(12) United States Patent
Norris et al.

(10) Patent No.: US 8,067,582 B2
(45) Date of Patent: Nov. 29, 2011

(54) FUSED HETEROCYCLIC COMPOUNDS USEFUL AS MODULATORS OF NUCLEAR HORMONE RECEPTOR FUNCTION

(75) Inventors: Derek J. Norris, Pennington, NJ (US); Ashvinikumar V. Gavai, Princeton Junction, NJ (US); James Aaron Balog, Lambertville, NJ (US); Joel F. Austin, Ewing, NJ (US); Weifang Shan, Princeton, NJ (US); Yufen Zhao, Pennington, NJ (US); Andrew James Nation, Scotch Plains, NJ (US); Wen-Ching Han, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/666,423

(22) PCT Filed: Jun. 26, 2008

(86) PCT No.: PCT/US2008/068272
§ 371 (c)(1), (2), (4) Date: Dec. 23, 2009

(87) PCT Pub. No.: WO2009/003077
PCT Pub. Date: Dec. 31, 2008

(65) Prior Publication Data
US 2010/0331324 A1    Dec. 30, 2010

Related U.S. Application Data

(60) Provisional application No. 60/946,486, filed on Jun. 27, 2007.

(51) Int. Cl.
C07D 517/00    (2006.01)
C07D 491/00    (2006.01)
A61K 31/40     (2006.01)

(52) U.S. Cl. .............................. 540/1; 548/421; 514/410

(58) Field of Classification Search .................. 514/410; 540/1; 548/421
See application file for complete search history.

(56) References Cited

U.S. PATENT DOCUMENTS

| | | |
|---|---|---|
| 6,953,679 B2 | 10/2005 | Salvati et al. |
| 6,960,474 B2 | 11/2005 | Salvati et al. |
| 7,087,636 B2 | 8/2006 | Salvati et al. |
| 7,141,578 B2 | 11/2006 | Salvati et al. |
| 7,432,267 B2 | 10/2008 | Salvati et al. |
| 2003/0181728 A1 | 9/2003 | Salvati et al. |
| 2004/0077605 A1 | 4/2004 | Salvati et al. |

FOREIGN PATENT DOCUMENTS

WO    WO 02/00617    1/2002

OTHER PUBLICATIONS

Anderson, J. 'The role of antiandrogen monotherapy in the treatment of prostate cancer' BJU International, vol. 91, p. 455-461, 2003.*
Cannon, J.G. 'Analog Design' Burger's Medicinal Chemistry and Drug Discovery, 5th Edition, vol. 1, Chapter 19, p. 783-802, 1995.*
Horig et al 'From bench to clinic and back: Perspective on the 1st IQPC Translational Research conference' Journal of Translational Medicine, 2(44), p. 1-8, 2004.*
Schafer et al 'Failure is an option: learning from unsuccessful proof-of-concept trials' Drug Discovery Today, 13(21/22), p. 913-916, 2008.*
Mondon, A. et al., Liebigs Ann. Chem., vol. 10, pp. 1760-1797 (1983).

* cited by examiner

*Primary Examiner* — Brandon Fetterolf
*Assistant Examiner* — Christopher R Stone
(74) *Attorney, Agent, or Firm* — Gary D. Greenblatt

(57) ABSTRACT

Disclosed are fused heterocyclic compounds of Formula (I) or pharmaceutically-acceptable salts or stereoisomers thereof. Also disclosed are methods of using such compounds in the treatment of at least one androgen receptor-associated condition, such as, for example, cancer, and pharmaceutical compositions comprising such compounds.

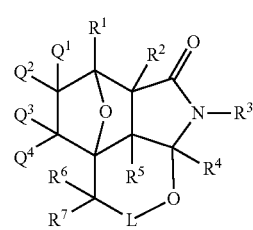

(I)

9 Claims, 8 Drawing Sheets

FUSED HETEROCYCLIC COMPOUNDS USEFUL AS MODULATORS OF NUCLEAR HORMONE RECEPTOR FUNCTION

FIELD OF THE INVENTION

The present invention generally relates to fused heterocyclic compounds, to methods of using such compounds in the treatment of androgen receptor-associated conditions such as cancer, and to pharmaceutical compositions comprising the compounds.

BACKGROUND OF THE INVENTION

Carcinoma of the prostate (CaP) is the second leading cause of cancer-related death in men. Reportedly, there were an estimated 221,000 new cases of CaP diagnosed in 2003 with an estimated 28,900 deaths. See American Cancer Society, Key Statistics about Prostate Cancer 2003; Jemal et al., CA Cancer J. Clin. Vol. 52 (2002), at p. 23-47. CaP presents a relatively high rate of morbidity and mortality necessitating prompt detection and effective treatment.

CaP has been commonly treated with surgery, i.e. radical prostatectomy. This procedure presents drawbacks in terms of surgical risks and impairment, and additionally, its usefulness may be limited to early-stage, organ-confined cancers. In advanced cases, the cancer may have spread beyond the bounds of the removed tissue, making it unlikely surgery will be a successful treatment. Radiation therapy also has been widely used as an alternative and/or supplement to surgery but with limited success.

In recent years, various treatment strategies have focused on inhibiting the role of androgens [testosterone (T) and dihydrotestosterone (DHT)] in prostate tumor growth. The androgen receptor (AR) is a ligand-binding transcription factor in the nuclear-hormone receptor (NHR) superfamily, and it is an important mediator of prostate cancer development and growth. The androgens (T and DHT) compete for binding to the AR (DHT having a higher binding affinity than T), and both T and DHT activate the AR, influencing cell function and stimulating growth of the prostate and other tissue, including prostate tumor cells.

Recent efforts for treating CaP have focused on developing compounds that act as androgen receptor modulators. A compound that binds to the AR and mimics the effect of the natural ligand (e.g., T or DHT) is referred to as an "agonist", while a compound that inhibits the effect of a natural ligand in binding to the AR is referred to as an "antagonist". AR antagonist and/or agonists (collectively "antiandrogens") have proven useful in the treatment of CaP.

However, AR is related to other members of the subfamily of NHR's, which share a sequence homology to one another. Other members of this sub-family include the estrogen receptor (ER), the progesterone receptor (PR), the glucocorticoid receptor (GR), the mineralcorticoid receptor (MR), and the aldosterone receptor (ALDR). Ligands to these receptors are known to play an important role in the health of men and women. Given the similarity in sequence homology of these NHR's, the development of compounds which have good specificity for one or more steroid receptors, but which have reduced or no cross-reactivity for other steroid receptors (thus reducing or avoiding undesirable side effects), has presented challenges. There are several known, approved non-steroidal antiandrogens including bicalutamide, Eulexin, and Anandrone. However, these antiandrogens may bind reversibly to the AR, and if treatment is continued for a period of years, tumors may become androgen independent. Androgen-independent tumors are not affected by the natural ligands (T and DHT), and thus, antiandrogens may lose effectiveness in treating androgen-independent tumors.

As may be appreciated, there remains a need for more potent AR antagonists and/or AR antagonist with a different pharmacological profile as compared with currently-known antiandrogens.

SUMMARY OF THE INVENTION

Described herein are compounds of Formula (I):

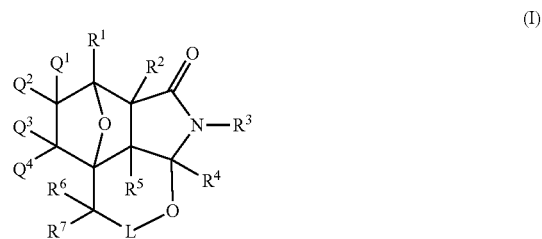

(I)

or pharmaceutically-acceptable salts or stereoisomers thereof, wherein:

L is a bond, $CR^8R^9$, or $CR^8R^9CR^{10}R^{11}$;

$R^1$ is H, alkyl, substituted alkyl, alkenyl, substituted alkenyl, alkynyl, substituted alkynyl, aryl, substituted aryl, heterocyclo, substituted heterocyclo, CN, —C(=O)$R^b$, —C(=O)N$R^bR^c$, or —C(=O)O$R^a$;

$R^2$ is H, alkyl, substituted alkyl, alkenyl, substituted alkenyl, alkynyl, substituted alkynyl, aryl, substituted aryl, heterocyclo, substituted heterocyclo, halo, CN, —C(=O)$R^b$, —C(=O)N$R^bR^c$, —C(=O)O$R^a$, —N$R^bR^c$, —N$R^a$C(=O)$R^a$, —N$R^a$C(=O)N$R^bR^c$, —N$R^a$C(=O)O$R^a$, —N$R^a$SO$_2R^a$, —N$R^a$SO$_2$N$R^bR^c$, —NO$_2$, —O$R^a$, or —SO$_2R^a$;

$R^3$ is aryl, substituted aryl, heteroaryl, or substituted heteroaryl, wherein $R^3$ is attached to the N atom of the core rings via a carbon atom of $R^3$;

$R^4$ is H, alkyl, or substituted alkyl;

$R^5$ is H, alkyl, substituted alkyl, cycloalkyl, substituted cycloalkyl, aryl, substituted aryl, heteroaryl, substituted heteroaryl, halo, CN, —C(=O)$R^b$, —C(=O)N$R^bR^c$, —N$R^bR^c$, —C(=O)O$R^a$, —N$R^a$C(=O)$R^a$, —N$R^a$C(=O)O$R^a$, —N$R^a$SO$_2R^a$; —NO$_2$, —O$R^a$, or —SO$_2R^a$;

$R^6$ and $R^7$ are each independently H, alkyl, substituted alkyl, cycloalkyl, substituted cycloalkyl, aryl, substituted aryl, heteroaryl, substituted heteroaryl, F, Cl, Br, CN, —C(=O)N$R^bR^c$, —C(=O)O$R^a$, —N$R^bR^c$, —N$R^a$C(=O)$R^a$, —N$R^a$C(=O)N$R^bR^c$, —N$R^a$C(=O)O$R^a$, —N$R^a$SO$_2R^a$, —N$R^a$SO$_2$N$R^bR^c$, NO$_2$, —O$R^a$, —OC(=O)$R^b$, —OC(=O)N$R^bR^c$, —SO$_2R^a$, and/or —SO$_2$N$R^bR^c$, provided that when L is a bond, $R^6$ and $R^7$ are not F, Cl, Br, —N$R^bR^c$, —N$R^a$C(=O)$R^a$, —N$R^a$C(=O)N$R^bR^c$, —N$R^a$C(=O)O$R^a$, —N$R^a$SO$_2R^a$, —N$R^a$SO$_2$N$R^bR^c$, NO$_2$, —O$R^a$, —OC(=O)$R^b$, —OC(=O)N$R^bR^c$, —SO$_2R^a$, or —SO$_2$N$R^bR^c$;

$R^8$ and $R^9$ are each independently H, alkyl, substituted alkyl, cycloalkyl, substituted cycloalkyl, aryl, substituted aryl, heteroaryl, substituted heteroaryl, F, Cl, Br, CN, —C(=O)N$R^bR^c$, —C(=O)O$R^a$, —N$R^bR^c$, —N$R^a$C(=O)$R^a$, —N$R^a$C(=O)N$R^bR^c$, —N$R^a$C(=O)O$R^a$, —N$R^a$SO$_2R^a$, —N$R^a$SO$_2$N$R^bR^c$, NO$_2$, —O$R^a$, —OC(=O)$R^b$, —OC(=O)N$R^bR^c$, —SO$_2R^a$, and/or —SO$_2$N$R^bR^c$, provided that when L is $CR^8R^9$, $R^8$ and $R^9$ are not F, Cl, Br,-

—NR$^b$R$^c$, —NR$^a$C(=O)R$^a$, —NR$^a$C(=O)NR$^b$R$^c$, —NR$^a$C(=O)OR$^a$, —NR$^a$SO$_2$R$^a$, —NR$^a$SO$_2$NR$^b$R$^c$, NO$_2$, —OR$^a$, —OC(=O)R$^b$, —OC(=O)NR$^b$R$^c$, —SO$_2$R$^a$, or —SO$_2$NR$^b$R$^c$;

R$^{10}$ and R$^{11}$ are each independently H, alkyl, substituted alkyl, cycloalkyl, substituted cycloalkyl, aryl, substituted aryl, heteroaryl, substituted heteroaryl, —C(=O)NR$^b$R$^c$, and/or —C(=O)OR$^a$;

Q$^1$, Q$^2$, Q$^3$, and Q$^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamide, thiol, alkylthio, substituted alkylthio, halo, CN, —C(=O)R$^b$, —C(=O)NR$^b$R$^c$, —C(=O)OR$^a$, —NR$^b$R$^c$, —NR$^b$OR$^a$, —NR$^a$C(=O)R$^a$, —NR$^a$C(=O)NR$^b$R$^c$, —NR$^a$C(=O)OR$^a$, —NR$^a$SO$_2$R$^a$, —NR$^a$SO$_2$NR$^b$R$^c$, N$_3$, NO$_2$, —OR$^a$, —OC(=O)R$^b$, —OC(=O)NR$^b$R$^c$, —SO$_2$R$^a$, —SO$_2$NR$^b$R$^c$, and/or —SO$_2$OR$^a$; or Q$^1$ and Q$^2$ together form =CR$^d$R$^d$, =O, =NR$^d$, =NOR$^b$, or =NNR$^c$R$^d$; and/or Q$^3$ and Q$^4$ together form =CR$^d$R$^d$, =O, =NR$^d$, =NOR$^b$, or =NNR$^c$R$^d$; or Q$^1$ and Q$^3$ together form —O— or NR$^b$, and Q$^2$ and Q$^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$;

each R$^a$ is independently H, alkyl, substituted alkyl, aryl, substituted aryl, heterocyclo, and/or substituted heterocyclo;

each R$^b$ is independently H, alkyl, substituted alkyl, aryl, substituted aryl, heterocyclo, and/or substituted heterocyclo;

each R$^c$ is independently H, alkyl, substituted alkyl, aryl, substituted aryl, heterocyclo, and/or substituted heterocyclo; or R$_b$ and R$_c$ together with the nitrogen atom to which they are attached, can form a 4-7 membered heterocyclo or substituted heterocyclo ring; and each R$^d$ is independently H, —C(=O)OR$^a$, —C(=O)NR$^b$R$^c$, —OR$_a$, —SO$_2$R$^a$, —SO$_2$NR$^b$R$^c$, alkyl, substituted alkyl, aryl, substituted aryl, heterocyclo, and/or substituted heterocyclo, and/or substituted heterocyclo.

Further described herein is at least one pharmaceutical composition comprising at least one compound of Formula (I) or a pharmaceutically-acceptable salt or stereoisomer thereof; and at least one pharmaceutically acceptable carrier and/or diluent.

Even further described herein is a method of modulating the function of at least one nuclear hormone receptor comprising administering to a patient in need thereof, an effective amount of at least one compound of Formula (I), or a pharmaceutically-acceptable salt or stereoisomer thereof.

Yet even further described herein is at least one method treating a condition or disorder comprising administering to a mammalian species in need thereof a therapeutically effective amount of at least one compound of Formula (I) or a pharmaceutically-acceptable salt or stereoisomer thereof.

BRIEF DESCRIPTION OF THE DRAWINGS

The invention is illustrated by reference to the accompanying drawings described below.

DETAILED DESCRIPTION OF THE INVENTION

Figure 1:
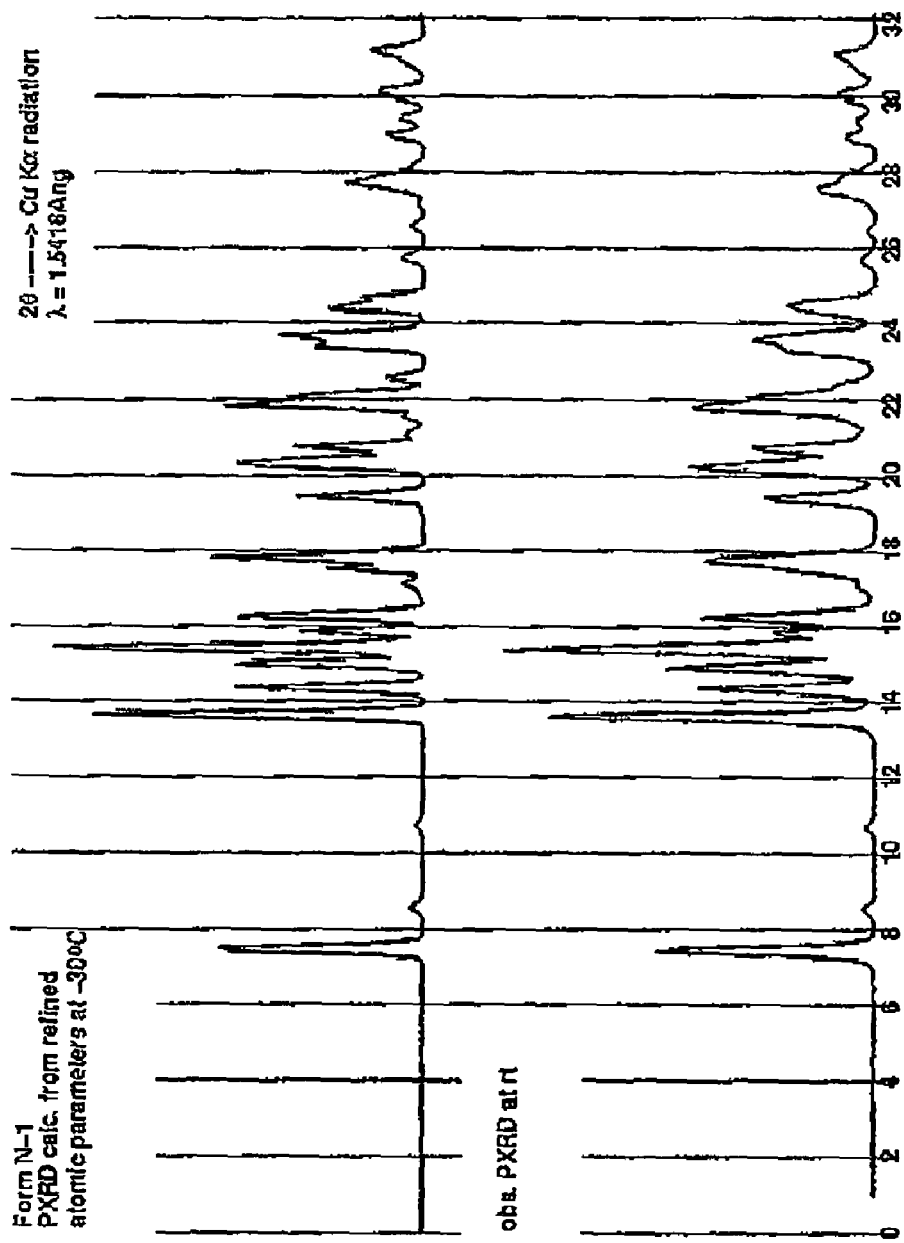
FIG. 1 shows observed (at r.t.) and simulated (at about −30° C.) PXRD patterns (CuKαλ=1.5418 Å) of the N-1 Form of the compound of Example 1.
Figure 2:
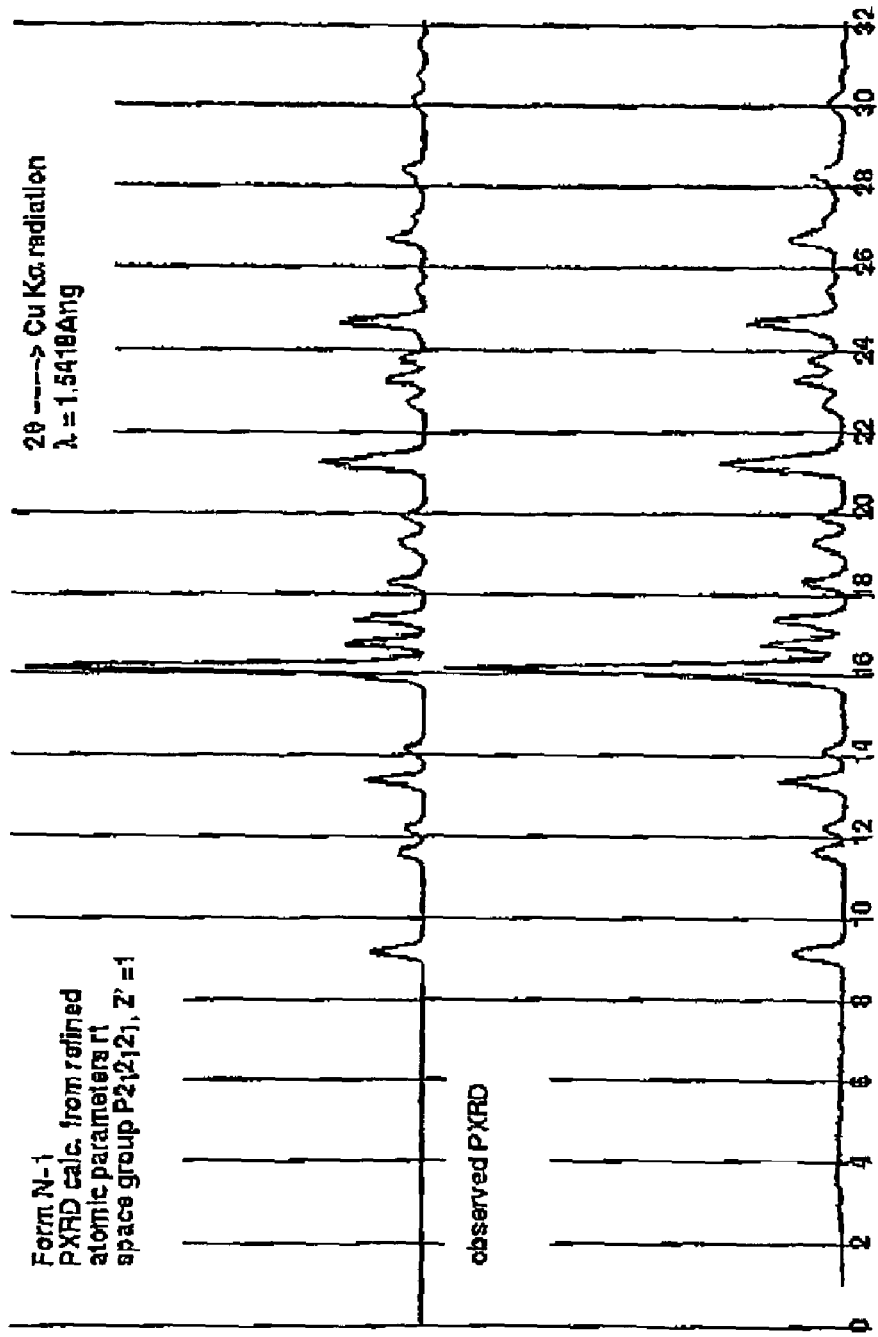
FIG. 2 shows observed (at room temperature (r.t.)) and simulated (at a Temperature (T) of about 25° C.) powder x-ray diffraction (PXRD) patterns (CuKαλ=1.5418 Å) of the N-1 Form of the compound of Example 3.

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group. Throughout the specification, groups and substituents thereof may be chosen by one skilled in the field to provide stable moieties and compounds.

The terms "alkyl" and "alk" refer to a straight or branched chain alkane (hydrocarbon) radical containing from 1 to 12 carbon atoms, preferably from 1 to 6 carbon atoms, and more preferably from 1 to 4 carbon atoms. Exemplary "alkyl" and/or "alk" groups include, but are not limited to, for example, methyl; ethyl; propyl; isopropyl; n-butyl; isobutyl; t-butyl; pentyl; hexyl; isohexyl; heptyl; 4,4-dimethylpentyl; diethylpentyl; octyl; 2,2,4-trimethylpentyl; nonyl; decyl; undecyl; and dodecyl.

The term "lower alkyl" refers to an "alkyl" and/or "alk" group containing from 1 to 4 carbon atoms and preferably from 1 to 2 carbon atoms. When a subscript is used with reference to an alkyl or other group, the subscript refers to the number of carbon atoms the group may contain. For example, the term "C$_{0-4}$alkyl" includes a bond and an alkyl group containing 1 to 4 carbon atoms, and the term "$C_{1-4}$alkyl" refers to alkyl groups containing 1 to 4 carbon atoms. Exemplary lower alkyl groups include, but are not limited to, for example, methyl; ethyl; propyl; isopropyl; n-butyl; t-butyl; and isobutyl.

The term "substituted alkyl" refers to an alkyl group substituted with at least one substituent, preferably 1 to 4 substituents, at any available and substitutable position. Exemplary substituents include, but are not limited to, for example, halo (e.g., a single halo substituent or multiple halo substituents forming, in the latter case, groups such as, for example, a perfluoroalkyl group or an alkyl group bearing —CCl$_3$ or —CF$_3$); alkoxy; alkylthio; hydroxyl; carboxy (i.e., —COOH); alkoxycarbonyl; alkylcarbonyloxy; CN; amino (i.e., —NH$_2$); alkylamino; dialkylamino; carbamoyl; carbamate; urea; amidinyl; thiol (i.e., —SH); heterocycle; cycloalkyl; heterocycloalkyl; —S-aryl; —S-heterocycle; —S(=O)-aryl; —S(=O)-heterocycle; arylalkyl-O—; —S(O)$_2$-aryl; —S(O)$_2$-heterocycle; —NHS(O)$_2$-aryl; —NHS(O)$_2$-heterocycle; —NHS(O)$_2$NH-heterocycle; —NHS(O)$_2$NH-aryl; —O-aryl; —O-heterocycle; —NH-aryl; —NH-heterocycle; —NHC(=O)-aryl; —NHC(=O)-alkyl; —NHC(=O)-heterocycle; —OC(=O)-aryl; —OC(=O)-heterocycle; —NHC(=O)NH-aryl; —NHC(=O)NH-heterocycle; —OC(=O)O-alkyl; —OC(=O)O-aryl; —OC(=O)O-heterocycle; —OC(=O)NH-aryl; —OC(=O)NH-heterocycle; —NHC(=O)O-aryl; —NHC(=O)O-heterocycle; —NHC(=O)O-alkyl; —C(=O)NH-aryl; —C(=O)NH-heterocycle; —C(=O)O-aryl; —C(=O)O-heterocycle; —N(alkyl)S(O)$_2$-aryl; —N(alkyl)S(O)$_2$-heterocycle; —N(alkyl)S(O)$_2$NH-aryl; —N(alkyl)S(O)$_2$NH-heterocycle; —N(alkyl)-aryl; —N(alkyl)-heterocycle; —N(alkyl)C(=O)-aryl; —N(alkyl)C(=O)-heterocycle; —N(alkyl)C(=O)NH-aryl; N(alkyl)C(=O)NH-heterocycle; —OC(=O)N(alkyl)-aryl; —OC(=O)N(alkyl)-heterocycle; —N(alkyl)C(=O)O-aryl; —N(alkyl)C(=O)O-heterocycle; —C(=O)N(alkyl)-aryl; —C(=O)N(alkyl)-heterocycle; —NHS(O)$_2$N(alkyl)-aryl; —NHS(O)$_2$N(alkyl)-heterocycle; —NHP(O)$_2$N(alkyl)-aryl; —NHC(=O)N(alkyl)-aryl; —NHC(=O)N(alkyl)-heterocycle; —N(alkyl)S(O)$_2$N(alkyl)-aryl; —N(alkyl)S(O)$_2$N(alkyl)-heterocycle; —N(alkyl)C(=O)N(alkyl)-aryl; —N(alkyl)C(=O)N(alkyl)-heterocycle; and —Si(alkyl)$_3$. In the aforementioned exemplary substituents, in each instance, groups such as "alkyl" and "cycloalkyl" can themselves be substituted with groups selected from —CF$_3$, halogen, —C≡CH, —CN, —NH$_2$, —OCF$_3$, and —NO$_2$. In the aforementioned exemplary substituents, in each instance, groups such as "aryl", and "heterocycle" can themselves be substituted with groups selected from methyl, cyclopropyl, —CF$_3$, halogen, —C≡CH, —CN, —NH$_2$, —OCF$_3$, and —NO$_2$.

The term "substituted lower alkyl" refers to a lower alkyl substituted at any available and substitutable position with at least one substituent described above in defining the term "substituted alkyl" as an exemplary alkyl substituent.

The term "aryl" refers to cyclic aromatic hydrocarbon groups having from 1 to 3 aromatic rings, especially monocyclic or bicyclic groups, such as, for example, phenyl, biphenyl, or naphthyl. When the aryl group contains two or more aromatic rings (e.g., bicyclic, etc.), the aromatic rings may be joined at a single point (e.g., biphenyl) or fused (e.g., naphthyl and phenanthrenyl).

The term "substituted aryl" refers to an aryl substituted with at least one substituent, preferably 1 to 5 substituents, at any available and substitutable ring position, or where valence allows on any rings fused or attached thereto. Exemplary substituents include, but are not limited to, for example, alkyl, substituted alkyl, or those recited hereinabove for substituted alkyl.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl. The term "substituted alkenyl" refers to an alkenyl substituted with at least one substituent, preferably 1 to 4 substituents, at any available point of attachment. Exemplary substituents include, but are not limited to, for example, substituted alkyl; alkenyl; and the substituents recited above in defining the term "substituted alkyl" as exemplary alkyl substituents.

The term "cycloalkyl" refers to a fully saturated hydrocarbon group containing from 1 to 4 rings and 3 to 8 carbons per ring. Exemplary cycloalkyl groups include, but are not limited to, for example, cyclopropyl, cyclobutyl, cyclopentyl, cyclohexyl, and cycloheptyl.

The term "substituted cycloalkyl" refers to a cycloalkyl substituted with at least one substituent, preferably 1 to 4 substituents, at any available point of attachment. Exemplary substituents include groups those recited for substituted alkyl.

The term "cycloalkenyl" refers to a partially saturated hydrocarbon group having at least one double bond in the ring and containing from 1 to 4 rings and 3 to 8 carbons per ring. Exemplary cycloalkenyl groups include, but are not limited to, for example, cyclobutenyl, cyclopentenyl, and cyclohexenyl.

The term "substituted cycloalkenyl" refers to a cycloalkenyl substituted with at least one substituent, preferably 1 to 4 substituents, at any available point of attachment. Exemplary substituents include, but are not limited to, for example, the substituents described above in defining the term "substituted alkenyl" as exemplary alkenyl substituents.

The term "alkylamino" refers to an amino group having one hydrogen atom replaced with an alkyl. Thus, alkylamino refers to the group —NH(alkyl).

The term "substituted alkylamino" refers to an alkylamino group having one hydrogen atom is replaced with a substituted alkyl. Thus, alkylamino refers to the group —NH(substituted alkyl).

The term "dialkylamino" refers to an amino group having both of the hydrogen atoms replaced with a group chosen from alkyl and/or substituted alkyl.

The terms "alkoxy" or "alkylthio" refers to an alkyl bonded through an oxygen linkage (—O—) or a sulfur linkage (—S—), respectively.

The terms "substituted alkoxy" or "substituted alkylthio" refer to a substituted alkyl bonded through an oxygen or sulfur linkage, respectively.

The term "carbonyl" refers to C(=O).

The term "alkoxycarbonyl" refers to an alkoxy bonded through a carbonyl. Thus, alkoxycarbonyl refers to the group —C(=O)O(alkyl).

The term "alkylcarbonyl" refers to an alkyl bonded through a carbonyl. Thus, alkylcarbonyl refers to the group —C(=O)(alkyl).

The term "alkylcarbonyloxy" refers to an alkylcarbonyl bonded through an oxygen linkage. Thus, alkylcarbonyloxy refers to the group —OC(=O)(alkyl).

The terms "heterocycle", heterocyclic" and "heterocyclo" refer to fully saturated, partially saturated, or fully unsaturated, aromatic (i.e., "heteroaryl") or nonaromatic cyclic groups that are, for example, 3 to 7 membered monocyclic, 7 to 11 membered bicyclic, or 10 to 16 membered tricyclic ring systems having at least one heteroatom in at least one carbon atom-containing ring. Each ring of the heterocycle, heterocyclic, or heterocyclo containing a heteroatom may have 1, 2, 3, or 4 heteroatoms selected from N, O, and/or S, where the N and/or S heteroatom(s) may optionally be oxidized and the N heteroatom(s) may optionally be quaternized. A heterocycle, heterocyclic, or heterocyclo may be attached to the remainder of the molecule at any heteroatom or carbon atom of the ring or ring system.

Exemplary groups containing a quaternized N include, but are not limited to, for example, a tetraalkylammonium group, such as, for example, tetramethylammonium and N-methylpyridinium; a protonated ammonium species, such as, for example, trimethylhydroammonium and N-hydropyridinium; an amine N-oxide, such as, for example, N-methylmorpholine-N-oxide and pyridine-N-oxide; and an N-aminoammonium group, such as, for example, N-aminopyridinium.

Exemplary monocyclic heterocycles, heterocyclics, or heterocyclos include, but are not limited to, for example, ethylene oxide; azetidinyl; pyrrolidinyl; pyrrolyl; pyrazolyl; oxetanyl; pyrazolinyl; imidazolyl; imidazolinyl; imidazolidinyl; oxazolyl; oxazolidinyl; isoxazolinyl; isoxazolyl; thiazolyl; thiadiazolyl; thiazolidinyl; isothiazolyl; isothiazolidinyl; furyl; tetrahydrofuryl; thienyl; oxadiazolyl; piperidinyl; piperazinyl; 2-oxopiperazinyl; 2-oxopiperidinyl; 2-oxopyrrolodinyl; 2-oxoazepinyl; azepinyl; hexahydrodiazepinyl; 4-piperidonyl; pyridyl; pyrazinyl; pyrimidinyl; pyridazinyl; triazinyl; triazolyl; tetrazolyl; tetrahydropyranyl; morpholinyl; thiamorpholinyl; thiamorpholinyl sulfoxide; thiamorpholinyl sulfone; 1,3-dioxolane; and tetrahydro-1,1-dioxothienyl.

Exemplary bicyclic heterocycles, heterocyclics, or heterocyclos include, but are not limited to, for example, indolyl; isoindolyl; benzothiazolyl; benzodioxolyl; benzoxazolyl; benzoxadiazolyl; benzothienyl; quinuclidinyl; quinolinyl; tetrahydroisoquinolinyl; isoquinolinyl; benzimidazolyl; benzopyranyl; indolizinyl; benzofuryl; benzofurazanyl; chromonyl; coumarinyl; benzopyranyl; cinnolinyl; quinoxalinyl; indazolyl; pyrrolopyridyl; furopyridinyl, such as, for example, furo[2,3-c]pyridinyl, furo[3,2-b]pyridinyl], and furo[2,3-b]pyridinyl; dihydrobenzodioxinyl; dihydrodioxidobenzothiophenyl; dihydroisoindolyl; dihydroindolyl; dihydroquinolinyl; dihydroquinazolinyl, such as, for example, 3,4-dihydro-4-oxo-quinazolinyl; triazinylazepinyl; and tetrahydroquinolinyl.

Exemplary tricyclic heterocycles, heterocyclics, or heterocyclos include, but are not limited to, for example, carbazolyl; benzidolyl; phenanthrolinyl; dibenzofuranyl; acridinyl; phenanthridinyl; and xanthenyl.

The terms "substituted heterocycle," "substituted heterocyclic," and "substituted heterocyclo" refer to a heterocycle, heterocyclic, or heterocyclo substituted at any available point of attachment with at least one substituent, preferably 1 to 4 substituents, selected from alkyl and those recited for substituted alkyl.

The term "heteroaryl" refers to an aromatic heterocycle, heterocyclic, or heterocyclo.

The term "substituted heteroaryl" refers to an aromatic heterocycle, heterocyclic, or heterocyclo substituted with at least one substituent, preferably 1 to 4 substituents, at any available point of attachment. Exemplary substituents include, but are not limited to, for example, the substituents describe above in defining the terms "substituted heterocycle," "substituted heterocyclic," and "substituted heterocyclo".

The term "nitro" refers to the group —$NO_2$.

The term "carbamoyl" refers to the group —C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "carbamate" refers to the group —O—C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "urea" refers to the group —NH—C(=O)NH— which is bonded on one end to the remainder of the molecule and on the other to hydrogen or an organic moiety, such as, for example, alkyl, substituted alkyl, aryl, substituted aryl, heterocycle, alkylcarbonyl, hydroxyl, and substituted nitrogen.

The term "amidinyl" refers to the group —C(=NH)($NH_2$).

The terms "substituted carbamoyl", "substituted carbamate", "substituted urea", and "substituted amidinyl" refer to a carbamoyl, carbamate, urea, and amidinyl, respectively, in which one more hydrogen group is replaced by an organic moiety, such as, for example, alkyl, substituted alkyl, aryl, substituted aryl, heterocycle, alkylcarbonyl, hydroxyl, and substituted nitrogen.

The terms "halogen" and "halo" refer to fluorine, chlorine, bromine, and iodine.

The term "salt(s)", as employed herein, denotes acidic and/or basic salts formed with inorganic and/or organic acids and/or bases, and such term, as used herein, further includes zwitterion(s) ("inner salts").

The terms "zwitterion(s)", as employed herein, denote compound(s) containing both a basic moiety, including but not limited to, for example, amine, pyridine and imidazole; and an acidic moiety including but not limited to, for example, a carboxylic acid.

The term "pharmaceutically acceptable", as employed herein, indicates the subject matter being identified as "pharmaceutically acceptable" is suitable and physiologically acceptable for administration to a patient. For example, the term "pharmaceutically acceptable salt(s)" denotes suitable and physiologically acceptable salt(s).

When a functional group is termed "protected", the functional group is in a modified form to mitigate, especially to preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991). The compounds of Formula (I) can also form salts. As a result, when a compound of Formula (I) is referred to herein, such reference includes, unless otherwise indicated, salts thereof. In one embodiment, the compounds of Formula (I) form pharmaceutically acceptable salts. In another embodiment, the compounds of Formula (I) form salts that can, for example, be used to isolate and/or purify the compounds of Formula (I). Salt(s) of the Formula (I) compounds can be formed by, for example, reacting a Formula (I) compound with, for example, an equivalent amount of acid or base in a medium that allows the thusly formed salt to, for example, either be precipitated out, or be isolated via lyophilization.

Exemplary acidic salt(s) that the compounds of Formula (I) can form with inorganic and/or organic acids include, but are not limited to, for example, include acetates, ascorbates, benzoates, benzenesulfonates, bisulfates, citrates, sulfates, hydrochlorides, hydrobromides, hydroiodides, maleates, methanesulfonates, nitrates, salicylates, succinates, tartrates, p-toluenesulfonates, and lactates. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

Prodrugs and solvates of the compounds of Formula (I) are also contemplated herein. The term "prodrug(s)", as employed herein, denotes a compound that, upon administration to a subject, undergoes chemical conversion via metabolic and/or chemical processes in vivo to yield a compound and/or derivative of Formula (I), or a salt and/or solvate thereof. Various forms of prodrug(s) are well known in the art. For examples of such prodrug derivatives, see:

a) Design of Prodrugs, edited by H. Bundgaard, (Elsevier, 1985) and Methods in Enzymology, Vol. 112, p. 309-396, edited by K. Widder, et al. (Academic Press, 1985);
b) A Textbook of Drug Design and Development, edited by Krosgaard-Larsen and H. Bundgaard, Chapter 5, "Design and Application of Prodrugs," by H. Bundgaard, p. 113-191 (1991); and
c) H. Bundgaard, Advanced Drug Delivery Reviews, 8, 1-38 (1992).

The term "solvate", as employed herein, denotes a compound produced by the chemical interaction of at least one solvent with at least one solute comprising at least one compound of Formula (I). Exemplary solvates include, but are not limited to, for example, hydrates.

All stereoisomers and geometric isomer(s) of the compounds of Formula (I), such as, for example, stereoisomer(s) that exist due to asymmetric carbons on various substituents, either in admixture or in pure or substantially pure form are further contemplated herein. In one embodiment, all enantiomers, tautomers, and diastereomers of the compounds of Formula (I), as well as mixtures, compounds, racemic compounds, racemic mixtures, and racemates produced therefrom are contemplated herein. In another embodiment, all optically active isomers of the compounds of Formula (I), including pure or substantially pure optically active isomers, i.e., optically active isomers substantially free of other isomers are contemplated herein.

When a compound containing a single enantiomer of a compound of Formula (I) is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of the compounds in accordance with Formula (I) can have the S or R configuration as defined by the IUPAC 1974 Recommendations.

In one embodiment, the compounds of Formula (I) are provided wherein L is a bond. The compounds of this embodiment have structures represented by Formula (Ia):

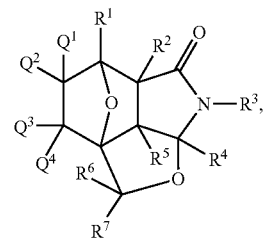

(Ia)

or a pharmaceutically-acceptable salt or stereoisomer thereof; wherein $Q^1$, $Q^2$, $Q^3$, $Q^4$, $R^1$, $R^2$, $R^3$, $R^4$, $R^5$, $R^6$, and $R^7$ are as defined hereinabove.

In another embodiment, the compounds of Formula (I) are provided wherein L is $CR^8R^9$. The compounds of this embodiment have structures represented by Formula (Ib):

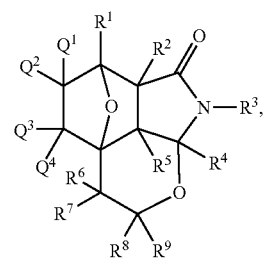

(Ib)

or a pharmaceutically-acceptable salt or stereoisomer thereof; wherein $Q^1$, $Q^2$, $Q^3$, $Q^4$, $R^1$, $R^2$, $R^3$, $R^4$, $R^5$, $R^6$, $R^7$, $R^8$, and $R^9$ are as defined hereinabove.

In a further embodiment, the compounds of Formula (I) are provided wherein L is $CR^8R^9CR^{10}R^{11}$. The compounds of this embodiment have structure represented by Formula (Ic):

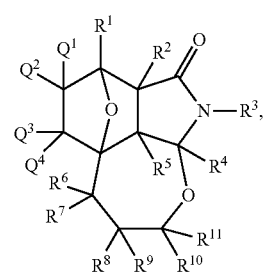

(Ic)

or a pharmaceutically-acceptable salt or stereoisomer thereof; wherein $Q^1$, $Q^2$, $Q^3$, $Q^4$, $R^1$, $R^2$, $R^3$, $R^4$, $R^5$, $R^6$, $R^7$, $R^8$, $R^9$, $R^{10}$, and $R^{11}$ are as defined hereinabove.

In one embodiment, the compounds of Formula (I) are provided wherein $R^4$ is H, methyl, or substituted methyl.

Preferably, $R^4$ is H or methyl, and more preferably, $R^4$ is H. For example, this embodiment provides compounds of Formula (I) wherein L is $CR^8R^9$ and $R^4$ is H.

In another embodiment, the compounds of Formula (I) are provided wherein $R^2$ is H, $C_{1-4}$alkyl, or substituted $C_{1-4}$alkyl. Examples of suitable $R^2$ groups include, but are not limited to, H, methyl, substituted methyl, ethyl, and substituted ethyl. Preferably, $R^2$ is H or methyl, and more preferably, $R^2$ is H. For example, this embodiment provides compounds of Formula (I) wherein L is $CR^8R^9$ and $R^2$ is H; as well as compounds of Formula (I) wherein L is $CR^8R^9$, $R^2$ is H, and $R^4$ is H.

In a further embodiment, the compounds of Formula (I) are provided wherein $R^5$ is H, $C_{1-4}$alkyl, or substituted $C_{1-4}$alkyl. Examples of suitable $R^5$ groups include, but are not limited to, H, methyl, substituted methyl, ethyl, and substituted ethyl. Preferably, $R^5$ is H or methyl, and more preferably, $R^5$ is H. For example, this embodiment provides compounds of Formula (I) wherein L is $CR^8R^9$ and $R^5$ is H; as well as compounds of Formula (I) wherein L is $CR^8R^9$, $R^5$ is H, and $R^4$ is H; and compounds of Formula (I) wherein L is $CR^8R^9$, $R^5$ is H, $R^4$ is H, and $R^2$ is H.

In a still further embodiment, the compounds of Formula (I) are provided wherein $R^1$ is H, —C(=O)$NR^bR^c$, $C_{1-4}$alkyl, or substituted $C_{1-4}$alkyl. Examples of suitable $R^1$ groups include, but are not limited to, H, methyl, substituted methyl, ethyl, substituted ethyl, and —C(=O)$NR^bR^c$ wherein $R^b$ is H, alkyl, or substituted alkyl, and $R^c$ is H, alkyl, or substituted alkyl, or $R_b$ and $R_c$ together with the nitrogen atom to which they are attached, can form a 4-7 membered heterocyclo or substituted heterocyclo ring. Preferably $R^1$ is H, methyl, or substituted methyl, and more preferably, $R^1$ is methyl. For example, this embodiment provides compounds of Formula (I) wherein L is $CR^8R^9$ and $R^1$ is methyl. Also, this embodiment provides compounds of Formula (I) wherein L is $CR^8R^9$, $R^1$ is methyl, and $R^4$ is H; as well as compounds of Formula (I) wherein L is $CR^8R^9$, $R^1$ is methyl, $R^4$ is H, and $R^5$ is H; and compounds of Formula (I) wherein L is $CR^8R^9$, $R^1$ is methyl, $R^5$ is H, $R^4$ is H, and $R^2$ is H.

According to one embodiment, the compounds of Formula (I) are provided wherein $R^3$ is substituted aryl, heteroaryl, or substituted heteroaryl, preferably substituted aryl or substituted heteroaryl, wherein $R^3$ is attached to the N atom of the core rings via a carbon atom of $R^3$. Examples of suitable groups for $R^3$ include, but are not limited to, substituted phenyl, substituted naphthyl, substituted pyridinyl, substituted quinoline, substituted isoquinoline, and substituted benzoxadiazol. Preferably, $R^3$ is substituted with 1, 2, or 3 substituents. Examples of suitable substituents include, but are not limited to, alkyl, substituted alkyl, cycloalkyl, substituted cycloalkyl, F, Cl, Br, CN, O-alkyl, and O-(substituted alkyl). Preferred substituents include —CH$_3$, —CF$_3$, F, Cl, CN, cyclopropanyl, and —OCF$_3$.

In one embodiment, the compounds of Formula (I) are provided wherein $R^3$ is a substituted aryl having the structure:

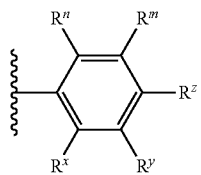

or a substituted heteroaryl having the structure:

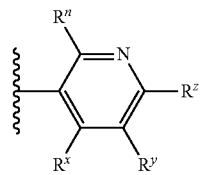

wherein: $R^n$, $R^m$, $R^x$, $R^y$, and $R^z$ are each independently H, $C_{1-4}$alkyl, substituted $C_{1-4}$alkyl, cyclopropyl, substituted cyclopropyl, alkynyl, substituted alkynyl, $OR^e$, halo, and/or CN, wherein $R^e$ is alkyl or substituted alkyl, provided that at least one of $R^n$, $R^m$, $R^x$, $R^y$, and $R^z$ is not H. In one example of this embodiment, $R^3$ is:

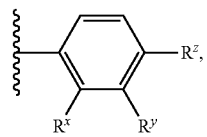

wherein $R^m$ is H; $R^n$ is H; $R^x$ is H, F, Cl, or —CH$_3$; $R^y$ is F, Cl, Br, I, —CF$_3$, —OCF$_3$, or —CH$_3$; and $R^z$ is CN, Cl, or Br. In another example of this embodiment, $R^3$ is:

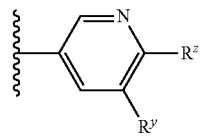

wherein $R^y$ is F, Cl, Br, I, —CF$_3$, —OCF$_3$, or —CH$_3$; and $R^z$ is CN, Cl, or Br. Examples of the $R^3$ include, but are not limited to:

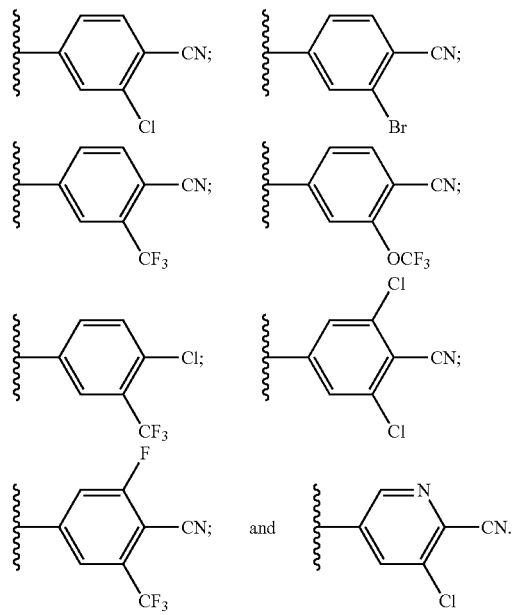

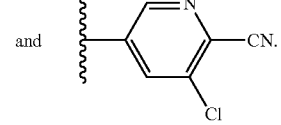

In another embodiment, compounds of Formula (I) are provided wherein $R^1$ is H, alkyl, or substituted alkyl. Preferably, $R^1$ is H, $C_{1-4}$alkyl, or substituted $C_{1-4}$alkyl, and more preferably, $R^1$ is H or $CH_3$.

In a further embodiment, compounds of Formula (I) are provided wherein $R^2$ is H, alkyl, substituted alkyl, or —C(=O)$NR^bR^c$.

In another embodiment, the compounds of Formula (I) are provided wherein $Q^1$, $Q^2$, $Q^3$, and $Q^4$ are each independently H, OH, —$NR^bR^c$, —$NR^bOR^a$, $N_3$, —NHC(=O)$R^a$, —$NHSO_2R^a$, and/or —NHC(=O)$OR^a$, provided that at least one of $Q^1$, $Q^2$, $Q^3$, and $Q^4$ is not H; or $Q^1$ and $Q^2$ together form =$CR^dR^d$, =O, =$NR^b$, =$NOR^b$, or =$NNR^bR^c$; and/or $Q^3$ and $Q^4$ together form =$CR^dR^d$, =, =$NR^b$, =$NOR^b$, or =$NNR^bR^c$; or $Q^1$ and $Q^3$ together form —O— or $NR^b$, and $Q^2$ and $Q^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)$R^b$, —C(=O)$NR^bR^c$, and/or —C(=O)$OR^a$; wherein each $R^a$ is independently H, alkyl, substituted alkyl, aryl, substituted aryl, heterocyclo, and/or substituted heterocyclo; each $R^b$ is independently H, alkyl, substituted alkyl, aryl, substituted aryl, heterocyclo, and/or substituted heterocyclo; and each $R^c$ is independently H, alkyl, substituted alkyl, aryl, substituted aryl, heterocyclo, and/or substituted heterocyclo. In this embodiment, preferably each $R^a$ is independently $C_{1-4}$alkyl, substituted $C_{1-4}$alkyl, phenyl, and/or substituted phenyl; each $R^b$ is independently H, alkyl, and/or substituted alkyl; and each $R^c$ is independently H, alkyl, and/or substituted alkyl.

One embodiment provides compounds of Formula (I) having the structure represented by Formula (Id):

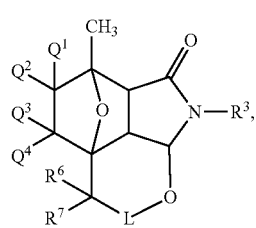

(Id)

wherein L, $R^3$, $R^6$, $R^7$, $Q^1$, $Q^2$, $Q^3$, and $Q^4$ are defined hereinabove.

In another embodiment, the compounds of Formula (Id) are provided wherein: $R^6$ is H; $R^7$ is H; $R^8$ and $R^9$, when present, are H; $R^3$ is substituted aryl or substituted heteroaryl, preferably substituted phenyl or substituted pyridinyl; $Q^1$, $Q^2$, $Q^3$, and $Q^4$ are each independently H, OH, —$NR^bR^c$, —$NR^bOR^a$, —$NR^aC$(=O)$R^a$, —$NR^aSO_2R^a$, and/or —$NR^aC$(=O)$OR^a$; or $Q^1$ and $Q^2$ together form =$CR^dR^d$, =O, =$NR^b$, =$NOR^b$, or =$NNR^bR^c$; and/or $Q^3$ and $Q^4$ together form =$CR^dR^d$, =O, =$NR^b$, =$NOR^b$, or =$NNR^bR^c$; or $Q^1$ and $Q^3$ together form —O— or $NR^b$, and $Q^2$ and $Q^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)$R^b$, —C(=O)$NR^bR^c$, and/or —C(=O)$OR^a$; each $R^a$ is independently $C_{1-4}$alkyl, substituted $C_{1-4}$alkyl, phenyl, and/or substituted phenyl; each $R^b$ is independently H, alkyl, and/or substituted alkyl; and each $R^c$ is independently H, alkyl, and/or substituted alkyl; or $R_b$ and $R_c$ together with the nitrogen atom to which they are attached, can form a 4-7 membered heterocyclo or substituted heterocyclo ring.

One embodiment provides compounds of Formula (Id) wherein $R^3$ is a substituted aryl having the structure:

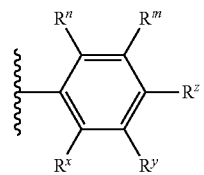

or a substituted heteroaryl having the structure:

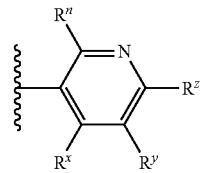

wherein: $R^n$, $R^m$, $R^x$, $R^y$, and $R^z$ are each independently H, $C_{1-4}$alkyl, substituted $C_{1-4}$alkyl, cyclopropyl, substituted cyclopropyl, alkynyl, substituted alkynyl, $OR^e$, halo, and/or CN, wherein $R^e$ is alkyl or substituted alkyl, provided that at least one of $R^n$, $R^m$, $R^x$, $R^y$, and $R^z$ is not H. In one example of this embodiment, $R^3$ is:

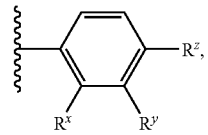

wherein $R^m$ is H; $R^n$ is H; $R^x$ is H, F, Cl, or —$CH_3$; $R^y$ is F, Cl, Br, I, —$CF_3$, —$OCF_3$, or —$CH_3$; and $R^z$ is CN, Cl, or Br. In another example of this embodiment, $R^3$ is:

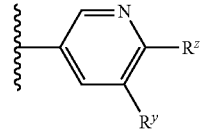

wherein $R^y$ is F, Cl, Br, I, —$CF_3$, —$OCF_3$, or —$CH_3$; and $R^z$ is CN, Cl, or Br.

In another embodiment, compounds are provided having the structure represented by Formula (Ie):

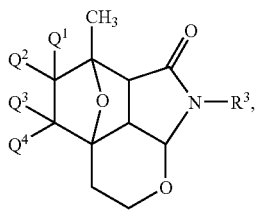

(Ie)

wherein: R³ is substituted aryl or substituted heteroaryl, preferably substituted phenyl or substituted pyridinyl, wherein R³ is attached to the N atom of the core rings via a carbon atom of R³; $Q^1$, $Q^2$, $Q^3$, and $Q^4$ are each independently H, OH, —NR$^b$R$^c$, —NR$^b$OR$^a$, —NHC(=O)R$^a$, —NHSO$_2$R$^a$, and/or —NHC(=O)OR$^a$; or $Q^1$ and $Q^2$ together form =CR$^d$R$^d$, =O, =NR$^b$, =NOR$^b$, or =NNR$^b$R$^c$; and/or $Q^3$ and $Q^4$ together form =CR$^d$R$^d$, =O, =NR$^b$, =NOR$^b$, or =NNR$^b$R$^c$; or $Q^1$ and $Q^3$ together form —O— or NR$^b$, and $Q^2$ and $Q^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$; each R$^a$ is independently C$_{1-4}$alkyl, substituted C$_{1-4}$alkyl, phenyl, and/or substituted phenyl; each R$^b$ is independently H, alkyl, and/or substituted alkyl; and each R$^c$ is independently H, alkyl, and/or substituted alkyl; or R$_b$ and R$_c$ together with the nitrogen atom to which they are attached, can form a 4- to 7-membered heterocyclo or substituted heterocyclo ring.

In another embodiment, compounds of Formula (Ie) are provided wherein R³ is a substituted aryl having the structure:

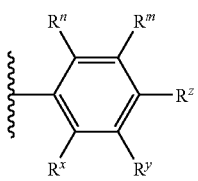

or a substituted heteroaryl having the structure:

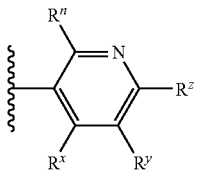

wherein: R$^n$, R$^m$, R$^x$, R$^y$, and R$^z$ are each independently H, C$_{1-4}$alkyl, substituted C$_{1-4}$alkyl, cyclopropyl, substituted cyclopropyl, alkynyl, substituted alkynyl, OR$^e$, halo, and/or CN, wherein R$^e$ is alkyl or substituted alkyl, provided that at least one of R$^n$, R$^m$, R$^x$, R$^y$, and R$^z$ is not H. In one example of this embodiment, R³ is:

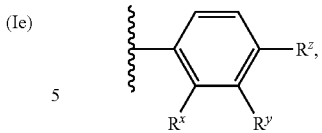

wherein R$^m$ is H; R$^n$ is H; R$^x$ is H, F, Cl, or —CH$_3$; R$^y$ is F, Cl, Br, I, —CF$_3$, —OCF$_3$, or —CH$_3$; and R$^z$ is CN, Cl, or Br. In another example of this embodiment, R³ is:

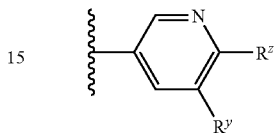

wherein R$^y$ is F, Cl, Br, I, —CF$_3$, —OCF$_3$, or —CH$_3$; and R$^z$ is CN, Cl, or Br.

In a further embodiment, compounds of Formula (Ie) are provided wherein: $Q^1$, $Q^2$, $Q^3$, and $Q^4$ are each independently H, OH, —NR$^b$R$^c$, —NR$^b$OR$^a$, —NHC(=O)R$^a$, —NHSO$_2$R$^a$, and/or —NHC(=O)OR$^a$; or $Q^1$ and $Q^2$ together form =CR$^d$R$^d$, =O, =NR$^b$, =NOR$^b$, or =NNR$^b$R$^c$; and/or $Q^3$ and $Q^4$ together form =CR$^d$R$^d$, =O, =NR$^b$, =NOR$^b$, or =NNR$^b$R$^c$; or $Q^1$ and $Q^3$ together form —O— or NR$^b$, and $Q^2$ and $Q^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$; each R$^a$ is independently C$_{1-4}$alkyl, substituted C$_{1-4}$alkyl, phenyl, and/or substituted phenyl; each R$^b$ is independently H, alkyl, and/or substituted alkyl; and each R$^c$ is independently H, alkyl, and/or substituted alkyl.

In another embodiment, compounds are provided having the structure represented by Formula (If):

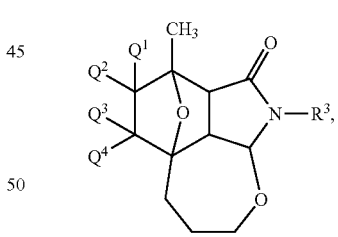

(If)

wherein: R³ is substituted aryl or substituted heteroaryl, preferably substituted phenyl or substituted pyrindinyl, wherein R³ is attached to the N atom of the core rings via a carbon atom of R³; $Q^1$, $Q^2$, $Q^3$ and $Q^4$ are each independently H, OH, —NR$^b$R$^c$, —NR$^b$OR$^a$, —NHC(=O)R$^a$, —NHSO$_2$R$^a$, and/or —NHC(=O)OR$^a$, provided that at least one of $Q^1$, $Q^2$, $Q^3$, and $Q^4$ is not H; or $Q^1$ and $Q^2$ together form =CR$^d$R$^d$, =O, =NR$^b$, =NOR$^b$, or =NNR$^b$R$^c$; and/or $Q^3$ and $Q^4$ together form =CR$^d$R$^d$, =O, =NR$^b$, =NOR$^b$, or =NNR$^b$R$^c$; or $Q^1$ and $Q^3$ together form —O— or NR$^b$, and $Q^2$ and $Q^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$; each R$^a$ is independently C$_{1-4}$alkyl, substituted C$_{1-4}$alkyl, phenyl, and/or substituted phenyl; each R$^b$ is independently H, alkyl, and/or substituted alkyl; and each R$^c$ is independently H, alkyl, and/or substituted alkyl; or R$_b$ and R$_c$ together with the nitrogen atom to which they are attached, can form a 4- to 7-membered heterocyclo or substituted heterocyclo ring.

One embodiment is directed towards compounds of Formula (I) wherein Q$^1$ and Q$^3$ together form —O— or NR$^b$, and Q$^2$ and Q$^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$. The compounds of this embodiment are represented by Formulas (Ig) and (Ih):

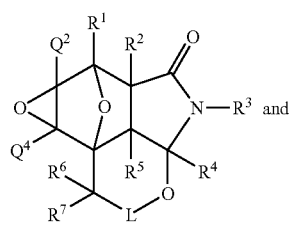

(Ig)

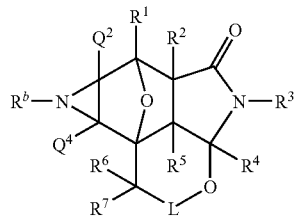

(Ih)

or pharmaceutically-acceptable salts or stereoisomers thereof; and L, R$^1$, R$^2$, R$^3$, R$^4$, R$^5$, R$^6$, R$^7$, R$^b$, and R$^d$ are as defined hereinabove.

In another embodiment, compounds of Formula (Id) are provided having the structure represented by Formula (If):

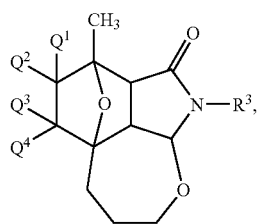

(If)

wherein: R$^3$ is substituted aryl or substituted heteroaryl, preferably substituted phenyl, wherein R$^3$ is attached to the N atom of the core rings via a carbon atom of R$^3$; Q$^1$, Q$^2$, Q$^3$, and Q$^4$ are each independently H, OH, —OC(=O)R$^b$, —OC(=O)NR$^b$R$^c$, —NR$^b$R$^c$, —NR$^b$OR$^a$, —NHC(=O)R$^a$, —NHSO$_2$R$^a$, and/or —NHC(=O)OR$^a$, provided that at least one of Q$^1$, Q$^2$, Q$^3$, and Q$^4$ is not H; or Q$^1$ and Q$^2$ together form =O, =NR$^b$, =NOR$^b$, or =NNR$^b$R$^c$; and/or Q$^3$ and Q$^4$ together form =O, =NR$^b$, =NOR$^b$, or =NNR$^b$R$^c$; or Q$^1$ and Q$^3$ together form —O— or NR$^b$, and Q$^2$ and Q$^4$ are each independently H, alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heterocyclo, substituted heterocyclo, hydroxylamine, CN, —C(=O)R$^b$, —C(=O)NR$^b$R$^c$, and/or —C(=O)OR$^a$; each R$^a$ is independently C$_{1-4}$alkyl, substituted C$_{1-4}$-alkyl, phenyl, and/or substituted phenyl; each R$^b$ is independently H, alkyl, and/or substituted alkyl; and each R$^c$ is independently H, alkyl, and/or substituted alkyl.

In one embodiment, compounds of Formula (I) are provided wherein:

L is a bond, CR$^8$R$^9$, or CR$^8$R$^9$CR$^{10}$R$^{11}$;

R$^1$ is H, alkyl, substituted alkyl, alkenyl, substituted alkenyl, alkynyl, substituted alkynyl, aryl, substituted aryl, heterocyclo, substituted heterocyclo, —CN, —C(=O)NR$^b$R$^c$, or —C(=O)OR$^a$;

R$^2$ is H, alkyl, substituted alkyl, aryl, substituted aryl, heterocyclo, substituted heterocyclo, —C(=O)NR$^b$R$^c$, or —C(=O)OR$^a$;

R$^3$ is 1- or 2-ring aryl or heteroaryl which is optionally substituted, wherein R$^3$ is attached to the N atom of the core rings via a carbon atom of R$^3$;

R$^4$, R$^5$, R$^6$, R$^7$, R$^8$, R$^9$, R$^{10}$, and R$^{11}$ are each independently H, alkyl, and/or substituted alkyl;

Q$^1$, Q$^2$, Q$^3$, and Q$^4$ are each independently H, alkyl, substituted alkyl, aryl, substituted aryl, heterocyclo, substituted heterocyclo, CN, —C(=O)R$^b$, —C(=O)NR$^b$R$^c$, —C(=O)OR$^a$, —NR$^b$R$^c$, —NR$^b$OR$^a$, —NR$^a$C(=O)R$^a$, —NR$^a$C(=O)NR$^b$R$^c$, —NR$^a$C(=O)OR$^a$, —NR$^a$SO$_2$R$^a$, —NR$^a$SO$_2$NR$^b$R$^c$, N$_3$, —OR$^a$, —OC(=O)R$^b$, —OC(=O)NR$^b$R$^c$, —SO$_2$R$^a$, —SO$_2$NR$^b$R$^c$, and/or —SO$_2$OR$^a$; or Q$^1$ and Q$^2$ together form =CR$^d$R$^d$, =O, =NR$^d$, =NOR$^b$, or =NNR$^c$R$^d$; and/or Q$^3$ and Q$^4$ together form =CR$^d$R$^d$, =O, =NR$^d$, =NOR$^b$, or =NNR$^c$R$^d$; or Q$^1$ and Q$^3$ together form —O— or NR$^b$, and Q$^2$ and Q$^4$ are each independently H, alkyl, substituted alkyl, aryl, substituted aryl, heterocyclo, substituted heterocyclo, CN, —C(=O)R$^b$, —C(=O)NR$^b$R$^c$, and/or —C(=O)OR$^a$;

each R$^a$ is independently H, alkyl, substituted alkyl, aryl, substituted aryl, heterocyclo, and/or substituted heterocyclo;

each R$^b$ is independently H, alkyl, substituted alkyl, aryl, substituted aryl, heterocyclo, and/or substituted heterocyclo;

each R$^c$ is independently H, alkyl, substituted alkyl, aryl, substituted aryl, heterocyclo, and/or substituted heterocyclo; or R$_b$ and R$_c$ together with the nitrogen atom to which they are attached, can form a 4-7 membered heterocyclo or substituted heterocyclo ring; and each R$^d$ is independently H, —C(=O)OR$^a$, —C(=O)NR$^b$R$^c$, —OR$_a$, —SO$_2$R$^a$, —SO$_2$NR$^b$R$^c$, alkyl, substituted alkyl, aryl, substituted aryl, heterocyclo, and/or substituted heterocyclo, and/or substituted heterocyclo.

In one embodiment, compounds of Formula (I) or a pharmaceutically-acceptable salts or stereoisomers thereof, are provided wherein:

L is a bond, CR$^8$R$^9$, or CR$^8$R$^9$CR$^{10}$R$^{11}$;

R$^1$ is H, C$_{1-4}$alkyl optionally substituted with OH, —C(=O)OR$^a$ wherein R$^a$ is H or C$_{1-4}$alkyl, or —C(=O)NR$^b$R$^c$ wherein R$^b$ and R$^c$ are independently H and/or C$_{1-4}$alkyl;

R$^2$ is i) H, ii) C$_{1-4}$alkyl optionally substituted with OH, iii) —C(=O)OR$^a$ wherein R$^a$ is C$_{1-4}$alkyl optionally substituted with aryl, or iv) —C(=O)NHR$^c$ wherein R$^c$ is phenyl or C$_{1-2}$alkyl optionally substituted with aryl or —CF$_3$;

R$^3$ is 1- or 2-ring aryl or heteroaryl which is optionally substituted with 1-3 substituents independently selected from methyl, cyclopropyl, —CF$_3$, halogen, —C≡CH, —CN, —NH$_2$, —NO$_2$, and/or —OR$_a$ wherein each R$_a$ is independently C$_{1-3}$ alkyl optionally substituted with 1 or more halogens, wherein R$^3$ is attached to the N atom of the core rings via a carbon atom of R$^3$;

R$^4$, R$^5$, R$^6$, R$^7$, R$^8$, R$^9$, R$^{10}$, and R$^{11}$ are independently H and/or C$_{1-4}$alkyl; and Q$^1$, Q$^2$, Q$^3$, and Q$^4$ are each independently:
i) H, ii) OH, iii) —N$_3$, iv) CN, v) C$_{1-4}$alkyl optionally substituted with OH, —C(=O)NHCH$_3$, or —C(=O)N(CH$_3$)$_2$, vi) monocyclic heterocycle, vii) —NHOR$^a$ wherein R$^a$ is C$_{1-4}$alkyl, viii) —C(=O)R$^b$ wherein R$^b$ is H or C$_{1-4}$alkyl; ix) —C(=O)OR$^a$ wherein R$^a$ is H or C$_{1-4}$alkyl, x) —C(=O)NR$^b$R$^c$ wherein R$^b$ and R$^c$ are independently H or C$_{1-4}$alkyl, xi) —NHC(=O)OR$^a$ wherein R$^a$ is C$_{1-4}$-alkyl optionally substituted with OH, OCH$_3$, or monocyclic heterocycle, xii) —NHC(=O)R$^a$ wherein R$^a$ is C$_{1-4}$alkyl optionally substituted with —OCH$_3$, —N(CH$_3$)$_2$, or monocyclic heterocycle, xiii) —NR$^b$R$^c$ wherein R$^b$ and R$^c$ are independently H or monocyclic heterocycle optionally substituted with halogen or —CF$_3$, xiv) —NHSO$_2$R$^a$ wherein R$^a$ is monocyclic heterocycle, C$_{1-4}$alkyl optionally substituted with —CF$_3$, C$_{3-6}$cycloalkyl, or phenyl, or phenyl optionally substituted with halogen or —NHC(=O)(C$_{1-4}$alkyl), xv) —NHSO$_2$NR$^b$R$^c$ wherein R$^b$ and R$^c$ are independently H and/or C$_{1-4}$alkyl, or xvi) —SO$_2$R$^a$ wherein R$^a$ is C$_{1-4}$alkyl or phenyl optionally substituted with halogen; or Q$^1$ and Q$^2$ together or Q$^3$ and Q$^4$ together are:
i) =CHR$^d$ wherein R$^d$ is H, —C(=O)OR$^a$ or —C(=O)NR$^b$R$^c$ wherein R$^a$, R$^b$, and R$^c$ are independently H and/or C$_{1-4}$alkyl, ii) =O, iii) =NOR$^b$ wherein R$^b$ is H, phenyl, monocyclic heterocycle, or C$_{1-4}$alkyl optionally substituted with phenyl, iv) =NR$^d$ wherein R$^d$ is monocyclic heterocycle, v) =NNR$^c$R$^d$ wherein R$^c$ and R$^d$ are independently H or C$_{1-4}$alkyl; or Q$^1$ and Q$^3$ together are =O wherein Q$^2$ and Q$^4$ are each H. In this embodiment, preferably at least two of Q$^1$, Q$^2$, Q$^3$, and Q$^4$ are H.

Preferably, R$^3$ is phenyl, naphthyl, pyridyl, or quinolinyl optionally substituted with 1-3 substituents independently selected from methyl, cyclopropyl, —CF$_3$, halogen, —C≡CH, —CN, —NH$_2$, —NO$_2$, and/or —OR$_a$ wherein each R$_a$ is independently C$_{1-3}$ alkyl optionally substituted with 1 or more halogens.

In one embodiment, compounds of Formula (I) or a pharmaceutically-acceptable salts or stereoisomers thereof, are provided wherein:

L is a bond, CR$^8$R$^9$, or CR$^8$R$^9$CR$^{10}$R$^{11}$;

R$^1$ is H, methyl, ethyl, —C(=O)NHCH$_3$, —C(=O)N(CH$_3$)$_2$, —CH$_2$OH, —C(=O)OH, or —C(=O)OCH$_3$;

R$^2$ is H, methyl, —CH$_2$OH, —C(=O)OCH$_2$-phenyl, —C(=O)NHCH$_2$-phenyl, —C(=O)NHCH$_2$CF$_3$, —C(=O)NHCH$_2$CH$_3$, or —C(=O)NH-phenyl;

R$^3$ is i) phenyl, or ii) phenyl, naphthyl, pyridyl, or quinolinyl substituted with 1-3 substituents independently selected from methyl, cyclopropyl, —CF$_3$, halogen, —C≡CH, —CN, —NH$_2$, —OCF$_3$, and —NO$_2$, wherein R$^3$ is attached to the N atom of the core rings via a carbon atom of R$^3$;

R$^4$ is H or methyl;

R$^5$, R$^6$, R$^7$, R$^{10}$, and R$^{11}$ are each H;

R$^8$ and R$^9$ are independently H and/or methyl; and

Q$^1$, Q$^2$, Q$^3$, and Q$^4$ are each independently H, OH, —CH$_3$, —CH$_2$OH, —CN, —N$_3$, —NH$_2$, —NHOCH$_3$, —C(=O)H, —C(=O)OH, —C(=O)NHCH$_3$, —C(=O)N(CH$_3$)$_2$, —NHC(=O)OCH$_3$, —NHC(=O)OCH$_2$CH$_3$, —NHC(=O)OCH(CH$_3$)$_2$, —NHC(=O)OCH$_2$CH$_2$OH, —NHC(=O)OCH$_2$CH$_2$OCH$_3$, —NHC(=O)CH$_3$, —NHC(=O)CH$_2$CH$_3$, —CH$_2$C(=O)NHCH$_3$, —CH$_2$C(=O)N(CH$_3$)$_2$, —NHC(=O)CH(CH$_3$)$_2$, —NHC(=O)CH$_2$OCH$_3$, —NHC(=O)CH$_2$N(CH$_3$)$_2$,

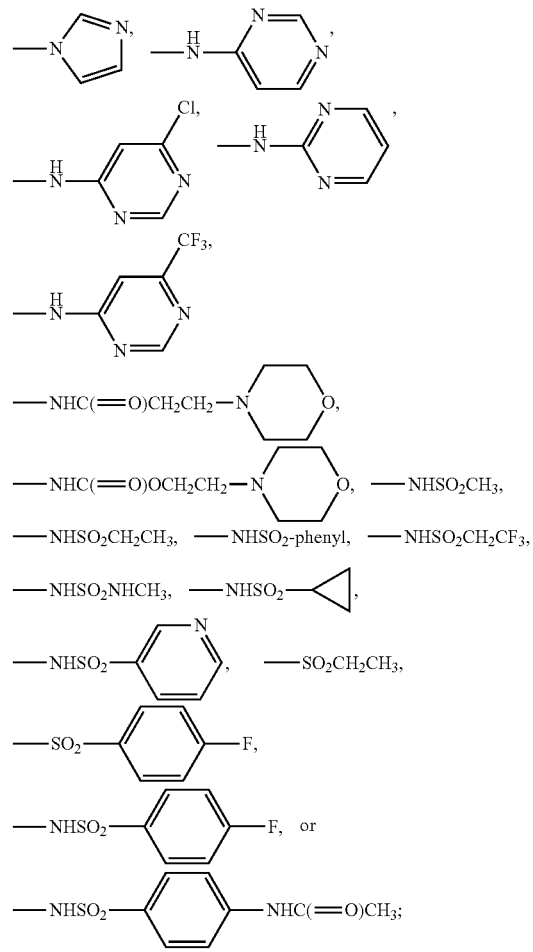

or Q$^1$ and Q$^2$ together or Q$^3$ and Q$^4$ together are =CH$_2$, =CHC(=O)OH, =CHC(=O)NHCH$_3$, =CHC(=O)OCH$_3$, =CHC(=O)N(CH$_3$)$_2$, =O, =NOH, =NOCH$_3$, =NOCH$_2$CH$_3$, =NOCH(CH$_3$)$_2$, =NOC(CH$_3$)$_3$, =N—O-phenyl, =N—NHCH$_3$,

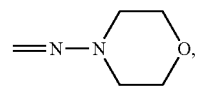

=N—OCH$_2$-phenyl, or

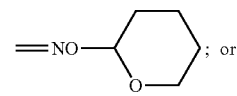; or

Q$^1$ and Q$^3$ together are =O wherein Q$^2$ and Q$^4$ are each H. In this embodiment, preferably at least two of Q$^1$, Q$^2$, Q$^3$, and Q$^4$ are H.

In one embodiment, a compound is provided having the formula:
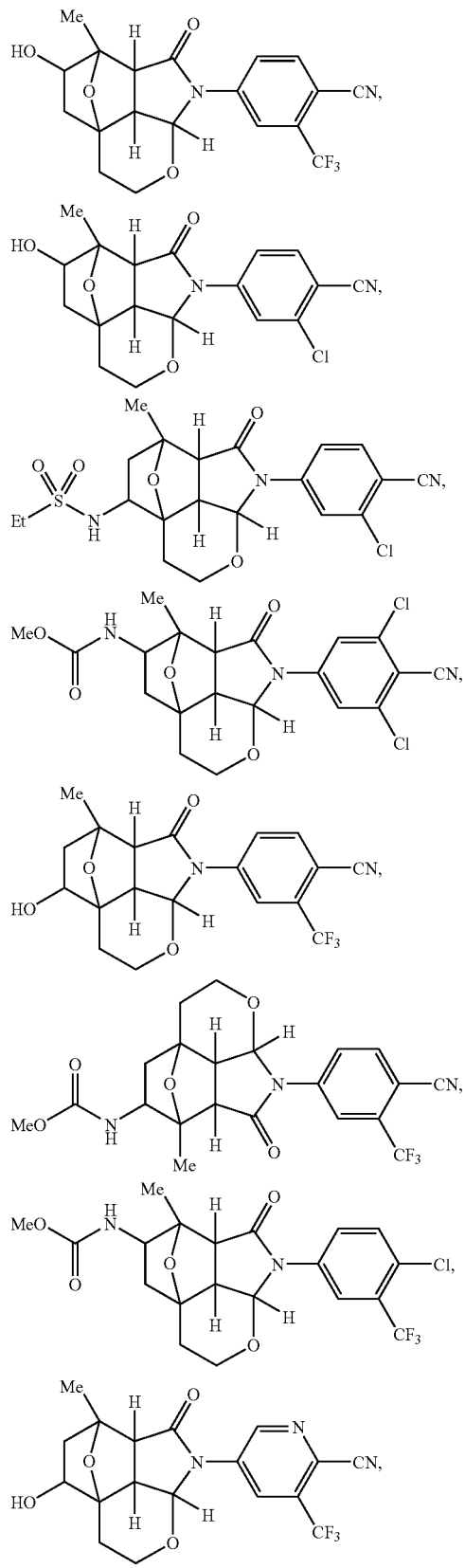
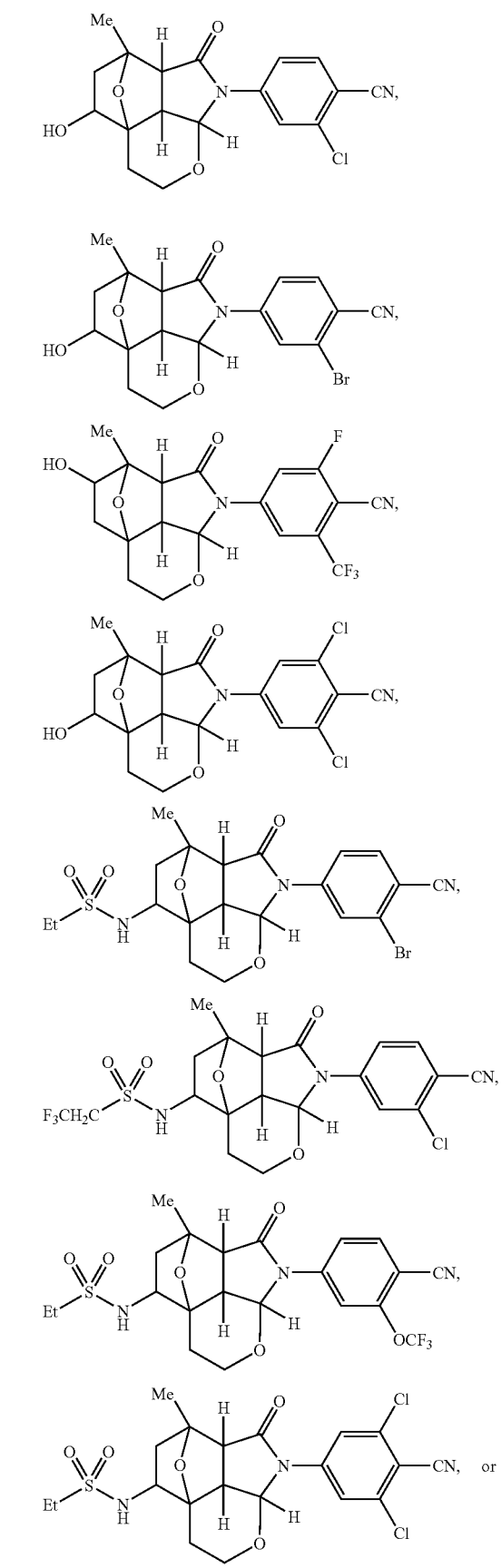

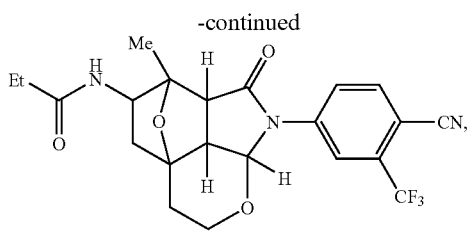

or pharmaceutically-acceptable salts thereof.

In another embodiment, compounds of Formula (I) wherein at least one of $Q^1$, $Q^2$, $Q^3$, and $Q^4$ is OH, may be provided as a prodrug. In this embodiment, the compounds of Formula (I) may be provided as prodrugs having Formula (Ik) or Formula (Im);

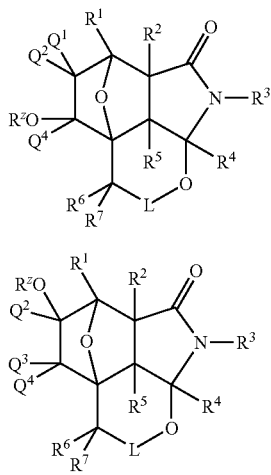

wherein $R^z$ is a group that cleaves during or after administration of the prodrug, to provide the compound of Formula (I) having an OH group for at least one of $Q^1$, $Q^2$, $Q^3$, and $Q^4$. Examples of suitable groups for $R^z$ include esters, amino acid esters, amides, ester linked peptides, alkoxy groups, phosphate (—P(=O)(OH)$_2$), or phosphate esters (—P(=O)(OR)$_2$ and —P(=O)(OH)(OR), wherein R is alkyl).

Crystal Form of the Compound of the Example 1

In one embodiment, the compound of Example 1 is provided as a crystalline material comprising a crystalline form. One crystalline form of the compound of Example 1 comprises a neat crystalline form referred to herein as "Form N-1" or "N-1 Form".

In one embodiment, the N-1 Form of compound of Example 1 is characterized by unit cell parameters approximately equal to the following:

Cell dimensions:
a=6.42 Å
b=11.54 Å
c=23.73 Å
α=90.0°
β=90.0°
γ=90.0°
Space group: P2$_1$2$_1$2$_1$
Molecules of Example 1/asymmetric unit: 1
Volume/Number of molecules in the unit cell=439 Å$^3$
Density (calculated)=1.491 g/cm$^3$, wherein the unit cell parameters of Form N-1 are measured at a temperature of about −30° C.

Figure 3:
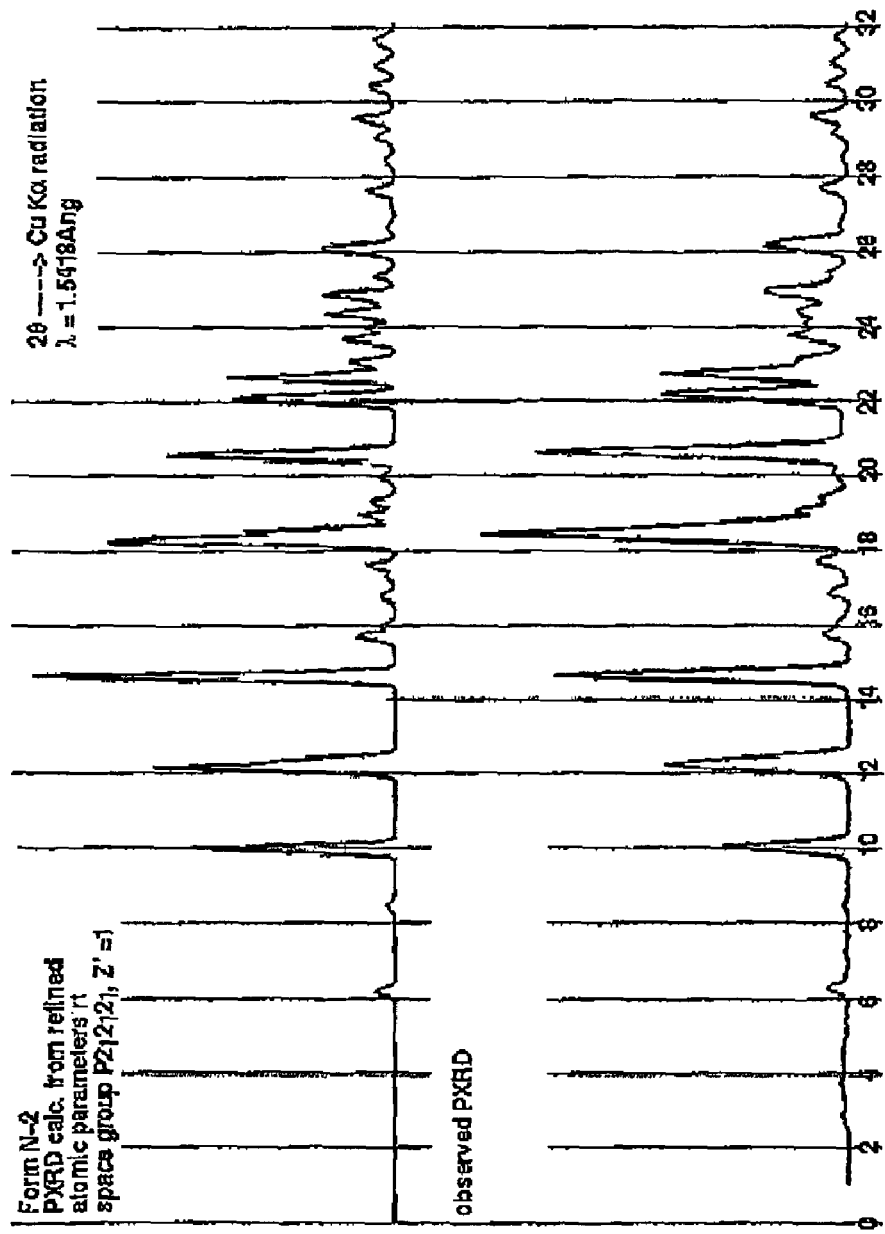
FIG. 3 shows observed (at r.t.) and simulated (at about 25° C.) PXRD patterns (CuKαλ=1.5418 Å) of the N-2 Form of the compound of Example 3.

In another embodiment, the N-1 Form of the compound of Example 1 is characterized by a simulated powder x-ray diffraction (PXRD) pattern substantially in accordance with the pattern shown in FIG. 3 and/or by an observed PXRD pattern substantially in accordance with the pattern shown in FIG. 3.

In yet another embodiment, the N-1 Form of the compound of Example 1 is characterized by a PXRD pattern (CuKαλ=1.5418 Å at a temperature of about 25° C.) comprising four or more, preferably five or more, 2θ values selected from: 7.4±0.2, 13.5±0.2, 14.3±0.2, 14.8±0.2, 15.3±0.2, 16.2±0.2, 19.4±0.2, 20.2±0.2, and 21.7±0.2, wherein the PXRD pattern of Form N-1 is measured at a temperature of about 25° C.

In still yet an even further embodiment, the N-1 form of the compound of Example 1 is substantially pure.

In still yet another embodiment, the N-1 form of the compound of Example 1 contains at least about 90 wt. %, preferably at least about 95 wt. %, and more preferably at least about 99 wt. %, based on weight of the Form N-1 of the compound of Example 1.

In yet another embodiment, a substantially pure Form N-1 of the compound of Example 1 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure crystalline form has substantially pure phase homogeneity with less than about 1% of the total peak area of the experimentally measured PXRD pattern arising from peaks that are absent from the simulated PXRD pattern.

In another embodiment, the crystalline form of the compound of Example 1 consists essentially of Form N-1. The crystalline form of this embodiment may comprise at least about 90 wt. %, preferably at least about 95 wt. %, and more preferably at least about 99 wt. %, based on the weight of the crystalline form, Form N-1 of the compound of Example 1.

In yet another embodiment, a pharmaceutical composition is provided comprising Form N-1 of the compound of Example 1; and at least one pharmaceutically-acceptable carrier and/or diluent.

In still another embodiment, a pharmaceutical composition comprises substantially pure Form N-1 of compound of Example 1; and at least one pharmaceutically-acceptable carrier and/or diluent.

In still an even further embodiment, a therapeutically effective amount of Form N-1 of the compound of Example 1 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 1, wherein the compound of Example 1 is provided in a crystalline form comprising Form N-1. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a crystalline form of the compound of Example 1 consisting essentially of Form N-1.

Crystal Forms of the Compound of Example 3

In one embodiment, the compound of Example 3

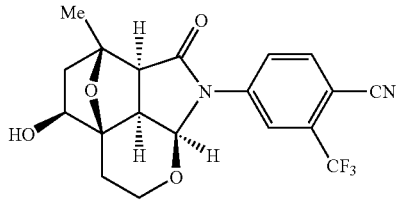

is provided as a crystalline material comprising one or more crystalline forms. Examples of suitable crystalline forms of the compound of Example 3 include Form N-1 and Form N-2.

A first crystalline form of the compound of Example 3 comprises a neat crystalline form referred to herein as "Form N-1" or "N-1 Form".

In one embodiment, the N-1 Form of Example 3 is characterized by unit cell parameters approximately equal to the following:

Cell dimensions:
a=8.34 Å
b=11.01 Å
c=19.45 Å
α=90.0°
β=90.0°
γ=90.0°
Space group: $P2_12_12_1$
Molecules of Example 3/asymmetric unit: 1
Volume/Number of molecules in the unit cell=447 Å$^3$
Density (calculated)=1.466 g/cm$^3$,
wherein the unit cell parameters of Form N-1 are measured at a temperature of about 25° C.

In another embodiment, the N-1 Form of Example 3 is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, the N-1 Form of Example 3 is characterized by a PXRD pattern (CuKαλ=1.5418 Å at a temperature of about 25° C.) comprising four or more, preferably five or more, 2θ values selected from: 9.1±0.2; 11.5±0.2, 13.3±0.2; 14.1±0.2; 16.1±0.2; 16.7±0.2, 17.3±0.2, 21.2±0.2 and 24.6±0.2; wherein the PXRD pattern of Form N-1 is measured at a temperature of about 25° C.

In yet an even further embodiment, the N-1 Form of Example 3 is characterized by fractional atomic coordinates substantially as listed in Table A.

TABLE A

Fractional Atomic Coordinates of Form N-1 of Example 3 (Calculated at a Temperature of about 25° C.)

| Atom | X | Y | Z | B(iso) | Occupancies |
|---|---|---|---|---|---|
| F21 | −0.0063(8) | 0.4269(6) | 0.5385(4) | 6.7 | 0.5 |
| F22 | −0.2114(6) | 0.3655(5) | 0.5937(5) | 5.2 | 0.5 |
| F23 | −0.0329(9) | 0.4663(5) | 0.6448(3) | 6.4 | 0.5 |
| F24 | −0.1052(14) | 0.4368(8) | 0.6568(4) | 6.2 | 0.25 |
| F25 | −0.2081(10) | 0.3512(8) | 0.5669(6) | 6.9 | 0.25 |
| F26 | 0.0238(12) | 0.4759(7) | 0.6168(6) | 5.9 | 0.25 |
| F27 | −0.058(2) | 0.3948(15) | 0.5235(8) | 9.3 | 0.25 |
| F28 | 0.0204(13) | 0.4628(10) | 0.5640(7) | 7.0 | 0.25 |
| F29 | −0.1894(16) | 0.3938(12) | 0.6319(9) | 6.5 | 0.25 |
| O2 | 0.8381(3) | 0.2720(2) | 0.90855(13) | 4.4 | 1 |
| O7 | 0.5394(2) | 0.30719(17) | 0.83321(9) | 3.1 | 1 |

TABLE A-continued

Fractional Atomic Coordinates of Form N-1 of Example 3 (Calculated at a Temperature of about 25° C.)

| Atom | X | Y | Z | B(iso) | Occupancies |
|---|---|---|---|---|---|
| O8 | 0.5332(3) | 0.07157(19) | 0.70766(11) | 4.0 | 1 |
| O10 | 0.1070(3) | 0.2438(2) | 0.82350(13) | 4.8 | 1 |
| N9 | 0.2875(3) | 0.1452(2) | 0.75367(13) | 3.6 | 1 |
| N24 | −0.1104(7) | 0.1581(5) | 0.4503(2) | 8.2 | 1 |
| C1 | 0.6257(3) | 0.1955(3) | 0.83209(14) | 3.2 | 1 |
| C2 | 0.7052(3) | 0.1922(3) | 0.90357(16) | 3.8 | 1 |
| C3 | 0.5704(4) | 0.2463(3) | 0.94718(15) | 4.4 | 1 |
| C4 | 0.4447(4) | 0.2834(3) | 0.89348(13) | 3.2 | 1 |
| C5 | 0.3561(3) | 0.1665(3) | 0.87030(14) | 3.4 | 1 |
| C6 | 0.4914(4) | 0.0976(3) | 0.83343(14) | 3.4 | 1 |
| C8 | 0.4267(4) | 0.0633(3) | 0.76217(17) | 3.5 | 1 |
| C10 | 0.2335(3) | 0.1913(3) | 0.81493(16) | 3.6 | 1 |
| C11 | 0.6258(4) | 0.1805(3) | 0.70561(15) | 4.1 | 1 |
| C12 | 0.7320(4) | 0.1903(3) | 0.76845(16) | 3.8 | 1 |
| C13 | 0.1994(4) | 0.1503(3) | 0.69092(16) | 3.5 | 1 |
| C14 | 0.1162(4) | 0.2560(3) | 0.67431(16) | 4.0 | 1 |
| C15 | 0.0312(4) | 0.2634(3) | 0.61376(17) | 3.9 | 1 |
| C16 | 0.0339(4) | 0.1650(3) | 0.56763(16) | 4.4 | 1 |
| C17 | 0.1174(5) | 0.0609(3) | 0.5859(2) | 5.0 | 1 |
| C18 | 0.2007(4) | 0.0553(3) | 0.6467(2) | 4.5 | 1 |
| C20 | −0.0539(5) | 0.3764(3) | 0.5972(2) | 5.0 | 1 |
| C24 | −0.0488(5) | 0.1638(5) | 0.5026(2) | 5.6 | 1 |
| C41 | 0.3440(4) | 0.3932(3) | 0.91222(17) | 4.5 | 1 |
| H2F | 0.9276 | 0.2453 | 0.8711 | — | 1 |

Numbers in parentheses are estimated standard deviations in the least significant digits.

In still yet an even further embodiment, the N-1 form of Example 3 is substantially pure.

In still yet another embodiment, the N-1 form of Example 3 contains at least about 90 wt. %, preferably at least about 95 wt. %, and more preferably at least about 99 wt. %, based on weight of the first crystalline form, Form N-1.

In yet another embodiment, a substantially pure first crystalline form of Example 3 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure first crystalline form has substantially pure phase homogeneity with less than about 1% of the total peak area of the experimentally measured PXRD pattern arising from peaks that are absent from the simulated PXRD pattern.

In another embodiment, the first crystalline form of Example 3 consists essentially of Form N-1. The first crystalline form of this embodiment may comprise at least about 90 wt. %, preferably at least about 95 wt. %, and more preferably at least about 99 wt. %, based on the weight of the first crystalline form, Form N-1.

In yet another embodiment, a pharmaceutical composition is provided comprising Form N-1 of the compound of Example 3; and at least one pharmaceutically-acceptable carrier and/or diluent.

In still another embodiment, a pharmaceutical composition comprises substantially pure first crystalline form of the compound of Example 3; and at least one pharmaceutically-acceptable carrier and/or diluent.

In still an even further embodiment, a therapeutically effective amount of Form N-1 of the compound of Example 3 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 3, wherein the compound of Example 3 is provided in a first crystalline form comprising Form N-1. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a first crystalline form of the compound of Example 3 consisting essentially of Form N-1.

A second crystalline form of the compound of Example 3 comprises a neat crystalline form referred to herein as "Form N-2" or "N-2 Form".

In one embodiment, the N-2 Form of the compound of Example 3 is characterized by unit cell parameters approximately equal to the following:

Cell dimensions:
a=5.39 Å
b=11.34 Å
c=28.82 Å
α=90.0°
β=90.0°
γ=90.0°
Space group: P2$_1$2$_1$2$_1$
Molecules of Example 3/asymmetric unit: 1
Volume/number of molecules in the unit cell=440 Å$^3$
Density (calculated)=1.488 g/cm$^3$, wherein the unit cell parameters of Form N-2 are measured at a temperature of about 25° C.

In another embodiment, the N-2 Form of Example 3 is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, the N-2 Form of Example 3 is characterized by a PXRD pattern (CuKαλ=1.5418 Å at a temperature of about 25° C.) comprising four or more, preferably five or more, 2θ values selected from: 6.1±0.2, 9.9±0.2; 12.1±0.2, 14.6±0.2; 18.2±0.2, 20.5±0.2; 22.0±0.2, 22.6±0.2, 26.0±0.2 and 29.5±0.2, wherein the PXRD pattern of Form N-2 is measured at a temperature of about 25° C.

In yet an even further embodiment, the N-2 Form of Example 3 is characterized by fractional atomic coordinates substantially as listed in Table B.

TABLE B

Fractional Atomic Coordinates of Form N-2 of Example 3 (Calculated at a Temperature of about 25° C.)

| Atom | X | Y | Z | B(iso) | Occupancy |
|------|---|---|---|--------|-----------|
| F21 | 1.0446(17) | 1.0084(7) | 0.3487(3) | 9.6 | 0.66 |
| F22 | 0.7519(19) | 1.0675(4) | 0.29868(18) | 10.0 | 0.67 |
| F23 | 0.6365(15) | 1.0449(5) | 0.3682(3) | 8.7 | 0.67 |
| F24F | 0.7282 | 1.0355 | 0.3786 | 5.1 | .2 |
| F25F | 0.6507 | 1.0616 | 0.3210 | 10.7 | .2 |
| F26F | 0.8204 | 1.0736 | 0.3130 | 5.8 | .2 |
| F27F | 1.0326 | 1.0042 | 0.3337 | 19.6 | .2 |
| F28F | 0.8785 | 1.0064 | 0.3763 | 12.9 | .2 |
| O2 | −0.0775(11) | 0.2456(5) | 0.47649(19) | 8.9 | 1 |
| O7 | 0.2454(8) | 0.4426(4) | 0.45423(14) | 5.5 | 1 |
| O8 | 0.4057(10) | 0.4495(4) | 0.35875(14) | 6.0 | 1 |
| O10 | 0.2146(14) | 0.7811(5) | 0.42623(19) | 8.9 | 1 |
| N9 | 0.2874(11) | 0.6444(4) | 0.36905(18) | 9.0 | 1 |
| N25 | 1.1924(17) | 0.9008(6) | 0.2413(3) | 5.0 | 1 |
| C1 | 0.0725(14) | 0.3878(6) | 0.4217(2) | 9.1 | 1 |
| C2I | −0.1335(16) | 0.3562(7) | 0.4549(3) | 5.5 | 1 |
| C3I | −0.1346(15) | 0.4586(7) | 0.4909(3) | 7.1 | 1 |

TABLE B-continued

Fractional Atomic Coordinates of Form N-2 of Example 3 (Calculated at a Temperature of about 25° C.)

| Atom | X | Y | Z | B(iso) | Occupancy |
|------|---|---|---|--------|-----------|
| C4 | 0.0833(15) | 0.5325(6) | 0.4732(2) | 6.1 | 1 |
| C5I | −0.0039(15) | 0.5957(7) | 0.4269(2) | 5.7 | 1 |
| C6I | −0.0025(14) | 0.4966(6) | 0.3917(3) | 5.9 | 1 |
| C8I | 0.1996(15) | 0.5273(6) | 0.3568(2) | 5.6 | 1 |
| C10 | 0.1746(16) | 0.6847(8) | 0.4094(2) | 6.4 | 1 |
| C11I | 0.3261(18) | 0.3295(6) | 0.3537(2) | 7.1 | 1 |
| C12I | 0.1963(16) | 0.2891(5) | 0.3960(3) | 6.2 | 1 |
| C13 | 0.4649(13) | 0.7041(6) | 0.3426(2) | 5.1 | 1 |
| C14I | 0.5361(14) | 0.8178(6) | 0.3527(2) | 5.1 | 1 |
| C15 | 0.7199(17) | 0.8718(5) | 0.3267(3) | 6.0 | 1 |
| C16 | 0.8363(15) | 0.8144(6) | 0.2894(2) | 5.9 | 1 |
| C17I | 0.7553(16) | 0.7021(7) | 0.2795(2) | 5.9 | 1 |
| C18I | 0.5739(16) | 0.6477(6) | 0.3043(2) | 5.6 | 1 |
| C19I | 0.2126(18) | 0.6056(8) | 0.5087(3) | 7.5 | 1 |
| C20 | 0.818(2) | 0.9983(7) | 0.3388(3) | 8.6 | 1 |
| C24 | 1.0320(18) | 0.8657(7) | 0.2622(3) | 6.3 | 1 |
| H2F | −0.2347 | 0.2192 | 0.4993 | — | 1 |

Numbers in parentheses are estimated standard deviations in the least significant digits.

In still yet an even further embodiment, the N-2 form of the compound of Example 3 is substantially pure.

In still yet another embodiment, the N-2 form of the compound of Example 3 contains at least about 90 wt. %, preferably at least about 95 wt. %, and more preferably at least about 99 wt. %, based on weight of the second crystalline form, Form N-2.

In yet another embodiment, a substantially pure second crystalline form of Example 3 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the compound of Example 3 consists essentially of Form N-2. The second crystalline form of this embodiment may comprise at least about 90 wt. %, preferably at least about 95 wt. %, and more preferably at least about 99 wt. %, based on the weight of the second crystalline form, Form N-2.

In yet another embodiment, a pharmaceutical composition is provided comprising Form N-2 of the compound of Example 3; and at least one pharmaceutically-acceptable carrier and/or diluent.

In still another embodiment, a pharmaceutical composition comprises substantially pure second crystalline form of compound of Example 3; and at least one pharmaceutically-acceptable carrier and/or diluent.

In still an even further embodiment, a therapeutically effective amount of Form N-2 of the compound of Example 3 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 3, wherein the compound of Example 3 is provided in a second crystalline form comprising Form N-2. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a second crystalline form of the compound of Example 3 consisting essentially of Form N-2.

Crystal Forms of the Compound Example 37

In one embodiment, the compound of Example 37 is provided as a crystalline material comprising one or more crystalline forms. Examples of suitable crystalline forms of the compound of Example 37 include Form N-1 and Form N-2.

A first crystalline form of the compound of Example 37 comprises a neat crystalline form referred to herein as "Form N-1" or "N-1 Form".

In one embodiment, the N-1 Form of Example 37 is characterized by unit cell parameters approximately equal to the following:

Cell dimensions:
a=8.16 Å
b=25.13 Å
c=27.76 Å
$\alpha$=90.0°
$\beta$=90.0°
$\gamma$=90.0°
Space group: $P2_12_12_1$
Molecules of Example 37/asymmetric unit: 3
Volume/Number of molecules in the unit cell=475 Å$^3$
Density (calculated)=1.429 g/cm$^3$,
wherein the unit cell parameters of Form N-1 are measured at a temperature of about −50° C.

Figure 4:
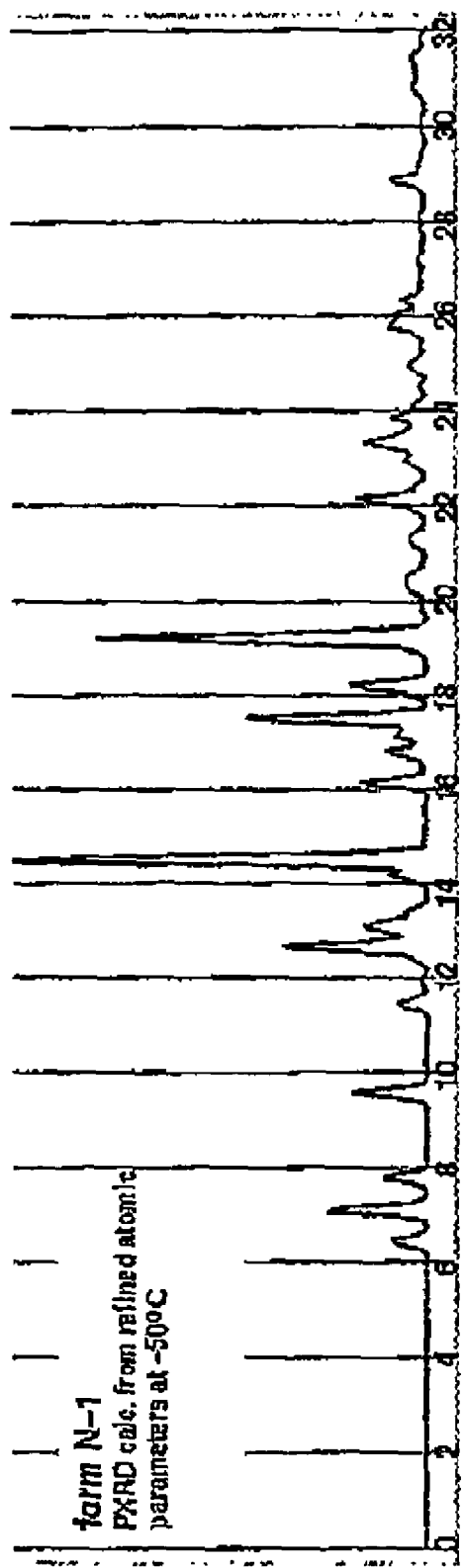
FIG. 4 shows simulated PXRD (at about −50° C.) of the N-1 Form the compound of Example 37.
Figure 5:
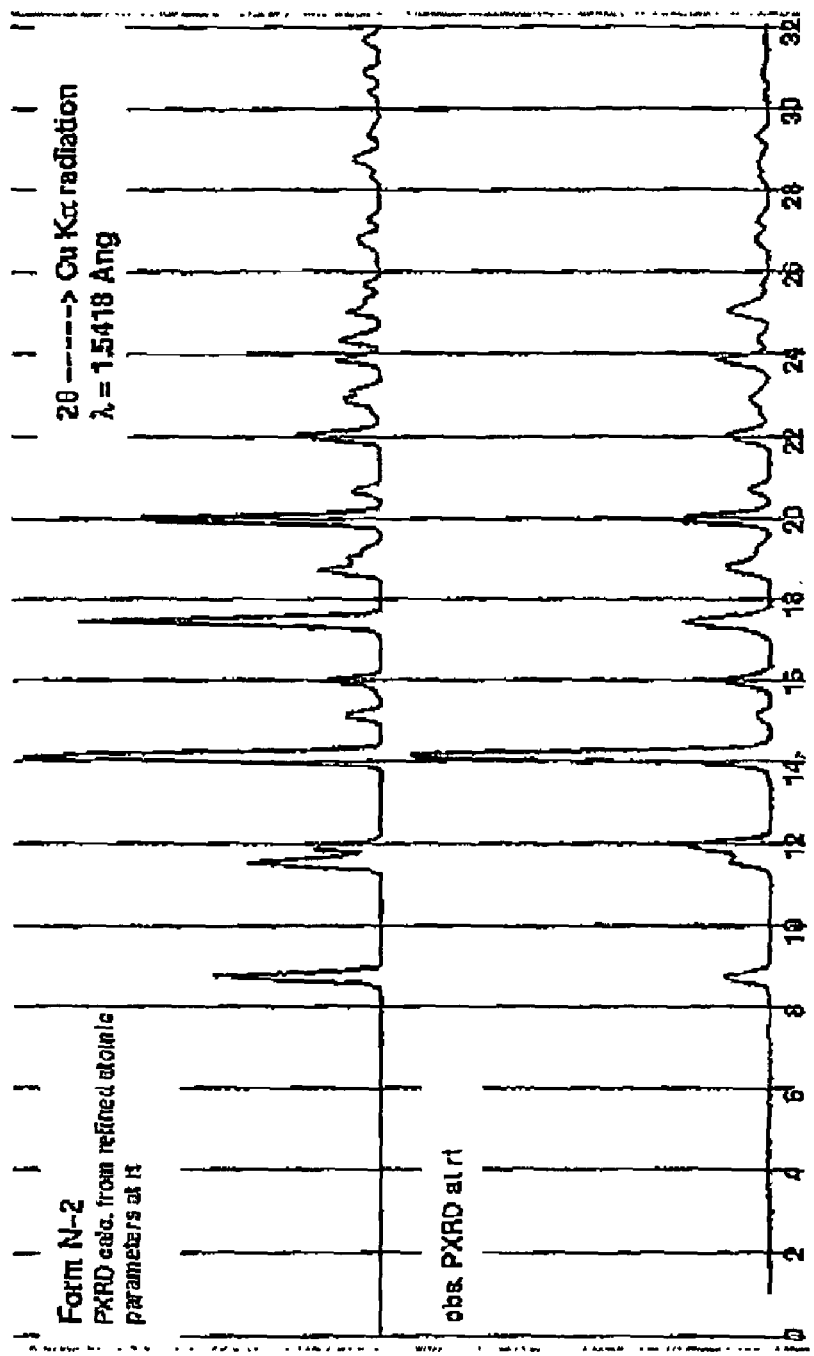
FIG. 5 shows simulated (at r.t.) and the observed (at r.t.) PXRD of the N-2 Form of the compound of Example 37.

In another embodiment, the N-1 Form of Example 37 is characterized by a simulated powder x-ray diffraction (PXRD) pattern substantially in accordance with the pattern shown in FIG. 4 and/or by an observed PXRD pattern substantially in accordance with the pattern shown in FIG. 4.

In yet another embodiment, the N-1 Form of Example 37 is characterized by a PXRD pattern (CuK$\alpha\lambda$=1.5418 Å at a temperature of about 25° C.) comprising four or more, preferably five or more, 2θ values selected from: 6.4±0.2, 7.0±0.2, 7.7±0.2, 9.5±0.2, 12.6±0.2, 14.4±0.2, 17.5±0.2, and 19.2±0.2, wherein the PXRD pattern of Form N-1 is measured at a temperature of about 25° C.

In still yet an even further embodiment, the N-1 form of the compound of Example 37 is substantially pure.

In still yet another embodiment, the N-1 form of the compound of Example 37 contains at least about 90 wt. %, preferably at least about 95 wt. %, and more preferably at least about 99 wt. %, based on weight of the first crystalline form, Form N-1 of the compound of Example 37.

In yet another embodiment, a substantially pure first crystalline form of the compound of Example 37 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure first crystalline form has substantially pure phase homogeneity with less than about 1% of the total peak area of the experimentally measured PXRD pattern arising from peaks that are absent from the simulated PXRD pattern.

In another embodiment, the first crystalline form of the compound of Example 37 consists essentially of Form N-1. The first crystalline form of this embodiment may comprise at least about 90 wt. %, preferably at least about 95 wt. %, and more preferably at least about 99 wt. %, based on the weight of the first crystalline form, Form N-1.

In yet another embodiment, a pharmaceutical composition is provided comprising Form N-1; and at least one pharmaceutically-acceptable carrier and/or diluent.

In still another embodiment, a pharmaceutical composition comprises substantially pure first crystalline form of compound of Example 37; and at least one pharmaceutically-acceptable carrier and/or diluent.

In still an even further embodiment, a therapeutically effective amount of Form N-1 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 37, wherein the compound of Example 37 is provided in a first crystalline form comprising Form N-1. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a first crystalline form of the compound of Example 37 consisting essentially of Form N-1.

A second crystalline form of the compound of Example 37 comprises a neat crystalline form referred to herein as "Form N-2" or "N-2 Form".

In one embodiment, the N-2 Form is characterized by unit cell parameters approximately equal to the following:

Cell dimensions:
a=8.03 Å
b=11.77 Å
c=20.40 Å
$\alpha$=90.0°
$\beta$=90.0°
$\gamma$=90.0°
Space group: $P2_12_12_1$
Molecules of Example 37/asymmetric unit: 1
Volume/number of molecules in the unit cell=482 Å$^3$
Density (calculated)=1.470 g/cm$^3$,
wherein the unit cell parameters of Form N-2 are measured at a temperature of about 25° C.

In another embodiment, the N-2 Form is characterized by a simulated powder x-ray diffraction (PXRD) pattern substantially in accordance with the pattern shown in FIG. 1 and/or by an observed PXRD pattern substantially in accordance with the pattern shown in FIG. 1.

In yet another embodiment, the N-2 Form is characterized by a PXRD pattern (CuK$\alpha\lambda$=1.5418 Å at a temperature of about 25° C.) comprising four or more, preferably five or more, 2θ values selected from: 8.7±0.2, 11.5±0.2, 11.8±0.2, 14.0±0.2, 15.9±0.2, 17.4±0.2, 20.0±0.2, 22.0±0.2, and 23.8±0.2, wherein the PXRD pattern of Form N-2 is measured at a temperature of about 25° C.

In still yet an even further embodiment, the N-2 form of the compound of Example 37 is substantially pure.

In still yet another embodiment, the N-2 form of the compound of Example 37 contains at least about 90 wt. %, preferably at least about 95 wt. %, and more preferably at least about 99 wt. %, based on weight of the second crystalline form, Form N-2.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the compound of Example 37 consists essentially of Form N-2. The second crystalline form of this embodiment may comprise at least about 90 wt. %, preferably at least about 95 wt. %, and more preferably at least about 99 wt. %, based on the weight of the second crystalline form, Form N-2.

In yet another embodiment, a pharmaceutical composition is provided comprising Form N-2; and at least one pharmaceutically-acceptable carrier and/or diluent.

In still another embodiment, a pharmaceutical composition comprises substantially pure second crystalline form of compound of Example 37; and at least one pharmaceutically-acceptable carrier and/or diluent.

In still an even further embodiment, a therapeutically effective amount of Form N-2 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 37, wherein the compound of Example 37 is provided in a second crystalline form comprising Form N-2. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a second crystalline form of the compound of Example 37 consisting essentially of Form N-2.

Crystal Form of the Compound of the Example 119

In one embodiment, the compound of Example 119 is provided as a crystalline material comprising a crystalline form. One crystalline form of the compound of Example 119 comprises a neat crystalline form referred to herein as "Form N-1" or "N-1 Form".

A first crystalline form of the compound of Example 119 comprises a neat crystalline form referred to herein as "Form N-1" or "N-1 Form".

In one embodiment, the N-1 Form of Example 119 is characterized by unit cell parameters approximately equal to the following:

Cell dimensions:
a=8.50 Å
b=9.69 Å
c=20.7 Å
α=90.0°
β=90.0°
γ=90.0°
Space group: $P2_12_12_1$
Molecules of Example 119/asymmetric unit: 1
Volume/Number of molecules in the unit cell=426 Å³
Density (calculated)=1.407 g/cm³,
wherein the unit cell parameters of Form N-1 are measured at a temperature of about 25° C.

Figure 6:
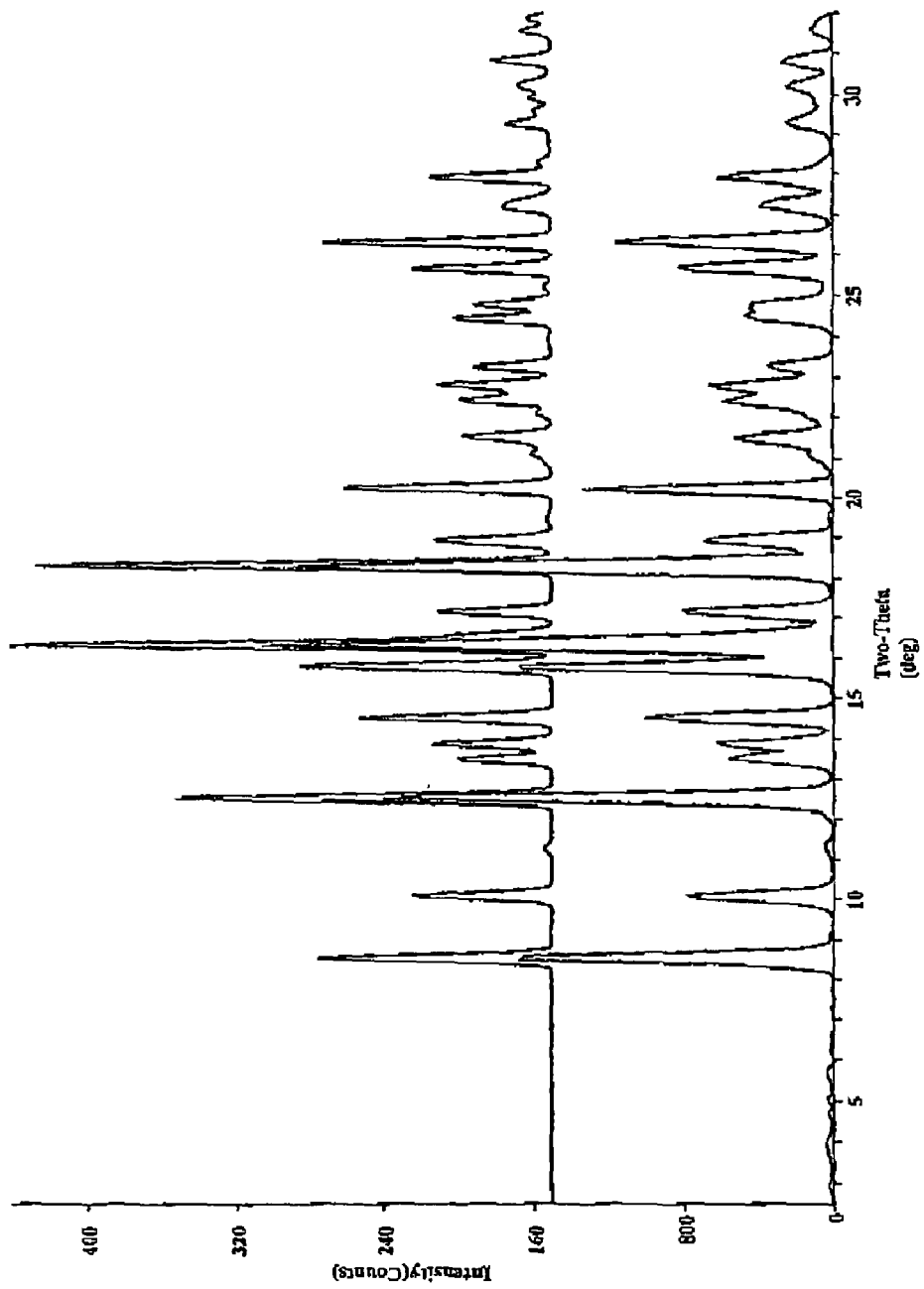
FIG. 6 shows simulated (top) and the observed (bottom) PXRD of the N-1 Form of the compound of Example 119 at about room temperature.

In another embodiment, the N-1 Form of Example 119 is characterized by a simulated powder x-ray diffraction (PXRD) pattern substantially in accordance with the pattern shown in FIG. 6 and/or by an observed PXRD pattern substantially in accordance with the pattern shown in FIG. 6.

In another embodiment, the N-1 Form of Example 119 is characterized by fractional atomic coordinates substantially as listed in Table C.

TABLE C

Fractional Atomic Coordinates of Form N-1 of Compound 119 Calculated at a Temperature of about 25° C.

| Atom | X | Y | Z |
|---|---|---|---|
| Cl1 | 0.2076 | 0.7826 | 0.0263 |
| N1 | 0.5914 | 0.4695 | 0.1454 |
| N2 | 0.0997 | 0.5658 | -0.1073 |
| O2 | 0.8313 | 0.4071 | 0.0944 |
| O4 | 0.8424 | 0.6320 | 0.2333 |
| O3 | 1.1405 | 0.5722 | 0.2950 |
| O1 | 0.4215 | 0.5643 | 0.2194 |
| C14 | 0.9290 | 0.5072 | 0.2194 |
| C13 | 1.0261 | 0.5264 | 0.1597 |
| C8 | 0.5440 | 0.5053 | 0.2070 |
| C4 | 0.3137 | 0.6319 | 0.0324 |
| C15 | 1.0114 | 0.4819 | 0.2840 |
| C11 | 0.7972 | 0.3965 | 0.2135 |
| C9 | 0.7302 | 0.3793 | 0.1453 |
| C17 | 0.7522 | 0.5822 | 0.2867 |
| C10 | 0.6665 | 0.4591 | 0.2542 |
| C2 | 0.2972 | 0.5319 | -0.0153 |
| C5 | 0.4853 | 0.3909 | 0.0421 |
| C12 | 0.9193 | 0.5324 | 0.1019 |
| C16 | 0.8805 | 0.5225 | 0.3309 |
| C7 | 0.4971 | 0.4901 | 0.0900 |
| C3 | 0.3875 | 0.4121 | -0.0096 |
| C1 | 0.1889 | 0.5510 | -0.0671 |
| C6 | 0.4115 | 0.6117 | 0.0839 |
| C18 | 0.6526 | 0.6947 | 0.3154 |
| H3 | 1.2168 | 0.5457 | 0.2741 |
| H13A | 1.0861 | 0.6113 | 0.1629 |
| H13B | 1.0993 | 0.4503 | 0.1551 |
| H15 | 1.0418 | 0.3850 | 0.2892 |
| H11 | 0.8316 | 0.3077 | 0.2312 |
| H9 | 0.6938 | 0.2839 | 0.1409 |
| H10 | 0.6247 | 0.3936 | 0.2859 |
| H5 | 0.5437 | 0.3099 | 0.0451 |
| H12A | 0.8471 | 0.6092 | 0.1067 |
| H12B | 0.9817 | 0.5483 | 0.0633 |
| H16A | 0.9170 | 0.5911 | 0.3615 |
| H16B | 0.8420 | 0.4428 | 0.3544 |
| H3A | 0.3810 | 0.3451 | -0.0416 |
| H6 | 0.4209 | 0.6801 | 0.1153 |
| H18A | 0.7192 | 0.7672 | 0.3312 |
| H18B | 0.5917 | 0.6578 | 0.3505 |
| H18C | 0.5833 | 0.7308 | 0.2829 |

In still yet an even further embodiment, the N-1 form of the compound of Example 119 is substantially pure.

In still yet another embodiment, the N-1 form of the compound of Example 119 contains at least about 90 wt. %, preferably at least about 95 wt. %, and more preferably at least about 99 wt. %, based on weight of the first crystalline form, Form N-1 of the compound of Example 119.

In yet another embodiment, a substantially pure first crystalline form of the compound of Example 119 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure first crystalline form has substantially pure phase homogeneity with less than about 1% of the total peak area of the experimentally measured PXRD pattern arising from peaks that are absent from the simulated PXRD pattern.

In another embodiment, the first crystalline form of the compound of Example 119 consists essentially of Form N-1. The first crystalline form of this embodiment may comprise at least about 90 wt. %, preferably at least about 95 wt. %, and more preferably at least about 99 wt. %, based on the weight of the first crystalline form, Form N-1.

In yet another embodiment, a pharmaceutical composition is provided comprising Form N-1; and at least one pharmaceutically-acceptable carrier and/or diluent.

In still another embodiment, a pharmaceutical composition comprises substantially pure first crystalline form of compound of Example 119; and at least one pharmaceutically-acceptable carrier and/or diluent.

In still an even further embodiment, a therapeutically effective amount of Form N-1 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 119, wherein the compound of Example 119 is provided in a first crystalline form comprising Form N-1. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a first crystalline form of the compound of Example 119 consisting essentially of Form N-1.

Crystalline Form of the Compound of Example 174

In one embodiment, the compound of Example 174 comprises a chloroform solvate crystalline form referred to herein as "Form CHF-1" or "CHF-1 Form". The CHF-1 Form comprises about one chloroform molecule for each molecule of Example 174.

In one embodiment, the CHF-1 Form is characterized by unit cell parameters approximately equal to the following:
Cell dimensions:
a=9.60 Å
b=12.64 Å
c=21.18 Å
α=90.0°
β=90.0°
γ=90.0°
Space group: $P2_12_12_1$
Molecules of Example 174/asymmetric unit: 1
Volume/number of molecules in the unit cell=642 Å$^3$
Density (calculated)=1.477 g/cm$^3$,
wherein the unit cell parameters of Form CHF-1 are measured at a temperature of about 25° C.

Figure 7:
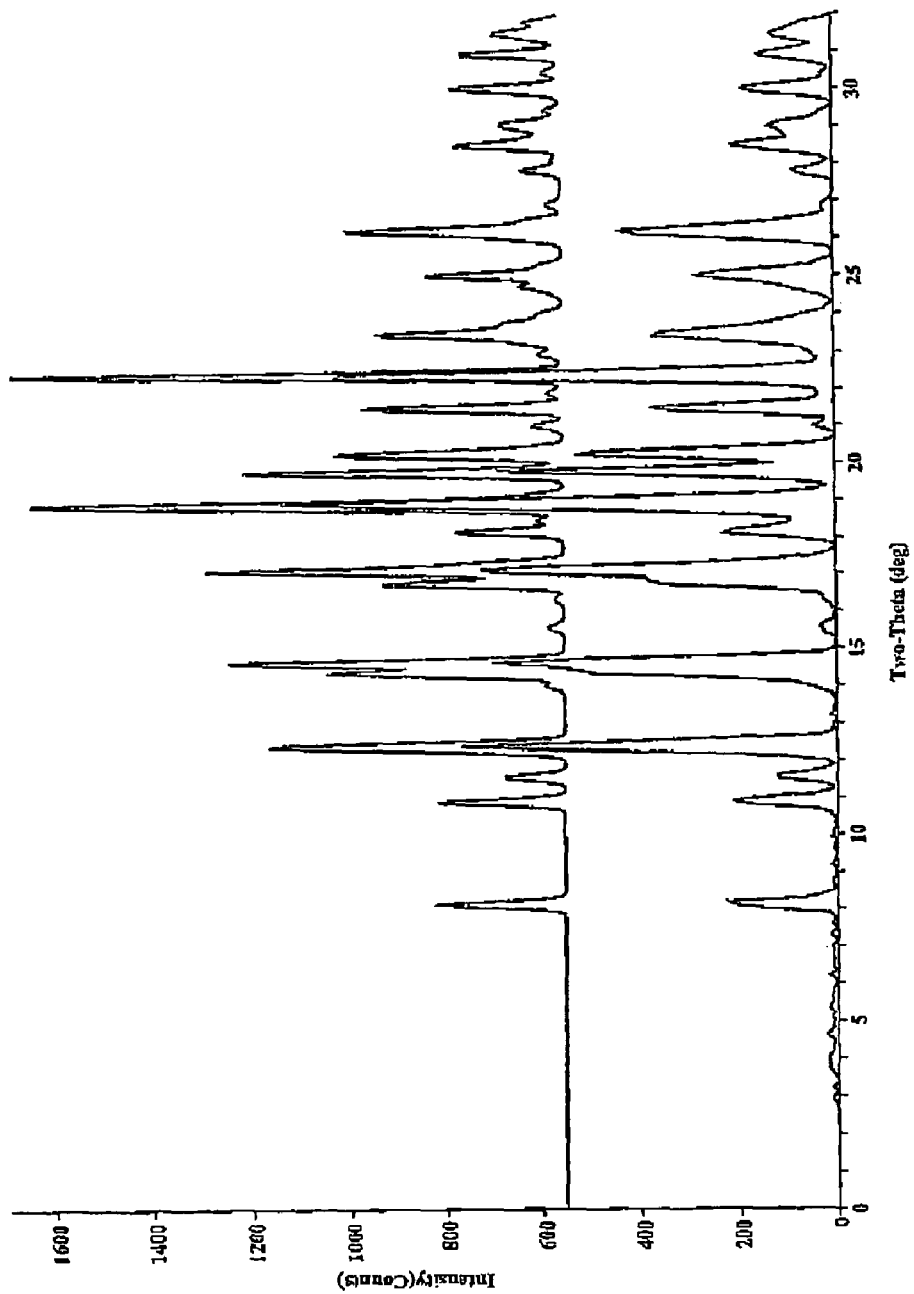
FIG. 7 shows simulated (top) and the observed (bottom) PXRD of the CHF-1 Form of the compound of Example 174 at about room temperature.

In another embodiment, the CHF-1 Form is characterized by a simulated powder x-ray diffraction (PXRD) pattern substantially in accordance with the pattern shown in FIG. 7 and/or by an observed PXRD pattern substantially in accordance with the pattern shown in FIG. 7.

In another embodiment, the CHF-1 Form of Example 174 is characterized by fractional atomic coordinates substantially as listed in Table D.

TABLE D

Fractional Atomic Coordinates of Form CHF-1 of Compound 174 Calculated at a Temperature of about 25° C.

| Atom | X | Y | Z |
|---|---|---|---|
| S1 | 0.4230 | 0.8766 | 0.2262 |
| Cl2 | 0.1060 | 0.0756 | 0.0420 |
| O4 | 0.3089 | 0.6813 | 0.0520 |
| O6 | 0.0258 | 0.5748 | −0.0465 |
| O8 | 0.2474 | 0.4286 | 0.1274 |
| C9 | 0.1406 | 0.3821 | 0.0009 |
| C11 | 0.0691 | 0.5675 | 0.0076 |
| N7 | 0.1214 | 0.4789 | 0.0344 |
| C12 | 0.0722 | 0.6563 | 0.0557 |
| N13 | 0.4001 | 0.8139 | 0.1605 |
| C15 | 0.2819 | 0.6543 | 0.1174 |
| C16 | 0.1352 | 0.6044 | 0.1152 |
| C17 | 0.1886 | 0.3804 | −0.0605 |
| C18 | 0.1816 | 0.7400 | 0.0396 |
| C19 | 0.1963 | 0.1903 | −0.0578 |
| C20 | 0.3922 | 0.5830 | 0.1435 |
| C21 | 0.1836 | 0.8224 | 0.0941 |
| C23 | 0.2359 | 0.0923 | −0.0871 |
| C24 | 0.2641 | 0.7669 | 0.1461 |
| C25 | 0.1347 | 0.4836 | 0.1032 |
| C26 | 0.3821 | 0.4735 | 0.1137 |
| C27 | 0.1414 | 0.1905 | 0.0022 |
| C28 | 0.1121 | 0.2878 | 0.0326 |
| C30 | 0.2163 | 0.2863 | −0.0896 |
| C31 | 0.3268 | 0.9969 | 0.2238 |
| C32 | 0.1800 | 0.7856 | −0.0255 |
| C34 | 0.3845 | 1.0749 | 0.1792 |
| O35 | 0.5659 | 0.9039 | 0.2290 |
| O36 | 0.3660 | 0.8130 | 0.2747 |
| N37 | 0.2738 | 0.0127 | −0.1092 |
| Cl3 | 0.1878 | 0.2373 | 0.3164 |
| Cl5 | 0.0079 | 0.2737 | 0.2133 |
| Cl1 | 0.0879 | 0.4479 | 0.2871 |
| C33 | 0.1414 | 0.3279 | 0.2576 |
| H34 | 0.3283 | 1.1377 | 0.1804 |
| H34 | 0.3839 | 1.0463 | 0.1373 |
| H34 | 0.4782 | 1.0921 | 0.1911 |
| H31 | 0.2327 | 0.9824 | 0.2112 |
| H31 | 0.3270 | 1.0283 | 0.2651 |
| H13 | 0.4757 | 0.8074 | 0.1312 |
| H24 | 0.2118 | 0.7610 | 0.1846 |
| H21 | 0.2301 | 0.8854 | 0.0802 |
| H21 | 0.0899 | 0.8394 | 0.1062 |
| H32 | 0.0889 | 0.8136 | −0.0339 |
| H32 | 0.2012 | 0.7313 | −0.0557 |
| H32 | 0.2477 | 0.8413 | −0.0287 |
| H20 | 0.4822 | 0.6130 | 0.1353 |
| H20 | 0.3789 | 0.5764 | 0.1883 |
| H16 | 0.0827 | 0.6217 | 0.1524 |
| H12 | −0.0202 | 0.6816 | 0.0642 |
| H25 | 0.0512 | 0.4555 | 0.1217 |
| H26 | 0.4537 | 0.4283 | 0.1303 |
| H26 | 0.3938 | 0.4807 | 0.0689 |
| H28 | 0.0746 | 0.2892 | 0.0746 |
| H17 | 0.2030 | 0.4456 | −0.0828 |
| H30 | 0.2486 | 0.2843 | −0.1324 |
| H33 | 0.2200 | 0.3414 | 0.2308 |
| — | — | — | — |

In still yet an even further embodiment, the CHF-1 form of the compound of Example 174 is substantially pure.

In still yet another embodiment, the CHF-1 form of the compound of Example 174 contains at least about 90 wt. %, preferably at least about 95 wt. %, and more preferably at least about 99 wt. %, based on weight of the second crystalline form, Form CHF-1.

In yet another embodiment, a substantially pure second crystalline form has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure second crystalline form has substantially pure phase homogeneity with less than about 1% of the total peak area of the experimentally measured PXRD pattern arising from peaks that are absent from the simulated PXRD pattern.

In another embodiment, the second crystalline form of the compound of Example 174 consists essentially of Form CHF-1. The second crystalline form of this embodiment may comprise at least about 90 wt. %, preferably at least about 95 wt. %, and more preferably at least about 99 wt. %, based on the weight of the second crystalline form, Form CHF-1.

Crystal Form of the Compound of the Example 185

In one embodiment, the compound of Example 185 is provided as a crystalline material comprising a crystalline form. One crystalline form of the compound of Example 185 comprises a neat crystalline form referred to herein as "Form N-1" or "N-1 Form".

In one embodiment, the N-1 Form of Example 185 is characterized by unit cell parameters approximately equal to the following:

Cell dimensions:
a=5.23 Å
b=11.11 Å
c=37.84 Å
α=90.0°
β=90.0°
γ=90.0°
Space group: $P2_12_12_1$
Molecules of Example 185/asymmetric unit: 1
Volume/Number of molecules in the unit cell=550 Å$^3$
Density (calculated)=1.527 g/cm$^3$, wherein the unit cell parameters of Form N-1 are measured at a temperature of about 25° C.

Figure 8:
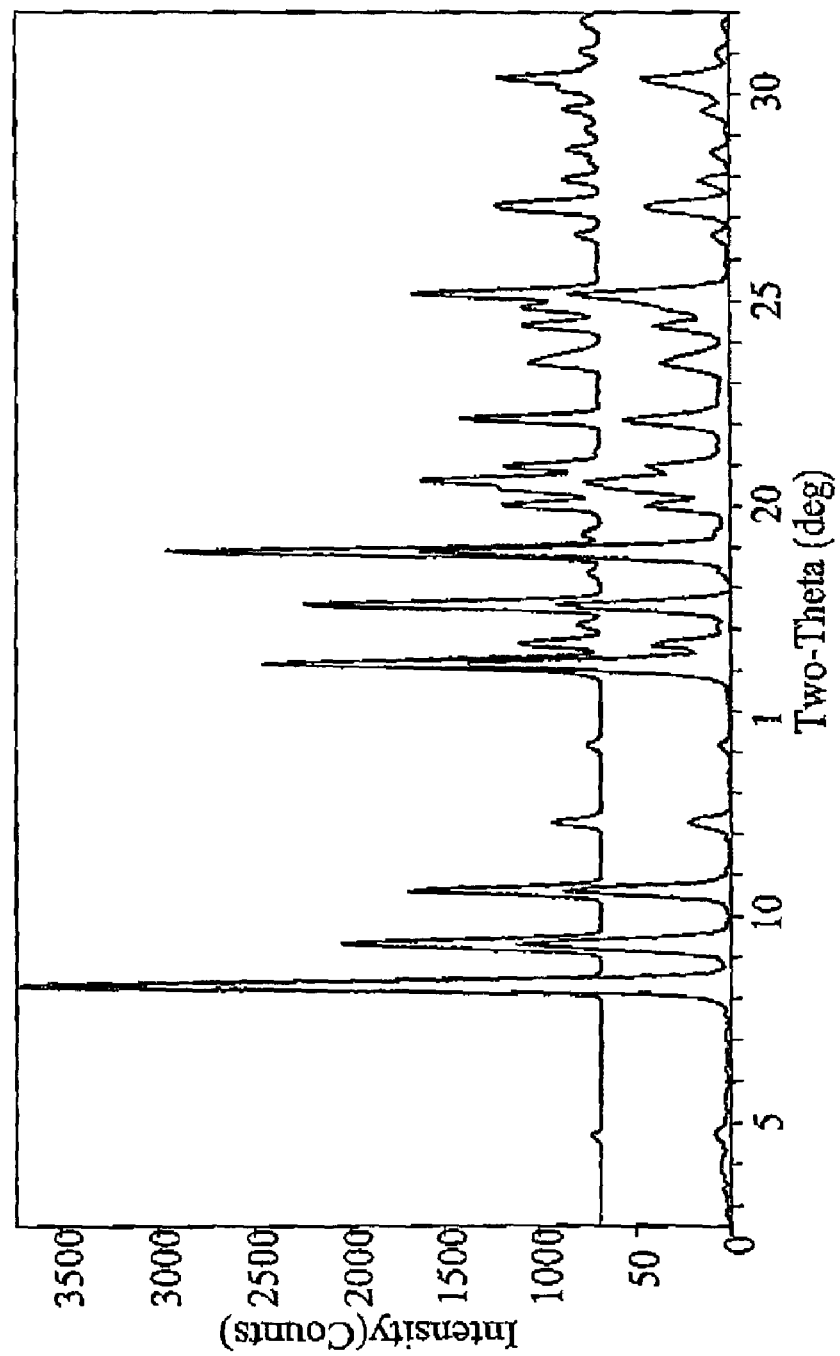
FIG. 8 shows simulated (top) and the observed (bottom) PXRD of the N-1 Form of the compound of Example 185 at about room temperature.

In another embodiment, the N-1 Form of Example 185 is characterized by a simulated powder x-ray diffraction (PXRD) pattern substantially in accordance with the pattern shown in FIG. 8 and/or by an observed PXRD pattern substantially in accordance with the pattern shown in FIG. 8.

In another embodiment, the N-1 Form of Example 185 is characterized by fractional atomic coordinates substantially as listed in Table E.

TABLE E

Fractional Atomic Coordinates of Form N-1 of Compound 185 Calculated at a Temperature of about 25° C.

| Atom | X | Y | Z |
|---|---|---|---|
| S1 | 0.4453 | 0.1224 | 0.0314 |
| Cl2 | −0.6228 | 0.6022 | 0.2646 |
| O3 | −0.0070 | 0.3662 | 0.1050 |
| O4 | 0.1640 | 0.2039 | 0.1843 |
| O5 | 0.7039 | 0.1324 | 0.0426 |
| N7 | 0.2813 | 0.2256 | 0.0495 |
| O9 | −0.0173 | 0.6080 | 0.1693 |
| C10 | −0.2556 | 0.4972 | 0.2268 |
| C11 | −0.0517 | 0.4175 | 0.2211 |
| C12 | 0.0202 | 0.3408 | 0.2485 |
| C13 | 0.1387 | 0.4763 | 0.0996 |
| N6 | 0.0751 | 0.4147 | 0.1883 |
| C8 | −0.3755 | 0.4998 | 0.2590 |
| C14 | 0.1076 | 0.1637 | 0.1219 |
| C15 | 0.2033 | 0.2864 | 0.1123 |
| C16 | −0.0128 | 0.1649 | 0.1582 |
| C17 | 0.3504 | 0.3509 | 0.1426 |
| C18 | 0.0942 | 0.5123 | 0.1656 |
| C19 | 0.2751 | 0.4830 | 0.1359 |
| C20 | 0.3703 | 0.3012 | 0.0790 |
| C21 | −0.3016 | 0.4249 | 0.2864 |
| O22 | 0.3875 | 0.1208 | −0.0054 |
| C23 | 0.3336 | 0.4350 | 0.0718 |
| C24 | 0.2607 | 0.3203 | 0.1798 |
| C25 | −0.1025 | 0.3454 | 0.2805 |

TABLE E-continued

Fractional Atomic Coordinates of Form N-1 of Compound 185 Calculated at a Temperature of about 25° C.

| Atom | X | Y | Z |
|---|---|---|---|
| C26 | −0.0229 | 0.5795 | 0.0890 |
| C27 | −0.4256 | 0.4284 | 0.3202 |
| C28 | 0.3305 | −0.0153 | 0.0494 |
| F29 | 0.3718 | −0.2225 | 0.0491 |
| N30 | −0.5224 | 0.4289 | 0.3474 |
| C31 | 0.4600 | −0.1277 | 0.0358 |
| F32 | 0.4040 | −0.1392 | 0.0018 |
| F33 | 0.6947 | −0.1239 | 0.0359 |
| H28A | 0.3488 | −0.0142 | 0.0747 |
| H28B | 0.1533 | −0.0240 | 0.0434 |
| H7 | 0.1131 | 0.2431 | 0.0408 |
| H23A | 0.2658 | 0.4491 | 0.0486 |
| H23B | 0.4890 | 0.4798 | 0.0747 |
| H26A | 0.0824 | 0.6493 | 0.0856 |
| H26B | −0.1461 | 0.5953 | 0.1072 |
| H26C | −0.1100 | 0.5610 | 0.0673 |
| H19 | 0.4266 | 0.5317 | 0.1359 |
| H17 | 0.5323 | 0.3419 | 0.1407 |
| H20 | 0.5427 | 0.2781 | 0.0844 |
| H14A | −0.0163 | 0.1381 | 0.1048 |
| H14B | 0.2483 | 0.1082 | 0.1221 |
| H16A | −0.0697 | 0.0852 | 0.1640 |
| H16B | −0.1565 | 0.2186 | 0.1579 |
| H24 | 0.4025 | 0.3255 | 0.1958 |
| H12 | 0.1572 | 0.2847 | 0.2450 |
| H25 | −0.0499 | 0.2931 | 0.2994 |
| H10 | −0.3057 | 0.5500 | 0.2080 |

In still yet an even further embodiment, the N-1 form of the compound of Example 185 is substantially pure.

In still yet another embodiment, the N-1 form of the compound of Example 185 contains at least about 90 wt. %, preferably at least about 95 wt. %, and more preferably at least about 99 wt. %, based on weight of the first crystalline form, Form N-1 of the compound of Example 185.

In yet another embodiment, a substantially pure first crystalline form of the compound of Example 185 has substantially pure phase homogeneity with less than about 10%, preferably less than about 5%, and more preferably less than about 2% of the total peak area of the experimentally measured PXRD pattern arising from peaks that are absent from the simulated PXRD pattern. Most preferably, a substantially pure first crystalline form has substantially pure phase homogeneity with less than about 1% of the total peak area of the experimentally measured PXRD pattern arising from peaks that are absent from the simulated PXRD pattern.

In another embodiment, the first crystalline form of the compound of Example 185 consists essentially of Form N-1. The first crystalline form of this embodiment may comprise at least about 90 wt. %, preferably at least about 95 wt. %, and more preferably at least about 99 wt. %, based on the weight of the first crystalline form, Form N-1.

In yet another embodiment, a pharmaceutical composition is provided comprising Form N-1; and at least one pharmaceutically-acceptable carrier and/or diluent.

In still another embodiment, a pharmaceutical composition comprises substantially pure first crystalline form of compound of Example 185; and at least one pharmaceutically-acceptable carrier and/or diluent.

In still an even further embodiment, a therapeutically effective amount of Form N-1 is combined with at least one pharmaceutically acceptable carrier and/or diluent to provide at least one pharmaceutical composition.

Still yet a further embodiment provides a method for treating a proliferative disease comprising administering to a patient in need thereof a therapeutically effective amount of the compound of Example 185, wherein the compound of Example 185 is provided in a first crystalline form comprising Form N-1. Preferably, the proliferative disease is cancer, and more preferably, breast cancer, endometrial cancer, uterine cancer, or prostate cancer.

In one embodiment, the patient is a human.

In another embodiment, the proliferative disease is prostate cancer.

In an even further embodiment, the method comprises administering a first crystalline form of the compound of Example 185 consisting essentially of Form N-1.

Methods of Preparation

In general, the compounds of Formula (I) can be prepared in accordance with the following Schemes and the general knowledge of one skilled in the art and/or using methods set forth in the Examples that follow. Solvents, temperatures, pressures, and other reaction conditions can readily be selected by one of ordinary skill in the art. Starting materials are commercially available or readily prepared by one skilled in the art. Combinatorial techniques can be employed in the preparation of compounds, for example, where the intermediates possess groups suitable for these techniques. In the schemes, the groups L, $Q^1$, $Q^2$, $Q^3$, $Q^4$, $R^1$, $R^2$, $R^3$, $R^4$, $R^5$, $R^6$, $R^7$, $R^8$, $R^9$, $R^{10}$, and $R^{11}$, are described hereinabove.

Scheme 1

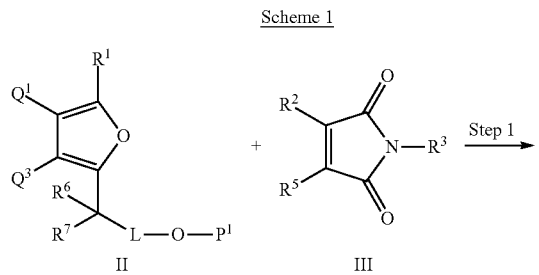

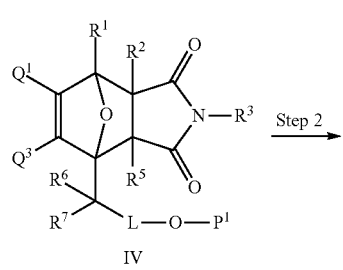

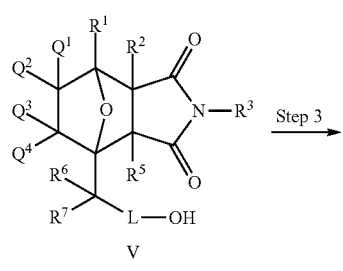

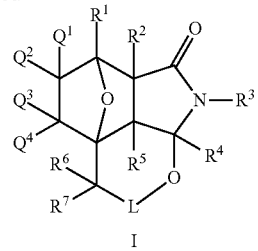

$P^1$ = Protecting group

Step 1

A diene of the general Formula II and a dienophile of the general Formula III can undergo a [4+2] cycloaddition under thermal or Lewis acidic conditions in a solvent, such as, for example, toluene, THF and/or isopropanol to generate compounds of the general Formula IV.

The diene II and the dienophile III can be obtained either from commercial sources, or can be readily made by one of skill in the art. $P^1$ is a suitable alcohol protecting group.

Step 2

A compound of the general formula V can be produced by functionalizing the olefin of the formula IV compound via a variety of methods known to one skilled in the art. Such functionalization methods include, but are not limited to, for example, dihydroxylation; aminohydroxylation; hydrogenation; hydroxylation; hydroboration and subsequent oxidation; epoxidation; aziridination; cyclopropanation; bromination; and chlorination. The resulting products may undergo further functional group manipulations, including, but not limited to, for example, converting a hydroxyl group to a fluoro functionality by treating with (diethylamino)sulfur trifluoride and reducing an azide to the corresponding amine and further derivatizing to alkyl carbamates, amides, sulfonamides or ureas. Other well-known methods for functionalizing an olefin can be found in standard synthetic organic references, such as, for example, Larock, R. C., *Comprehensive Organic Transformations*, VCH Publishers, New York (1989) and March, J., *Advanced Organic Chemistry*, John Wiley & Sons Inc. USA (1985).

For example, compound IV may be treated with an agent such as $BH_3 \cdot THF$ in a solvent such as THF. Further treatment with a reagent such as hydrogen peroxide can provide compounds V where $Q^2$ or $Q^4$ is OH, after removal of the protecting group $P^1$ under suitable conditions. For instance, if $P^1$ is a t-butyldimethylsilyl group, reaction with an acid, such as aqueous HCl, in a solvent, such as THF, can result in removal of the protecting group to provide the alcohol V.

Step 3

Compounds of general formula V may be treated under reductive conditions, such as, for example, sodium borohydride in a solvent system such as THF/MeOH and the resulting products can be cyclized under appropriate conditions, such as, for example, reaction with aqueous HCl to afford the corresponding compounds in accordance with formula I.

When $R^2$=H, a compound of Formula I can be treated with a strong base, such as, for example, lithium diisopropylamide to generate an anion that can react with various electrophiles, such as, for example, methyl iodide and methyl chloroformate, to produce a compound of the general formula I where $R^3$ is the corresponding alkyl or acyl group.

Scheme 2

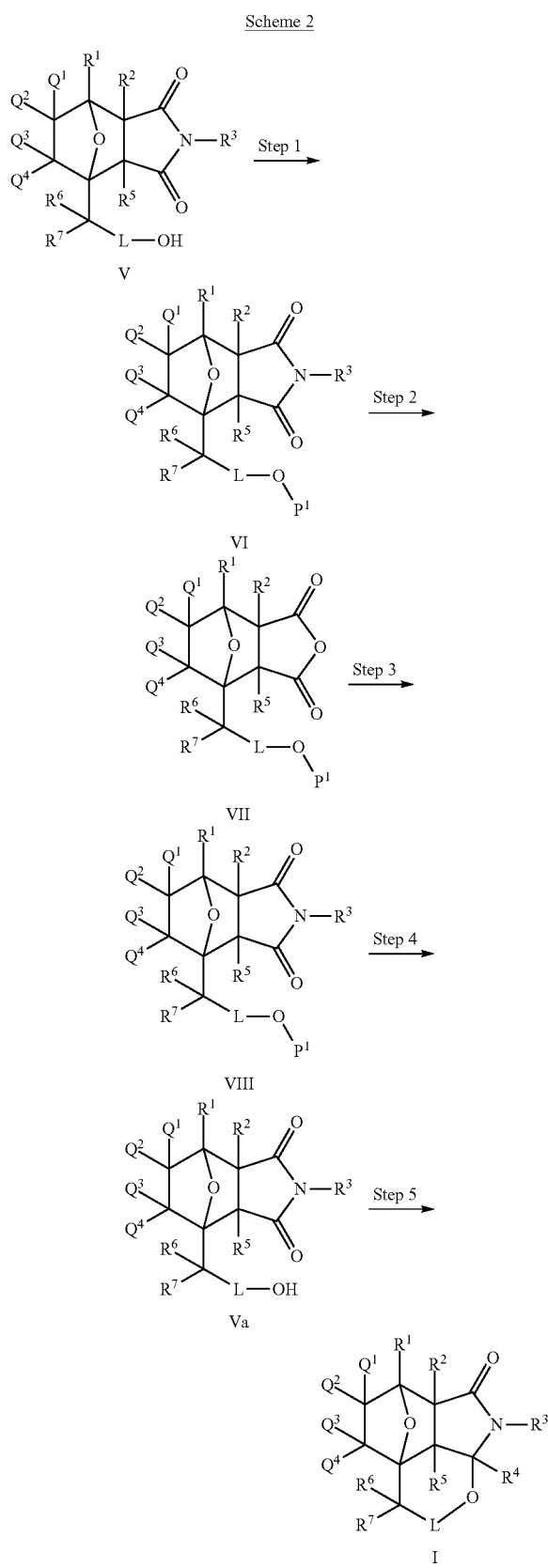

P¹ = Protecting group

Scheme 2 illustrates an alternative method for synthesizing compounds represented by general formula I. A compound of the general formula V can be prepared by the general procedure outlined in Scheme I.

Step 1

The alcohol in compound V may be suitably protected to provide the corresponding compound VI. For example, compound V can be treated with reagents such as t-butyldimethylsilyl chloride and imidazole in a solvent such as DMF to give compound VI, where P¹ is a t-butyldimethylsilyl group.

Step 2

The imide VI may be converted to the corresponding anhydride VII by methods known in the literature. For example, compound VI can be reacted with a base such as aqueous sodium hydroxide in a solvent such as THF. Subsequent treatment with an acid such as aqueous HCl can provide the intermediate amido acid. Further treatment of the amido acid intermediate with a reagent such as glacial acetic acid in a solvent such as THF at an elevated temperature (e.g., 60° C.) can afford the desired anhydride VII.

Step 3

The anhydride VII can be treated with the appropriate reagent NH₂R³ in the presence of a base such as triethylamine in a solvent such as toluene at appropriate temperatures (e.g., 175° C. in a pressure tube) to give the corresponding imide VIII.

Step 4

The protecting group P¹ may be removed under standard conditions known in the literature to provide the corresponding alcohol Va. For instance, if P¹ is a t-butyldimethylsilyl group, reaction of the imide VIII with an acid, such as aqueous HCl, in a solvent, such as THF, can result in removal of the protecting group to provide the alcohol Va.

Step 5

The alcohol Va may be treated under conditions described in step 3 of Scheme I to generate the desired compounds represented by general formula I.

The nuclear hormone receptor (NHR) family includes the androgen receptor (AR), the estrogen receptor (ER), the progesterone receptor (PR), the glucocorticoid receptor (GR), the mineralocorticoid receptor (MR), the steroid and xenobiotic receptor (SXR), other steroid binding NHRs, the Orphan receptors, as well as other NHRs.

The terms "modulate", "modulates", "modulating", or "modulation", as used herein, refer to, for example, the activation (e.g., agonist activity) or inhibition (e.g., antagonist activity) of at least one NHR.

The term "NHR-associated condition(s)", as used herein, denotes a condition or disorder that can be treated by modulating the function of at least one NHR associated with the condition or disorder. The treatment comprises preventing, partially alleviating, or curing the condition or disorder. Modulation may occur either locally, for example, within certain tissues of the subject being treated, or more extensively throughout the subject.

The compounds of Formula (I) are useful for modulating the function of a nuclear hormone receptor specifically, the androgen receptor (AR). Formula (I) compounds are useful to treat AR-associated conditions. In one embodiment, at least one compound of Formula (I) selectively modulates the androgen receptor within the NHR family.

Compounds of Formula (I) may be used to treat a variety of medical conditions and/or disorders associated with the AR pathway. Formula (I) compounds can modulate the function of the AR by, for example, agonizing, partially agonizing, antagonizing, and/or partially antagonizing the AR. In one embodiment, at least one compound of Formula (I) selectively modulates the function of at least one AR. In another embodiment, at least one compound of Formula (I) agonizes or partially agonizes the function of at least one AR. In still another embodiment, at least one compound of Formula (I) antagonizes or partially antagonizes the function of at least one AR.

Medical conditions associated with the AR pathway include, but are not limited to, for example, benign prostate hyperplasia, hirsutism, acne, hyperpilosity, seborrhea, endometriosis, polycystic ovary syndrome, androgenic alopecia, adenomas and neoplasies of the prostate, benign or malignant tumor cells containing the androgen receptor, hypogonadism, osteoporosis, suppression of spermatogenesis, libido, cachexia, anorexia, androgen supplementation for age related decreased testosterone levels in men, prostate cancer, breast cancer, endometrial cancer, uterine cancer, hot flashes, and Kennedy's disease. For example, pan AR modulation is contemplated, with prostate selective AR modulation ("SARM") being particularly preferred, such as for the treatment of early stage prostate cancers. In one embodiment, Compound (I) is used to treat prostate cancer by being employed as an antagonist or partial antagonist of the AR.

Formula (I) compounds can be used to antagonize, preferably selectively antagonize, mutated ARs found, for example, in many tumor cell lines. Exemplary mutated ARs, include, but are not limited to, those found in prostate tumor cell lines, such as, for example, LNCap (T877A mutation, *Biophys. Acta,* 187, 1052 (1990)); PCa2b (L701H & T877A mutations, *J. Urol.,* 162, 2192 (1999)); and CWR22 (H874Y mutation, *Mol. Endo.,* 11, 450 (1997)).

One embodiment provides a pharmaceutical composition comprising at least one compound in accordance with Formula (I), or a pharmaceutically-acceptable salt or stereoisomer thereof; optionally at least one pharmaceutically-acceptable carrier and/or diluent; and optionally at least one other anti-cancer agent.

A still further embodiment provides a method for treating at least one condition or disorder comprising administering to a patient in need thereof a therapeutically effective amount of at least one compound of Formula (I), or a pharmaceutically-acceptable salt or stereoisomer thereof; optionally administering either simultaneously or sequentially at least one other anti-cancer agent, and optionally administering either simultaneously or sequentially at least one other anti-cancer treatment.

The phrase "other anti-cancer agent" includes any known agent useful for treating cancer, preferably prostate cancer.

In treating cancer, a combination of chemotherapeutic agents and/or other treatments (e.g., radiation therapy) is often advantageous. The other anti-cancer agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, the compounds of formula (I) (or other formulae disclosed herein) may be administered in combination with other anti-cancer agents and treatments useful in the treatment of cancer or other proliferative diseases. The invention herein further comprises use of the compounds of formula I herein (or other formulae disclosed herein), in preparing medicaments for the treatment of cancer, and/or it comprises the packaging of the compounds of formula (I) herein together with instructions that the compounds be used in combination with other anti-cancer agents and treatments for the treatment of cancer. The present invention further comprises combinations of the compounds of formula (I) and one or more additional agents in kit form, e.g., where they are packaged together or placed in separate packages to be sold together as a kit, or where they are packaged to be formulated together.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disrupter agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Additionally, the compounds of Formula (I) can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

The above other therapeutic agents, when employed in combination with the compounds of the present invention, can be used, for example, in those amounts indicated in the Physicians' Desk Reference (PDR) or as otherwise determined by one of ordinary skill in the art.

The phrase "anti-cancer treatment" includes but is not limited to, for example, radiation therapy and surgery, e.g. castration.

In one embodiment, at least one compound of Formula (I) is used to treat cancer.

The cancers that can be treated using Formula (I) compound(s) include, but are not limited to, for example, carcinoma, including, for example, that of the bladder, breast, colon, kidney, liver, lung (including small cell lung cancer), esophagus, gall bladder, ovary, pancreas, stomach, cervix, thyroid, prostate, and skin (including squamous cell carcinoma); hematopoietic tumors of lymphoid lineage, such as, for example, leukemia, acute lymphocytic leukemia, acute lymphoblastic leukemia, B-cell lymphoma, T-cell lymphoma, Hodgkin lymphoma, non-Hodgkin lymphoma, hairy cell lymphoma, and Burkett's lymphoma; hematopoietic tumors of myeloid lineage, such as, for example, acute and chronic myelogenous leukemia, myelodysplastic syndrome, and promyelocytic leukemia; tumors of mesenchymal origin, including, for example, fibrosarcoma and rhabdomyosarcoma; tumors of the central and peripheral nervous system, including, for example, astrocytoma, neuroblastoma, glioma, and schwannomas; and other tumors, such as, for example, melanoma, seminoma, teratocarcinoma, osteosarcoma, xeroderma pigmentosum, keratoacanthoma, thyroid follicular cancer, and Kaposi's sarcoma.

In another embodiment, at least one compound of Formula (I) is used to treat prostate cancer, breast cancer, uterine cancer, and/or endometrial cancer.

In another embodiment, at least one compound of Formula (I) is used to treat prostate cancer.

In yet another embodiment, at least one compound of Formula (I) is used to treat adenoma(s) and neoplasie(s) of the prostate.

In one embodiment, the patient is a mammal, including, but not limited to, for example, humans and domestic animals, such as, for example, dogs, cats, and horses.

In yet a further embodiment, the patient is a human.

Compounds in accordance with Formula (I) may be used, for example, in combination with known therapies for treating advanced metastatic prostate cancer including, but not limited to, for example, "complete androgen ablation therapy" wherein tumor growth is inhibited by controlling the supply of androgen to the prostate tissues via chemical castration followed by the administration of at least one AR antagonist. The compounds of Formula (I) can be employed as AR antagonists in complete ablation therapy, alone or in combination with other AR antagonists such as Flutamide, bicalutamide, Nilutamide, or Cyproterone acetate.

The compounds of Formula (I) may further be employed adjuvant to surgery.

Compounds in accordance with Formula (I) may be used, for example, either in combination with antibody therapy including, but not limited to, for example, antibody therapy against PSCA, or in concert with vaccine/immune modulating agents used to treat cancer.

Compounds in accordance with Formula (I) can be administered by any means suitable for the condition to be treated, which can depend on the need for site-specific treatment or quantity of Formula (I) compound to be delivered.

Any pharmaceutical composition contemplated herein can, for example, be delivered orally via any acceptable and suitable oral preparations. Exemplary oral preparations, include, but are not limited to, for example, tablets; troches; lozenges; aqueous or oily suspensions; dispersible powders or granules; emulsions; hard or soft capsules; syrups; and elixirs. Pharmaceutical compositions intended for oral administration can be prepared according to any methods known in the art for manufacturing pharmaceutical compositions intended for oral administration. In order to provide pharmaceutically elegant and palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinylpyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and a hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oil phase can be provided by, but is not limited to, for example, a vegetable oil, such as, for example, olive oil and arachis oil; a mineral oil, such as, for example, liquid paraffin; and mixtures thereof. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. An emulsion can also contain a sweetening agent, a flavoring agent, a preservative, and/or an antioxidant.

Any pharmaceutical composition contemplated herein can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleagenous suspensions.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Any pharmaceutical composition contemplated herein can, for example, further be administered via any acceptable and suitable rectal preparation, including, but not limited to, for example, a suppository. A suppository can be prepared by mixing at least one compound of Formula (I) with at least one suitable non-irritating excipient that is liquid at rectal temperatures but solid at a temperature below rectal temperature. Exemplary non-irritating excipients include, but are not limited to, for example, cocoa butter; glycerinated gelatin; hydrogenated vegetable oils; mixtures of polyethylene glycols of various molecular weights; and fatty acid esters of polyethylene glycol.

Any pharmaceutical composition contemplated herein can, for example, be administered via any acceptable and suitable topical preparations including, but not limited to, for example, creams; ointments; jellies; solutions; suspensions; transdermal patches; and intranasal inhalers. For purposes of this application, topical preparations include mouth washes and gargles.

Exemplary compositions for nasal aerosol or inhalation administration include solutions that may contain, for example, benzyl alcohol or other suitable preservatives, absorption promoters to enhance absorption and/or bioavailability, and/or other solubilizing or dispersing agents such as those known in the art An "effective amount" of Formula (I) compound may be determined by one of ordinary skill in the art, and includes exemplary dosage amounts for a mammal of from about 1 to about 500 mg/day, preferably from about 5 to about 300 mg/day, and more preferably, from about 10 to about 200 mg/day, in a single dose or in or in the form of individual divided doses. Exemplary dosage amounts for an adult human are from about 20, 40, 60, 80, 100, and 120 mg active compound per day, which can be administered in a single dose or in the form of individual divided doses, such as from 1 to 4 times per day.

The specific dose level and frequency of dosage for any particular subject, however, may be varied and generally depends on a variety of factors, including, but not limited to, for example, the bioavailability of the specific Formula (I) compound(s) in the administered form; metabolic stability and length of action of the specific Formula (I) compound(s); species, age, body weight, general health, sex, and diet of the subject; mode and time of administration; rate of excretion; drug combination; and severity of the particular condition.

The compounds of Formula (I) can also be formulated or co-administered with other therapeutic agents that are selected for their particular usefulness in administering therapies associated with the aforementioned conditions. For example, the compounds of the invention may be formulated with agents to prevent nausea, hypersensitivity, and/or gastric irritation, such as, for example, antiemetics and $H_1$ and $H_2$ antihistaminics.

The above other therapeutic agents, when employed in combination with the compounds of Formula (I), can be used, for example, in those amounts indicated in the Physicians' Desk Reference (PDR) or as otherwise determined by one of ordinary skill in the art.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

ABBREVIATIONS

Ac acetate
AcOH acetic acid
$Ac_2O$ acetic anhydride
$CH_2Cl_2$ dichloromethane
DMAP dimethylaminopyridine
DIEA diisopropylethylamine
DMF dimethylformamide
DMSO dimethylsulfoxide
Et ethyl
$Et_2O$ diethyl ether
EtOAc ethyl acetate
EtOH ethanol
$Et_3N$ triethyl amine
$Et_3SiH$ triethylsilane h hour
HATU O-(7-azabenzotriazol-1-yl)-N,N,N',N'-tetramethyl-uroniumhexafluorophosphate
HCl hydrochloric acid
iPr isopropyl
iPrOH isopropanol
LiHMDS lithium bis(trimethylsilyl)amide
mCPBA 3-chloroperoxybenzoic acid
Me methyl
MeOH methanol
min minute
NBS N-bromosuccinimide
n-BuLi n-butyl lithium
NaOMe sodium methoxide
PMe$_3$ trimethyl phosphine
RT retention time
TBDMSCl tert-butyldimethylsilylchloride
TEA triethylamine
TFA trifluoroacetic acid
Tf$_2$O trifluoromethylsulfonic anhydride
THF tetrahydrofuran
VCD vibrational circular dichroism

EXPERIMENTAL

Example 1 and Example 2

4-((1S,3R,4S,5S,8S,12R)-3-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (1) and 4-((1R,3S,4R,5R,8R,12S)-3-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (2)

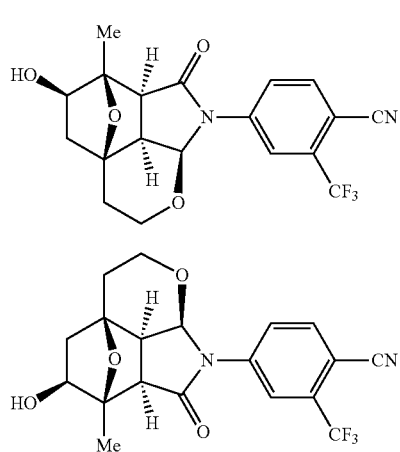

Preparation 1A: 5-Methyl-2-furanethanol

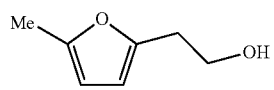

A solution of n-BuLi (83.0 mL, 133 mmol, 1.6 M in hexanes) was added to a stirred solution of 2-methylfuran (10.0 mL, 111 mmol) in THF (85 mL) at 0° C. under nitrogen. The reaction mixture was stirred for 4 h at room temperature and cooled to 0° C. Ethylene oxide (8.30 mL, 166 mmol) was added drop wise and the reaction mixture was allowed to warm to room temperature over 16 h. Saturated aqueous ammonium chloride was added, the resulting layers were separated, and the aqueous layer was extracted with diethyl ether (2×250 mL). The combined organic layers were dried over anhydrous Na$_2$SO$_4$ and concentrated under reduced pressure. Distillation at atmospheric pressure (170-185° C.) gave 10.1 g (80.3 mmol, 72%) of Preparation 1A as a light yellow oil.

Preparation 1B: 2-[2-[[(1,1-Dimethylethyl)dimethylsilyl]oxy]ethyl]-5-methylfuran

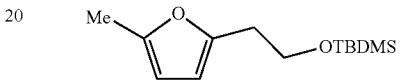

To a solution of Preparation 1A (2.00 g, 15.9 mmol) in DMF (50 mL) were added successively imidazole (1.62 g, 23.9 mmol) and tert-butyldimethylsilyl chloride (2.63 g, 17.5 mmol). After 2 h of stirring at 25° C., the reaction mixture was poured into diethyl ether (300 mL) and washed with water (1×100 mL), aq. 1 N HCl (1×100 mL), water (1×100 mL), brine (1×50 mL) and dried over anhydrous MgSO$_4$. Preparation 1B (3.85 g, 100%) was analyzed by LCMS and NMR. HPLC: 4.35 min (RT) (YMC S5 ODS column 4.6×50 mm eluting with 10-90% aqueous MeOH over 4 minutes containing 0.1% TFA, 4 mL/min, monitoring at 220 nm).

Preparation 1C

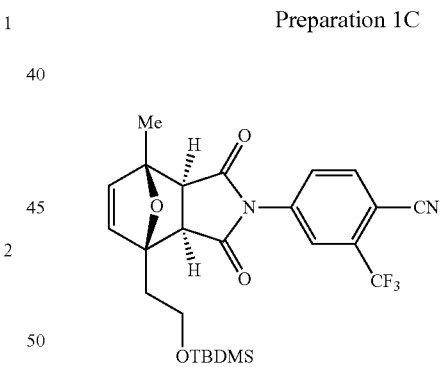

A mixture of 4-(2,5-dioxo-2,5-dihydro-1H-pyrrol-1-yl)-2-(trifluoro)benzonitrile (140 g, 526 mmol) (for synthesis, refer to US Patent Application Publication No. 2005/0192253 A1) and Preparation 1B (190 g, 790 mmol) in isopropanol (500 mL) and THF (50 mL) was heated at 80° C. for 1.5 h. The reaction mixture was allowed to cool to 50° C. over 30 min and seeded with previously prepared product (seeds can be prepared by concentrating a small aliquot of the reaction mixture and allowing to crystallize, or by isolating with column chromatography). The reaction mixture was allowed to cool to room temperature for 12 h and further cooled in an ice bath for 1 h. The solid material was collected by filtration, rinsed with cold isopropanol, and dried to give 215.8 g (81%) of the Preparation 1C. HPLC: 3.90 min (RT) (Chromolith column 4.6×50 mm eluting with 10-90% aqueous MeOH over 4 minutes containing 0.1% TFA, 4 mL/min, monitoring at 220 nm).

Preparation 1D and Preparation 1E

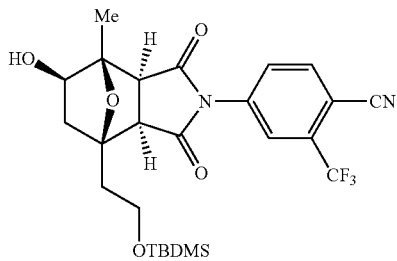

1D

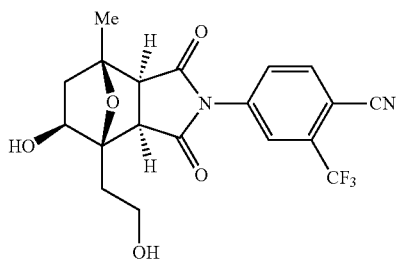

1E

To a solution of Preparation 1C (100 g, 197 mmol) in THF (500 mL) at 0° C. was added drop wise 1M solution of BH$_3$-THF in THF (500 mL, 500 mmol) over 30 min. After the addition was complete, the reaction mixture was stirred at 0° C. for an additional 15 min. Next, the reaction was quenched by drop wise addition of an aqueous pH 7.2 phosphate buffer (700 mL) with the evolution of hydrogen gas. Aqueous hydrogen peroxide (30%, 350 mL) was added to the cooled reaction mixture and the reaction mixture was stirred for an additional 30 min. The reaction mixture was diluted with brine (0.8 L) and extracted with EtOAc (0.8 L). The organic layer was cooled at 0° C. and stirred with 20% aqueous Na$_2$S$_2$O$_3$ solution (1.0 L) for 30 min. The organic layer tested negative for peroxides on EM QUANT Peroxide Test Strip. Brine (0.8 L) was added and the layers were separated. The organic layer was dried over anhydrous magnesium sulfate, filtered, and the solvent removed under reduced pressure to afford a thick oil. The crude mixture was dissolved in EtOAc (170 mL) and seeded with some previously prepared product (seeds can be prepared by purifying a sample with column chromatography). The mixture was stirred for 5 min and hexane (350 mL) was added slowly to the resulting suspension. The resulting mixture was stirred for 12 h and more hexane (400 mL) was slowly added. After an additional one hour of stirring, the mixture was filtered and the solid rinsed with 4:1 hexane/EtOAc (500 mL) to give 30.8 g (37%) of Preparation 1E. The mother liquor was concentrated under reduced pressure and purified on silica gel (330 g ISCO column) eluting with a gradient from CH$_2$Cl$_2$ to 40% EtOAc/CH$_2$Cl$_2$ over 50 min. (100 mL/min) The product was collected and concentrated under reduced pressure to give 36 g (35%) Preparation 1D. HPLC: 3.673 min (RT) (Preparation 1D). HPLC: 1.987 min (RT) (Preparation 1E) (Chromolith column 4.6×50 mm eluting with 10-90% aqueous MeOH over 4 minutes containing 0.1% TFA, 4 mL/min, monitoring at 220 nm).

Examples 1 and 2

To Preparation 1D (29 g, 55 mmol) in MeOH (50 mL) cooled in a water bath was added 2% conc. HCl in MeOH (200 mL). The reaction mixture was stirred for 10 min and then concentrated in vacuo. The residue was dissolved in EtOAc, washed with brine, and then dried over MgSO$_4$, filtered and concentrated. The crude material was dissolved in THF (200 mL) and MeOH (100 mL) and cooled in an ice bath. To the reaction was added NaBH$_4$ (5.35 g, 141 mmol) in portions. The reaction was stirred for 30 min and then slowly quenched with saturated aq. NH$_4$Cl (300 mL) followed by addition of water (200 mL) and brine (400 mL). The mixture was extracted twice with EtOAc and then the organic layer was dried over MgSO$_4$, filtered, and concentrated. The crude material was suspended in CH$_2$Cl$_2$ (100 mL) and cooled in a water bath. To the mixture was added TFA (100 mL) and the resulting solution was stirred for 15 min, followed by the addition of Et$_3$SiH (30 mL). After stirring for 1 h, the reaction was concentrated in vacuo and to the residue was added 1N NaOH (300 mL) cooled in an ice bath. To the mixture was added brine (400 mL) and extracted twice with EtOAc. The organic layer was dried over MgSO$_4$, filtered and concentrated. The crude material was purified on silica gel using 330 g ISCO column eluting with 100% CH$_2$Cl$_2$ to 100% EtOAc. The product was collected and concentrated, then triturated with cold EtOAc/hexane filtered with cold EtOAc/hexane rinse and dried under vacuo to give 9.95 g racemic material.

The enantiomers (4.68 g racemic material) were separated on a chiral OJ prep eluting with 30% (1:1 EtOH/MeOH) in heptane. The two enantiomers were collected and concentrated in vacuo to give Example 1 and Example 2.

Example 1

2.16 g. HPLC: 2.137 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. Chiral HPLC: 6.48 min (RT) (OJ column eluting with 30% (1:1 EtOH/MeOH) in heptane, 1 mL/min, monitoring at 220 nm). [α]$_D$=−29.20 deg in MeOH at 25° C. (10.5 mg/mL). Relative configuration confirmed by X-ray crystallography and absolute stereochemistry confirmed by VCD analysis.

Example 2

2.22 g. HPLC: 2.131 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. Chiral HPLC: 17.62 min (RT) (OJ column eluting with 30% (1:1 EtOH/MeOH) in heptane, 1 mL/min, monitoring at 220 nm). $^1$H NMR (500 MHz, CDCl$_3$) δ ppm 8.07 (1H, d, J=2.20 Hz), 7.91 (1H, dd), 7.81 (1H, d, J=8.80 Hz), 5.82 (1H, d, J=7.70 Hz), 3.99 (1H, dd, J=7.15, 3.85 Hz), 3.64-3.72 (1H, m), 3.55-3.62 (1H, m), 2.70 (1H, d, J=7.70 Hz), 2.46 (1H, t, J=7.70 Hz), 2.25 (1H, dd, J=13.20, 7.15 Hz), 1.97-2.08 (2H, m), 1.69 (3H, s), 1.50 (1H, dd, J=12.92, 3.57 Hz).

Examples 3 and 4

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (3) and 4-((1S,2R,4S,5R,8R,12S)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (4)

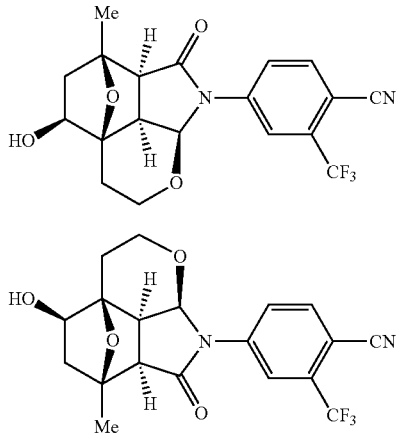

To a solution of Preparation 1E (25 g, 60.9 mmol) in THF (225 mL) and MeOH (25 mL) at −5° C. was added in portions sodium borohydride (4.6 g, 122 mmol) over a period of 20 min. The reaction mixture was stirred for 2 h and quenched with a drop-wise addition of aqueous 2M HCl (200 mL). The reaction mixture was concentrated in vacuo until an oil started to come out of the solution. THF (5 mL) was added to make a homogeneous solution. To the reaction mixture was added aq. 2M HCl (200 mL) and stirring continued for 18 h. The reaction mixture was cooled at 0° C. for 30 min, filtered, and the solid was washed with cold (0° C.) water (100 mL). The solid was dried to give 15.7 g (65.4%) of the racemic mixture of Example 3 and Example 4. HPLC: 2.03 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. The 15.7 g was combined with another 24.5 g prepared similarly and the enantiomers were separated by preparatory column chromatography (Chiralcel OJ 5 cm×50 cm 20μ, by Chiral Technologies Inc.) eluting with 30% (1:1 EtOH/MeOH) in heptane. Concentration of the appropriate fractions provided 19.9 g of Example 3 as a white solid and 19 g of Example 4 as a white solid.

Example 3

HPLC: 2.03 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. Chiral HPLC: 5.46 min (RT) [Chiralcel OJ 5 cm×50 cm 20μ, by Chiral Technologies Inc. (800 North Five Points Road, West Chester, Pa. 19380, USA) eluting with 30% (1:1 EtOH/MeOH) in heptane, 1 mL/min, monitoring at 220 nm]. Enantiomeric purity: >99.9%; Specific rotation Example 3 [α]$_D$=−29.674 deg in MeOH at 25° C. (10.15 mg/mL). Example 3: $^1$H NMR (500 MHz, DMSO-d$_6$) δ ppm 8.19 (1H, d, J=8.80 Hz), 8.14 (1H, d, J=1.65 Hz), 7.94 (1H, dd, J=8.52, 1.92 Hz), 6.08 (1H, d, J=7.70 Hz), 4.84 (1H, d, J=6.05 Hz), 3.67-3.75 (1H, m), 3.50-3.58 (1H, m), 3.35-3.42 (1H, m), 2.82 (1H, d, J=8.25 Hz), 2.42 (1H, t, J=7.70 Hz), 2.22 (1H, dd, J=13.47, 6.87 Hz), 1.92 (1H, d, J=14.85 Hz), 1.73-1.82 (1H, m), 1.59 (3H, s), 1.36 (1H, dd, J=13.20, 1.65 Hz). Relative configuration confirmed by X-ray crystallography and absolute stereochemistry confirmed by VCD analysis.

Example 4

HPLC: 2.00 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. Chiral HPLC: 12.11 min (RT) [Chiralcel OJ 5 cm×50 cm 20μ, by Chiral Technologies Inc. (800 North Five Points Road, West Chester, Pa. 19380, USA) eluting with 30% (1:1 EtOH/MeOH) in heptane, 1 mL/min, monitoring at 220 nm]. Enantiomeric purity: >99.9%; Specific rotation Example 4 [α]$_D$=+27.651 deg in MeOH at 25° C. (10.04 mg/mL). Example 4 $^1$H NMR (500 MHz, DMSO-d$_6$) δ ppm 8.19 (1H, d, J=8.80 Hz), 8.14 (1H, d, J=1.65 Hz), 7.94 (1H, dd, J=8.52, 1.92 Hz), 6.08 (1H, d, J=7.70 Hz), 4.84 (1H, d, J=6.05 Hz), 3.67-3.75 (1H, m), 3.50-3.58 (1H, m), 3.35-3.42 (1H, m), 2.82 (1H, d, J=8.25 Hz), 2.42 (1H, t, J=7.70 Hz), 2.22 (1H, dd, J=13.47, 6.87 Hz), 1.92 (1H, d, J=14.85 Hz), 1.73-1.82 (1H, m), 1.59 (3H, s), 1.36 (1H, dd, J=13.20, 1.65 Hz).

Example 3

Preparation of Crystalline Form N-1

A mixture of Example 3 (19.9 g) in ethanol (250 mL) was heated to reflux for 1 hour. The resulting solution was filtered while hot with hot ethanol (10 mL) rinse. To the solution was added H$_2$O (250 mL) and let cool to room temperature with stirring to crystallize. The mixture was stirred at room temperature for 18 hours then cooled to 0° C. and another 300 mL H$_2$O was added. After stirring for 1 hour the crystals were collected by filtration and rinsed with cold 3:1 H$_2$O:EtOH (200 mL). The crystals were dried under reduced pressure at 65° C. for 1 hour to give 18.2 g Example 3: HPLC: 2.03 min (RT) (Chromolith column 4.6×50 mm eluting with 10-90% aqueous MeOH over 4 minutes containing 0.1% TFA, 4 mL/min, monitoring at 220 nm). (M+H)$^+$: 395. Chiral HPLC: 6.02 min (RT) [Chiralcel OJ 5 cm×50 cm 20μ, by Chiral Technologies Inc. (800 North Five Points Road, West Chester, Pa. 19380, USA) eluting with 30% (1:1 EtOH/MeOH) in heptane, 1 mL/min, monitoring at 220 nm]. Enantiomeric purity: >99.9%

Example 3

Preparation of Crystalline Form N-2

A solution of Example 3 (3.5 g) in minimum amount of 2:1 MeOH/DMSO was run on preparative reverse phase HPLC, eluting with 10-90% aqueous MeOH over 15 minutes containing 0.1% TFA. The product fractions were collected and the methanol was removed under reduced pressure at 32° C. (bath temperature). Crystallization occurred and the mixture was cooled to room temperature and neutralized with aq NaHCO₃. The crystals were collected by filtration, rinsed with water and then dried to give 2.52 g Example 3. HPLC: 1.98 min (RT) (Chromolith column 4.6×50 mm eluting with 10-90% aqueous MeOH over 4 minutes containing 0.1% TFA, 4 mL/min, monitoring at 220 nm).

Preparation 1F and Preparation 1G

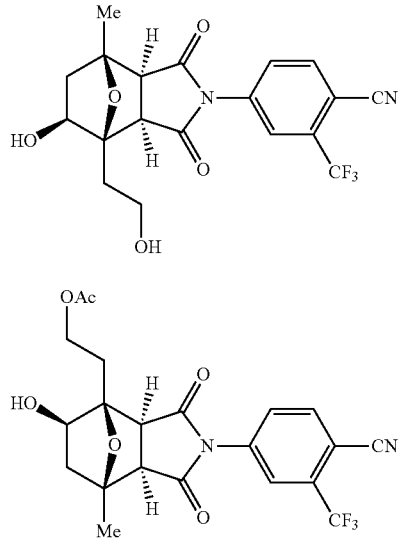

To a solution of Preparation 1E (50 g, 24.4 mmol) in anhydrous tetrahydrofuran (THF, 1 L) was added vinyl acetate (300 mL) and then Lipase (100 g) (Lipase from porcine pancreas, Type II). The reaction was stirred at 42° C. under nitrogen for 92 h. Then the reaction mixture was cooled to room temperature and filtered through a medium porosity fritted funnel rinsing with THF. The solid material was transferred to a 1 L beaker; THF (500 mL) was added and was stirred at room temperature for 20 min. Then it was filtered again. The solid was rinsed with THF (5×100 mL). The combined filtrate was concentrated in vacuo to give the crude material which was purified by flash chromatography on silica gel. The crude material was dissolved in CH₂Cl₂ (120 mL) was loaded on two 330 g silica gel columns (7 cm×23 cm). Each column had been equilibrated with 10% acetone in CH₂Cl₂. Preparation 1G was fully eluted with 10% acetone in CH₂Cl₂ (2.5 L). Preparation 1F was then eluted with 80% acetone in CH₂Cl₂ (1 L) to give 24 g of Preparation 1F and 26 g of Preparation 1G, each as a light yellow solid.

Preparation 1F: HPLC: 2.483 min (RT) (YMC ODS-A column 4.6×50 mm eluting with 10-90% aqueous MeOH over 4 minutes containing 0.1% H₃PO₄, 4 mL/min, monitoring at 220 nm). Chiral HPLC: >99.9% ee @ 16.26 min (RT) (Chiral OJ NP 10 um 4.6×250 mm eluting with 15% EtOH/ 15% MeOH/70% heptane). The opposite enantiomer has a (RT) of ~6.5 min.

Preparation 1G: HPLC: 2.801 min (RT) (YMC ODS-A column 4.6×50 mm eluting with 10-90% aqueous MeOH over 4 minutes containing 0.1% H₃PO₄, 4 mL/min, monitoring at 220 nm). MS (ES): m/z=453.0 [M+H]⁺; Chiral HPLC:>99% ee @ 5.99 min (RT) (Chiral OJ NP 10 um 4.6×250 mm eluting with 20% EtOH/20% MeOH/60% heptane).

Example 3

4-((1R,2S,4R,5S,8S,12R)-2-hydroxy-4-methyl-6-oxo-9,13-dioxa-7-azatetracyclo[6.3.1.1$^{1,4}$.0$^{5,12}$] tridec-7-yl)-2-(trifluoromethyl)benzonitrile (3)

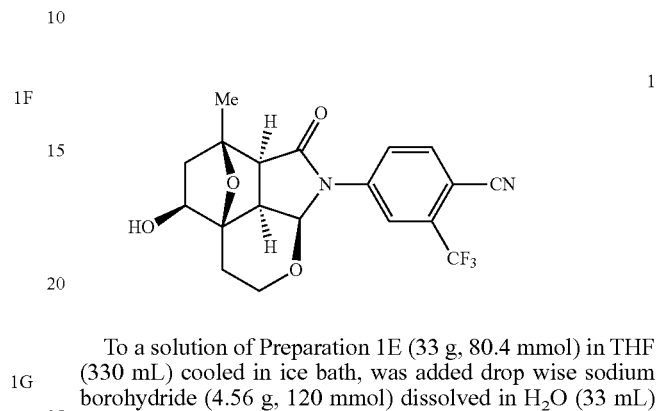

To a solution of Preparation 1E (33 g, 80.4 mmol) in THF (330 mL) cooled in ice bath, was added drop wise sodium borohydride (4.56 g, 120 mmol) dissolved in H₂O (33 mL) over a period of 30 min. The reaction mixture was stirred for 5 h and quenched with a drop wise addition of acetone (30 mL). The reaction mixture was stirred for 20 min and then concentrated in vacuo. To the resulting residue was added aq. 6M HCl (500 mL) and the reaction mixture was stirred for 18 h. The reaction mixture was then cooled at 0° C. for 30 min, filtered and the solid was washed with cold (0° C.) water (100 mL). The solid was dried to give 20.77 g (65.5%) of Example 3.

HPLC: 2.00 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]⁺; Chiral HPLC: 5.31 min (RT) [Chiralcel OJ 5 cm×50 cm 20μ, by Chiral Technologies Inc. (800 North Five Points Road, West Chester, Pa. 19380, USA) eluting with 30% (1:1 EtOH/MeOH) in heptane, 1 mL/min, monitoring at 220 nm]. Enantiomeric purity: >99.9%; Specific rotation [α]$_D$=−29.674° deg in MeOH at 25° C. (10.15 mg/mL); ¹H NMR (500 MHz, DMSO-d₆) δ ppm 8.19 (1H, d, J=8.80 Hz), 8.14 (1H, d, J=1.65 Hz), 7.94 (1H, dd, J=8.52, 1.92 Hz), 6.08 (1H, d, J=7.70 Hz), 4.84 (1H, d, J=6.05 Hz), 3.67-3.75 (1H, m), 3.50-3.58 (1H, m), 3.35-3.42 (1H, m), 2.82 (1H, d, J=8.25 Hz), 2.42 (1H, t, J=7.70 Hz), 2.22 (1H, dd, J=13.47, 6.87 Hz), 1.92 (1H, d, J=14.85 Hz), 1.73-1.82 (1H, m), 1.59 (3H, s), 1.36 (1H, dd, J=13.20, 1.65 Hz).

Example 5

4-((1R,4R,5S,8S,12R)-4-methyl-2,6-dioxo-9,13-dioxa-7-azatetracyclo[6.3.1.1$^{1,4}$.0$^{5,12}$]tridec-7-yl)-2-(trifluoromethyl)benzonitrile (5)

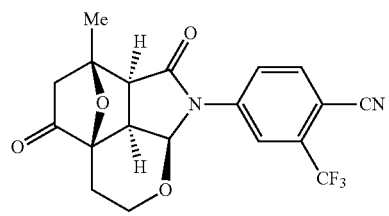

Dess-Martin periodinane (12 g, 28.3 mmol) was added to a solution of Example 3 (3.0 g, 7.6 mmol) in THF (20 mL) and CH$_2$Cl$_2$ (30 mL) at room temperature. The reaction mixture was stirred at room temperature for 18 h and CH$_2$Cl$_2$ (50 mL), aq. 15% Na$_2$S$_2$O$_3$ solution (25 mL), and aq. 2M Na$_2$CO$_3$ solution (25 mL) were added. The mixture was stirred for 1 h and the layers were separated. The organic layer was dried over anhydrous magnesium sulfate, filtered, and concentrated under reduced pressure to give 2.9 g (97%) of the Example 5.

HPLC: 2.62 min (RT) (Chromolith column 4.6×50 mm eluting with 10-90% aqueous MeOH over 4 minutes containing 0.1% TFA, 4 mL/min, monitoring at 220 nm). MS (ES): m/z=393 [M+H]$^+$.

Example 6

4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (6)

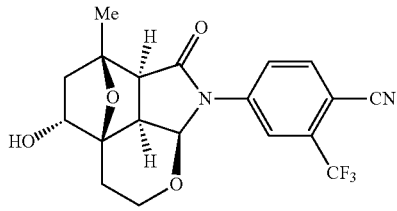

Sodium borohydride (0.56 g, 14.7 mmol) was added in portions to a solution of Example 5 (2.9 g, 7.39 mmol) in THF (10 mL) and MeOH (10 mL) at 0° C. The reaction mixture was stirred for 15 min and quenched with drop-wise addition of aqueous saturated ammonium chloride (20 mL). The organic solvents were removed in vacuo and the residue was extracted with EtOAc. The organic layer was dried over anhydrous magnesium sulfate, filtered, and concentrated. The crude material was purified by silica gel chromatography using an 80 g ISCO column eluting with 0-100% EtOAc in CH$_2$Cl$_2$ at 70 mL/min. Concentration of appropriate fractions provided 2.9 g (99%) of Example 6 as a white solid.

HPLC: 2.43 min (RT) (Chromolith column 4.6×50 mm eluting with 10-90% aqueous MeOH over 4 minutes containing 0.1% TFA, 4 mL/min, monitoring at 220 nm). MS (ES): m/z=395 [M+H]$^+$. $^1$H NMR (500 MHz, CDCl$_3$) δ ppm 8.12 (1H, d, J=1.65 Hz), 7.94 (1H, dd, J=8.52, 1.92 Hz), 7.83 (1H, d, J=8.80 Hz), 5.98 (1H, d, J=7.70 Hz), 4.02-4.08 (1H, m), 3.59-3.64 (1H, m), 3.32 (1H, t, J=7.70 Hz), 2.90 (1H, d, J=7.70 Hz), 2.18 (1H, dd, J=13.20, 9.90 Hz), 2.04-2.13 (1H, m), 1.99 (1H, d, J=4.40 Hz), 1.79 (1H, d, J=14.30 Hz), 1.68 (3H, s), 1.54 (1H, d, J=4.40 Hz).

Example 7

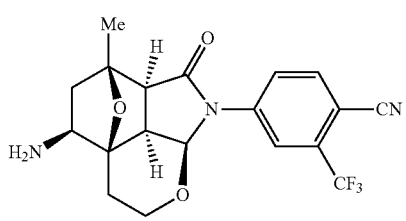

To a solution of Example 6 (2.9 g, 7.3 mmol) in CH$_2$Cl$_2$ (20 mL) at 0° C. were added successively pyridine (0.728 mL, 9 mmol) and trifluoromethanesulfonic anhydride (1.3 mL, 8.2 mmol). The reaction mixture was stirred for 10 min., water (15 mL) was added, and the layers were separated. The organic layer was washed with aq. 1N HCl (5 mL), dried over anhydrous magnesium sulfate, filtered, and concentrated. The residue was dissolved in DMF (10 mL) and sodium azide (1.5 g, 22 mmol) was added. The reaction mixture was heated at 60° C. for 1 h, allowed to cool to room temperature, and poured into ice cold water (50 mL) with aq. 2M sodium carbonate (5 mL). The mixture was stirred at 0° C. for 10 min, the solid was collected by filtration, rinsed with cold water, and dried under vacuum. The resulting crude azide product was dissolved in THF (15 mL), trimethylphosphine (1M THF, 20 mL, 20 mmol) was added and stirring was continued for 30 min. The reaction mixture was concentrated to half of its original volume and MeOH (15 mL) was added followed by aq. 50% NaOH (3 mL). The reaction mixture was concentrated under reduced pressure, diluted with aq. saturated bicarbonate, and extracted twice with EtOAc. The organic layer was dried over anhydrous magnesium sulfate, filtered, and concentrated in vacuo to give 2.6 g (90%) of Example 7 as a white solid.

HPLC: 1.70 min (RT) (Chromolith column 4.6×50 mm eluting with 10-90% aqueous MeOH over 4 minutes containing 0.1% TFA, 4 mL/min, monitoring at 220 nm). MS (ES): m/z=394 [M+H]$^+$.

Example 8

Methyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (8)

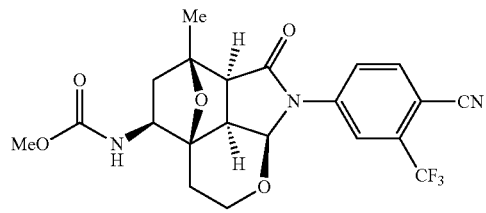

A solution of Example 7 (2.5 g, 6.3 mmol) in THF (20 mL) was added drop-wise over 10 min. to a solution of carbonyldiimidazole (4 g, 24.6 mmol) in THF (30 mL) at room temperature. The reaction mixture was stirred for 10 min and MeOH (30 mL) was added, followed by sodium methoxide (0.68 g, 12.6 mmol). The reaction mixture was stirred for a further 5 min and concentrated under reduced pressure. The resulting residue was stirred with cold (0° C.) aq. 2M HCl (50 mL) for 30 min. The solid precipitate was collected by filtration, washed with cold (0° C.) water and dried to give 2.1 g (74%) of Example 8.

HPLC: 2.44 min (RT) (Chromolith column 4.6×50 mm eluting with 10-90% aqueous MeOH over 4 minutes containing 0.1% TFA, 4 mL/min, monitoring at 220 nm). MS (ES): m/z=452 [M+H]$^+$. $^1$H NMR (500 MHz, CDCl$_3$) δ ppm 8.09 (1H, s), 7.91 (1H, dd, J=8.80, 1.65 Hz), 7.81 (1H, d, J=8.25 Hz), 4.75 (1H, d, J=9.90 Hz), 3.95-4.01 (1H, m), 3.67 (3H, s), 3.58-3.64 (1H, m), 3.50-3.58 (1H, m), 2.80 (1H, d, J=7.70 Hz), 2.56 (1H, t, J=7.70 Hz), 2.39 (1H, dd, J=13.75, 8.25 Hz), 1.99-2.08 (1H, m), 1.89-1.96 (1H, m), 1.74 (3H, s), 1.43 (1H, dd, J=14.30, 2.20 Hz).

Example 9

N-((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (9)

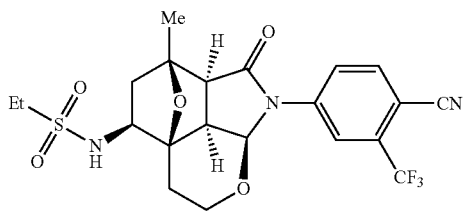

To a solution of Example 7 (320 mg, 0.81 mmol) in CH$_2$Cl$_2$ (5 mL) at room temperature were added successively triethylamine (0.34 mL, 2.44 mmol) and ethylsulfonyl chloride (0.085 mL, 0.89 mmol). The reaction mixture was stirred for 30 min, washed with aq. 1M HCl, dried over anhydrous magnesium sulfate, and concentrated. The crude material was purified by silica gel chromatography with a 40 g ISCO column with gradient elution from 100% CH$_2$Cl$_2$ to 100% EtOAc. The appropriate fractions were concentrated under reduced pressure to afford 234 mg (59%) of Example 9.

HPLC: 2.19 min (RT) (Chromolith column 4.6×50 mm eluting with 10-90% aqueous MeOH over 4 minutes containing 0.1% TFA, 4 mL/min, monitoring at 220 nm). MS (ES): m/z=486 [M+H]$^+$. $^1$H NMR (500 MHz, CDCl$_3$) δ ppm 8.19 (1H, d, J=8.80 Hz), 8.13 (1H, d, J=1.65 Hz), 7.93 (1H, dd, J=8.80, 1.65 Hz), 7.15 (1H, d, J=8.80 Hz), 6.09 (1H, d, J=7.70 Hz), 3.48-3.60 (2H, m), 3.36 (1H, t, J=11.00 Hz), 2.98 (2H, q, J=7.33 Hz), 2.88 (1H, d, J=7.70 Hz), 2.60 (1H, t, J=7.70 Hz), 2.37 (1 H, dd, J=13.20, 8.25 Hz), 1.90-1.97 (1H, m), 1.77-1.87 (1H, m), 1.59 (3H, s), 1.54 (1H, dd, J=13.20, 2.20 Hz), 1.17 (3H, t, J=7.42 Hz).

Example 10

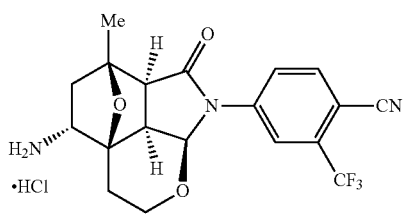

To a cold (0° C.) solution of Example 3 (1 g, 2.53 mmol) in CH$_2$Cl$_2$ (10 mL) were added successively pyridine (0.24 mL, 3.29 mmol) and trifluoromethanesulphonic anhydride (0.457 mL, 2.78 mmol). The reaction mixture was stirred for 10 min and washed with water (15 mL) and aq. 1N HCl (5 mL). The organic layer was dried over anhydrous magnesium sulfate, filtered, and concentrated under reduced pressure. The residue was dissolved in THF (10 mL) and stirred at room temperature for 3 h with tetrabutylammonium azide (1.44 g, 5.07 mmol). Trimethylphosphine (1M in THF, 7 mL) was then added and stirring continued for an additional 30 min. The reaction mixture was concentrated to half of its original volume and MeOH (3 mL) was added followed by aq. 1M NaOH (3 mL). The reaction mixture was concentrated under reduced pressure, diluted with aq saturated sodium bicarbonate, and extracted with EtOAc. The organic layer was dried over anhydrous magnesium sulfate, filtered, and concentrated under reduced pressure. The residue was dissolved in CH$_2$Cl$_2$ (10 mL) and 4N HCl in dioxane (1.5 mL) was added. The resulting precipitate was filtered to give 1.0 g of Example 10.

HPLC: 1.98 min (RT) (Chromolith column 4.6×50 mm eluting with 10-90% aqueous MeOH over 4 minutes containing 0.1% TFA, 4 mL/min, monitoring at 220 nm). MS (ES): m/z=394 [M+H]$^+$.

Example 11

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)propanamide (11)

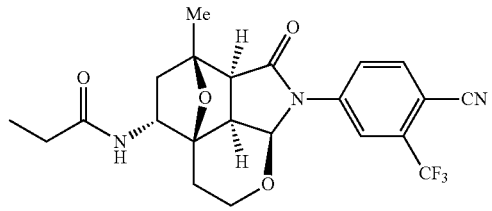

A solution-suspension of Example 10 (22 mg, 0.051 mmol), triethylamine (21 µL, 0.153 mmol), and propionic anhydride (9.9 µL, 0.076 mmol) in CH$_2$Cl$_2$ (0.5 mL) was stirred at room temperature for 1 h. The reaction mixture was washed with aq. 1M HCl, and the organic layer was dried over anhydrous magnesium sulfate, filtered, and concentrated. The residue was purified by silica gel chromatography (12 g ISCO column) eluting with a gradient from 100% CH$_2$Cl$_2$ to 100% EtOAc. Concentration of the appropriate fractions afforded 19.3 mg of Example 11.

HPLC: 2.47 min (RT) (Chromolith column 4.6×50 mm eluting with 10-90% aqueous MeOH over 4 minutes containing 0.1% TFA, 4 mL/min, monitoring at 220 nm). MS (ES): m/z=450 [M+H]$^+$. $^1$H NMR (500 MHz, CDCl$_3$) δ ppm 8.07 (1H, d, J=2.20 Hz), 7.91 (1H, dd, J=8.80, 2.20 Hz), 7.82 (1H, d, J=8.25 Hz), 5.94 (1H, d, J=7.70 Hz), 4.22-4.29 (1H, m), 3.52-3.62 (2H, m), 2.85 (1H, d), 2.79 (1H, t, J=7.70 Hz), 2.22-2.34 (3H, m), 2.04-2.13 (1H, m), 1.92-1.97 (1H, m), 1.69 (3H, s), 1.39 (1H, dd, J=13.20, 6.05 Hz), 1.19 (3H, t, J=7.42 Hz).

Example 12

4-((1S,3R,4R,5R,8R,12S)-3-azido-4-methyl-6-oxo-9,13-dioxa-7-azatetracyclo[6.3.1.1$^{1,4}$.0$^{5,12}$]tridec-7-yl)-2-(trifluoromethyl)benzonitrile (12)

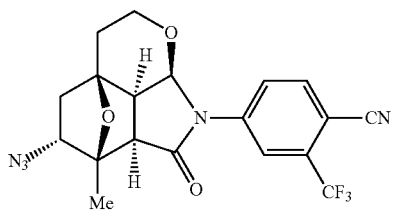

To a solution of Example 2 (9.95 g, 0.025 mol) in CH$_2$Cl$_2$ (100 mL) placed in a water bath was added pyridine (2.43 mL, 0.030 mol) followed by trifluoromethanesulfonic anhydride (4.6 mL, 0.028 mol). After stirring for 10 min, the reaction mixture was washed with water acidified with 1N HCl (aq). The organic phase was dried over MgSO$_4$, filtered, and then concentrated in vacuo. The residue was dissolved in DMF (30 mL) and NaN$_3$ (3.25 g, 0.050 mol) was added. The mixture was heated to 50° C. for 1 hour then cooled to room temperature. The reaction mixture was diluted with EtOAc and washed twice with 10% LiCl (aq). The organic layer was concentrated in vacuo and the resulting solid was stirred in H$_2$O (100 mL) for 30 min. The solid was filtered, rinsed with H$_2$O, and dried to give 10.3 g of Example 12.

HPLC: 2.938 min (RT) (Chromolith column 4.6×50 mm eluting with 10-90% aqueous MeOH over 4 minutes containing 0.1% TFA, 4 mL/min, monitoring at 220 nm). MS (ES): m/z=420 [M+H]$^+$.

Example 13

4-((1S,3R,4R,5R,8R,12S)-3-amino-4-methyl-6-oxo-9,13-dioxa-7-azatetracyclo[6.3.1.1$^{1,4}$.0$^{5,12}$]tridec-7-yl)-2-(trifluoromethyl)benzonitrile (13)

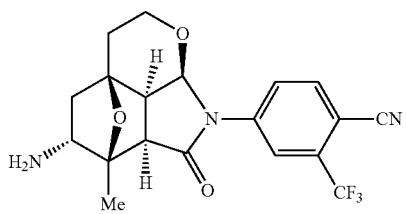

To Example 12 (10.3 g, 0.0246 mol) in THF (50 mL) cooled in a water bath was added PMe$_3$ (49 mL, 1M in THF). The mixture was stirred for 10 min then the solvent was removed in vacuo. The residue was dissolved in MeOH (30 mL) and 50% NaOH (0.7 mL, aq) was added. The mixture was stirred for 30 min and then concentrated in vacuo. To the residue was added water and brine and then extracted twice with EtOAc. The organic layer was dried over MgSO$_4$, filtered and concentrated in vacuo. The resulting solid was triturated with EtOAc/hexane (100 mL, 1:1) and filtered with EtOAc/hexane rinse, then dried to afford 8.8 g of Example 13.

HPLC: 2.107 min (RT) (Chromolith column 4.6×50 mm eluting with 10-90% aqueous MeOH over 4 minutes containing 0.1% TFA, 4 mL/min, monitoring at 220 nm). MS (ES): m/z=394 [M+H]$^+$.

Example 14

Methyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (14)

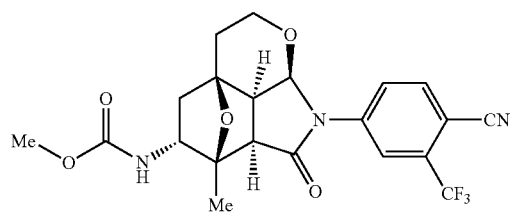

Example 13 (1.18 g, 3.0 mmol) in THF (10 mL) was added drop wise over 10 min to a solution of carbonyldiimidazole (1.5 g, 9.25 mmol) in THF (10 mL). The mixture was stirred for 30 min. Next, MeOH (20 mL) was added followed by the addition of NaOMe (0.162 g, 3 mmol). The reaction mixture was stirred for 5 min and then concentrated in vacuo. To the residue was added EtOAc and washed twice with 1M HCl and once with sat. NaHCO$_3$ aq. The organic layer was dried over MgSO$_4$, filtered, and then concentrated in vacuo. The residue was purified by silica gel chromatography on a 120 g ISCO column eluting with a gradient from 100% CH$_2$Cl$_2$ up to 6% MeOH/CH$_2$Cl$_2$. The product was collected, concentrated in vacuo, and dried to give 1.2 g of Example 14.

HPLC: 2.638 min (RT) (Chromolith column 4.6×50 mm eluting with 10-90% aqueous MeOH over 4 minutes containing 0.1% TFA, 4 mL/min, monitoring at 220 nm). MS (ES): m/z=452 [M+H]$^+$. $^1$H NMR (500 MHz, CDCl$_3$) δ ppm 8.05 (1H, d, J=2.20 Hz), 7.92 (1H, dd, J=8.52, 1.92 Hz), 7.82 (1H, d, J=8.25 Hz), 5.86 (1H, d, J=7.15 Hz), 4.71 (1H, s), 4.03-4.13 (1H, m), 3.70 (3H, s), 3.63-3.67 (1H, m), 3.54-3.61 (1H, m), 3.16 (1H, d, J=7.70 Hz), 2.60 (1H, t, J=7.70 Hz), 2.29 (1H, t, J=12.10 Hz), 1.97-2.06 (1H, m), 1.88-1.94 (1H, m), 1.73 (3H, s), 1.38 (1H, dd, J=12.65, 2.75 Hz).

Example 15

(1R,2S,4R,5S,8S,12R)-7-(3-chloro-4-fluorophenyl)-2-hydroxy-4-methyl-9,13-dioxa-7-azatetracyclo[6.3.1.1$^{1,4}$.0$^{5,12}$]tridecan-6-one (15)

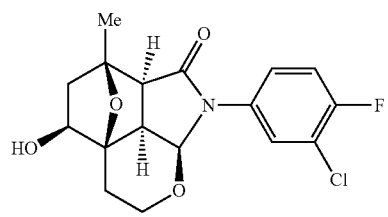

Preparation 15A

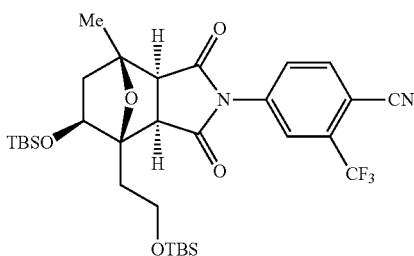

To a solution of Preparation 1F (3.6 g, 8.8 mmol) in DMF (9 mL) was added TBSCl (2.7 g, 18 mmol) and imidazole (1.5 g, 22 mmol). The reaction mixture was stirred at 22° C. for 4 h. The reaction mixture was diluted with EtOAc (200 mL) and washed with water (3×50 mL), dried over anhydrous MgSO$_4$ and filtered. The filtrate was concentrated in vacuo to give 5.5 g of Preparation 15A as a white solid.

HPLC: 4.985 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=639.1 [M+H]$^+$.

Preparation 15B

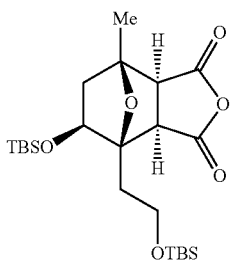

To a solution of Preparation 15A (5.5 g, 8.6 mmol) in THF (50 mL) was added 1N NaOH (50 mL, 50 mmol). The reaction mixture was stirred at 22° C. for 60 min and then THF (100 mL) was added followed by the addition of 1 N HCl (52 mL, 52 mmol, pH<4) over a 30 minute period. The solution was then diluted with EtOAc (100 mL) and the organic layer was separated, washed with brine (100 mL), dried over MgSO$_4$, filtered, and concentrated and dried in vacuo to give the intermediate amido acid as a white solid (5.0 g).

HPLC: 4.558 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=657.6 [M+H]$^+$.

The crude amido acid (5.0 g, 7.2 mmol) was suspended in THF (50 mL) and then glacial acetic acid (25 mL) was added. The reaction mixture was heated at 60° C. in a sealed pressure tube for 10 h followed by cooling to 22° C. The mixture was concentrated in vacuo followed by repeated azeotroping with heptane to remove acetic acid. The crude product was purified by flash chromatography on silica using an ISCO automated system (120 g column, flow rate: 85 mL/min solvent A: Hexane, solvent B: EtOAc, 0% B to 50% B in 25 min) to give 1.43 g of Preparation 15B as a white solid.

MS (ES): m/z=529.6 [M+OAc]$^-$. $^1$H NMR (500 MHz, CDCl$_3$) δ ppm 3.86 (2H, m), 3.62 (1H, m), 3.00 (1H, d, J=7.5 Hz), 2.90 (1H, d, J=7.5 Hz), 2.32 (1H, m), 2.11 (2H, m), 1.54 (3H, s), 1.49 (1H, m), 0.81 (9H, s), 0.80 (9H, s), 0.00 (3H, s), −0.01 (3H, s), −0.02 (3H, s), −0.03 (3H, s).

Preparation 15C

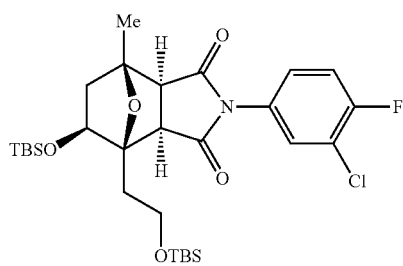

To a solution of Preparation 15B (1.3 g, 2.76 mmol) in toluene (12 mL) in a pressure tube was added 3-chloro-4-fluoroaniline (1.0 g, 6.9 mmol) and Et$_3$N (1.3 mL) followed by MgSO$_4$ (1.3 g). The pressure tube was sealed and the mixture was stirred at 175° C. for 30 h and then cooled to room temperature. The resulting brown mixture was diluted with EtOAc (30 mL), filtered through celite rinsing with EtOAc. The organics were then washed with water (2×50 mL), brine (1×100 mL), dried over MgSO$_4$, and concentrated to give the crude product which was purified by flash chromatography on silica (ISCO automated system 80 g column, flow rate: 60 mL/min, solvent A: hexane, solvent B: EtOAc, 0% B to 60% B in 25 min) to give 1.1 g of Preparation 15C as a white solid. (67% yield).

HPLC: 5.13 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=598.1 [M+H]$^+$.

Preparation 15D

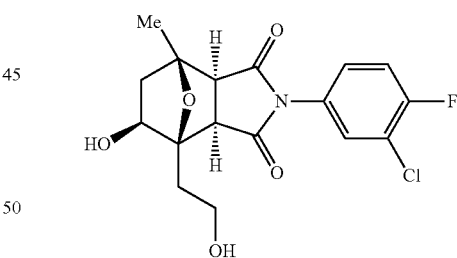

To a solution of Preparation 15C (1.1 g, 1.8 mmol) in THF (100 mL) was added 12 N HCl (2.5 mL). The reaction mixture was stirred at 22° C. for 3 h and then it was concentrated in vacuo and azeotroped with toluene to give 0.75 g of Preparation 15D as a white solid.

HPLC: 2.41 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=370 [M+H]$^+$.

Example 15

Example 15 was prepared from Preparation 15D by the general procedure described in Example 3.

HPLC: 2.39 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=354.1 [M+H]$^+$.

Example 16

2-Chloro-4-((1S,3R,4S,5S,8S,12R)-3-hydroxy-4-methyl-6-oxo-9,13-dioxa-7-azatetracyclo[6.3.1.1$^{1,4}$.0$^{5,12}$]tridec-7-yl)benzonitrile (16)

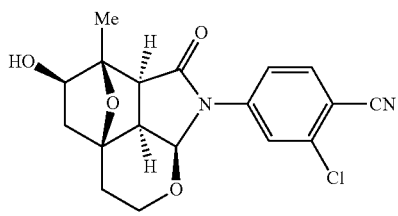

Preparation 16A

Preparation 16A was prepared from Preparation 1D by the general procedure described for Preparation 15D.

HPLC: 1.787 min (RT) (Chromolith SpeedROD column 4.6×50 mm eluting with 10-90% aqueous MeOH over 4 minutes containing 0.1% TFA, 4 mL/min, monitoring at 220 nm). MS (ES): m/z=411 [M+H]$^+$.

Preparations 16B and 16C

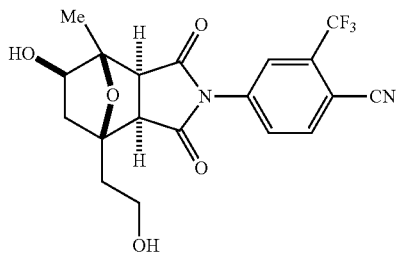

16B

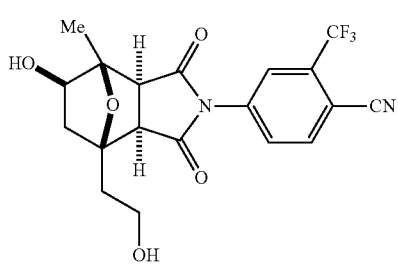

16C

Preparation 16A (7.5 g, 18.3 mmol) was dissolved in 40 mL of THF and 250 mL of methyl tert-butylether. To this mixture was added 90 mL (0.95 mol) of vinyl acetate and 12 g of Porcine Pancrease Lipase type II (Sigma Aldrich). The resulting slurry was heated to 40° C. for 60 h at which point the reaction had progressed to approximately 55% conversion with 99% enantiomeric excess as determined by chiral HPLC monitoring.

Preparation 16B: HPLC: 2.721 min (RT) (YMC S-50DS-A column 4.6×50 mm eluting with 10-90% aqueous MeOH over 4 min containing 0.1% H$_3$PO$_4$, 4 mL/min, monitoring at 220 nm). Chiral HPLC: 6.13 min (undesired enantiomer) and 8.30 min (desired enantiomer) [Chiralcel OJ column 10 um 4.6×250 mm eluting with 10-90% (1:1 EtOH:MeOH)/heptane over 20 min, monitoring at 220 nm].

Preparation 16C: HPLC: 3.158 min (RT) (YMC S-50DS-A column 4.6×50 mm eluting with 10-90% aqueous MeOH over 4 minutes containing 0.1% H$_3$PO$_4$, 4 mL/min, monitoring at 220 nm). Chiral HPLC: 8.43 min (RT) [Chiralcel OJ column 10 um 4.6×250 mm eluting with 10-90% (1:1 EtOH: MeOH)/heptane over 20 min, monitoring at 220 nm].

At this time the slurry was filtered through a pad of celite and concentrated in vacuo. The resulting product was purified via silica gel chromatography with an eluent system of 0-5% MeOH/CH$_2$Cl$_2$. Preparation 16B was attained (3.2 g, 7.8 mmol, 43% yield) as a white solid. All characterization is identical to that of the racemate.

Preparation 16D

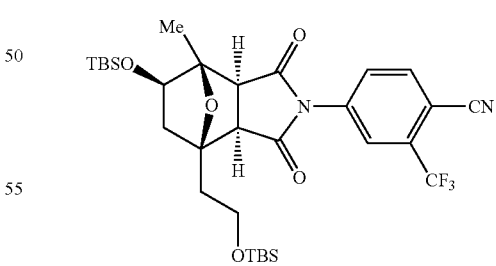

To a solution of Preparation 16B (30 g, 57.2 mmol) in DMF (50 mL) was added imidazole (5.84 g, 85.8 mmol), TBSCl (11.2 g, 74.3 mmol) and a catalytic amount of DMAP. The reaction was stirred at 22° C. for 18 h. The reaction mixture was then added to ice-water, and extracted twice with ether. The combined extracts were washed with 10% LiCl and brine, dried over anhydrous MgSO$_4$ and filtered. The filtrate was concentrated and purified by flash column on silica gel (330 g ISCO column, EtOAc/Hexane 0-40%). Preparation 16A (34.5 g) was obtained as a colorless sticky oil.

HPLC: 4.430 min (RT) (Chromolith SpeedROD column 4.6×50 mm eluting with 10-90% aqueous MeOH over 4 minutes containing 0.1% TFA, 4 mL/min, monitoring at 220 nm). MS (ES): m/z=639.5 [M+H]+.

Preparation 16E

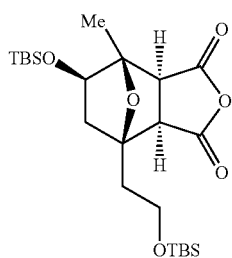

To a solution of Preparation 16D (34.5 g, 54.1 mmol) in THF (300 mL) was added 1N NaOH (300 mL, 300 mmol). The reaction mixture was stirred at 22° C. for 50 min, EtOAc (500 ml) added, and the resulting mixture was slowly acidified with 1 N HCl (225 mL, 225 mmol, pH=5) while stirring. The organic layer was separated, washed with brine, dried over MgSO₄, filtered and concentrated and dried in vacuo to give the intermediate amido acid as a colorless sticky oil.

HPLC: 4.266 min (RT) (Chromolith SpeedROD column 4.6×50 mm eluting with 10-90% aqueous MeOH over 4 minutes containing 0.1% TFA, 4 mL/min, monitoring at 220 nm). MS (ES): m/z=657.7 [M+H]+.

The crude amido acid was dissolved in THF (300 mL) and then glacial acetic acid (150 mL) was added. The reaction mixture was heated at 60° C. for 20 h followed by cooling to 22° C. The mixture was concentrated in vacuo followed by repeated azeotroping with heptane to remove acetic acid. The crude product was purified by flash chromatography on silica using an ISCO automated system (330 g column, EtOAc/ Hexane 0-40%) to give 18.5 g of Preparation 16E as a white solid.

MS (ES): m/z=471 [M+H]+. ¹H NMR (CDCl₃) 3.88-3.91 (m, 2H), 3.79-3.81 (m, 1H), 3.20 (d, J=7.6 Hz, 1H), 2.91 (d, J=7.6 Hz, 1H), 2.23-2.30 (m, 2H), 2.12-2.17 (m, 1H), 1.74-1.78 (m, 1H), 0.88 (s, 18H), 0.04-0.06 (m, 12H)

Example 16

Example 16 was prepared from Preparation 16E and 4-cyano-3-chloroaniline by the general procedure described for the preparation of Example 15 from Preparation 15B.

HPLC: 1.853 min (RT) (Chromolith SpeedROD column 4.6×50 mm eluting with 10-90% aqueous MeOH over 4 minutes containing 0.1% TFA, 4 mL/min, monitoring at 220 nm). MS (ES): m/z=361 [M+H]+.

Example 17

(1R,2S,4R,5S,8S,12R)-7-(4-Cyano-3-(trifluoromethyl)phenyl)-N-ethyl-2-hydroxy-4-methyl-6-oxo-9,13-dioxa-7-azatetracyclo[6.3.1.1$^{1,4}$.0$^{5,12}$]tridecane-5-carboxamide (17)

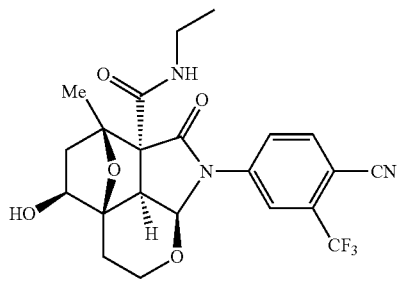

Preparation 17A

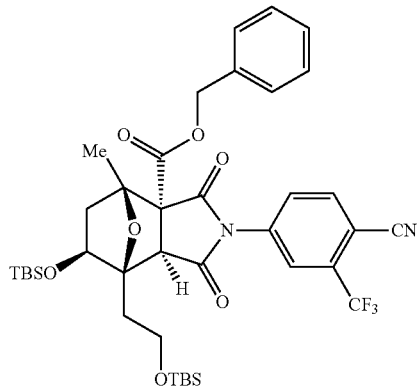

To a solution of Preparation 15A (2.10 g, 3.29 mmol) and benzyl chloroformate (95%, 0.695 mL, 4.93 mmol) in THF (30 mL) at −78° C. was added LiHMDS (1.0 M in THF, 6.58 mL, 6.58 mmol) over a 5 minute period. After 3 h at −78° C., the reaction was quenched with sat. aq. NH₄Cl (50 mL) and brine (25 mL). After warming to room temperature, the mixture was extracted with EtOAc (2×50 mL). The combined organics were washed once with brine and dried over anhydrous MgSO₄. The crude material was purified by flash chromatography on silica eluting with 0-20% EtOAc in heptane to give 1.58 g of Preparation 17A as a white foam.

HPLC: 5.68 min (RT) (YMC ODS-A column 4.6×50 mm eluting with 10-90% aqueous MeOH over 4 minutes containing 0.1% H₃PO₄, 4 mL/min, monitoring at 220 nm).

Preparation 17B

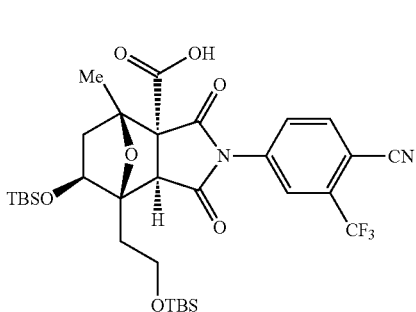

To a solution of Preparation 17A (5.20 g, 11.5 mmol) in EtOAc (100 mL) in a pressure bottle was added Pd/C (De-Gussa, 10% Pd, 1.00 g). The bottle was sealed and 50 psi of H$_2$ was introduced. After 4 h, the pressure was released and the bottle purged with nitrogen. The solution was then filtered thru celite, rinsing with EtOAc, and concentrated at 22° C. to give 4.81 g of Preparation 17B as a white foam.

HPLC: 5.03 min (RT) (YMC ODS-A column 4.6×50 mm eluting with 10-90% aqueous MeOH over 4 minutes containing 0.1% H$_3$PO$_4$, 4 mL/min, monitoring at 220 nm).

Preparation 17C

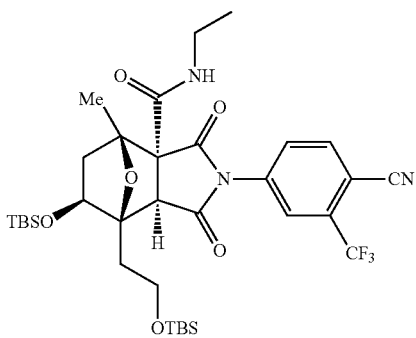

To a solution of Preparation 17B (0.50 g, 0.73 mmol) in DMF (8.0 mL) was added in succession 1-(3-(dimethylamino)propyl)-3-ethyl-carbodiimide hydrochloride (0.211 g, 1.1 mmol), 1-hydroxy-7-azabenzotriazole (0.150 g, 1.1 mmol), DIEA (0.384 mL, 2.19 mmol) and ethylamine hydrochloride (0.090 g, 1.09 mmol). The resulting mixture was stirred at room temperature for 16 h and then diluted with EtOAc (75 mL) and washed once with 1 N HCl (25 ml), once with sat. aq. NaHCO$_3$ (25 mL), once with brine (25 mL) and dried over anhydrous MgSO$_4$. Filtration and concentration gave 0.577 g of Preparation 17C as a yellow solid.

HPLC: 5.241 min (RT) (YMC ODS-A column 4.6×50 mm eluting with 10-90% aqueous MeOH over 4 minutes containing 0.1% H$_3$PO$_4$, 4 mL/min, monitoring at 220 nm).

Preparation 17D

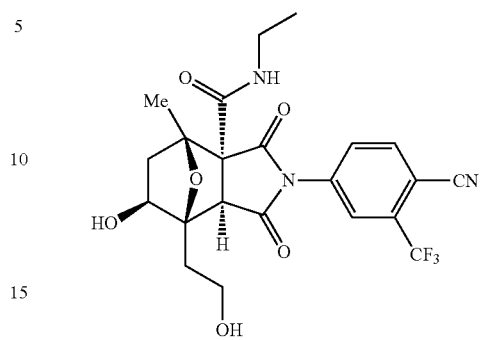

To a solution of crude Preparation 17C (0.57 g) in THF (20 mL) was added 12 N HCl (1.0 mL) and the resulting mixture was stirred at room temperature for 3 h. The mixture was then diluted with EtOAc (50 mL) and quenched with sat. aq. NaHCO$_3$ (25 mL) and brine (25 mL). The mixture was then extracted with EtOAc (3×25 mL). The combined organics were then dried over anhydrous MgSO$_4$, filtered and concentrated in vacuo to give 0.330 mg of Preparation 17D as a yellow foam.

HPLC: 2.746 min (RT) (YMC ODS-A column 4.6×50 mm eluting with 10-90% aqueous MeOH over 4 minutes containing 0.1% H$_3$PO$_4$, 4 mL/min, monitoring at 220 nm).

Example 17

Example 17 was prepared from Preparation 17D by the general method described in Example 3.

HPLC: 2.90 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=524.1 [M+OAc]$^-$; $^1$H NMR (500 MHz, acetone-d$_6$) δ ppm 8.23 (1H, d, J=1.7 Hz), 8.11 (1H, d, J=8.2 Hz), 8.05 (1H, dd, J=1.7, 8.2 Hz), (7.31 (1H, bs), 6.18 (1H, d, 7.7 Hz), 3.85 (1H, dd, J=2.2, 7.1 Hz), 3.57 (1H, ddd, J=1.7, 5.0, 11.0 Hz), 3.51 (1H, dt, J=2.2, 8.1 Hz), 3.31 (1H, m), 3.01 (1H, m), 3.12 (1H, d, J=7.7 Hz), 2.53 (1H, dd, J=6.6, 13.2 Hz), 1.95 (1H, m), 1.70 (3H, s), 1.38 (1H, dd, J=2.2, 13.8 Hz), 1.05 (3H, t, J=7.1 Hz).

Example 18

Benzyl (1S,3R,4S,5R,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$]tridecane-5-carboxylate (18)

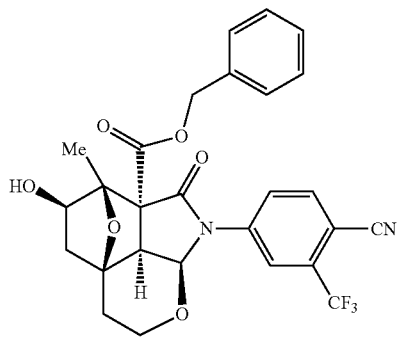

Preparation 18A

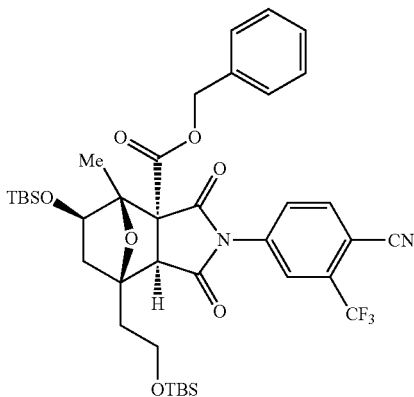

To a solution of racemic Preparation 16D (2.10 g, 3.29 mmol) and benzyl chloroformate (95%, 0.695 mL, 4.93 mmol) in THF (30 mL) at −78° C. was added LiHMDS (1.0 M in THF, 6.58 mL, 6.58 mmol) over a 5 minute period. After 3 h at −78° C., the reaction was quenched with sat. aq. NH$_4$Cl (50 mL) and brine (25 mL). After warming to room temperature, the mixture was extracted with EtOAc (2×50 mL). The combined organics was washed once with brine and dried over anhydrous MgSO$_4$. The crude material was purified by flash chromatography on silica eluting with 0-20% EtOAc in heptane to give 1.66 g of Preparation 18A as a white foam.

HPLC: 5.86 min (RT) (YMC ODS-A column 4.6×50 mm eluting with 10-90% aqueous MeOH over 4 minutes containing 0.1% H$_3$PO$_4$, 4 mL/min, monitoring at 220 nm).

Preparation 18B

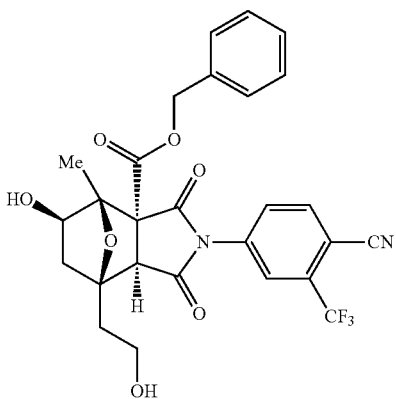

Preparation 18B was prepared from Preparation 18A by the general procedure described in Preparation 15D.

HPLC: 3.20 min (RT) (YMC ODS-A column 4.6×50 mm eluting with 10-90% aqueous MeOH over 4 minutes containing 0.1% H$_3$PO$_4$, 4 mL/min, monitoring at 220 nm).

Example 18

To a solution of Preparation 18B (2.1 g, 3.83 mmol) in THF (50 mL) at −78° C. was added lithium triethylborohydride (1.0 M, 11.5 mL, 11.5 mmol) over a 10 minute period. After 2 h at −78° C., the starting imide was absent by LC analysis and the reaction was carefully quenched with sat. aq. NH$_4$Cl (25 mL) and then diluted with brine (25 mL). The mixture was then extracted with EtOAc (3×30 mL). The combined organics were then dried over anhydrous MgSO$_4$, filtered and concentrated to a yellow foam. The crude hemiaminal intermediate was then suspended in CH$_2$Cl$_2$ (50 mL) at 22° C. and TFA (2.0 mL) was added resulting in a yellow homogenous solution. After 6 h, the aminal was absent by LC analysis and the reaction was diluted with toluene (30 mL) and concentrated in vacuo to a yellow foam. The crude product was purified by flash chromatography on silica eluting with 0-20% acetone in CH$_2$Cl$_2$ to give 0.98 g of Example 18 as a white foam.

HPLC: 3.31 min (RT) (YMC ODS-A column 4.6×50 mm eluting with 10-90% aqueous MeOH over 4 minutes containing 0.1% H$_3$PO$_4$, 4 mL/min, monitoring at 220 nm). $^1$H NMR (500 MHz, acetone-d$_6$) δ ppm 8.23 (1H, d, J=1.7 Hz), 8.11 (1H, d, J=8.2 Hz), 8.05 (1H, dd, J=1.7, 8.2 Hz), 7.33 (5H, m), 6.20 (1H, d, J=7.7 Hz), 5.18 (2H, dd, J=12.6, 19.8 Hz), 4.25 (1H, dd, J=4.4, 7.7 Hz), 3.57 (2H, m), 3.02 (1H, d, J=7.1 Hz), 2.31 (1H, dd, J=7.1, 12.1 Hz), 2.09 (1H, m), 1.88 (1H, d, J=14.9 Hz), 1.76 (3H, s), 1.48 (1H, dd, J=3.9, 12.6 Hz).

Example 19

(1R,3S)—N-((1R,2S)-2-(((4S)-4-(4-Chlorophenyl)-4-hydroxy-3,3-dimethyl-1-piperidinyl)carbonyl)cyclohexyl)-3-hydroxycyclopentanecarboxamide (19)

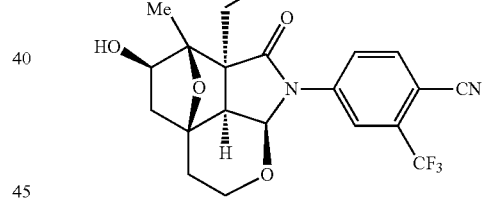

To a solution of Preparation 18B (0.8 g, 1.52 mmol) in THF (20 mL) and MeOH (2.0 mL) at 0° C. was added sodium borohydride (0.150 g, 2.0 mmol). After 1 h at 0° C., the starting imide was absent by LC analysis and the reaction was carefully quenched with sat. aq. NH$_4$Cl (10 mL) and then diluted with brine (10 mL). The mixture was then extracted with EtOAc (3×20 mL). The combined organics were then dried over anhydrous MgSO$_4$, filtered and concentrated to a yellow foam. A crude LC-MS measurement showed reduction of the imide as well as reduction of the benzyl ester to the primary alcohol. The crude hemiaminal diol intermediate was then suspended in CH$_2$Cl$_2$ (20 mL) at 22° C. and TFA (0.5 mL) was added resulting in a yellow homogenous solution. After 6 h, the aminal was absent by LC analysis and the reaction was diluted with toluene (30 mL) and concentrated in vacuo to a yellow foam. The crude product was purified by flash chromatography on silica eluting with 0-30% acetone in CH$_2$Cl$_2$ to give 0.218 g of Example 19 as a white foam.

HPLC: 2.45 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=483 [M+OAc]⁻.

Example 20

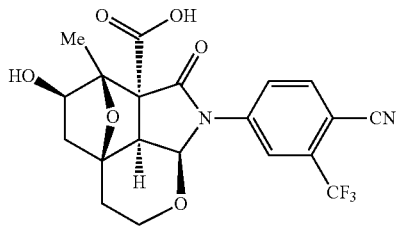

Racemic Example 20 was prepared from Example 18 by the general method described in Preparation 17B.

HPLC: 2.56 min (RT) (YMC ODS-A column 4.6×50 mm eluting with 10-90% aqueous MeOH over 4 minutes containing 0.1% $H_3PO_4$, 4 mL/min, monitoring at 220 nm).

Examples 21 and 22

(1S,3R,4S,5S,8S,12R)-7-(4-Cyano-3-(trifluoromethyl)phenyl)-N-ethyl-3-hydroxy-4-methyl-6-oxo-9,13-dioxa-7-azatetracyclo[6.3.1.1$^{1,4}$.0$^{5,12}$]tridecane-5-carboxamide (21) and (1R,3S,4R,5R,8R,12S)-7-(4-Cyano-3-(trifluoromethyl)phenyl)-N-ethyl-3-hydroxy-4-methyl-6-oxo-9,13-dioxa-7-azatetracyclo[6.3.1.1$^{1,4}$.0$^{5,12}$]tridecane-5-carboxamide (22)

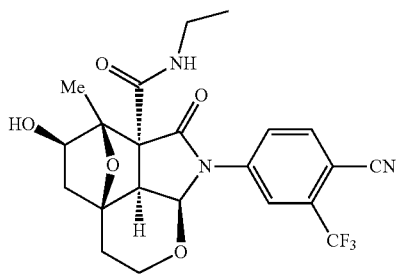

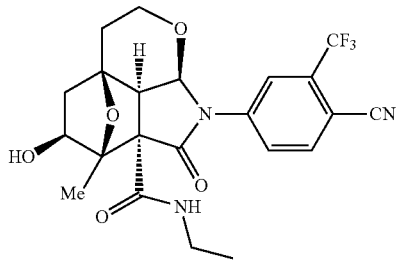

Example 21 and 22 were prepared from Example 20 by the general method described in Preparation 17C. The individual antipodes were separated by chiral normal phase chromatography. Chiracel OJ column 4.6×250 mm, eluting with 25% 1:1 EtOH/MeOH in heptane at 80 mL/min and monitoring at 220 nm.

Example 21

Chiral HPLC: >99% ee @ 10.5 min (RT) (Chiracel OJ column, 4.6×250 mm, 25% 1:1 EtOH/MeOH in heptane, 1 mL/min, monitoring at 220 nm). HPLC: 2.86 min (RT) (YMC ODS-A column 4.6×50 mm eluting with 10-90% aqueous MeOH over 4 minutes containing 0.1% $H_3PO_4$, 4 mL/min, monitoring at 220 nm). MS: [M+OAc]⁻=524.1; ¹H NMR (500 MHz, acetone-d$_6$) δ ppm 8.23 (1H, d, J=2.2 Hz), 8.11 (1H, d, J=8.8 Hz), 8.05 (1H, dd, J=2.2, 8.8 Hz), (7.40 (1H, bs), 6.13 (1H, d, 7.7 Hz), 4.17 (1H, dd, J=3.3, 7.1 Hz), 3.55 (2H, m), 3.32 (1H, m), 3.15 (1H, m), 3.12 (1H, d, J=7.7 Hz), 2.27 (1H, dd, J=1.7, 5.5 Hz), 2.06 (1H, m), 1.87 (1H, d, J=14.3 Hz), 1.67 (3H, s), 1.47 (1H, dd, J=3.8, 12.6 Hz), 1.07 (3H, t, J=7.2 Hz). The absolute stereochemistry of Example 21 has not been established. Although the compound represents a single antipode, the nomenclature and structure shown does not reflect the absolute stereochemistry of the compound.

Example 22

Chiral HPLC: >99% ee @ 17.3 min (RT) (Chiracel OJ column, 4.6×250 mm, 25% 1:1 EtOH/MeOH in heptane, 1 mL/min, monitoring at 220 nm). HPLC: 2.86 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=524.1 [M+OAc]⁻; ¹H NMR (500 MHz, acetone-d$_6$) δ ppm 8.23 (1H, d, J=2.2 Hz), 8.11 (1H, d, J=8.8 Hz), 8.05 (1H, dd, J=2.2, 8.8 Hz), (7.40 (1H, bs), 6.13 (1H, d, 7.7 Hz), 4.17 (1H, dd, J=3.3, 7.1 Hz), 3.55 (2H, m), 3.32 (1H, m), 3.15 (1H, m), 3.12 (1H, d, J=7.7 Hz), 2.27 (1H, dd, J=1.7, 5.5 Hz), 2.06 (1H, m), 1.87 (1H, d, J=14.3 Hz), 1.67 (3H, s), 1.47 (1H, dd, J=3.8, 12.6 Hz), 1.07 (3H, t, J=7.2 Hz). The absolute stereochemistry of Example 22 has not been established. Although the compound represents a single antipode, the nomenclature and structure shown does not reflect the absolute stereochemistry of the compound.

Example 23

Benzyl (1R,2S,4R,5R,8S,12R)-7-(4-cyano-3-(trifluoromethyl)phenyl)-2-hydroxy-4-methyl-6-oxo-9,13-dioxa-7-azatetracyclo[6.3.1.1$^{1,4}$.0$^{5,12}$]tridecane-5-carboxylate (23)

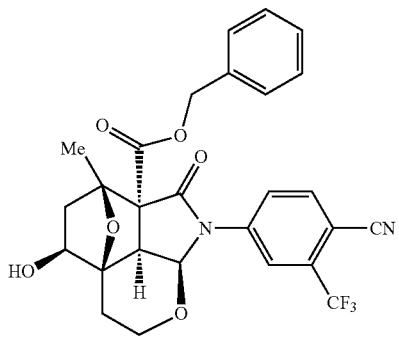

Example 23 was prepared from Preparation 17A by the general method described in Example 18.

HPLC: 3.37 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=587.1 [M+OAc]$^-$; $^1$H NMR (400 MHz, acetone-d$_6$) δ ppm 8.05 (1H, d, J=1.9 Hz), 7.89 (1H, d, J=1.9 Hz), 7.84 (1H, d, J=8.6 Hz), 7.34 (2H, m), 7.33 (3H, m), 5.98 (1H, d, J=7.3 Hz), 5.17 (2H, s), 3.79 (1H, t, J=8.6 Hz), 3.65 (1H, m), 3.55 (1H, m), 2.64 (1H, d, J=7.3 Hz), 2.53 (1H, dd, J=6.8, 14.9 Hz), 2.06 (1H, m), 1.98 (1H, m), 1.68 (1H, d, J=9.4 Hz), 1.57 (3H, s), 1.53 (1H, dd J=1.7, 14.9 Hz).

Example 24

4-((1R,2S,4R,5R,8S,12R)-2-hydroxy-5-(hydroxymethyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (24)

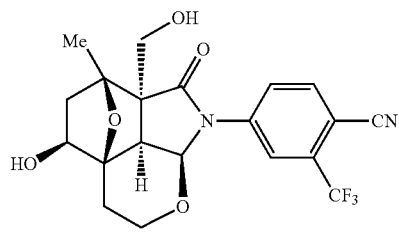

Example 24 was prepared from Preparation 17A by the general method described in Example 19.

HPLC: 2.36 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=483.2 [M+OAc]$^-$.

Examples 25 and 26

4-((1S,3R,4S,5S,8S,12R)-3-hydroxy-4,8-dimethyl-6-oxo-9,13-dioxa-7-azatetracyclo[6.3.1.1$^{1,4}$.0$^{5,12}$]tridec-7-yl)-2-(trifluoromethyl)benzonitrile (25) and 4-((1R,3S,4R,5R,8R,12S)-3-hydroxy-4,8-dimethyl-6-oxo-9,13-dioxa-7-azatetracyclo[6.3.1.1$^{1,4}$.0$^{5,12}$]tridec-7-yl)-2-(trifluoromethyl)benzonitrile (26)

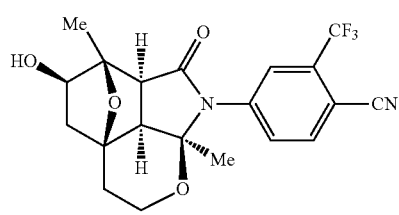

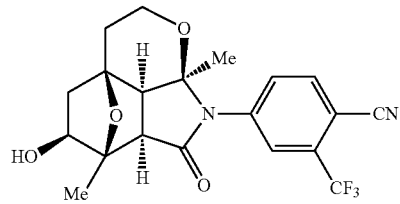

A solution of racemic Preparation 16A (2.5 g; 4.8 mmol) in 50 mL dry THF was cooled to −78° C. under an inert atmosphere. Methyllithium (1.6 M in Et$_2$O, 7.5 mL, 12 mmol) was added slowly via addition funnel, and stirred 10 min at −78° C. The pale yellow solution was quenched with 10 mL saturated aqueous ammonium chloride and diluted with 50 mL CH$_2$Cl$_2$. The layers were separated and the aqueous phase extracted twice with 25 mL CH$_2$Cl$_2$. Organic extracts were combined, dried over anhydrous sodium sulfate, and concentrated in vacuo revealing 2.65 g of a mixture of hemiaminals as an off-white foam in 90% purity.

The resulting crude isomeric mixture was dissolved in 45 mL dry CH$_2$Cl$_2$ and cooled to 0° C. in an ice bath. Trifluoroacetic acid (5 mL) was added slowly via syringe, and the solution stirred at 0° C. for 20 minutes. Volatiles were removed under reduced pressure at ambient temperature, and the remaining viscous amber oil was dissolved in CH$_2$Cl$_2$ and treated with 15 mL of 1N NaOH. After allowing the yellow, biphasic mixture to stir 10 minutes, the layers were separated and the aqueous phase extracted three times with 20 mL CH$_2$Cl$_2$. The organic layers were combined and dried over anhydrous sodium sulfate. Filtration and concentration afforded an off-white foam which was purified on silica gel (5-20% acetone/CH$_2$Cl$_2$ eluted desired product cleanly; 60-90% acetone/CH$_2$Cl$_2$ eluted exo methylene side product) to afford 0.728 g (37%) of Example 25 as a white foam.

HPLC: 2.663 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=409 [M+H]$^+$. $^1$H NMR (400 MHz, CDCl$_3$) δ ppm 8.02 (1H, s), 7.85 (2H, s), 4.01-3.93 (2H, m), 3.85-3.82 (1H, m), 2.77 (1H, d, J=7.6 Hz), 2.24 (1H, dd, J=12.8, 7.2 Hz), 2.14 (1H, d, J=8.0 Hz), 2.09-2.06 (2H, m), 1.8-1.76 (1H, br s), 1.64 (3H, s), 1.52 (1H, dd, J=12.8, 3.6 Hz), 1.38 (3H, s).

The individual antipodes were separated by chiral normal-phase HPLC (Chiralpak AD column semiprep column (2×50 cm) isocratic run with 15% EtOH/MeOH (1:1) in heptane at 20 mL/min, monitoring at 256 nm).

Example 25

RT=16.0 minutes. The 1H NMR and LC-MS match that for the racemate. The absolute stereochemistry of Example 25 has not been established. Although the compound represents a single antipode, the nomenclature and structure shown does not reflect the absolute stereochemistry of the compound.

Example 26

RT=23.0 minutes. The 1H NMR and LC-MS match that for the racemate. The absolute stereochemistry of Example 26 has not been established. Although the compound represents a single antipode, the nomenclature and structure shown does not reflect the absolute stereochemistry of the compound.

Example 27

4-((1R,2E,4R,5S,8S,12R)-2-(hydroxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (27)

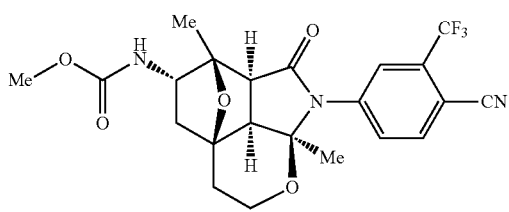

Example 27 was prepared from Example 25 by the general procedure described for the conversion of Example 2 to Example 14.

HPLC: 3.02 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=466.4 [M+H]$^+$. $^1$H NMR (400 MHz, CDCl$_3$) δ ppm 8.00 (1H, s), 7.85 (2H, s), 5.80 (1H, br s), 4.15-4.00 (1H, m), 3.89-4.00 (1H, m), 3.88-3.80 (1H, m), 3.71 (3H, s), 3.24 (1H, d, J=8.0 Hz), 2.28-2.34 (2H, m), 1.95-2.05 (2H, m), 1.67 (3H, s), 1.41 (3H, s), 1.26 (1H, dd, J=7.2, 3.6 Hz). The absolute stereochemistry of Example 27 has not been established. Although the compound represents a single antipode, the nomenclature and structure shown does not reflect the absolute stereochemistry of the compound.

Example 28

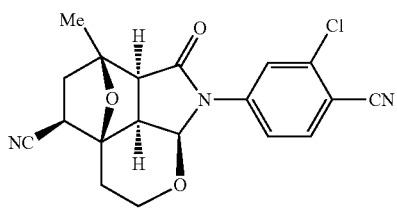

Preparation 28A

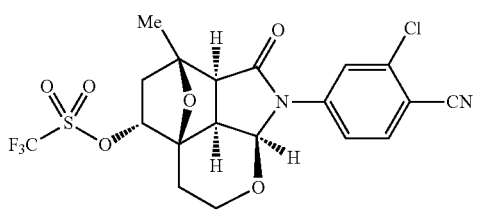

Preparation 28A was prepared from Example 132 by the general method described for Preparation 34A.

HPLC: 3.516 min (RT) (YMC ODS column 4.6×50 mm eluting with 10-90% aqueous methanol containing 0.2% H$_3$PO$_4$ over 4 minutes, 4 mL/min, monitoring at 220 nm). MS (ES): m/z=409 [M+H]$^+$. $^1$H NMR (400 MHz, CDCl$_3$) δ ppm 7.77 (1H, d, J=2.01 Hz), 7.56-7.65 (1H, m), 7.53 (1H, dd, J=8.60, 2.01 Hz), 5.88 (1H, d, J=7.55 Hz), 4.78 (1H, dd, J=10.07, 4.28 Hz), 3.50-3.64 (2H, m), 3.05 (1H, t, J=7.68 Hz), 2.90 (1H, d, J=7.81 Hz), 2.34 (1H, dd, J=13.98, 10.20 Hz), 2.02-2.16 (1H, m), 1.76-1.92 (2H, m), 1.65 (3H, s)

Example 28

To a solution of Preparation 28A (30 mg; 0.06 mmol) in 1.5 mL DMSO at ambient temperature under nitrogen atmosphere was added tetraethylammonium cyanide (60 mg, 0.38 mmol). The solution was heated to 60° C. for 2 hours. The reaction mixture was cooled and diluted with water and EtOAc. The organic layer was washed four times with water and brine, and then dried over anhydrous magnesium sulfate, filtered, and concentrated in vacuo affording a colorless film which was purified on silica gel using 0-20% acetone/CH$_2$Cl$_2$ as the mobile phase. Example 28 (0.011 g, 50%) was afforded as a white film.

HPLC: 2.760 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=428 [M+OAc]$^-$. $^1$H NMR (400 MHz, CDCl$_3$) δ ppm 7.73 (1H, s), 7.60 (1H, d, J=8.6 Hz), 7.53 (1H, d, J=8.6 Hz), 5.79 (1H, d, J=7.6 Hz), 3.65-3.58 (2H, m), 2.80 (1H, d, J=7.8 Hz), 2.75 (1H, dd, J=8.8, 3.7 Hz), 2.45 (1H, t, J=7.6 Hz), 2.28-2.23 (2H, m), 2.06-2.00 (2H, m), 1.73 (3H, s).

Example 29

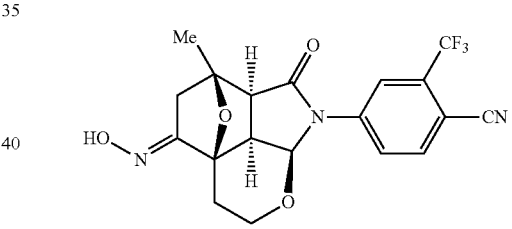

To a stirring solution of Example 3 (791 mg, 2.02 mmol) in 16 mL of pyridine was added 278 mg of hydroxylamine hydrochloride (4.04 mmol, 2 eq). The resulting solution was heated to 114° C. for 1 h. The reaction was judged to be complete by HPLC as verified by the disappearance of the starting material. The reaction was allowed to cool to room temperature and was then diluted with 20 mL EtOAc, 4 mL H$_2$O and 0.5 mL of 1N HCl. The organics were extracted and twice rinsed with 4 mL H$_2$O and 0.5 mL of 1N HCl. The organics were then rinse with brine, dried over anhydrous Na$_2$SO$_4$ and concentrated in vacuo. The resulting product was purified via silica gel chromatography with an eluent system of 0-5% MeOH/CH$_2$Cl$_2$ to afford Example 29 (640 mg, 1.57 mmol, 78% yield) as a white solid.

MS (ES): m/z=466.10 [M+OAc]$^-$. HPLC: 3.286 min (RT) (YMC S-5 ODS-A 4.6×50 mm column with eluent conditions of 10-90% MeOH/water with H$_3$PO$_4$ counter-ion 5 min run). HPLC: 16.52 min (RT) (Sunfire C18 3.5 u 4.6×150 mm low pH column (30 min run)). $^1$H NMR d$_6$DMSO: 10.67 ppm (1H, s), 8.20 ppm (1H, d, J=8.52 Hz), 8.12 ppm (1H, d, J=1.65 Hz), 7.93 ppm (1H, dd, J=8.66, 2.06 Hz), 6.08 ppm (1H, d, J=7.7 Hz), 3.60 ppm (1H, m), 3.49 ppm (1H, m), 3.16 ppm (1H, d, J=7.97 Hz), 2.65 ppm (2H, m), 2.39 ppm (1H, d), 2.15 ppm (1H, m), 1.86 ppm (1H, m), 1.62 ppm (3H, s).

Example 30

4-((1R,2E,4R,5S,8S,12R)-2-(methoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (30)

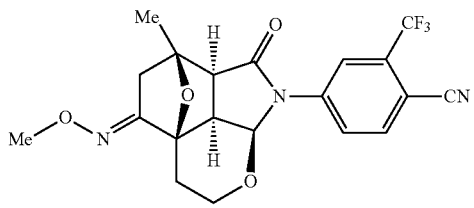

To a stirring solution of Example 29 (1.0 g, 2.55 mmol) in 30 mL of pyridine was added 320 mg of methoxylamine hydrochloride (3.83 mmol, 1.5 eq). The resulting solution was heated to 40° C. for 0.5 hr. The reaction was judged to be complete by HPLC as verified by the disappearance of the starting material. The reaction was allowed to cool to room temperature and was then diluted with 100 mL EtOAc, 20 mL of H$_2$O and 10 mL of 1N HCl. The organics were extracted and twice rinsed with 20 ml H$_2$O and 10 mL of 1N HCl. The organics were then rinse with Brine, dried over anhydrous Na$_2$SO$_4$ and concentrated in vacuo. The resulting product was purified via silica gel chromatography with an eluent system of 0-5% MeOH/DCM. Example 30 was attained (1.01 g, 2.4 mmol, 94% yield) as a white solid.

MS (ES): m/z=422.40 [M+H]$^+$. HPLC: 3.680 min (RT) (YMC S-50DS-A 4.6×50 mm column with eluent conditions of 10-90% MeOH/water with H$_3$PO$_4$ counter-ion (5 min run)). HPLC: 20.842 min (RT) (Sunfire C18 3.5 u 4.6×150 mm low pH column (30 min run)). $^1$H NMR d$_6$-DMSO: 8.20 ppm (1H, d, J=8.52 Hz), 8.13 ppm (1H, d, J=1.65 Hz), 7.93 ppm (1H, dd, J=8.52 Hz, 1.92 Hz), 6.09 ppm (1H, d, J=7.7 Hz), 3.78 ppm (3H, s), 3.60 ppm (1H, m), 3.50 ppm (1H, m), 3.17 ppm (1H, d), 2.71 ppm (2H, m), 2.43 ppm (1H, d), 2.15 ppm (1H, m), 1.86 ppm (1H, m), 1.62 ppm (3H, s).

Example 31

Rac-4-((1R,2S,3R,4S,5S,8S,12R)-2,3-dihydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (31)

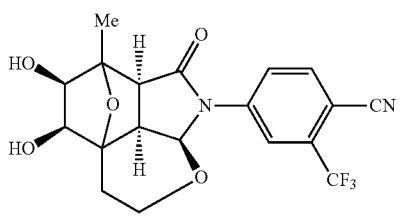

Preparation 31A

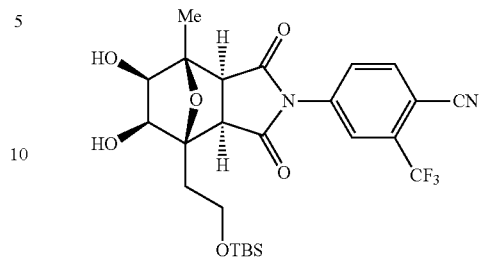

To a solution of racemic Preparation 1C (40.0 g, 79.0 mmol) in acetone (200 mL) at 22° C. was added 4-methyl morpholine-N-oxide (31.0 g, 60% in water, 158.0 mmol), followed by OsO$_4$ (1.5% soln in H$_2$O, 10.0 mL, 0.80 mmol). The reaction was stirred at 22° C. for 2 h and then solvent was removed in vacuo. Isopropyl alcohol (200 mL) was added and the solid was isolated by filtration to give 34 g of racemic Preparation 31A as an off white solid.

HPLC: 3.93 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z 541.5 [M+H]$^+$.

Preparation 31B

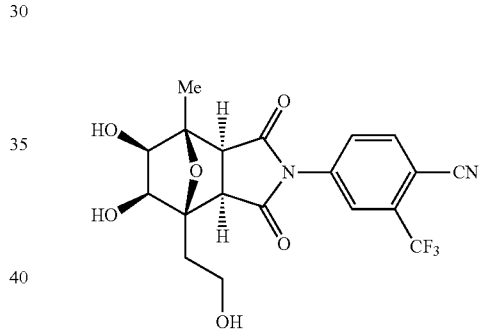

Preparation 31A (34.0 g, 63.0 mmol) was suspended in a solution of 5% 12N HCl in MeOH (60 mL) and stirred at 22° C. for 1 h. The suspension was then isolated by filtration to give 26 g of racemic Preparation 31A as an off white solid.

HPLC: 2.4 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=429.4 [M+H]$^+$.

Example 31

To a solution of Preparation 31B (26.0 g, 61.0 mmol) in THF (225 mL) and MeOH (25 mL) at 0° C. was added NaBH$_4$ (4.5 g, 122.0 mmol). The reaction mixture was stirred at 0° C. for 1 h. Next, the reaction mixture was acidified by addition of saturated NH$_4$Cl solution (200 mL) and extracted with EtOAc (3×250 mL). The organic phases were combined, washed with brine and dried over anhydrous magnesium sulfate and filtered. The filtrate was concentrated in vacuo to give the crude reduced imide intermediate as a white solid.

The above solid was added to 5% TFA in CH$_2$Cl$_2$ at 22° C. and stirred at 22° C. for 2 h. Toluene (100 mL) was added. The reaction mixture was concentrated in vacuo to give crude material, which was purified with flash chromatography in ISCO using 330 g column, Flow rate: 100 mL/min, solvent A: $CH_2Cl_2$, solvent B: MeOH. Gradient: 0% B to 30% B in 25 minutes to give 11 g of white solid as boron complex. The boron complex was divided into 1 g samples and each sample was dissolved in 10 mL MeOH and 5 mL of 90% $H_2O$/10% MeOH/0.1% TFA. The samples were repurified with C18 reverse phase chromatography in ISCO using 130 g column, Flow rate: 50 mL/min, solvent A: 90% $H_2O$/10% MeOH/0.1% TFA solvent B: 10% $H_2O$/90% MeOH/0.1% TFA. 0% B to 100% B in 30 minutes to afford 8.8 g of racemic Example 31 as a white solid.

HPLC: 2.5 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=411.3 [M+H]$^+$.

Example 32 and Example 33

Rac-4-((1R,2S,3R,4S,5S,8S,12R)-3-((tert-butyl(dimethyl)silyl)oxy)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (32) and Rac-4-((1R,2S,3R,4S,5S,8S,12R)-2-((tert-butyl(dimethyl)silyl)oxy)-3-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (33)

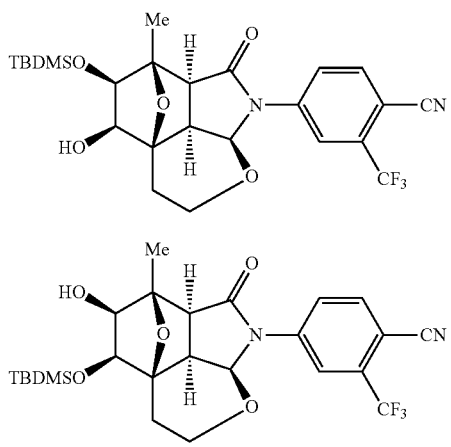

To a suspension of Example 31 (8.8 g, 21.5 mmol) in $CH_2Cl_2$ (100 mL) at −78° C. was added 2,6-lutidine (5.0 mL, 42.9 mmol) followed by tert-butyldimethylsilyl trifluoromethanesulfonate (5.4 mL, 23.6 mmol). The reaction mixture was stirred at −78° C. for 30 min and then acidified by addition of saturated 10% citric acid (200 mL) and extracted with $CH_2Cl_2$ (3×250 mL). The organic phases were combined, washed with brine and dried over anhydrous magnesium sulfate and filtered. The filtrate was concentrated in vacuo to give the crude material which was divided into two portions and purified with flash chromatography in ISCO using 330 g column, Flow rate: 100 mL/min, solvent A: $CH_2Cl_2$, solvent B: EtOAc. Gradient: 0% B to 30% B in 25 minutes to give 6.4 g of white solid as racemic Example 32 and 2.0 g of white solid as racemic Example 33.

Example 32

HPLC: 3.95 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=525.2 [M+H]$^+$. $^1$H NMR: CDCl$_3$ (ppm) 7.91 (1H, d, J=1.8 Hz), 7.79 (1H, m), 7.69 (1H, m), 5.73 (1H, d, J=7.6 Hz), 3.75 (1H, d, J=5.9 Hz), 3.48 (2H, m), 2.82 (1H, d, J=6.7 Hz), 2.52 (1H, d, J=7.8 Hz), 2.25 (1H, m), 2.05 (H, m), 1.85 (1H, m), 1.47 (3H, s) 0.81 (9H, s), 0.01 (6H, d, J=11.4 Hz).

Example 33

HPLC: 3.95 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=525.2 [M+H]$^+$. $^1$H NMR: CDCl$_3$ (ppm) 7.87 (1H, d, J=1.8 Hz), 7.75 (1H, m), 7.66 (1H, m), 5.69 (1H, d, J=7.6 Hz), 3.64 (1H, d, J=5.9 Hz), 3.60 (1H, m), 3.46 (2H, m), 2.78 (1H, d, J=8.9 Hz), 2.52 (1H, d, J=7.8 Hz), 2.20 (1H, m), 1.87 (H, m), 1.65 (1H, m), 1.50 (3H, s) 0.78 (9H, s), 0.01 (6H, d, J=6.6 Hz).

Example 34

Rac-N-((1R,2R,3R,4S,5S,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-4-fluorobenzenesulfonamide (34)

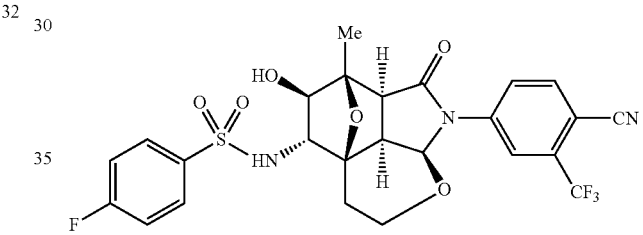

Preparation 34A (1R,2S,3R,4S,5S,8S,12R)-3-((tert-butyl(dimethyl)silyl)oxy)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl rac-trifluoromethanesulfonate (34A):

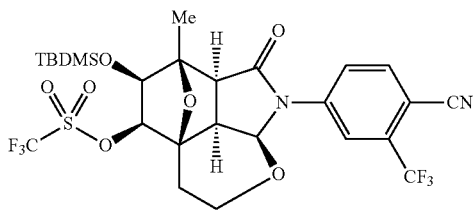

To a solution of Example 32 (6.4 g, 12.2 mmol) in $CH_2Cl_2$ (150 mL) at 0° C. was added pyridine (2.5 mL, 30.5 mmol) followed by trifluoromethanesulfonic anhydride (4.1 mL, 24.4 mmol). The reaction mixture was stirred at 0° C. for 2 h. Next, water (200 mL) was added and extracted with $CH_2Cl_2$ (3×250 mL). The organic phases were combined, washed with brine and dried over anhydrous magnesium sulfate and filtered. The filtrate was concentrated in vacuo to give 7.5 g of racemic Preparation 34A as a white solid.

HPLC: 4.32 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=715.1 [M+OAc]$^-$.

Preparation 34B: Rac-4-((1R,2R,3R,4S,5S,8S,12R)-2-azido-3-((tert-butyl(dimethyl)silyl)oxy)-4-methyl-6-oxo-9,13-dioxa-7-azatetracyclo[6.3.1.1$^{1,4}$.0$^{5,12}$]tridec-7-yl)-2-(trifluoromethyl)benzonitrile (34B)

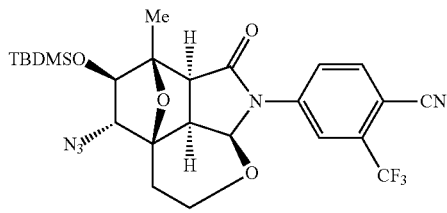

To a suspension of Preparation 34A (7.5 g, 11.4 mmol) in toluene (100 mL) at 22° C. was added tetrabutyl ammonium azide (12 g, 42.7 mmol). The reaction was stirred at 70° C. under nitrogen for 17 h. Then solvent was removed by rotavap and the crude material was purified with flash chromatography in ISCO using 120 g column, Flow rate: 85 mL/min, solvent A: Hexane, solvent B: EtOAc. Gradient: 0% B to 60% B in 25 minutes to give 6.0 g of racemic Preparation 34B as a white solid.

HPLC: 4.3 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=608.2 [M+OAc]$^-$.

Preparations 34C and 34D

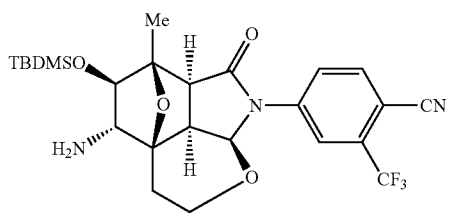

34C

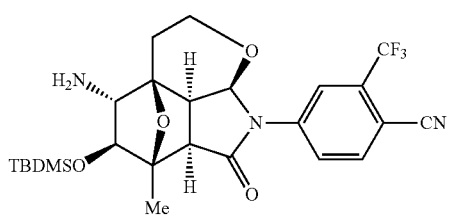

34D

To Preparation 34B (6.0 g, 10.9 mmol) was added PMe$_3$ (1M solution in THF, 35.0 mL, 35.0 mmol). The reaction was stirred at 22° C. under nitrogen for 2 h. Next, 1N NaOH (30 mL) was added. The reaction was stirred at 50° C. under nitrogen for 5 h and allowed to remain at 22° C. for 17 h. EtOAc (200 mL) and water (200 mL) were added. The organic layer was separated, washed with brine, and dried over anhydrous magnesium sulfate and filtered. The filtrate was concentrated in vacuo and the crude material was purified with flash chromatography in ISCO using 120 g column, Flow rate: 85 mL/min, solvent A: $CH_2Cl_2$, solvent B: EtOAc. Gradient: 0% B to 100% B in 25 minutes to give 5.0 g of the racemic mixture of Preparation 34C and 34D as a white solid.

HPLC: 3.4 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=524.1 [M+H]$^+$.

The mixture of Preparation 34C and 34D (6.0 g) was separated by SFC chiral HPLC. A Chiracel OD-H column (0.46 Cm×25 cm) was used at 100 bar, eluting with 80/20 $CO_2$/MeOH at 3.0 mL/min (35° C.), monitoring at 270 nm.

Preparation 34C: 2.3 g obtained, RT=4.79 min. The absolute stereochemistry of Preparation 34C has not been established. Although the compound represents a single antipode, the nomenclature and structure shown does not reflect the absolute stereochemistry of the compound.

Preparation 34D: 2.3 g obtained, (RT)=3.32 min. The absolute stereochemistry of Preparation 34D has not been established. Although the compound represents a single antipode, the nomenclature and structure shown does not reflect the absolute stereochemistry of the compound.

Example 34

To a solution of Preparation 34C (0.070 g, 0.13 mmol) in $CH_2Cl_2$ (1 mL) at 0° C. was added Hunig's base (0.094 mL, 0.54 mmol) followed by 4-fluorobenzene-1-sulfonyl chloride (0.052 g, 0.27 mmol). The reaction mixture was stirred at 22° C. for 17 h. Next, 1N HCl (3 mL) was added and the reaction mixture was stirred at 22° C. for 8 h. Then water (10 mL) was added and extracted with $CH_2Cl_2$ (3×15 mL). The organic phases were combined, washed with brine and dried over anhydrous magnesium sulfate and filtered. The filtrate was concentrated in vacuo and the crude material was purified with flash chromatography in ISCO using 12 g column, flow rate: 30 mL/min, solvent A: $CH_2Cl_2$, solvent B: acetone Gradient: 0% B to 60% B in 25 minutes to give 0.070 g of Example 34 as a white solid.

HPLC: 3.1 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=566.1 [M−H]$^-$. $^1$H NMR: CDCl$_3$ (ppm) 7.98 (1H, d, J=1.8 Hz), 7.91 (2H, m), 7.89 (1H, m), 7.77 (1H, m), 7.21 (2H, m), 5.84 (1H, d, J=7.4 Hz), 5.36 (1H, m), 3.68 (1H, m), 3.50 (2H, m), 3.0 (1H, m), 2.76 (1H, m), 2.69 (1H, d, J=7.8 Hz), 2.20 (1H, m), 1.90 (H, m), 1.65 (1H, m), 1.57 (3H, s). The absolute stereochemistry of Example 34 has not been established. Although the compound represents a single antipode, the nomenclature and structure shown does not reflect the absolute stereochemistry of the compound.

Example 35

N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1$^{1,4}$.0$^{5,12}$]tridec-3-yl)-4-fluorobenzenesulfonamide (35)

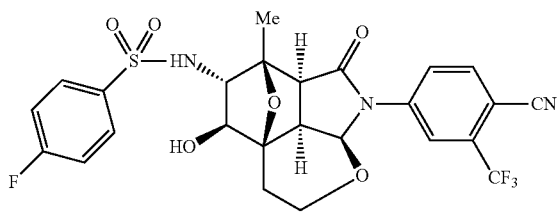

Preparations 35A and 35B

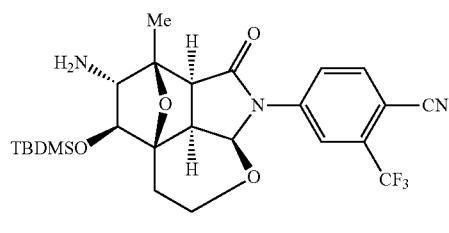

35A

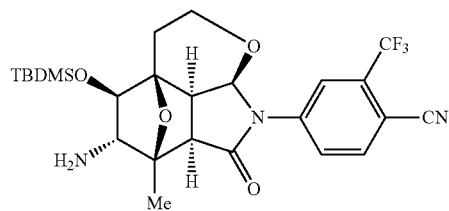

35B

The racemic mixture of Preparation 35A and 35B was prepared from Example 33 by the general procedure described for Example 34.

HPLC: 3.5 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=524.1 [M+H]$^+$.

The mixture of Preparation 35C and 35D (1.0 g) was separated by SFC chiral HPLC. A Chiracel AD-H column (0.46 cm×25 cm) was used at 100 bar, eluting with 80/20 CO$_2$/IPA at 2.0 mL/min (35° C.), monitoring at 270 nm.

Preparation 35A: 0.47 g obtained, (RT)=1.88 min. The absolute stereochemistry of Preparation 35A has not been established. Although the compound represents a single antipode, the nomenclature and structure shown does not reflect the absolute stereochemistry of the compound.

Preparation 35B: 0.47 g obtained, (RT)=3.50 min. The absolute stereochemistry of Preparation 35B has not been established. Although the compound represents a single antipode, the nomenclature and structure shown does not reflect the absolute stereochemistry of the compound.

Example 35

Example 35 was prepared from Preparation 35A according to the general procedure used for Example 34.

HPLC: 3.0 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=566.0 [M–H]$^+$. The absolute stereochemistry of Example 35 has not been established. Although the compound represents a single antipode, the nomenclature and structure shown does not reflect the absolute stereochemistry of the compound.

Example 36

4-((1R,2S,4R,5S,8S,10S,12R)-2-hydroxy-4,10-dimethyl-6-oxo-9,13-dioxa-7-azatetracyclo[6.3.1.1$^{1,4}$.0$^{5,12}$]tridec-7-yl)-2-(trifluoromethyl)benzonitrile (36)

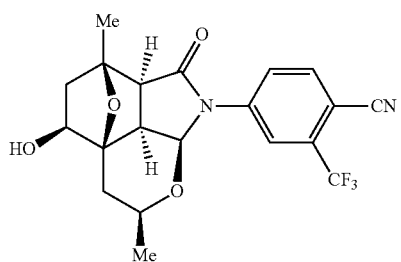

Preparation 36A

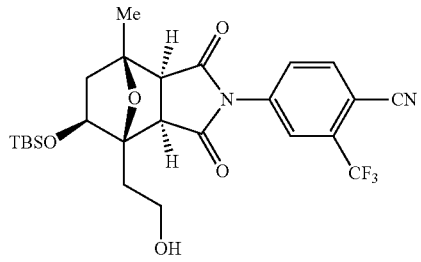

A mixture of Preparation 15A (1.28 g, 2.004 mmol) in 20 mL of acetic acid/water/THF (3/1/1.5) was heated at 100° C. in microwave reactor for 30 min. Solid sodium carbonate was added to the reaction mixture to quench the acid. The reaction mixture was then partitioned between EtOAc (40 mL) and saturated sodium bicarbonate (30 mL). The layers were separated and the organic layer was washed with saturated sodium bicarbonate, dried over magnesium sulfate, and purified by flash column chromatography, eluting with 10-60% EtOAc/hexane to give 0.87 g of Preparation 36A as a white solid HPLC: 2.04 minutes (RT) (Phenomenex Luna 5 u C18 column, 4.6×30 mm eluting with 10-90% aqueous MeOH over 2 minutes containing 0.1% TFA, 5 mL/min, monitoring at 254 nm). MS (ES): m/z=525 [M+H]$^+$. $^1$H NMR (500 MHz, CDCl$_3$) δ ppm 7.87 (d, J=8.52 Hz, 1H), 7.76 (d, J=1.65 Hz, 1H), 7.65 (dd, J=8.25, 1.92 Hz, 1H), 4.10 (dd, J=6.87, 2.75 Hz, 1H), 3.83-3.89 (m, 1H), 3.71 (dt, J=11.27, 3.85 Hz, 1H), 3.23 (d, J=7.15 Hz, 1H), 2.89 (d, J=7.15 Hz, 1H), 2.35 (dt, J=14.29, 3.85 Hz, 1H), 2.20 (dd, J=12.92, 6.87 Hz, 1H), 2.03-2.10 (m, 1H), 1.57 (s, 3H), 1.54 (dd, J=13.06, 2.89 Hz, 1H), 0.81 (s, 9H), 0.029 (s, 3H), 0.00 (s, 3H).

Preparation 36B

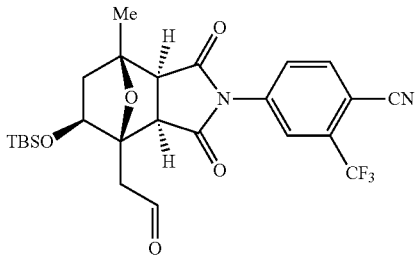

Dess-Martin Periodinane (428 mg, 1.009 mmol) was added to a solution of Preparation 36A (353 mg, 0.673 mmol) in $CH_2Cl_2$ (6 mL) at room temperature. The reaction mixture was stirred for 20 min. The reaction mixture was then partitioned between EtOAc (30 mL) and water (10 mL), the layers were separated and the organic layer was washed once with water, dried with magnesium sulfate, and purified by flash column chromatography, eluting with 0-50% EtOAc/$CH_2Cl_2$ to give Preparation 36B as a white solid (326 mg, 0.624 mmol, 93% yield).

HPLC: 2.04 minutes (RT) (Phenomenex Luna 5 u C18 column, 4.6×30 mm eluting with 10-90% aqueous MeOH over 2 minutes containing 0.1% TFA, 5 mL/min, monitoring at 254 nm). MS (ES): m/z=523 [M+H]$^+$. $^1$H NMR (500 MHz, CDCl$_3$) δ ppm 9.76 (s, 1H), 7.89 (d, J=8.25 Hz, 1H), 7.79 (d, J=1.92 Hz, 1H), 7.68 (dd, J=8.39, 2.06 Hz, 1H), 4.25 (dd, J=7.01, 3.16 Hz, 1H), 3.41 (d, J=7.14 Hz, 1H), 3.62 (d, J=18.97 Hz, 1H), 3.01 (d, J=18.70 Hz, 1H), 2.93 (d, J=7.42 Hz, 1H), 2.24 (dd, J=12.92, 7.15 Hz, 1H), 1.61 (s, 3H), 1.50-1.57 (m, 4H), 0.82 (s, 9H), 0.0 (s, 3H), −0.04 (s, 3H)

Preparation 36C

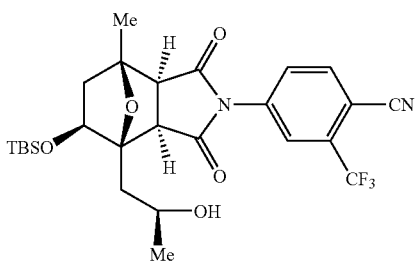

Methylmagnesium bromide (3.0 M soln, 0.624 ml, 1.871 mmol) was added dropwise to a solution of Preparation 36B (0.326 g, 0.624 mmol) in THF (10 mL) at −78° C. and the reaction mixture was stirred for 1 h. The reaction mixture was then quenched with saturated NH$_4$Cl (10 mL) and extracted with EtOAc (2×20 mL). The combined organic layers were dried over magnesium sulfate, concentrated and purified by flash column chromatography, eluting with 10-100% EtOAc/hexane to afford Preparation 36C (196 mg, 0.364 mmol, 58.3% yield) as a colorless oil.

HPLC: 2.16 minutes (RT) (Phenomenex Luna 5 u C18 column, 4.6×30 mm eluting with 10-90% aqueous MeOH over 2 minutes containing 0.1% TFA, 5 mL/min, monitoring at 254 nm). MS (ES): m/z=539 [M+H]$^+$. $^1$H NMR (500 MHz, CDCl$_3$) δ ppm 7.87 (d, J=8.25 Hz, 1H), 7.75 (d, J=1.65 Hz, 1H), 7.64 (dd, J=8.39, 1.79 Hz, 1H), 4.14 (dd, J=6.87, 2.75 Hz, 1H), 3.83-3.93 (m, 1H), 3.37 (d, J=7.15 Hz, 1H), 2.88 (d, J=7.15 Hz, 1H), 2.31 (dd, J=14.02, 2.47 Hz, 1H), 2.20 (dd, J=12.92, 6.87 Hz, 1H), 1.82 (dd, J=14.30, 11.27 Hz, 1H), 1.57 (s, 3H), 1.54 (dd, J=13.06, 2.61 Hz, 1H), 1.15-1.21 (m, 4H), 0.79-0.82 (s, 9H), 0.03 (s, 3H), 0.00 (s, 3H)

Example 36

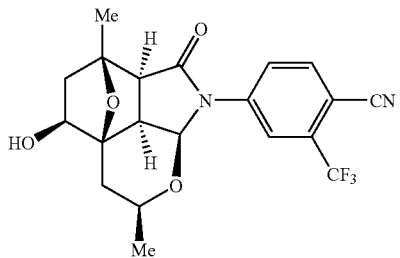

To a mixture of Preparation 36C (196 mg, 0.364 mmol) in THF (5 mL) and MeOH (0.500 mL) cooled in an ice/MeOH bath was added in portions NaBH$_4$ (27.5 mg, 0.728 mmol). The reaction was stirred cold for 2 hour and then 2M aqueous HCl (4 mL) was added slowly to the reaction mixture. The resulting solution was stirred at room temperature for 2 days. The reaction mixture was extracted 3 times with EtOAc and the combined organic layers were dried over magnesium sulfate, concentrated in vacuo and purified by flash column chromatography, eluting with 0-10% MeOH/$CH_2Cl_2$ to give Example 36 (110 mg, 0.269 mmol, 74.0% yield) as a white solid.

LC/MS Rt 1.43 min, MS (ES): m/z=409 [M+H]$^+$ (Phenomenex Luna 5 u C18 column, 4.6×30 mm eluting with 10-90% aqueous MeOH over 2 minutes containing 0.1% TFA, 5 mL/min, monitoring at 220 nm). Chiral HPLC: 7.27 min (RT) (Chiralcel OJ column 4.6×250 mm, eluting with 30% (1:1 EtOH/MeOH) in heptane, 1 mL/min, monitoring at 220 and 254 nm). X-ray crystallography confirmed the assignment of the methyl containing stereocenter on the pyran. $^1$H NMR (500 MHz, CDCl$_3$) δ ppm 8.27 (d, J=1.92 Hz, 1H), 8.10 (dd, J=8.52, 2.20 Hz, 1H), 7.74 (d, J=8.80 Hz, 1H), 5.64 (d, J=7.70 Hz, 1H), 3.74-3.83 (m, 2H), 2.72 (d, J=8.52 Hz, 1H), 2.39 (t, J=7.98 Hz, 1H), 2.21-2.28 (m, 2H), 1.93 (dd, J=15.53, 9.76 Hz, 1H), 1.63 (s, 3H), 1.56 (d, J=9.90 Hz, 1H), 1.50 (s, 5H), 1.46 (dd, J=13.88, 2.34 Hz, 1H), 1.27 (d, J=6.32 Hz, 3H).

Example 37

4-((1R,2R,4R,5S,8S,12R)-2-hydroxy-2,4-dimethyl-6-oxo-9,13-dioxa-7-azatetracyclo[6.3.1.1$^{1,4}$.0$^{5,12}$]tridec-7-yl)-2-(trifluoromethyl)benzonitrile (37)

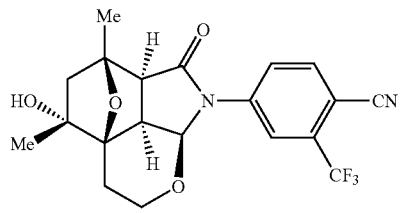

Methylmagnesium bromide (3M in ether, 0.476 mL, 1.427 mmol) was added drop wise to a solution of Example 3 (280 mg, 0.714 mmol) in THF (10 mL) at −30° C. The resulting reaction mixture was stirred for 1 h. The reaction mixture was quenched with saturated ammonium chloride (10 mL) and extracted with EtOAc (2×20 mL). The combined organic layers were dried over magnesium sulfate, concentrated in vacuo and purified by flash chromatography on silica gel using an automated ISCO system (40 g column, eluting with 10-100% EtOAc/hexane, Flow rate: 40 mL/min) to give Example 37 (64 mg, 22% yield) as a white solid along with 204 mg of recovered starting material.

LC/MS Rt 1.642 min, MS (ES): m/z=409 [M+H]$^+$ (Phenomenex Luna 5 u C18 column, 4.6×30 mm eluting with 10-90% aqueous MeOH over 2 minutes containing 0.1% TFA, 5 mL/min, monitoring at 220 nm). Chiral HPLC: 7.05 min (RT) (Chiralcel OJ column 4.6×250 mm, eluting with 30% (1:1 EtOH/MeOH) in heptane, 1 mL/min, monitoring at 220 and 254 nm). X-ray crystallography confirmed the stereochemical assignment of the newly formed tertiary alcohol. $^1$H NMR (500 MHz, CDCl$_3$) δ ppm 8.10 (d, J=1.65 Hz, 1H), 7.94 (dd, J=8.52, 1.92 Hz, 1H), 7.83 (d, J=8.52 Hz, 1H), 5.97 (d, J=7.97 Hz, 1H), 3.57-3.64 (m, 2H), 3.54 (t, J=7.97 Hz, 1H), 2.87 (d, J=7.97 Hz, 1H), 1.75-1.93 (m, 3H), 1.66 (s, 3H), 1.60 (br s, 2H), 1.35 (s, 3H)

Example 38 and Example 39

4-((1S,4S,7S,8R,10S,11R)-10-Hydroxy-8-methyl-6-oxo-3,12-dioxa-5-azatetracyclo[5.3.1.1$^{1,8}$.0$^{4,11}$]dodec-5-yl)-2-(trifluoromethyl)benzonitrile (38) and 4-((1S,4S,7S,8R,10S,11R)-10-Hydroxy-8-methyl-6-oxo-3,12-dioxa-5-azatetracyclo[5.3.1.1$^{1,8}$.0$^{4,11}$]dodec-5-yl)-2-(trifluoromethyl)benzonitrile (39)

38

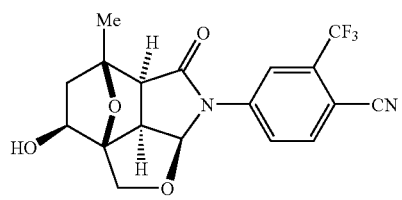

39

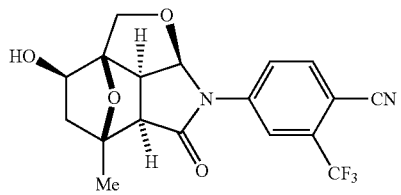

Preparation 38A

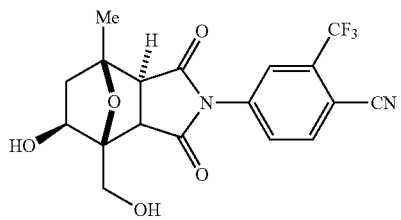

The racemic Preparation 38A was prepared from 5-methyl-2-hydroxymethylfuran and 4-(2,5-dioxo-2,5-dihydro-1H-pyrrol-1-yl)-2-(trifluoro)benzonitrile (for synthesis, refer to US Patent Application Publication No. 2005/0192253 A1) by the general procedure demonstrated in Example 3.

HPLC: 1.872 min (RT) (Chromolith column 4.6×50 mm eluting with 10-90% aqueous MeOH over 4 minutes containing 0.1% TFA, 4 mL/min, monitoring at 220 nm). MS (ES): m/z=397 [M+H]$^+$.

Examples 38 and 39

To a stirred mixture of Preparation 38A (212 mg, 0.53 mmol) in 2 mL of 15% MeOH in THF at −15° C. was added NaBH$_4$ (40.6 mg, 1.06 mmol). This mixture was stirred at −15° C. for 20 min upon which time another batch of NaBH$_4$ (40.6 mg, 1.06 mmol) was added. The mixture was then stirred at −15° C. for 20 min and quenched with 10 mL of saturated aqueous NH$_4$Cl solution. The quenched mixture was stirred at room temperature for 30 min, diluted with 5 mL of water and saturated with solid NaCl. The mixture was then extracted with EtOAc (3×30 mL). The combined EtOAc extracts were dried (MgSO$_4$), filtered and concentrated in vacuo to give the crude lactaminol intermediate. The lactaminol intermediate was dissolved in 12 mL of 20% TFA in CH$_2$Cl$_2$, stirred at room temperature for 30 min, then diluted with 100 mL of anhydrous toluene and concentrated in vacuo. It was purified by an ISCO auto flash chromatography system using 12 g silica gel column, eluted at 35 mL/min with CH$_2$Cl$_2$/EtOAc solvent and a 20 min 0% to 100% gradient elution to give 122 mg of the racemic mixture of Examples 38 and 39 as a white solid.

This racemic mixture (100 mg) was subsequently subjected to chiral HPLC on a Chiralpak OJ (2×25 cm) column. Elution with 30% heptane:MeOH:EtOH (50:25:25) afforded Example 38 (23.8 mg) and Example 39 (31.2 mg).

Example 38

Chiral HPLC: >99% ee, @ 5.88 min (RT) (Chiralpak OJ 250×4.6 mm, 10 micro column, 30% isocratic elution, heptane/(EtOH:MeOH) 1:1, 1 mL/min, monitoring at 254 nm).

LC/MS: MS (ES): m/z=439 [M+H]+. HPLC: 2.02 min (RT) (Chromolith SpeedROD column 4.6×50 mm, 10-90% aqueous MeOH over 4 minutes containing 0.2% phosphoric acid, 4 mL/min, monitoring at 220 nm). $^1$H NMR: 400 MHz, DMSO-d$_6$) δ ppm 8.41 (s, 1H) 8.10-8.22 (m, 2H) 5.96 (d, J=7.55 Hz, 1H) 5.08 (d, J=4.78 Hz, 1H) 4.02-4.18 (m, 3H) 3.12 (t, J=7.43 Hz, 1H) 2.86 (d, J=7.55 Hz, 1H) 2.26 (dd, J=13.35, 6.55 Hz, 1H) 1.53 (s, 3H) 1.41 (d, J=13.35 Hz, 1H). The absolute stereochemistry of Example 38 has not been established. Although the compound represents a single antipode, the nomenclature and structure shown does not reflect the absolute stereochemistry of the compound.

Example 39

Chiral HPLC: 96% ee @ 8.60 min (RT) (Chiralpak OJ 250×4.6 mm, 10 micro column, 30% isocratic elution, heptane/(EtOH:MeOH) 1:1, 1 mL/min, monitoring at 254 nm). MS (ES): m/z=439 [M+H]+. HPLC: 2.03 min (RT) (Chromolith SpeedROD column 4.6×50 mm, 10-90% aqueous MeOH over 4 minutes containing 0.2% phosphoric acid, 4 mL/min, monitoring at 220 nm). $^1$H NMR: (400 MHz, DMSO-d$_6$) δ ppm 8.41 (s, 1H) 8.03-8.29 (m, 2H) 5.96 (d, J=7.55 Hz, 1H) 5.08 (d, J=5.04 Hz, 1H) 3.95-4.22 (m, 3H) 3.12 (t, J=7.55 Hz, 1H) 2.86 (d, J=7.55 Hz, 1H) 2.26 (dd, J=13.35, 6.55 Hz, 1H) 1.53 (s, 3H) 1.42 (d, J=13.35 Hz, 1H). The absolute stereochemistry of Example 39 has not been established. Although the compound represents a single antipode, the nomenclature and structure shown does not reflect the absolute stereochemistry of the compound.

Example 40

2-Cyclopropyl-4-41R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (40)

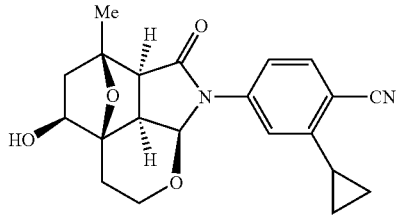

Preparation 40A

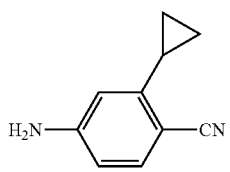

To a stirred mixture of 4-amino-2-bromobenzonitrile (2.00 g, 10.2 mmol), cyclopropyl boronic acid (1.18 g, 13.7 mmol) and K$_3$PO$_4$ (3.23 g, 15.2 mmol) in the mixed solvents of EtOH/H$_2$O/toluene (2 mL/2 mL/12 mL) under nitrogen was added PdCl$_2$(PPh$_3$)$_2$ (0.72 g, 1.03 mmol). This mixture was heated at 80° C. for 19 h and cooled to room temperature. Next, the mixture was diluted with 150 mL of EtOAc and filtered through a pad of silica gel topped with a layer of celite. This pad was further rinsed with EtOAc (2×100 mL). The filtrate was washed with 25 mL of brine, dried over MgSO$_4$, filtered and concentrated in vacuo to give the crude amine The crude amine was purified by an ISCO auto flash chromatographer using 120 g silica gel column, eluted with hexanes/CH$_2$Cl$_2$ solvents in a 25 min 50% to 100% gradient elution to give 0.75 g of Preparation 40A as a white solid in 47% yield.

HPLC: 1.55 min (RT) (Chromolith SpeedROD column 4.6×50 mm, 10-90% aqueous MeOH over 4 minutes containing 0.2% phosphoric acid, 4 mL/min, monitoring at 220 nm). MS (ES): m/z=159 [M+H]+. $^1$H NMR of 4-amino-2-cyclopropyl-benzonitrile (400 MHz, CDCl$_3$) δ ppm 7.34 (d, J=8.31 Hz, 1H) 6.44 (dd, J=8.31, 2.27 Hz, 1H) 6.12 (d, J=2.01 Hz, 1H) 4.01 (s, 2H) 2.13-2.24 (m, 1H) 1.02-1.12 (m, 2H) 0.68-0.76 (m, 2H).

Example 40

Example 40 was prepared from Preparation 40A and Preparation 15B by the general procedure described in Example 15.

HPLC: 1.94 min (RT) (Chromolith SpeedROD column 4.6×50 mm, 10-90% aqueous MeOH over 4 minutes containing 0.2% phosphoric acid, 4 mL/min, monitoring at 220 nm). MS (ES): m/z=367 [M+H]+.

Examples 41 and 42

4-((1R,2S,4R,5S,8S,13R)-2-Hydroxy-4-methyl-6-oxo-9,14-dioxa-7-azatetracyclo[6.4.1.1$^{1,4}$.0$^{5,13}$]tetradec-7-yl)-2-(trifluoromethyl)benzonitrile (42)

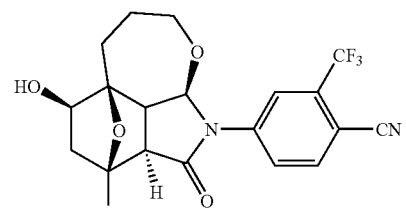

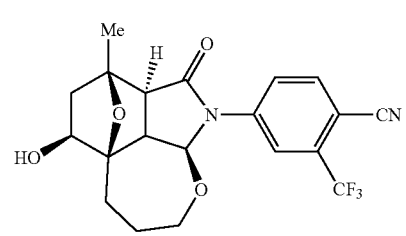

Preparation 41A

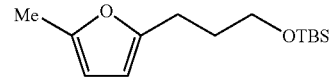

To a stirred solution of 2-methylfuran (10.35 g, 126 mmol) in THF (100 mL) under nitrogen in an ice bath was added dropwise 2.5 M n-butyllithium (48.2 mL, 121 mmol) in 10 min. This mixture was then stirred at 0° C. for 1 h and at room temperature for 2 h. tert-butyl(3-iodopropoxy)dimethylsilane (32.9 g, 110 mmol) was added at 0° C. dropwise over 20 min. The resulting mixture was stirred at 0° C. for 4 h and quenched with 30 mL of saturated $NH_4Cl$ solution. This mixture was concentrated in vacuo and partitioned between 30 mL of water and EtOAc (3×60 mL). Combined EtOAc extracts were dried ($MgSO_4$), filtered and concentrated in vacuo. This was loaded onto 350 g of silica and eluted with 1 L 20% $CH_2Cl_2$/hexanes, 1 L 30% $CH_2Cl_2$/hexanes, followed by 2 L 40% $CH_2Cl_2$/hexanes to give Preparation 41A (tert-butyldimethyl(3-(5-methylfuran-2-yl)propoxy)silane) (23.7 g, 93 mmol, 85% yield).

HPLC: 4.14 min (RT) (Chromolith SpeedROD column 4.6×50 mm, 10-90% aqueous methanol over 4 minutes containing 0.2% phosphoric acid, 4 mL/min, monitoring at 220 nm). $^1$H NMR (400 MHz, DMSO-$d_6$) δ ppm 5.90 (s, 2H) 3.59 (t, J=6.17 Hz, 2H) 2.56 (t, J=7.55 Hz, 2H) 2.18 (s, 3H) 1.65-1.81 (m, 2H) 0.85 (s, 9H) 0.01 (s, 6H); MS (ES): m/z=255 $[M+H]^+$.

Preparations 41B and 41C

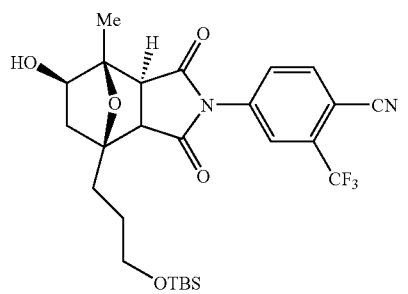

41B

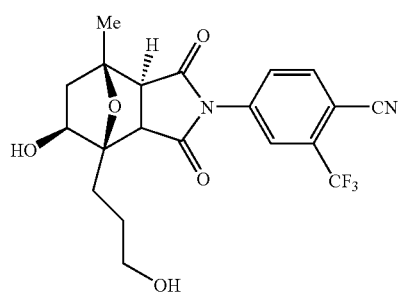

41C

Preparations 41B and 41C were prepared from Preparation 41A by the general method described for Preparations 1D and 1E.

Preparation 41B: MS (ES): m/z=539 $[M+H]^+$; HPLC: 3.67 min (RT) (Chromolith SpeedROD column 4.6×50 mm, 10-90% aqueous methanol over 4 minutes containing 0.2% phosphoric acid, 4 mL/min, monitoring at 220 nm).

Preparation 41C: MS (ES): m/z=425 $[M+H]^+$; HPLC: 2.08 min (RT) (Chromolith SpeedROD column 4.6×50 mm, 10-90% aqueous methanol over 4 minutes containing 0.2% phosphoric acid, 4 mL/min, monitoring at 220 nm).

Examples 41 and 42

The racemic mixture of Examples 41 and 42 was prepared from Preparation 41C by the general method described for Example 3.

The racemic mixture (0.45 g) was separated using preparative chiral HPLC on a Chiralpak IA (0.46×25 cm) column. Elution with 20% methanol/$CO_2$ afforded Example 41 (186 mg) and Example 42 (173 mg).

Racemic mixture: $^1$H NMR (500 MHz, CDCl$_3$) δ ppm 8.32 (s, 1H) 8.17 (d, J=8.80 Hz, 1H) 7.96 (dd, J=8.80, 2.20 Hz, 1H) 5.89 (d, J=7.15 Hz, 1H) 4.97 (d, J=6.60 Hz, 1H) 3.74-3.85 (m, 1H) 3.67-3.74 (m, 1H) 3.57-3.66 (m, 1H) 2.80 (d, J=9.35 Hz, 1H) 2.72 (dd, J=8.81, 7.05 Hz, 1H) 2.20 (dd, J=12.37, 7.42 Hz, 1H) 2.12-2.18 (m, 1H) 1.94-2.02 (m, 1H) 1.74-1.82 (m, 1H) 1.66-1.73 (m, 1H) 1.48 (s, 3H) 1.22 (dd, J=12.37, 3.57 Hz, 1H).

Example 41

MS (ES): m/z=409 $[M+H]^+$; HPLC: 2.14 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 5.73 min (Chiralpak OJ 250×4.6 mm, 10 micro column, 30% isocratic elution, heptane/(EtOH:MeOH 1:1), 1 mL/min, monitoring at 254 nm). The absolute stereochemistry of Example 41 has not been established. Although the compound represents a single antipode, the nomenclature and structure shown does not reflect the absolute stereochemistry of the compound.

Example 42

MS (ES): m/z=409 $[M+H]^+$; HPLC: 2.14 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 7.87 min (Chiralpak OJ 250×4.6 mm, 10 micron, 30% isocratic elution, heptane/(EtOH:MeOH 1:1), 1 mL/min, monitoring at 254 nm). The absolute stereochemistry of Example 42 has not been established. Although the compound represents a single antipode, the nomenclature and structure shown does not reflect the absolute stereochemistry of the compound.

Examples 43 and 44

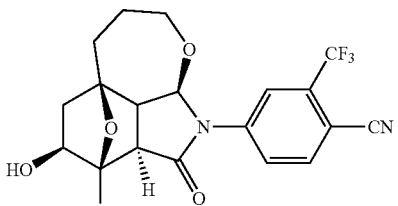

43

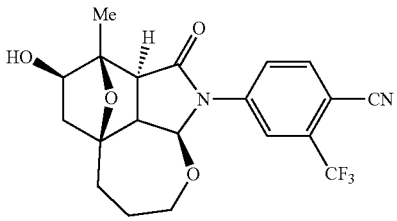

44

The racemic mixture of Examples 43 and 44 was prepared from Preparation 41B by the general method described for Example 1.

¹H NMR (400 MHz, DMSO-d₆) δ ppm 8.35 (s, J=2.01 Hz, 1H) 8.17 (d, J=8.81 Hz, 1H) 7.96 (dd, J=8.69, 2.14 Hz, 1H) 5.79 (d, J=6.80 Hz, 1H) 4.86 (d, J=6.04 Hz, 1H) 3.78-3.87 (m, 1H) 3.54-3.69 (m, 2H) 2.79 (dd, J=8.81, 7.05 Hz, 1H) 2.70 (d, 1H) 2.25 (dd, J=13.09, 7.05 Hz, 1H) 1.97-2.16 (m, 2H) 1.76-1.89 (m, 1H) 1.68 (dd, J=9.95, 4.41 Hz, 1H) 1.37 (s, 3H) 1.26 (dd, J=13.09, 2.01 Hz, 1H).

The racemic mixture (0.41 g) was subsequently subjected to chiral HPLC on a Chiralpak 1A (2×25 cm) column. Elution with 15% methanol/CO₂ afforded Enantiomer A (173 mg) and Enantiomer B (165 mg).

Example 43

MS (ES): m/z=409 [M+H]⁺; HPLC: 2.07 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: >99% ee @ 5.59 min (RT) (Chiralpak OJ 250×4.6 mm, 10 micron column, 30% isocratic elution, heptane/(EtOH:MeOH 1:1), 1 mL/min, monitoring at 254 nm). The absolute stereochemistry of Example 43 has not been established. Although the compound represents a single antipode, the nomenclature and structure shown does not reflect the absolute stereochemistry of the compound.

Example 44

MS (ES): m/z=409 [M+H]⁺; HPLC: 2.06 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: >99% ee, at 7.49 min (Chiralpak OJ 250×4.6 mm, 10 micro column, 30% isocratic elution, heptane/(EtOH:MeOH 1:1), 1 mL/min, monitoring at 254 nm). The absolute stereochemistry of Example 44 has not been established. Although the compound represents a single antipode, the nomenclature and structure shown does not reflect the absolute stereochemistry of the compound.

Example 45

4-((1R,2S,4R,5S,8S,12R)-2-amino-4-methyl-6-oxo-9,13-dioxa-7-azatetracyclo[6.3.1.1¹,⁴.0⁵,¹²]tridec-7-yl)-2-chlorobenzonitrile (45)

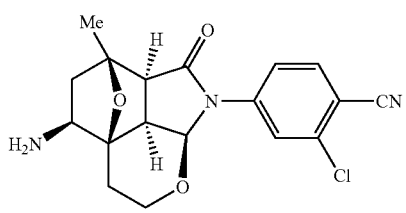

Example 45 was prepared from 4-cyano-3-chloroaniline and Preparation 15B by the sequential application of the general procedures described in Examples 15, 3, 4 and 5.

HPLC: 1.56 min (RT) (YMC ODS column 4.6×50 mm eluting with 10-90% aqueous MeOH containing 0.2% H₃PO₄ over 4 minutes, 4 mL/min, monitoring at 220 nm). MS (ES): m/z=360.0 [M+H]⁺.

Example 46

2-Chloro-4-((1R,2S,4R,5S,8S,12R)-2-((6-chloro-4-pyrimidinyl)amino)-4-methyl-6-oxo-9,13-dioxa-7-azatetracyclo[6.3.1.1¹,⁴.0⁵,¹²]tridec-7-yl)benzonitrile (46)

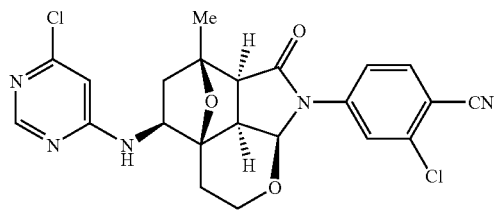

To a solution of Example 45 (0.050 g; 0.14 mmol) in dry DMF (0.2 mL) under nitrogen in a sealed tube apparatus was added 4,6-dichloropyrimidine (0.042 g; 0.28 mmol) at 22° C. The resulting pale yellow solution was heated to 100° C. in an oil bath overnight.

HPLC showed a 1:1 ratio of desired product to starting material. The solution was cooled to room temperature and diluted with 5 mL water and 10 mL EtOAc. The aqueous layer was backextracted with EtOAc (3×10 mL) and the organic layers were combined, dried over anhydrous magnesium sulfate, and filtered. The resulting filtrate was concentrated in vacuo revealing a viscous brown oil which was purified using a 4 g ISCO silica gel column, eluting with 0-30% acetone/CH₂Cl₂, to afford Example 46 (0.023 g (35%) as a white solid.

HPLC: 2.995 min (RT)(YMC ODS column 4.6×50 mm eluting with 10-90% aqueous MeOH containing 0.2% H₃PO₄ over 4 minutes, 4 mL/min, monitoring at 220 nm). MS (ES): m/z=471.9 [M+H]⁺. ¹H NMR (400 MHz, CDCl₃) δ ppm 8.31 (1H, s), 7.78 (1H, s), 7.78 (1H, s), 7.57 (2H, dd, J=20, 8 Hz), 6.32 (1H, s), 5.82 (1H, d, J=8 Hz), 4.90-4.50 (1H, br s), 3.51-3.48 (2H, m), 2.77 (1H, d, J=8 Hz), 2.58-2.54 (1H, m), 1.92-1.80 (2H, m), 1.72 (3H, s), 1.47-1.44 (2H, m).

Example 47

N-((1R,2S,4R,5S,8S,12R)-7-(3-Chloro-4-cyanophenyl)-4-methyl-6-oxo-9,13-dioxa-7-azatetracyclo[6.3.1.1¹,⁴.0⁵,¹²]tridec-2-yl)-N'-methylsulfamide (47)

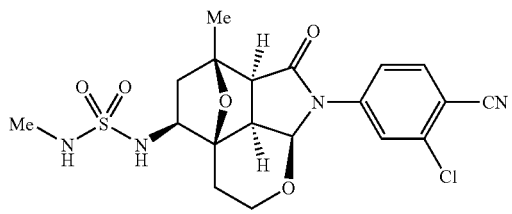

To a solution of chlorosulfonylisocyanate (0.052 mL; 0.6 mmol) in dry CH₂Cl₂ (4.0 mL) at 0° C. under nitrogen was added 2-chloroethanol (0.040 mL; 0.6 mmol) slowly via syringe. The pale yellow solution was stirred for 2 h at 0° C. The solution was then transferred via cannula to a solution containing Example 45 (0.225 g; 0.6 mmol) in dry CH$_2$Cl$_2$ (4.0 mL) at 0° C. Resulting solution was slowly warmed to room temperature and stirred overnight, with a precipitate slowly forming. The resulting suspension was concentrated in vacuo revealing a white solid, half of which was dissolved in dry acetonitrile (1.5 mL) in a sealed tube apparatus and treated with N,N-diisopropylethylamine (0.1 mL; 0.6 mmol) and methylamine solution (2M in THF, 0.45 mL, 0.9 mmol). The resulting solution was heated to 90° C. overnight. The mixture was cooled and concentrated in vacuo. The remaining residue purified using a 4 g SiO$_2$ column. The desired product eluted as a colorless band using 20% acetone/CH$_2$Cl$_2$ as eluent, to afford 0.005 g (4%) of Example 47 as a colorless film.

HPLC: 2.373 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=450.9 [M−H]$^-$.

Example 48

4-((1S,3S,4S,5S,8S,12R)-3-hydroxy-3,4-dimethyl-6-oxo-9,13-dioxa-7-azatetracyclo[6.3.1.1$^{1,4}$.0$^{5,12}$]tridec-7-O-2-(trifluoromethyl)benzonitrile (48)

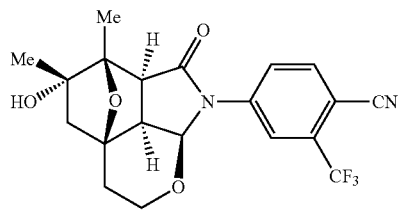

Example 48 was prepared from Example 271 by the general procedure used in Example 37.

HPLC: 2.67 min (RT) (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=409 [M+H]$^+$.

Example 49

4-((1R,4S,5S,8S,12R)-4-methyl-3-methylene-6-oxo-9,13-dioxa-7-azatetracyclo[6.3.1.1$^{1,4}$.0$^{5,12}$]tridec-7-yl)-2-(trifluoromethyl)benzonitrile (49)

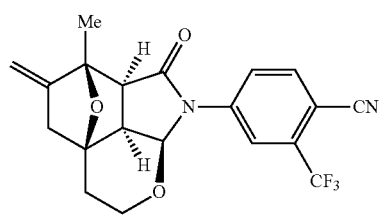

A suspension of methyltriphenylphosphonium bromide with sodium amide (2.4 mmol/g, 2.5 g, 6 mmol) in dry toluene (30 mL) was heated to reflux under nitrogen for 3 h. The mixture was cooled to room temperature and allowed to remain at room temperature for 1.5 h. The golden supernatant was then isolated by syringe and used in the following olefination reaction.

The above solution (1.9 mL, 0.38 mmol) was added to a solution of Example 269 (100 mg, 0.26 mmol) in dry THF (2 mL). The reaction mixture was stirred at room temperature overnight, then concentrated and purified by ISCO column (4 g column, EtOAc/Hexane=0-100%, 10 mL/min) to give Example 49 (89.7 mg, 90%) as a white solid.

HPLC: 2.84 min (RT) (Chromolith column 4.6×50 mm eluting with 10-90% aqueous MeOH over 4 minutes containing 0.1% TFA, 4 mL/min, monitoring at 220 nm). MS (ES): m/z=391 [M+H]$^+$. $^1$H NMR (500 MHz, CDCl$_3$) δ ppm 8.08 (d, J=2.20 Hz, 1H) 7.93 (dd, J=8.25, 2.20 Hz, 1H) 7.82 (d, J=8.80 Hz, 1H) 5.88 (d, J=7.70 Hz, 1H) 5.03-5.08 (m, 1H) 4.97-5.02 (m, 1H) 3.64-3.73 (m, 1H) 3.55-3.62 (m, 1H) 2.83 (d, J=7.70 Hz, 1H) 2.58 (t, J=7.70 Hz, 1H) 2.40-2.48 (m, 1H) 2.31-2.37 (m, 1H) 2.05-2.14 (m, 1H) 1.95-2.02 (m, 1H) 1.78 (s, 3H)

Example 50 and Example 51

4-((1R,4R,5S,8S,12R)-4-methyl-6-oxo-9,13-dioxa-7-azatetracyclo[6.3.1.1$^{1,4}$.0$^{5,12}$]tridec-7-yl)-2-(trifluoromethyl)benzonitrile (50) and 4-((1S,4S,5R,8R,12S)-4-methyl-6-oxo-9,13-dioxa-7-azatetracyclo[6.3.1.1$^{1,4}$.0$^{5,12}$]tridec-7-yl)-2-(trifluoromethyl)benzonitrile (51)

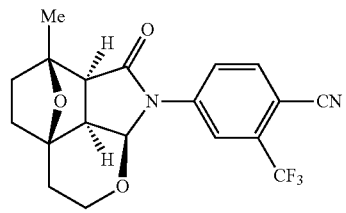

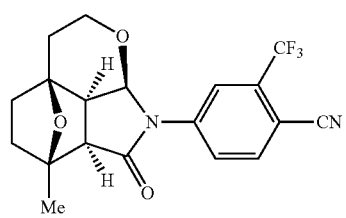

Preparation 50A

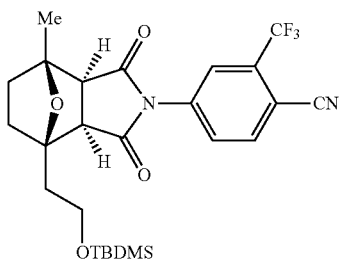

A mixture of Preparation 1C (10 g, 19.7 mmol) and 10% Pd/C (1.7 g) in EtOAc (100 mL) was stirred at room temperature under 1 atmosphere hydrogen gas. After stirring 2 hours under hydrogen, the reaction mixture was filtered through a 0.45 micron filter membrane with EtOAc rinse. The solvent was removed under reduced pressure to afford 10 g of racemic Preparation 50A as a white foam.

HPLC: 3.901 min (RT) (Chromolith column 4.6×50 mm eluting with 10-90% aqueous MeOH over 4 minutes containing 0.1% TFA, 4 mL/min, monitoring at 220 nm). MS (ES): m/z=509 [M+H]$^+$.

Examples 50 and 51

The racemic mixture of Examples 50 and 51 was prepared from Preparation 50A by the general method described in Example 3 transforming Preparation 1E to the mixture of Examples 3 and 4. The enantiomers were separated by preparatory column chromatography (Chiralcel OJ 5 cm×50 cm 20μ, by Chiral Technologies Inc.) eluting with at 80 mL/min with 25% (1:1 EtOH/MeOH) in heptane.

Example 50

HPLC: 2.595 min (RT) (Chromolith column 4.6×50 mm eluting with 10-90% aqueous MeOH over 4 minutes containing 0.1% TFA, 4 mL/min, monitoring at 220 nm). MS (ES): m/z=379 [M+H]$^+$. Chiral HPLC: 5.16 min (RT) (OJ column eluting with 25% (1:1 EtOH/MeOH) in heptane, 1 mL/min, monitoring at 220 nm). Absolute stereochemistry confirmed by VCD analysis.

Example 51

HPLC: 2.585 min (RT) (Chromolith column 4.6×50 mm eluting with 10-90% aqueous MeOH over 4 minutes containing 0.1% TFA, 4 mL/min, monitoring at 220 nm). MS (ES): m/z=379 [M+H]$^+$. Chiral HPLC: 14.76 min (RT) (OJ column eluting with 25% (1:1 EtOH/MeOH) in heptane, 1 mL/min, monitoring at 220 nm).

Examples 52 and 53

4-((1R,4R,5S,8S,12R)-6-oxo-9,13-dioxa-7-azatetracyclo[6.3.1.1$^{1,4}$.0$^{5,12}$]tridec-7-yl)-2-(trifluoromethyl)benzonitrile (52) and 4-((1S,4S,5R,8R,12S)-6-oxo-9,13-dioxa-7-azatetracyclo[6.3.1.1$^{1,4}$.0$^{5,12}$]tridec-7-yl)-2-(trifluoromethyl)benzonitrile (53)

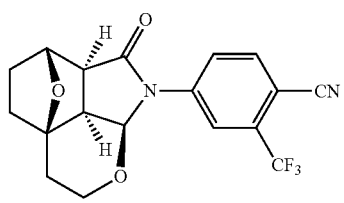

52

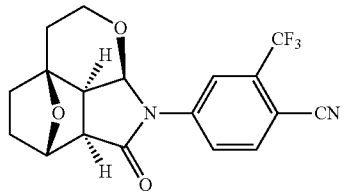

53

Preparation 52A

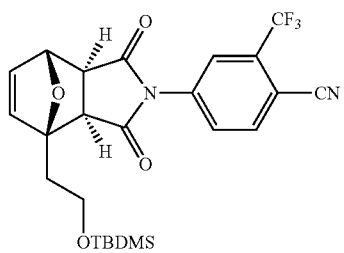

Preparation 52A was prepared from furan and 4-(2,5-dioxo-2,5-dihydro-1H-pyrrol-1-yl)-2-(trifluoro)benzonitrile (140 g, 526 mmol) according to the general procedure described in Example 1 of U.S. Patent Application Publication No. 2005/0192253 A1).

Preparation 52B

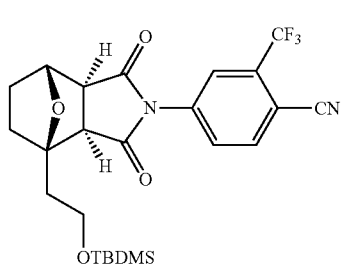

Preparation 52B was prepared from Preparation 52A by the general method described for Preparation 50A.

Examples 52 and 53

The racemic mixture of Examples 52 and 53 was prepared from Preparation 52B by the general method described in Example 3 for transforming Preparation 1E to the mixture of Examples 3 and 4. The enantiomers were separated by preparatory column chromatography (Chiralcel OJ 5 cm×50 cm 20 μm, by Chiral Technologies Inc.) eluting with at 80 mL/min with 30% (1:1 EtOH/MeOH) in heptane.

Example 52

HPLC: 2.445 min (RT) (Chromolith column 4.6×50 mm eluting with 10-90% aqueous MeOH over 4 minutes containing 0.1% TFA, 4 mL/min, monitoring at 220 nm). MS (ES): m/z=365 [M+H]$^+$. Chiral HPLC: 6.98 min (RT) (OJ column eluting with 30% (1:1 EtOH/MeOH) in heptane, 1 mL/min, monitoring at 220 nm). The absolute stereochemistry of Example 52 has not been established. Although the compound represents a single antipode, the nomenclature and structure shown does not reflect the absolute stereochemistry of the compound.

Example 53

HPLC: 2.445 min (RT) (Chromolith column 4.6×50 mm eluting with 10-90% aqueous MeOH over 4 minutes containing 0.1% TFA, 4 mL/min, monitoring at 220 nm). MS (ES): m/z=365 [M+H]$^+$. Chiral HPLC: 13.37 min (RT) (OJ column eluting with 30% (1:1 EtOH/MeOH) in heptane, 1 mL/min, monitoring at 220 nm). The absolute stereochemistry of Example 53 has not been established. Although the compound represents a single antipode, the nomenclature and structure shown does not reflect the absolute stereochemistry of the compound.

Example 54 and Example 55

4-((1R,2S,4R,5S,8S,12R)-2-hydroxy-6-oxo-9,13-dioxa-7-azatetracyclo[6.3.1.1$^{1,4}$.0$^{5,12}$]tridec-7-yl)-2-(trifluoromethyl)benzonitrile (54) and 4-((1S,2R,4S,5R,8R,12S)-2-hydroxy-6-oxo-9,13-dioxa-7-azatetracyclo[6.3.1.1$^{1,4}$.0$^{5,12}$]tridec-7-yl)-2-(trifluoromethyl)benzonitrile (55)

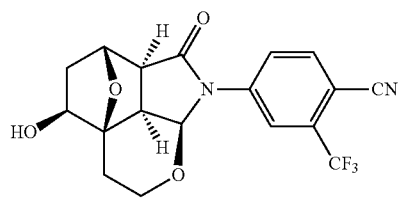

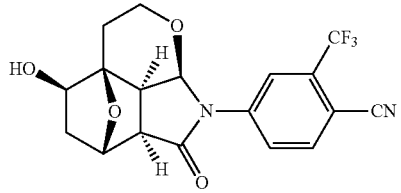

The racemic mixture of Examples 54 and 55 was prepared from Preparation 52A by the general procedures described in Examples 1 and 2. The enantiomers were separated by preparatory column chromatography (Chiralcel OJ 5 cm×50 cm 20 μm, by Chiral Technologies Inc.) eluting with at 80 mL/min with 25% (1:1 EtOH/MeOH) in heptane.

Example 54

HPLC: 1.875 min (RT) (Chromolith column 4.6×50 mm eluting with 10-90% aqueous MeOH over 4 minutes containing 0.1% TFA, 4 mL/min, monitoring at 220 nm). MS (ES): m/z=381 [M+H]$^+$. Chiral HPLC: 9.41 min (RT) (OJ column eluting with 25% (1:1 EtOH/MeOH) in heptane, 1 mL/min, monitoring at 220 nm). The absolute stereochemistry of Example 54 has not been established. Although the compound represents a single antipode, the nomenclature and structure shown does not reflect the absolute stereochemistry of the compound.

Example 55

HPLC: 1.885 min (RT) (Chromolith column 4.6×50 mm eluting with 10-90% aqueous MeOH over 4 minutes containing 0.1% TFA, 4 mL/min, monitoring at 220 nm). MS (ES): m/z=381 [M+H]$^+$. Chiral HPLC: 14.75 min (RT) (OJ column eluting with 25% (1:1 EtOH/MeOH) in heptane, 1 mL/min, monitoring at 220 nm). The absolute stereochemistry of Example 55 has not been established. Although the compound represents a single antipode, the nomenclature and structure shown does not reflect the absolute stereochemistry of the compound.

Example 56 and Example 57

4-((1S,3R,4S,5S,8S,12R)-3-hydroxy-6-oxo-9,13-dioxa-7-azatetracyclo[6.3.1.1$^{1,4}$.0$^{5,12}$]tridec-7-yl)-2-(trifluoromethyl)benzonitrile (56) and 4-((1R,3S,4R,5R,8R,12S)-3-hydroxy-6-oxo-9,13-dioxa-7-azatetracyclo[6.3.1.1$^{1,4}$.0$^{5,12}$]tridec-7-yl)-2-(trifluoromethyl)benzonitrile (57)

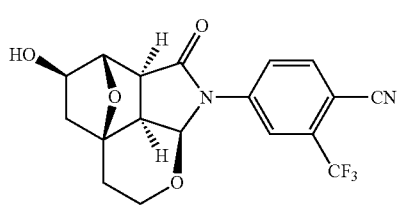

-continued

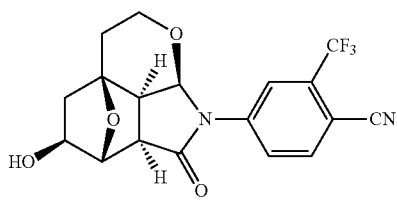

57

Examples 56 and 57 were prepared from Preparation 52A according to the general procedures described in Examples 1 and 2. The enantiomers were separated by preparatory column chromatography (Chiralcel OJ 5 cm×50 cm 20 μm, by Chiral Technologies Inc.) eluting with at 80 mL/min with 30% (1:1 EtOH/MeOH) in heptane.

Example 56

HPLC: 1.992 min (RT) (Chromolith column 4.6×50 mm eluting with 10-90% aqueous MeOH over 4 minutes containing 0.1% TFA, 4 mL/min, monitoring at 220 nm). MS (ES): m/z=381 [M+H]$^+$. Chiral HPLC: 5.35 min (RT) (OJ column eluting with 30% (1:1 EtOH/MeOH) in heptane, 1 mL/min, monitoring at 220 nm). The absolute stereochemistry of Example 56 has not been established. Although the compound represents a single antipode, the nomenclature and structure shown does not reflect the absolute stereochemistry of the compound.

Example 57

HPLC: 1.978 min (RT) (Chromolith column 4.6×50 mm eluting with 10-90% aqueous MeOH over 4 minutes containing 0.1% TFA, 4 mL/min, monitoring at 220 nm). MS (ES): m/z=381 [M+H]$^+$. Chiral HPLC: 16.10 min (RT) (OJ column eluting with 30% (1:1 EtOH/MeOH) in heptane, 1 mL/min, monitoring at 220 nm). The absolute stereochemistry of Example 57 has not been established. Although the compound represents a single antipode, the nomenclature and structure shown does not reflect the absolute stereochemistry of the compound.

Example 58 and Example 59

4-((1R,2S,4R,5S,8S,12R)-4-ethyl-2-hydroxy-6-oxo-9,13-dioxa-7-azatetracyclo[6.3.1.1$^{1,4}$.0$^{5,12}$]tridec-7-yl)-2-(trifluoromethyl)benzonitrile (58) and 4-((1S,2R,4S,5R,8R,12S)-4-ethyl-2-hydroxy-6-oxo-9,13-dioxa-7-azatetracyclo[6.3.1.1$^{1,4}$.0$^{5,12}$]tridec-7-yl)-2-(trifluoromethyl)benzonitrile (59)

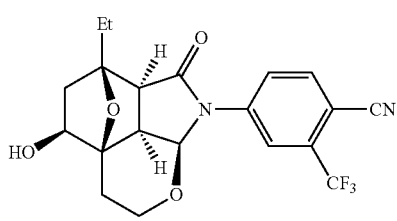

58

-continued

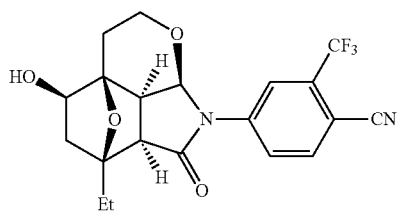

59

The racemic mixture of Examples 58 and 59 was prepared from 2-ethylfuran according to the general procedures described in Examples 1 and 2. The enantiomers were separated by preparatory column chromatography (Chiralcel OJ 5 cm×50 cm 20 μm, by Chiral Technologies Inc.) eluting with at 80 mL/min with 30% (1:1 EtOH/MeOH) in heptane.

Example 58

HPLC: 2.258 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]$^+$. (M+H)$^+$. Chiral HPLC: 5.14 min (RT) (OJ column eluting with 30% (1:1 EtOH/MeOH) in heptane, 1 mL/min, monitoring at 220 nm). The absolute stereochemistry of Example 58 has not been established. Although the compound represents a single antipode, the nomenclature and structure shown does not reflect the absolute stereochemistry of the compound.

Example 59

HPLC: 2.265 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]$^+$. Chiral HPLC: 15.8 min (RT) (OJ column eluting with 30% (1:1 EtOH/MeOH) in heptane, 1 mL/min, monitoring at 220 nm). The absolute stereochemistry of Example 59 has not been established. Although the compound represents a single antipode, the nomenclature and structure shown does not reflect the absolute stereochemistry of the compound.

Example 60 and Example 61

4-((1S,3R,4S,5S,8S,12R)-4-ethyl-3-hydroxy-6-oxo-9,13-dioxa-7-azatetracyclo[6.3.1.1$^{1,4}$.0$^{5,12}$]tridec-7-yl)-2-(trifluoromethyl)benzonitrile (60) and 4-((1R,3S,4R,5R,8R,12S)-4-ethyl-3-hydroxy-6-oxo-9,13-dioxa-7-azatetracyclo[6.3.1.1$^{1,4}$.0$^{5,12}$]tridec-7-yl)-2-(trifluoromethyl)benzonitrile (61)

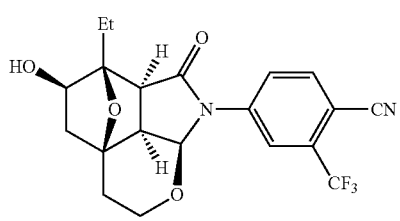

60

-continued

61

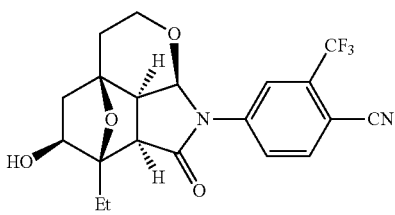

The racemic mixture of Examples 60 and 61 was prepared from 2-ethylfuran according to the general procedures used in Examples 1 and 2. The enantiomers were separated by preparatory column chromatography (Chiralcel OJ 5 cm×50 cm 20 μm, by Chiral Technologies Inc.) eluting with at 80 mL/min with 30% (1:1 EtOH/MeOH) in heptane.

Example 60

HPLC: 2.290 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]+. Chiral HPLC: 6.2 min (RT) (OJ column eluting with 30% (1:1 EtOH/MeOH) in heptane, 1 mL/min, monitoring at 220 nm). The absolute stereochemistry of Example 60 has not been established. Although the compound represents a single antipode, the nomenclature and structure shown does not reflect the absolute stereochemistry of the compound.

Example 61

HPLC: 2.280 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]+. Chiral HPLC: 29.2 min (RT) (OJ column eluting with 30% (1:1 EtOH/MeOH) in heptane, 1 mL/min, monitoring at 220 nm). The absolute stereochemistry of Example 61 has not been established. Although the compound represents a single antipode, the nomenclature and structure shown does not reflect the absolute stereochemistry of the compound.

Example 62

2-Ethynyl-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (62)

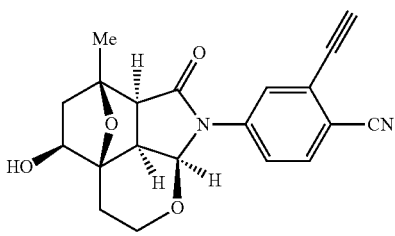

To a solution of Example 118 (300 mg, 0.66 mmol) in THF (3 mL) and Et$_3$N (3 mL), was added trimethylsilylacetylene (326 mg, 3.3 mmol), Pd(Cl)$_2$(PPH$_3$)$_2$ (92.6 mg, 0.132 mmol), CuI (12.6 mg, 0.066 mmol) under an inert atmosphere. The mixture was heated to 50° C. for 15 min, then cooled to room temperature. To the reaction mixture was added EtOAc and water and the mixture was filtered through celite with EtOAc rinse. Brine was added and the mixture extracted. The organic layer was dried over MgSO$_4$, filtered and then the solvent removed under reduced pressure. The residue was suspended in MeOH (5 mL) and saturated aq K$_2$CO$_3$ (200 mL) was added at room temperature. The mixture was stirred for 15 min and filtered through celite with MeOH rinse. After removal of the solvent, the crude mixture was purified on silica gel (12 g ISCO column) eluting with a gradient from 100% CH$_2$Cl$_2$ to 100% EtOAc over 15 min. The product peak was collected and concentrated under reduced pressure and the resulting solid triturated with EtOAc/Et$_2$O (1:1) and filtered to give 89.9 mg of Example 62 as a white foam.

HPLC: 1.610 min (RT) (Chromolith column 4.6×50 mm eluting with 10-90% aqueous MeOH over 4 minutes containing 0.1% TFA, 4 mL/min, monitoring at 220 nm). MS (ES): m/z=351 [M+H]+. $^1$H NMR (500 MHz, CDCl$_3$) δ ppm 7.83 (1H, d, J=1.65 Hz), 7.62-7.71 (2H, m), 5.86 (1H, d, J=7.15 Hz), 3.80 (1H, t, J=7.42 Hz), 3.54-3.66 (2H, m), 3.46 (1H, s), 2.71 (1H, d, J=7.70 Hz), 2.35 (1H, t, J=7.70 Hz), 2.30 (1H, dd, J=13.75, 6.60 Hz), 2.07-2.13 (1H, m), 1.92-2.01 (1H, m), 1.76 (3H, s), 1.68 (1H, d, J=9.90 Hz)

Example 63

(1R,2S,4R,5S,8S,12R)-7-(4-chloro-3-ethynylphenyl)-2-hydroxy-4-methyl-9,13-dioxa-7-azatetracyclo[6.3.1.1$^{1,4}$.0$^{5,12}$]tridecan-6-one (63)

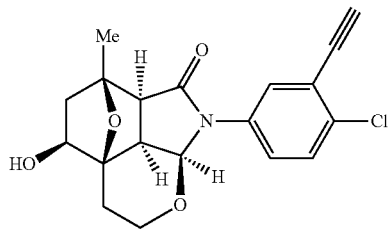

Example 63 was prepared from Example 114 according to the general method described in Example 62.

HPLC: 2.015 min (RT) (Chromolith column 4.6×50 mm eluting with 10-90% aqueous MeOH over 4 minutes containing 0.1% TFA, 4 mL/min, monitoring at 220 nm). MS (ES): m/z=360 [M+H]+.

Example 64

2-Fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (64)

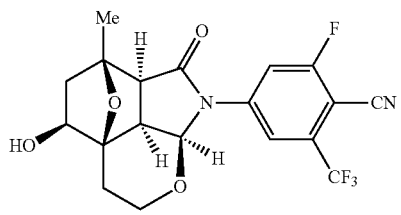

Preparation 64A

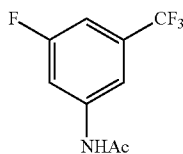

To a solution of 3-fluoro-5-(trifluoromethyl)aniline (39.32 g, 219.5 mmol) in EtOH (210 mL) was added Ac₂O (24.9 mL, 263.4 mmol) dropwise. The reaction mixture was stirred for 1 h and then concentrated to afford Preparation 64A as a light yellow solid (56.5 g, 100%. contains some Ac₂O).

HPLC: 2.518 min (RT) (Chromolith SpeedROD 4.6×50 mm, A linear gradient using 10% MeOH, 90% water, and 0.1% TFA (Solvent A) and 90% MeOH, 10% water, and 0.1% TFA (Solvent B); t=0 min., 0% B, t=4 min., 100% B (5 min.) was employed. Flow rate was 4 ml/min and UV detection was set to 220). MS (ES): m/z=220 [M–H]⁻.

Preparation 64B

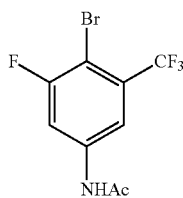

To a solution of Preparation 64A (28.8 g, 130 mmol) in HOAc (300 mL) at 0° C., Br₂ (36.6 mL, 715 mmol) was added dropwise over 1 h. The reaction mixture was allowed to warm to room temperature and stirred for 4 days after which time the mixture was poured into stirring ice-water resulting in an orange solid precipitate. The solid was collected by filtration, washed with water, dried under high vacuum to give Preparation 64B (32.6 g, 83%) as yellow solid.

HPLC: 2.938 min (RT) (Chromolith SpeedROD 4.6×50 mm, a linear gradient using 10% MeOH, 90% water, and 0.1% TFA (Solvent A) and 90% MeOH, 10% water, and 0.1% TFA (Solvent B); t=0 min., 0% B, t=4 min., 100% B (5 min.) was employed. Flow rate was 4 ml/min and UV detection was set to 220). MS (ES): m/z=300 [M–H]⁻.

Preparation 64C

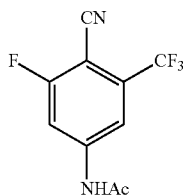

A mixture of Preparation 64B (2.4 g, 8 mmol), CuCN (0.896 g, 10 mmol) in DMF (10 mL) was heated at 150° C. under nitrogen overnight. Next, the reaction mixture was cooled to room temperature and then poured into ice water. EtOAc was added, and the insoluble solid was filtered off and rinsed with copious EtOAc. The organic layer was separated, and the aqueous layer was extracted with EtOAc once. The combined extracts were washed with saturated aqueous NaHCO₃, 10% LiOH and brine, and dried over MgSO₄. The resulting material was concentrated and purified by ISCO column (80 g, 10-100% EtOAc/hexane) to afford Preparation 64C (1.45 g, 75%) as light yellow solid.

HPLC: 2.362 min (RT) (Chromolith SpeedROD 4.6×50 mm, A linear gradient using 10% MeOH, 90% water, and 0.1% TFA (Solvent A) and 90% MeOH, 10% water, and 0.1% TFA (Solvent B); t=0 min., 0% B, t=4 min., 100% B (5 min.) was employed. Flow rate was 4 mL/min and UV detection was set to 220). MS (ES): m/z=245 [M–H]⁻.

Preparation 64D

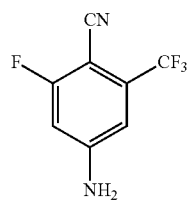

To a solution of Preparation 64C (1.45 g, 5.89 mmol) in EtOH (10 mL) was added concentrated HCl (12 N, 10 mL). The mixture was heated to reflux for 1 h and then concentrated to give white solid. The solid was dissolved in EtOAc, washed with saturated aqueous NaHCO₃, dried over MgSO₄ and concentrated to give Preparation 64D (1.11 g, 93%) as white solid.

HPLC: 1.970 min (RT) (Chromolith SpeedROD 4.6×50 mm, A linear gradient using 10% MeOH, 90% water, and 0.1% TFA (Solvent A) and 90% MeOH, 10% water, and 0.1% TFA (Solvent B); t=0 min., 0% B, t=4 min., 100% B (5 min.) was employed. Flow rate was 4 ml/min and UV detection was set to 220). MS (ES): m/z=205 [M+H]⁺.

Example 64

Example 64 was prepared from Preparation 64D according to the general method described in Example 15.

HPLC: 2.75 min (RT) (Chromolith SpeedROD 4.6×50 mm, A linear gradient using 10% MeOH, 90% water, and 0.1% TFA (Solvent A) and 90% MeOH, 10% water, and 0.1% TFA (Solvent B); t=0 min., 0% B, t=4 min., 100% B (5 min.) was employed. Flow rate was 4 ml/min and UV detection was set to 220). MS (ES): m/z=413.2 [M+H]⁺.

Example 65

2-Chloro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (65)

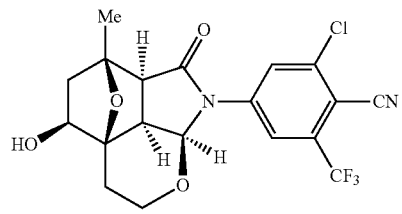

Preparation 65A

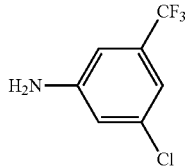

To a stirred mixture of 1-chloro-3-nitro-5-(trifluoromethyl)benzene (2.90 g, 12.9 mmol.) in 120 mL of EtOAc, was added $SnCl_2$ dihydrate (12.0 g, 51.6 mmol.). This mixture was heated to reflux for 3 h and cooled to room temperature. Next, the mixture was diluted with 100 mL of EtOAc and washed with 2.5N NaOH solution (1×150 mL). The aqueous layer was separated and extracted with EtOAc (1×200 mL). Combined EtOAc layers were washed with brine (1×40 mL), dried ($MgSO_4$), filtered and concentrated in vacuo to give 2.51 g of Preparation 65A (3-chloro-5-(trifluoromethyl) aniline) as a yellow solid in quantitative yield.

HPLC: 2.57 min (RT) (Chromolith SpeedROD column 4.6×50 mm, 10-90% aqueous MeOH over 4 minutes containing 0.2% phosphoric acid, 4 mL/min, monitoring at 220 nm). MS (ES): m/z=196 $[M+H]^+$.

Preparation 65B

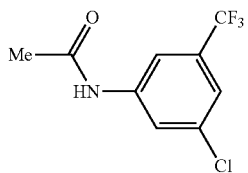

To a stirred mixture of Preparation 65A (2.51 g, 12.9 mmol.) in EtOH (130 mL) was added acetic anhydride (15.0 mL, 159 mmol.). The mixture was stirred at room temperature for 17 h. The mixture was then poured into a mixture of 40 mL of ice, 10 mL of saturated $NaHCO_3$ solution and 60 mL of EtOAc. The aqueous layer was separated and extracted with EtOAc (1×60 mL). The combined EtOAc layers were washed with brine (1×20 mL), dried ($MgSO_4$), filtered and concentrated in vacuo to give 2.88 g of Preparation 65B in 94% yield.

HPLC: 2.84 min (RT)(Chromolith SpeedROD column 4.6×50 mm, 10-90% aqueous MeOH over 4 minutes containing 0.2% phosphoric acid, 4 mL/min, monitoring at 220 nm). MS (ES): m/z=238 $[M+H]^+$. $^1$H NMR (400 MHz, DMSO-$d_6$) δ ppm 10.4 (s, 1H, NH) 7.96 (s, 1H) 7.91 (s, 1H) 7.50 (s, 1H), 2.09 (s, 3H).

Preparation 65C

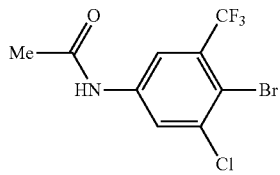

To a stirred solution of Preparation 65B (2.88 g, 12.1 mmol.) in 40 mL of HOAc was added $Br_2$ (3.00 mL, 58.5 mmol.). The reaction progress was monitored by LC. The reaction took 3 days to complete and approximately 1.5 mL $Br_2$ was added at about each 12 h interval. The mixture was then poured into a mixture of 80 mL of ice and water. The precipitate was filtered off and rinsed with water (3×20 mL). The precipitate was dried under pump vacuum and purified by a CombiFlash ISCO Chromatographer using 80 g column eluting with $CH_2Cl_2$/EtOAc solvents from 0% to 100% in 20 min gradient elution to give 3.21 g of Preparation 65C in 84% yield.

HPLC: 3.16 min (RT) (Chromolith SpeedROD column 4.6×50 mm, 10-90% aqueous MeOH over 4 minutes containing 0.2% phosphoric acid, 4 mL/min, monitoring at 220 nm). MS (ES): m/z=316 $[M+H]^+$. $^1$H NMR (400 MHz, DMSO-$d_6$) δ ppm 10.7 (s, 1H, NH) 8.23 (s, 1H) 8.06 (s, 1H) 2.10 (s, 3H).

Preparation 65D

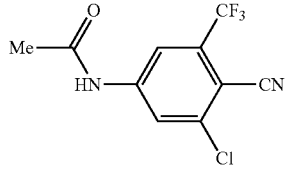

To a stirred mixture of Preparation 65C (0.87 g, 2.75 mmol.) in 2.5 mL of DMF was added CuCN (0.74 g, 8.25 mmol.). This mixture was heated at 155° C. for 3 h and another batch of CuCN (0.32 g, 3.57 mmol.) was added. Heating was continued for 20 h. The cooled reaction mixture was diluted with 40 mL of EtOAc and filtered through a pad of Celite rinsing with EtOAc (3×50 mL). The filtrate was concentrated in vacuo and purified by the CombiFlash ISCO Chromatographer using 40 g column eluting with $CH_2Cl_2$/EtOAc solvents from 0% to 50% in 20 min gradient elution to give 0.87 g of Preparation 65D in 58% yield.

HPLC: 2.58 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=261 $[M+H]^+$. $^1$H NMR (400 MHz, DMSO-$d_6$) δ ppm 10.9 (s, 1H, NH) 8.23 (s, 1H) 8.06 (s, 1H) 2.10 (s, 3H).

Preparation 65E

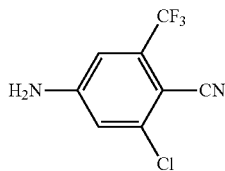

To a stirred mixture of Preparation 65D (0.86 g, 3.28 mmol.) in 3.6 mL of EtOH was added 3.6 mL of 12N HCl. This mixture was heated to reflux for 40 min and cooled to room temperature. The mixture was concentrated in vacuo and then diluted with 40 mL of saturated $NaHCO_3$ solution. The aqueous layer was further basified by solid $NaHCO_3$ and extracted with EtOAc (3×80 mL). The combined EtOAc extracts were washed with brine (1×20 mL), dried ($MgSO_4$), filtered and concentrated in vacuo. This crude aniline was mixed with 10 mL of $CH_2Cl_2$ and the precipitate was filtered off. The precipitate (0.47 g) was Preparation 65E. The filtrate was directly loaded unto a 4 g ISCO column and purified by the CombiFlash ISCO Chromatographer by eluting with $CH_2Cl_2$/hexanes solvents from 0% to 100% in 20 min gradient elution to give 0.23 g of desired Preparation 65E. Total yield for Preparation 65E was 0.70 g (97%).

HPLC: 2.01 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=221 $[M+H]^+$. $^1H$ NMR (400 MHz, DMSO-$d_6$) δ ppm 7.05 (s, 2H, $NH_2$) 7.00 (s, 1H) 6.95 (s, 1H).

Example 65

Example 65 was prepared from Preparation 65E according to the general method described in Example 15.

HPLC: 2.47 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=429 $[M+H]^+$.

Example 66

2-Bromo-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (66)

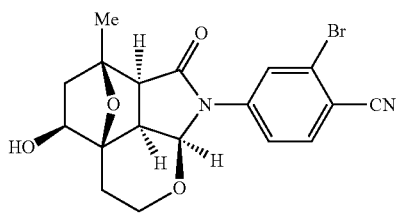

Preparation 66A

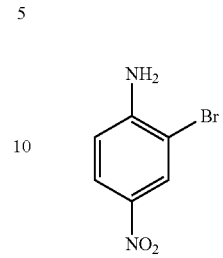

4-nitroaniline (10.0 g, 72 mmol) was dissolved in $CH_2Cl_2$ (300 mL) and MeOH (175 mL) and tetrabutylammonium bromide (38 g, 79.4 mmol) were added. After 5 minutes at room temperature, 10% aq $Na_2SO_3$ was added with vigorous stirring. The organic layer was then separated and it was washed once with water, once with brine and dried over $MgSO_4$. The crude material was passed through a plug of $SiO_2$ eluting with ether. Concentration gave Preparation 66A as an orange solid (15 g).

Preparation 66B

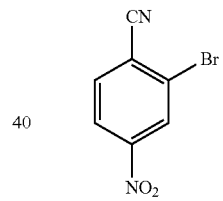

Preparation 66A (25 g, 115.7 mmol) was dissolved in a mixture of 50 mL 12 N HCl in 100 mL water and then cooled to 0° C. To this mixture, a solution of sodium nitrite (15.9 g, 230.7 mmol) in 25 mL water was slowly added while maintaining the reaction temperature at 0° C. The reaction was stirred for 1 h at 0° C. and then slowly added to a mechanically stirred solution of freshly prepared cuprous cyanide (8.25 g, 92.2 mmol) and potassium cyanide (18.8 g, 288.4 mmol) in water (125 mL) at 50° C. The reaction was stirred for 1 h at 50° C., and then allowed to cool to 25° C. The aqueous mixture was then extracted with $CH_2Cl_2$ (3×150 mL). The organic layer was dried over sodium sulfate, filtered and concentrated in vacuo to get the crude product. The crude product was purified by chromatography on silica gel eluting with 10% EtOAc-pet ether to yield Preparation 66B (11.0 g) as a white solid.

HPLC: 4.22 minutes (RT) (Eclipse XDB C18 column, 4.6×150 mm eluting with 50-90% aqueous acetonitrile over 15 minutes (0.01M ammonium acetate), 1.0 mL/min, monitoring at 280 nm).

Preparation 66C

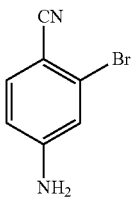

To a solution of Preparation 66B (8.39 g, 37.12 mmol) in acetic acid (42 mL) and EtOAc (42 mL) maintained at 80° C., iron powder (8.3 g, 150.3 mmol) was added with mechanical stirring. The reaction mixture was maintained at 80° C. until all starting material was consumed (4 h). The reaction mixture was cooled, filtered through Celite and the residue was washed with EtOAc. The filtrate was then neutralized with sat. NaHCO$_3$ and the organic layer was washed with water, brine, dried over sodium sulfate, and concentrated in vacuo to yield Preparation 66C (6.5 g) as an off white solid. No purification was necessary.

HPLC: 4.22 minutes (RT) (Eclipse XDB C18 column, 4.6×150 mm eluting with 50-90% aqueous acetonitrile over 15 minutes (0.01M ammonium acetate), 1.0 mL/min, monitoring at 280 nm).

Example 66

Example 66 was prepared from Preparation 66C and Preparation 15B according to the general method described in Example 15.

HPLC: 2.29 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=464.2 [M+OAc]$^-$.

Example 67

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethoxy)benzonitrile (67)

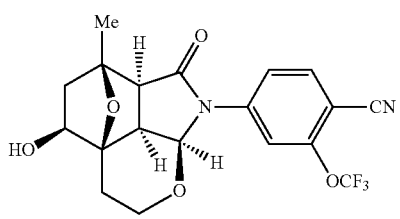

Preparation 67A

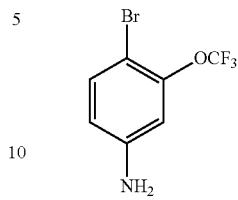

A solution of NBS (20.1 g, 111.9 mmol) in DMF (40 mL) was added drop wise to a solution of 3-trifluoromethylaniline (20.0 g, 112.9 mmol) in DMF (80 mL) at room temperature over 40 minutes. The reaction mixture was stirred overnight. After 12 h, the reaction mixture was poured into water and extracted with EtOAc and the organic layer was dried over anhydrous Na$_2$SO$_4$. Concentration in vacuo gave 26 g of Preparation 67A.

MS (ES): m/z=256.2 [M+1]$^+$.

Preparation 67B

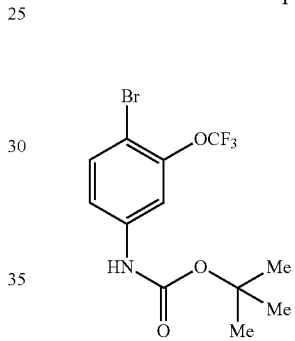

An aqueous solution of NaOH (10.2 g, 254 mmol in 20 mL water) was added to a solution of Preparation 67A in t-butanol (100 mL). Next, a solution of di-tert-butyldicarbonate (60.1 mL, 254 mmol) in t-butanol was added at room temperature and the resulting mixture was stirred for 4 days. The reaction mixture became a suspension and was filtered. The residue was washed with a small amount of water. The filtrate was concentrated to half its volume and then extracted with EtOAc (2×200 mL). The organic layer was washed with brine solution and dried over anhydrous Na$_2$SO$_4$. Removal of solvent in vacuo gave Preparation 67B (31.0 g) as a white solid.

Preparation 67C

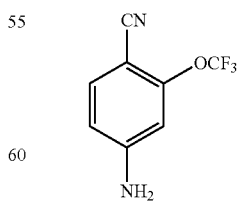

Copper cyanide (36 g, 402 mmol) was added to a solution of Preparation 67B (54 g, 152 mmol) in DMF (700 mL) at room temperature and the resulting mixture was heated to reflux in an oil bath and stirred. After 5 h at reflux, additional CuCN (18 g, 200 mmol)) was added and the mixture was maintained under reflux for 5 more hours. The reaction was cooled and FeCl$_3$.6H$_2$O (99 g) and 1 N HCl (982 mL) were added and the mixture stirred for 1.5 h. The mixture was extracted with EtOAc (2×300 mL). The organic layer was then washed with water, brine, dried over Na$_2$SO$_4$. Removal of solvent in vacuo gave the crude Preparation 67C, which was purified by column chromatography using silica gel (100-200 mesh) eluting with 16% EtOAc in hexanes, to afford 18 g of Preparation 67C as a pale yellow solid.

HPLC: 2.29 min (RT) (Zorbax SB-C18 column 4.6×50 mm eluting with 30-90% aqueous acetonitrile containing with 0.25% TFA over 4 minutes, 1 mL/min, monitoring at 280 nm). MS (ES): m/z=203.0 [M+H]$^+$.

Example 67

Example 67 was prepared from Preparation 67B and Preparation 15B according to the general procedure described in Example 15.

HPLC: 2.60 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=469.1 [M+OAc]$^-$.

Example 68

3-Fluoro-4-((1R,2S,4R,5S,8S,12R)-2-hydroxy-4-methyl-6-oxo-9,13-dioxa-7-zatetracyclo[6.3.1.1$^{1,4}$.0$^{5,12}$]tridec-7-yl)-2-(trifluoromethyl)benzonitrile (68)

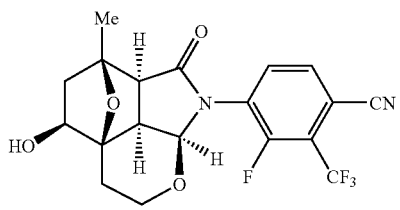

Preparation 68A

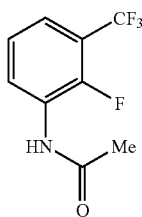

Preparation 68A was prepared from 2-fluoro-3-trifluoromethylaniline according to the general procedure described for Preparation 64B.

Preparation 68B

To a solution of Preparation 68A (15.0 g, 67.8 mmol) in conc. H$_2$SO$_4$ (35 mL) cooled to −5° C., was added fuming nitric acid (4.35 mL, 101.8 mmol) drop wise. The reaction was slowly warmed to room temperature and stirred for 3 h. The reaction was quenched by pouring into ice water and then the mixture was extracted into EtOAc. The EtOAc layer was washed with water, sat. aq.NaHCO$_3$ solution and then with brine and dried over Na$_2$SO$_4$. Removal of solvent in vacuo afforded Preparation 68B (17 g) as a yellow solid.

Preparation 68C

Preparation 68C was prepared from Preparation 68B according to the general method described for Preparation 66C.

Preparation 68D

Concentrated H$_2$SO$_4$ (5.2 mL, 101.7 mmol) was added drop wise to a solution of Preparation 68C (12.0 g, 50.8 mmol) in acetic acid (60 mL) and water (24 mL). The resulting solution was cooled to 0° C. and a solution of NaNO$_2$ (7.0 g, 101.7 mmol) in 30 mL of water was then added drop wise with stirring while maintaining the temperature in the range of from −5° C. to 0° C. The reaction mixture was stirred for 90 min and then a solution of KI (25.2 mL, 152 mmol in 20 mL water) was then added at −5° C. The reaction mixture was allowed to attain room temperature and stirred at room temperature for 6 h. Ice was then added to the reaction mixture and the resulting mixture was extracted into EtOAc. The organic layer was washed with water, brine and dried over anhydrous $Na_2SO_4$. Removal of solvent in vacuo gave crude Preparation 65D, which was purified by column chromatography using silica gel (100-200 mesh eluting with 8-10% EtOAc-pet ether) to give 15 g of Preparation 68D as a red oil.

Preparation 68E

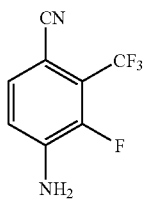

Preparation 68E was prepared from Preparation 68D according to the general methods described in Preparations 67C and 65E.

HPLC: 2.96 min (RT) (Zorbax SB-C18 column 4.6×50 mm eluting with 30-90% aqueous acetonitrile containing with 0.25% TFA over 4 minutes, 1 mL/min, monitoring at 280 nm). MS (ES): m/z=205.0 $[M+H]^+$.

Example 68

Example 68 was prepared from Preparation 68E and Preparation 15B according to the general method described in Example 15.

HPLC: 2.07 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=413 $[M+H]^+$.

Example 69

2-Chloro-6-fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (69)

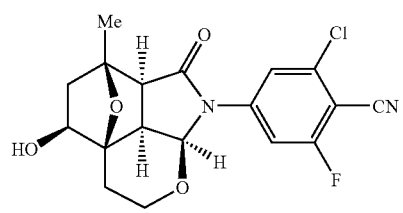

Preparation 69A

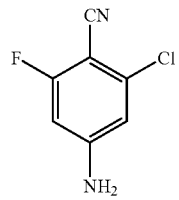

Preparation 69A was prepared from 3-chloro-5-fluoroaniline according to the general method described for Preparation 67C.

HPLC: 2.97 min (RT) (Zorbax SB-C18 column 4.6×50 mm eluting with 30-90% aqueous acetonitrile containing with 0.25% TFA over 4 minutes, 1 mL/min, monitoring at 280 nm). MS (ES): m/z=171.0 $[M+H]^+$.

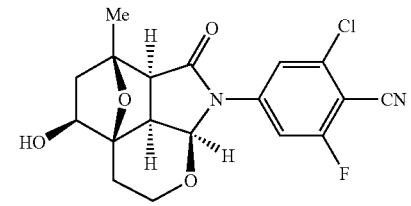

Example 69

Example 69 was prepared from Preparation 69A and Preparation 15B according to the general method described in Example 15.

HPLC: 3.008 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=379.2 $[M+H]^+$.

Example 70

2,6-Dichloro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (70)

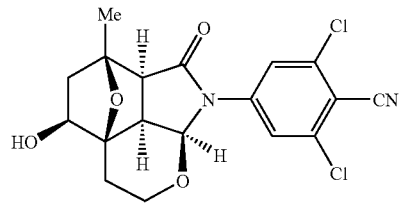

Preparation 70A

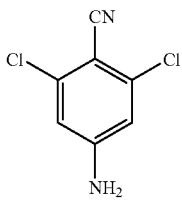

Preparation 70A was prepared from 3,5-dichloroaniline according to the general method described in Example 64.

Example 70

Example 70 was prepared from Preparation 70A and Preparation 15B according to the general method described in Example 15.

HPLC: 2.75 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=453.0 [M+OAc]$^-$.

Example 71

Rac-4-((1R,5S,8S,9S,10R,12S,13R)-9-methyl-7-oxo-4,11,14-trioxa-6-azapentacyclo[6.4.1.1$^{1,9}$.0$^{5,13}$.0$^{10,12}$]tetradec-6-yl)-2-(trifluoromethyl)benzonitrile (71)

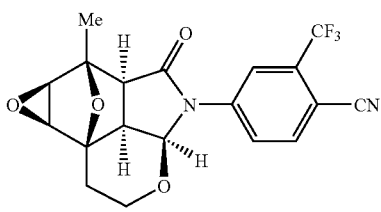

Preparation 71A

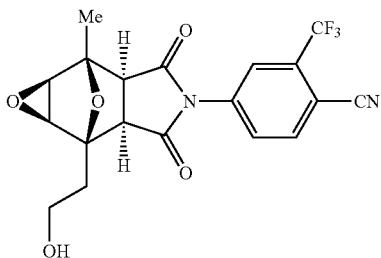

To a solution of racemic Preparation 1C (5.00 g, 9.90 mmol) in methylene chloride (100 mL) was added mCPBA (~70%, 7.3 g, 29.6 mmol) and the resulting mixture was stirred at room temperature for 19 h. 3-hydroxypyridine (0.94 g, 9.9 mmol) was then added resulting in a mild exotherm. After 20 min, sat. aq. NaHCO$_3$ (100 mL) was added and the mixture stirred vigorously for 30 min. The resulting layers were separated and the organic phase washed once with sat. aq. NaHCO$_3$ (30 mL), once with brine (30 mL) and dried over anhydrous sodium sulfate. The crude epoxide was then dissolved in THF (100 mL) and 12 N HCl (5 mL) was added. After 3 h at room temperature, the mixture was diluted with EtOAc (100 mL) and neutralized with sat. aq. NaHCO$_3$ (40 mL). The resulting mixture was extracted three times with EtOAc (100 mL) and dried over anhydrous magnesium sulfate. Filtration and concentration in vacuo gave 4.36 g of Preparation 71A as a white solid.

HPLC: 2.300 min (RT) (YMC ODS-A column 4.6×50 mm eluting with 10-90% aqueous MeOH over 4 minutes containing 0.1% $H_3PO_4$, 4 mL/min, monitoring at 220 nm).

Example 71

Example 71 was prepared from Preparation 71A by the general method described for the preparation of Example 3 from Preparation 1D.

HPLC: 2.604 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=451.2 [M+OAc]$^-$.

Example 72

4-((1S,3S,4S,5S,8S,12R)-3-hydroxy-3-(hydroxymethyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (72)

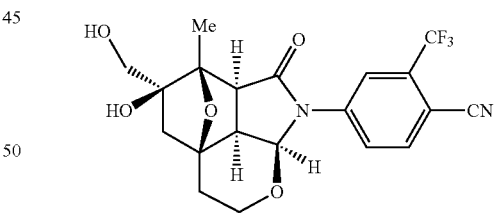

Example 72 was prepared from Example 49 by the general method described for Preparation 31A.

HPLC: 1.972 min (RT) (Chromolith column 4.6×50 mm eluting with 10-90% aqueous MeOH over 4 minutes containing 0.1% TFA, 4 mL/min, monitoring at 220 nm). MS (ES): m/z=425 [M+H]$^+$. $^1$H NMR (400 MHz, CDCl$_3$) δ ppm 8.08 (s, 1H), 7.93 (dd, J=8.8, 2.0 Hz, 1H) 7.85 (d, J=8.80 Hz, 1H) 5.87 (d, J=7.6 Hz, 1H), 3.59-3.78 (m, 4H) 3.0 (d, J=7.6 Hz, 1H), 2.50 (t, J=7.6 Hz, 1H) 2.42 (s, 1H) 2.24-2.52 (m, 4H) 1.75 (s, 3H).

Example 73

4-((1S,3R,4S,5S,8S,12R)-3-hydroxy-4,5-dimethyl-6-oxo-9,13-dioxa-7-azatetracyclo[6.3.1.1$^{1,4}$.0$^{5,12}$]tridec-7-yl)-2-(trifluoromethyl)benzonitrile (73)

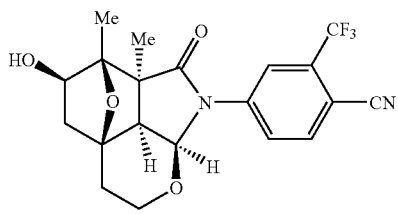

Preparation 73A

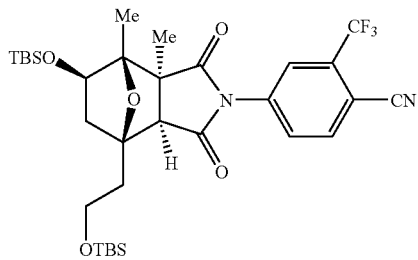

Preparation 73A was prepared from Preparation 16D by the general method shown for Preparation 17A using methyl iodide as an electrophile.

HPLC: 4.463 min (RT) (Chromolith column 4.6×50 mm eluting with 10-90% aqueous MeOH over 4 minutes containing 0.1% TFA, 4 mL/min, monitoring at 220 nm). MS (ES): m/z=653 [M+H]$^+$.

Example 73

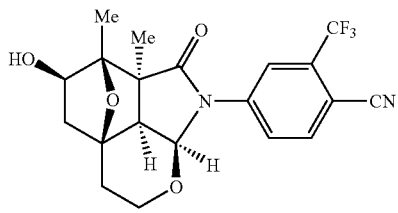

Example 73 was prepared from Preparation 73A by the general methods shown for Example 17.

HPLC: 2.50 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]$^+$.

Example 74

Methyl ((1R,3S,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$]tridec-3-yl)carbamate (74)

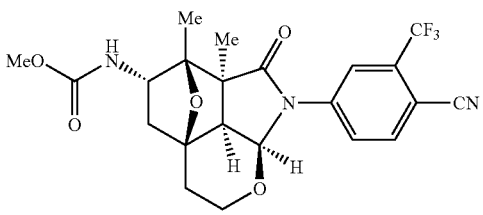

Example 74 was prepared from Example 73 by the general methods shown for Examples 12-14.

HPLC: 2.611 min (RT) (Chromolith column 4.6×50 mm eluting with 10-90% aqueous MeOH over 4 minutes containing 0.1% TFA, 4 mL/min, monitoring at 220 nm). MS (ES): m/z=466 [M+H]$^+$.

Example 75

4-((1S,3S,4S,5S,8S,12R)-3-hydroxy-4,5-dimethyl-6-oxo-9,13-dioxa-7-azatetracyclo[6.3.1.1$^{1,4}$.0$^{5,12}$]tridec-7-yl)-2-(trifluoromethyl)benzonitrile (75)

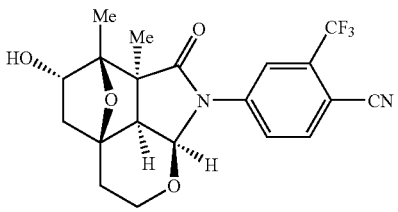

Example 75 was prepared from Example 73 by the general methods shown for Examples 3 and 4.

HPLC: 2.482 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]$^+$.

Example 76

4-((1R,3R,4S,5S,8S,12R)-3-azido-4,5-dimethyl-6-oxo-9,13-dioxa-7-azatetracyclo[6.3.1.1$^{1,4}$.0$^{5,12}$]tridec-7-yl)-2-(trifluoromethyl)benzonitrile (76)

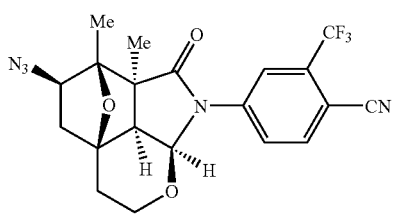

Example 76 was prepared from Example 75 by the general method shown for Example 12.

HPLC: 3.001 min (RT) (Chromolith column 4.6×50 mm eluting with 10-90% aqueous MeOH over 4 minutes containing 0.1% TFA, 4 mL/min, monitoring at 220 nm). MS (ES): m/z=434 [M+H]$^+$.

Example 77

Methyl ((1R,3R,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$]tridec-3-yl)carbamate (77)

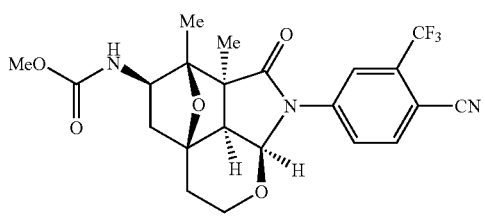

Example 77 was prepared from Example 76 by the general method shown for Examples 13 and 14.

HPLC: 2.498 min (RT) (Chromolith column 4.6×50 mm eluting with 10-90% aqueous MeOH over 4 minutes containing 0.1% TFA, 4 mL/min, monitoring at 220 nm). MS (ES): m/z=466 [M+H]$^+$.

Example 78

Isopropyl ((1R,3R,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$]tridec-3-yl)carbamate (78)

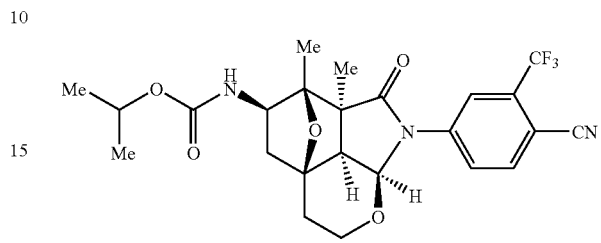

Example 78 was prepared from Example 76 by the general method shown for Examples 13 and 14.

HPLC: 2.865 min (RT) (Chromolith column 4.6×50 mm eluting with 10-90% aqueous MeOH over 4 minutes containing 0.1% TFA, 4 mL/min, monitoring at 220 nm). MS (ES): m/z=494 [M+H]$^+$.

Example 79

4-((1R,2S,4R,5S,8S,12R)-2-hydroxy-4,5-dimethyl-6-oxo-9,13-dioxa-7-azatetracyclo[6.3.1.1$^{1,4}$.0$^{5,12}$]tridec-7-yl)-2-(trifluoromethyl)benzonitrile (79)

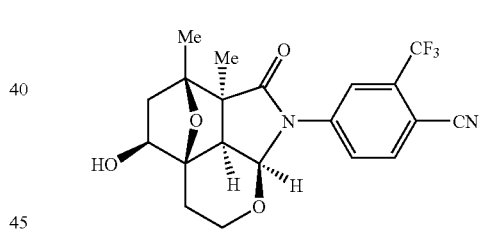

Preparation 79A

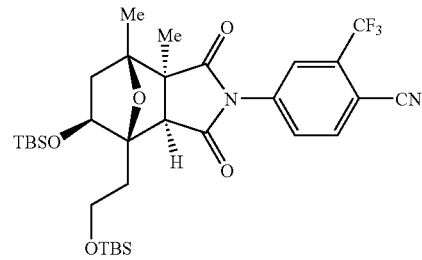

Preparation 79A was prepared from Preparation 15A by the general method shown for Preparation 17A using methyl iodide as an electrophile.

HPLC: 3.90 min (RT) (Chromolith column 4.6×50 mm eluting with 10-90% aqueous MeOH over 4 minutes containing 0.1% TFA, 4 mL/min, monitoring at 220 nm). MS (ES): m/z=653 [M+H]+.

Example 79

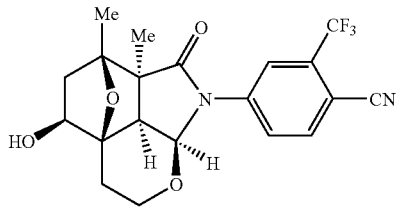

Example 79 was prepared from Preparation 79A by the general methods shown for Example 17.
HPLC: 2.123 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]+.

Example 80

(1R,3S,4S,5S,8S,12R)-3-azido-7-(4-chloro-3-(trifluoromethyl)phenyl)-4-methyl-9,13-dioxa-7-azatetracyclo[6.3.1.1$^{1,4}$.0$^{5,12}$]tridecan-6-one (80)

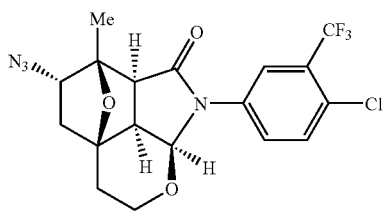

Example 80 was prepared from Example 136 by the general method shown for Example 12.
HPLC: 3.180 min (RT) (Chromolith column 4.6×50 mm eluting with 10-90% aqueous MeOH over 4 minutes containing 0.1% TFA, 4 mL/min, monitoring at 220 nm). MS (ES): m/z=429 [M+H]+.

Example 81

4-((1R,3R,4S,5S,8S,12R)-3-azido-4-methyl-6-oxo-9,13-dioxa-7-azatetracyclo[6.3.1.1$^{1,4}$.0$^{5,12}$]tridec-7-yl)-2-(trifluoromethyl)benzonitrile (81)

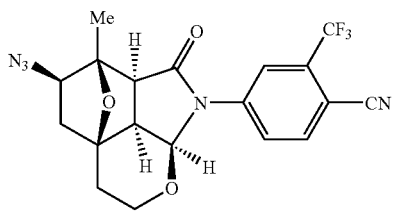

Example 81 was prepared from Example 156 by the general method shown for Example 12.
HPLC: 2.943 min (RT) (Chromolith column 4.6×50 mm eluting with 10-90% aqueous MeOH over 4 minutes containing 0.1% TFA, 4 mL/min, monitoring at 220 nm). MS (ES): m/z=420 [M+H]+.

Example 82

4-((1R,3S,4S,5S,8S,12R)-3-azido-4-methyl-6-oxo-9,13-dioxa-7-azatetracyclo[6.3.1.1$^{1,4}$.0$^{5,12}$]tridec-7-yl)-2-(trifluoromethyl)benzonitrile (82)

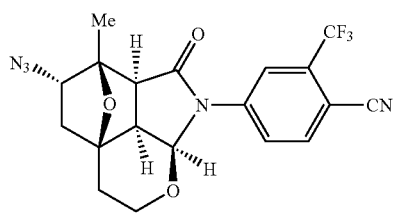

Example 82 was prepared from Example 1 by the general method shown for Example 12.
HPLC: 2.865 min (RT) (Chromolith column 4.6×50 mm eluting with 10-90% aqueous MeOH over 4 minutes containing 0.1% TFA, 4 mL/min, monitoring at 220 nm). MS (ES): m/z=420 [M+H]+.

Example 83

4-((1R,3R,4S,5S,8S,12R)-3-azido-4-methyl-6-oxo-9,13-dioxa-7-azatetracyclo[6.3.1.1$^{1,4}$.0$^{5,12}$]tridec-7-yl)-2,6-dichlorobenzonitrile (83)

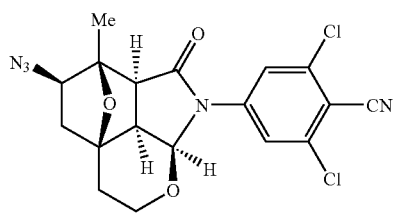

Example 83 was prepared from Example 158 by the general method shown for Example 12.
HPLC: 3.120 min (RT) (Chromolith column 4.6×50 mm eluting with 10-90% aqueous MeOH over 4 minutes containing 0.1% TFA, 4 mL/min, monitoring at 220 nm). MS (ES): m/z=478 [M+H]+.

Example 84

(1R,2S,4R,5S,8S,12R)-2-azido-7-(4-chloro-3-(trifluoromethyl)phenyl)-4-methyl-9,13-dioxa-7-azatetracyclo[6.3.1.1$^{1,4}$.0$^{5,12}$]tridecan-6-one (84)

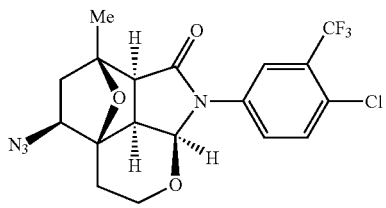

Example 84 was prepared from Example 110 by the sequential application of the methods described in Examples 3, 4 and 12.

HPLC: 3.236 min (RT) (Chromolith column 4.6×50 mm eluting with 10-90% aqueous MeOH over 4 minutes containing 0.1% TFA, 4 mL/min, monitoring at 220 nm). MS (ES): m/z=429 [M+H]$^+$.

Example 85

2-Chloro-4-((1R,2S,4R,5S,8S,12R)-4-methyl-6-oxo-2-((4-(trifluoromethyl)-2-pyrimidinyl)amino)-9,13-dioxa-7-azatetracyclo[6.3.1.1$^{1,4}$.0$^{5,12}$]tridec-7-yl)benzonitrile (85)

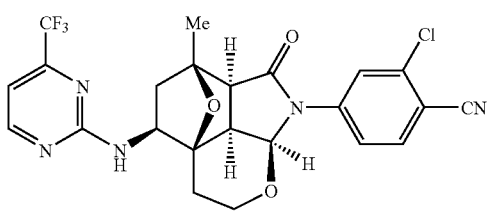

Example 85 was prepared from Example 45 and 2-chloro-4-trifluoromethylpyrimidine by the general method described in Example 46.

HPLC: 3.358 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=504.0 [M−H]$^-$.

Example 86

2-Chloro-4-((1R,2S,4R,5S,8S,12R)-4-methyl-6-oxo-2-(2-pyrimidinylamino)-9,13-dioxa-7-azatetracyclo[6.3.1.1$^{1,4}$.0$^{5,12}$]tridec-7-yl)benzonitrile (86)

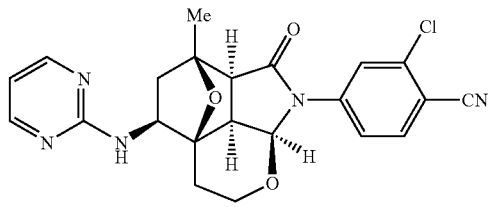

Example 86 was prepared from Example 45 and 2-chloropyrimidine by the general method shown for Example 46.

HPLC: 2.503 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=438.0 [M+H]$^+$.

Example 87

2-Chloro-4-((1R,2S,4R,5S,8S,12R)-4-methyl-6-oxo-2-(4-pyrimidinylamino)-9,13-dioxa-7-azatetracyclo[6.3.1.1$^{1,4}$.0$^{5,12}$]tridec-7-yl)benzonitrile (87)

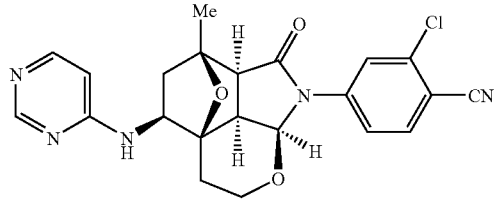

Example 87 was prepared from Example 45 and 4-chloropyrimidine by the general method described for Example 46.

HPLC: 1.908 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=438.1 [M+H]$^+$.

Example 88

2-Chloro-4-((1R,2S,4R,5S,8S,12R)-2-((4-fluorophenyl)sulfonyl)-4-methyl-6-oxo-9,13-dioxa-7-azatetracyclo[6.3.1.1$^{1,4}$.0$^{5,12}$]tridec-7-yl)benzonitrile (88)

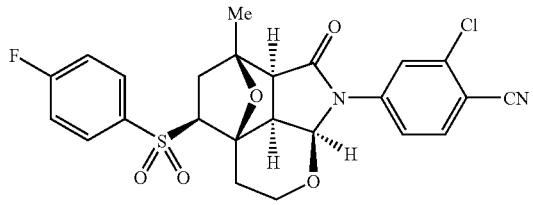

To a suspension of NaH (1.785 mg, 0.045 mmol) in dry DMSO (800 μL) at 22° C. under nitrogen, was added 4-fluorobenzenethiol (4.54 μL, 0.043 mmol). Following cessation of gas evolution, a solution of Preparation 28A (20 mg, 0.041 mmol) in 0.4 mL DMSO was added and the reaction mixture was stirred at room temperature. After 1.5 h, the reaction mixture was diluted with 1 mL EtOAc and 0.5 mL water. The layers were separated and the aqueous layer was backextracted with EtOAc (2×5 mL). The colorless organic layer was washed with water and brine, and then combined and dried over anhydrous magnesium sulfate. Filtration and concentration in vacuo afforded a colorless oil.

The crude sulfide was purified by flash chromatography eluting with 0-10% acetone/$CH_2Cl_2$ as the mobile phase, to afford 0.020 g as a white foam.

To a solution of thioether (19 mg, 0.040 mmol) in dry $CH_2Cl_2$ (403 μL) at 22° C. under nitrogen was added mCPBA (20.89 mg, 0.121 mmol) and the resulting colorless solution was stirred at room temperature. After 1.5 h, the sulfide was not present as measured by HPLC. LCMS indicated correct m/z for desired sulfone. The reaction mixture was diluted with 0.5 mL $CH_2Cl_2$ and quenched with 0.4 mL 10% aq. $Na_2SO_3$ and 0.4 mL saturated aq. $NaHCO_3$. The biphasic mixture was stirred vigorously 30 min (until clear, colorless). The organic and aqueous layers separated and the aqueous layer was backextracted with $CH_2Cl_2$ (2×5 mL). The colorless organics were combined and dried over anhydrous $Na_2SO_4$. Filtration and concentration in vacuo afforded 0.021 g of Example 88 as a white solid.

HPLC: 2.990 min (RT) (YMC ODS column 4.6×50 mm eluting with 10-90% aqueous methanol containing 0.2% $H_3PO_4$ over 4 minutes, 4 mL/min, monitoring at 220 nm). MS (ES): m/z=561.2 [M+OAc]$^-$. $^1$H NMR (400 MHz, DMSO-$d_6$) δ ppm 7.93-8.01 (3H, m), 7.81 (1H, d, J=2.01 Hz), 7.59 (1H, dd, J=8.69, 1.89 Hz), 7.51 (2H, t, J=8.81 Hz), 6.01 (1H, d, J=7.81 Hz), 4.10 (1H, dd, J=8.94, 4.41 Hz), 3.49-3.57 (1H, m), 3.34-3.40 (1H, m), 2.95 (1H, d, J=7.81 Hz), 2.74 (1H, t, J=7.81 Hz), 2.24-2.34 (1H, m), 2.07-2.19 (2H, m), 1.79 (1H, dd, J=13.60, 4.78 Hz), 1.53 (3H, s).

Example 89

N-(5-cyclopropyl-1H-pyrazol-3-yl)-2-(3-(3-pyridinyl)-1-pyrrolidinyl)pyrrolo[2,1-f][1,2,4]triazin-4-amine (89)

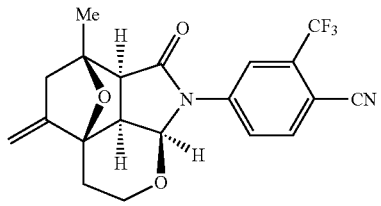

Example 89 was prepared from Example 3 by the general method described for Example 49.

HPLC: 2.860 min (RT) (Chromolith column 4.6×50 mm eluting with 10-90% aqueous MeOH over 4 minutes containing 0.1% TFA, 4 mL/min, monitoring at 220 nm). MS (ES): m/z=391 [M+H]$^+$.

Examples 90 and 91

4-((1R,2S,4R,5S,8S,12R)-2-(Methoxyamino)-4-methyl-6-oxo-9,13-dioxa-7-azatetracyclo[6.3.1.1$^{1,4}$.0$^{5,12}$]tridec-7-yl)-2-(trifluoromethyl)benzonitrile (90) and 4-((1R,2R,4R,5S,8S,12R)-2-(Methoxyamino)-4-methyl-6-oxo-9,13-dioxa-7-azatetracyclo[6.3.1.1$^{1,40}$.0$^{5,12}$]tridec-7-yl)-2-(trifluoromethyl)benzonitrile (91)

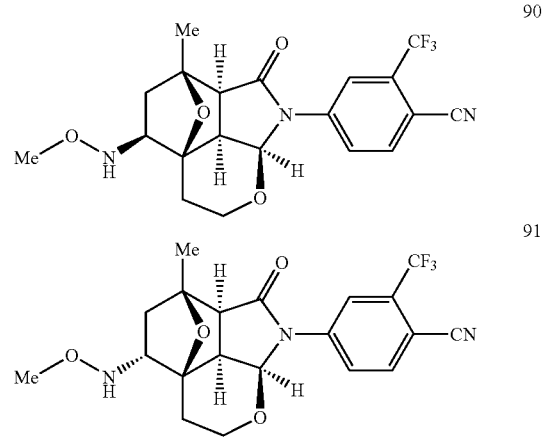

Example 30 (100 mg, 0.237 mmol) was dissolved in DCE (2 mL) at room temperature. To this mixture was added acetic acid (0.14 mL) followed by addition of sodium cyanoborohydride (150 mg, 1.187 mmol) and stirred for 20 h. The reaction was judged completed by LCMS. Two new peaks were observed: peak 1 at 3.080 min and peak 2 at 3.306 min. The reaction mixture was diluted with ethyl acetate (30 ml) and was extracted with sodium bicarbonate (2×30 ml). The ethyl acetate layer was then washed with brine, dried over anhydrous sodium sulfate, filtered and concentrated under reduced pressure. The crude was purified on Isco (120 g column) 0-20% EtOAc-DCM to give Example 91 (peak 1) (42 mg, 0.099 mmol) and Example 90 (peak 2) (10 mg, 0.023 mmol). The NOE characterization of both the peak revealed that Example 91 and Example 90 were endo and exo isomers respectively.

Example 90

MS (ES): m/z=424.23 [M+H]$^+$; HPLC (RT): 3.65 min (YMC ODS column 4.6×50 mm eluting with 10-90% aqueous MeOH containing 0.2% $H_3PO_4$ over 4 minutes, 4 mL/min, monitoring at 220 nm); $^1$H NMR (500 MHz, $CD_3OD$) δ ppm 1.61 (s, 3H) 1.76 (dd, J=13.47, 5.77 Hz, 1H) 1.90 (d, J=14.30 Hz, 1H) 2.22 (t, 1H) 2.39-2.58 (m, 1H) 3.00 (s, 2H) 3.48-3.67 (m, 3H) 3.78-3.94 (m, 3H) 6.07-6.25 (m, 1H) 7.90-8.04 (m, 2H) 8.16 (s, 1H).

Example 91

MS (ES): m/z=424.25 [M+H]$^+$; HPLC (RT): 3.461 min (YMC ODS column 4.6×50 mm eluting with 10-90% aqueous MeOH containing 0.2% $H_3PO_4$ over 4 minutes, 4 mL/min, monitoring at 220 nm); $^1$H NMR (500 MHz, $CD_3OD$) δ ppm 1.26 (dd, J=12.65, 6.05 Hz, 1H) 1.51 (s, 3H) 1.71 (d, J=14.85 Hz, 1H) 1.82-1.90 (m, 1H) 2.07-2.25 (m, 1H) 2.80 (d, J=8.25 Hz, 1H) 3.21 (dd, J=10.45, 6.05 Hz, 1H) 3.34 (t, J=7.70 Hz, 1H) 3.39-3.58 (m, 5H) 6.01 (d, J=7.70 Hz, 1H) 7.77-7.98 (m, 2H) 8.09 (s, 1H).

Example 92

4-((1R,2E,4R,5S,8S,12R)-4-Methyl-2-(4-morpholinylimino)-6-oxo-9,13-dioxa-7-azatetracyclo[6.3.1.1$^{1,4}$.0$^{5,12}$]tridec-7-yl)-2-(trifluoromethyl)benzonitrile (92)

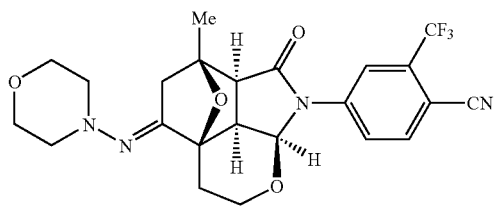

To a stirring solution of Example 3 (85 mg, 0.216 mmol) in pyridine (2 mL) was added. N-aminomorpholine hydrochloride (0.287 mmol, 1.5 eq). The mixture was stirred at 50° C. for 1 h. The reaction was judged completed by LCMS. The reaction mixture was cooled to room temperature. It was then diluted with EtOAc (6 ml) and extracted with 1N HCl (2×10 ml). The ethyl acetate layer was then washed with brine, dried over anhydrous sodium sulfate, filtered and concentrated under reduced pressure. The crude was purified on Isco (12 g column) 0-5% MeOH-DCM to give Example 92 (59 mg, 58%, 0.133 mmol).

HPLC: 3.541 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=477.3 [M+H]$^+$; $^1$H NMR (500 MHz, $CD_3OD$) δ ppm 1.72 (s, 3H) 1.86 (d, J=14.85 Hz, 1H) 2.29-2.43 (m, 1H) 2.56 (d, J=17.32 Hz, 1H) 2.65-2.90 (m, 6H) 3.10 (d, J=7.97 Hz, 1H) 3.64 (dd, J=7.56, 2.06 Hz, 2H) 3.72-3.91 (m, 4H) 6.03 (d, J=7.70 Hz, 1H) 7.89-8.11 (m, 2H) 8.17 (s, 1H).

Example 93

4-((1R,3E,4S,5S,8S,12R)-4-Methyl-3-(4-morpholinylimino)-6-oxo-9,13-dioxa-7-azatetracyclo[6.3.1.1$^{1,4}$.0$^{5,12}$]tridec-7-yl)-2-(trifluoromethyl)benzonitrile (93)

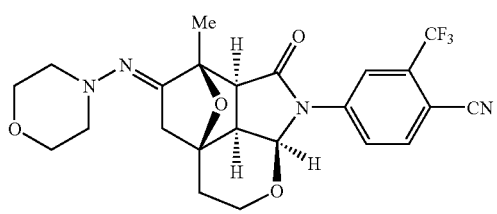

Example 93 was prepared from Example 271 by the general method described for Example 92.

HPLC: 3.491 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=477.4 [M+H]$^+$. $^1$H NMR d$^6$ DMSO: 8.20 ppm (1H, d, J=8.52 Hz), 8.14 ppm (1H, d, J=1.65 Hz), 7.94 ppm (1H, d), 6.07 ppm (1H, d, J=7.7 Hz), 3.65 ppm (4H, t, J=4.67 Hz), 3.52 ppm (2H, s), 2.84 ppm (1H, d, J=7.97 Hz), 2.76-2.82 ppm (2H, m), 2.68-2.76 ppm (3H, m), 2.60 (1H, d, J=16.22 Hz), 2.40-2.46 (1H, m), 1.99-2.08 (1H, m), 1.87-1.95 (1H, m), 1.59 ppm (3H, s).

Example 94

4-((1R,2E,4R,5S,8S,12R)-4-Methyl-2-(methylhydrazono)-6-oxo-9,13-dioxa-7-azatetracyclo[6.3.1.1$^{1,4}$.0$^{5,12}$]tridec-7-yl)-2-(trifluoromethyl)benzonitrile (94)

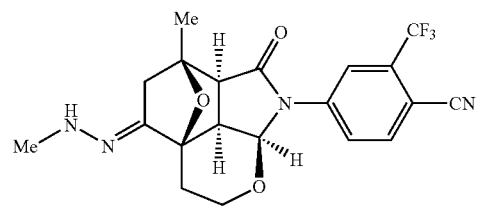

Example 94 was prepared from Example 3 by the general method described for Example 92.

HPLC: 3.078 min (RT) (YMC ODS column 4.6×50 mm eluting with 10-90% aqueous MeOH containing 0.2% $H_3PO_4$ over 4 minutes, 4 mL/min, monitoring at 220 nm). MS (ES): m/z=421.2 [M+H]$^+$.

Example 95

2-Chloro-4-((1R,4S,5S,8S,12R)-4-methyl-3-methylene-6-oxo-9,13-dioxa-7-azatetracyclo[6.3.1.1$^{1,4}$.0$^{5,12}$]tridec-7-yl)benzonitrile (95)

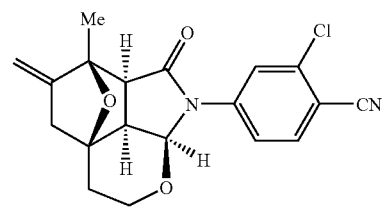

Example 95 was prepared by the general method described in Example 49.

HPLC: 2.658 min (RT) (Chromolith column 4.6×50 mm eluting with 10-90% aqueous MeOH over 4 minutes containing 0.1% TFA, 4 mL/min, monitoring at 220 nm). MS (ES): m/z=357 [M+H]$^+$.

Example 96

2-Chloro-4-((1R,2S,4R,5S,8S,12R)-2-(1H-imidazol-1-yl)-4-methyl-6-oxo-9,13-dioxa-7-azatetracyclo[6.3.1.1$^{1,4}$.0$^{5,12}$]tridec-7-yl)benzonitrile (96)

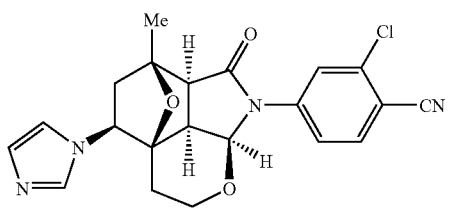

To a suspension of Example 45 in 0.5 mL water was added 85% phosphoric acid (0.05 mL), resulting in a solution having a pH=2. Paraformaldehyde (0.005 g, 0.17 mmol) was then added. Glyoxal (40% in water; 0.025 mL; 0.17 mmol) was added and the resulting milky suspension was heated to 80° C. After 15 minutes, 0.030 mL saturated aq. NH$_4$Cl was added and the solution was heated to 100° C. overnight. The reaction mixture was diluted with water and saturated aq. NaHCO$_3$ was added, followed by the addition of EtOAc. The aqueous layer was extracted three times with 5 mL EtOAc and washed with brine to reduce emulsion. The organic portions were combined, dried (MgSO$_4$), filtered, and concentrated in vacuo to afford 0.040 g (57%) of Example 96 as a tan solid.

HPLC: 1.920 min (RT) (YMC ODS column 4.6×50 mm eluting with 10-90% aqueous methanol containing 0.2% H$_3$PO$_4$ over 4 minutes, 4 mL/min, monitoring at 220 nm). MS (ES): m/z=411.0 [M+H]$^+$. $^1$H NMR (400 MHz, CDCl$_3$) δ ppm 7.74 (1H, app s), 7.60 (1H, d, J=8.60 Hz), 7.53 (1H, dd, J=8.60, 2.01 Hz), 7.49 (1H, s), 7.01 (1H, s), 6.95 (1H, s), 5.83 (1H, d, J=7.55 Hz), 4.22-4.21 (1H, m), 3.47 (2H, d, J=7.8 Hz), 2.85 (1H, d, J=7.8 Hz), 2.55-2.49 (2H, m), 2.01-1.96 (1H, m), 1.82 (3H, s), 1.69-1.61 (1H, m), 1.29-1.25 (1H, m).

Example 97

4-((1R,2R,4R,5S,8S,12R)-2-((4-Fluorophenyl)sulfonyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (97)

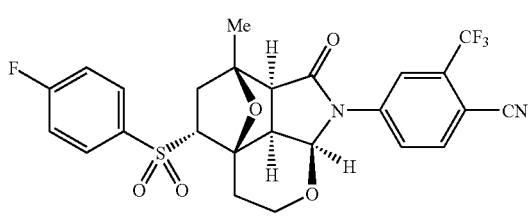

Example 97 prepared from Example 3 by the general method described in Example 88.

HPLC: 3.361 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=595.1 [M+OAc]$^-$.

Example 98

4-((1R,2R,4R,5S,8S,12R)-2-(Ethylsulfonyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (98)

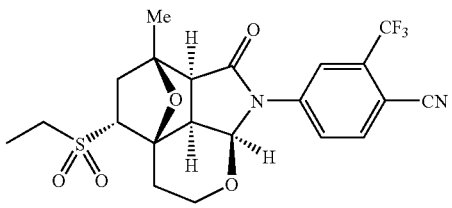

Example 98 prepared from Example 3 by the general method described in Example 88.

HPLC: 2.861 min (RT) (YMC ODS column 4.6×50 mm eluting with 10-90% aqueous MeOH containing 0.2% H$_3$PO$_4$ over 4 minutes, 4 mL/min, monitoring at 220 nm). MS (ES): m/z=529.1 [M+OAc]$^-$.

Examples 99 and 100

(1S,3R,4S,5S,8S,12R)-7-(4-Cyano-3-(trifluoromethyl)phenyl)-3-hydroxy-4-methyl-6-oxo-N-(2,2,2-trifluoroethyl)-9,13-dioxa-7-azatetracyclo[6.3.1.1$^{1,4}$.0$^{5,12}$]tridecane-5-carboxamide (99) and (1S,3R,4S,5S,8S,12R)-7-(4-Cyano-3-(trifluoromethyl)phenyl)-3-hydroxy-4-methyl-6-oxo-N-(2,2,2-trifluoroethyl)-9,13-dioxa-7-azatetracyclo[6.3.1.1$^{1,4}$.0$^{5,12}$]tridecane-5-carboxamide (100)

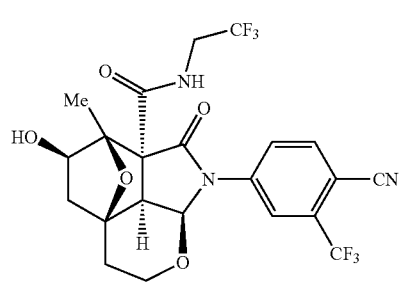

99

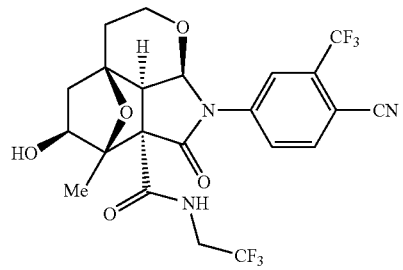

100

Examples 99 and 100 were prepared from Example 20 by the general method described in Preparation 17C. The individual antipodes were separated by chiral normal phase chromatography. Chiracel OJ column 4.6×250 mm, eluting with 30% 1:1 EtOH/MeOH in heptane at 80 mL/min and monitoring at 220 nm.

Example 99

Chiral HPLC: >99% ee, rt=7.76 min, Chiracel OJ column, 4.6×250 mm, 25% 1:1 EtOH/MeOH in heptane, 1 mL/min, 220 nm. HPLC: 2.915 min (RT) (YMC ODS-A column 4.6×50 mm eluting with 10-90% aqueous MeOH over 4 minutes containing 0.1% $H_3PO_4$, 4 mL/min, monitoring at 220 nm). MS: [M–H]$^-$=518.0. The absolute stereochemistry of Example 99 has not been established. Although the compound represents a single antipode, the nomenclature and structure shown does not reflect the absolute stereochemistry of the compound.

Example 100

Chiral HPLC: >99% ee @ 15.3 min (RT) (Chiracel OJ column, 4.6×250 mm, 25% 1:1 EtOH/MeOH in heptane, 1 mL/min, 220 nm). HPLC: 2.915 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=518.1 [M+H]$^+$. The absolute stereochemistry of Example 100 has not been established. Although the compound represents a single antipode, the nomenclature and structure shown does not reflect the absolute stereochemistry of the compound.

Example 101

(1R,2S,4R,5S,8S,12R)—N-Benzyl-7-(4-cyano-3-(trifluoromethyl)phenyl)-2-hydroxy-4-methyl-6-oxo-9,13-dioxa-7-azatetracyclo[6.3.1.1$^{1,4}$.0$^{5,12}$]tridecane-5-carboxamide (101)

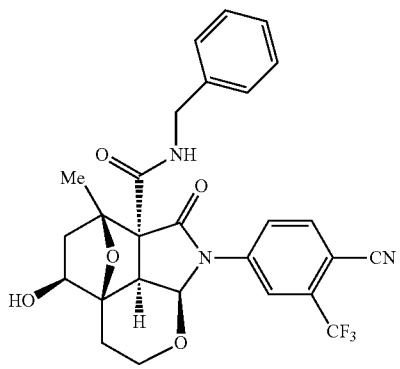

Example 101 was prepared from Example 17B by the general method described in Example 17.

HPLC: 3.313 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=526.2 [M–H]$^-$.

Example 102

3a,6-Epoxy-3aH-pyrano[2,3,4-cd]isoindole-6a(4H)-carboxamide, 8-[4-cyano-3-(trifluoromethyl)phenyl] octahydro-4-hydroxy-6-methyl-7-oxo-N-phenyl-, (3aR,4S,6R,6aS,8aS,8bR)— (102)

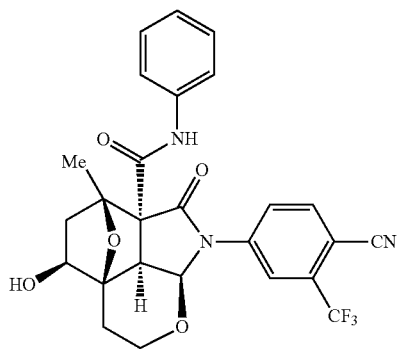

Example 102 was prepared from Example 17B by the general method described in Example 17.

HPLC: 3.431 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=512.0 [M–H]$^-$.

Example 103

Methyl (2E)-((1R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-ylidene)acetate (103)

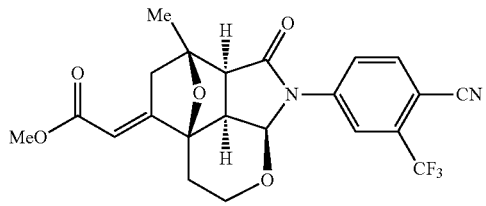

To a solution of Example 3 (50 mg, 0.128 mmol) in THF (2 mL) was added methyl(triphenylphosphoranylidene)acetate (51 mg, 0.153 mmol). The reaction mixture was stirred for 3 days and then concentrated in vacuo. The resulting residue was purified by ISCO column (4.0 g column, EtOAc/hexane=0-80%, 10 mL/min) to give Example 103 (40.5 mg, 71%) as a yellow solid.

HPLC: 3.023 min (RT) (YMC ODS-A column 4.6×50 mm eluting with 10-90% aqueous MeOH over 4 minutes containing 0.1% $H_3PO_4$, 4 mL/min, monitoring at 220 nm). MS (ES): m/z=440 [M+H]$^+$; $^1$H NMR (500 MHz, CDCl$_3$) δ ppm 8.08 (d, J=2.20 Hz, 1H) 7.93 (dd, J=8.25, 2.20 Hz, 1H) 7.83 (d, J=8.80 Hz, 1H) 5.89 (d, J=7.7 Hz, 1H) 5.70 (s, 1H) 3.70-3.75

(m, 5H), 2.82-3.05 (m, 3H) 2.58 (t, J=7.7 Hz, 1H) 2.20-2.27 (m, 1H) 1.98 (d, J=14.3 Hz, 1H) 1.81 (s, 3H).

Example 104

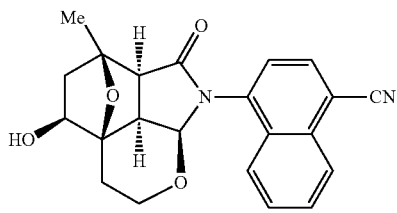

Example 104 was prepared from 4-cyano-1-naphthalamine and Preparation 15B by the general method described in Example 15.

HPLC (RT): 2.663 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=377.22 $[M+H]^+$.

Example 105

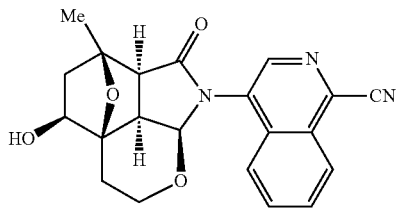

Example 105 was prepared from 2-cyano-7-aminoquinoline and Preparation 15B by the general method described in Example 15.

HPLC (RT): 2.483 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=378.2 $[M+H]^+$.

Examples 106 and 107

4-((1R,2S,4R,5S,8S,12R)-2-Hydroxy-2,4-dimethyl-6-oxo-9,13-dioxa-7-azatetracyclo[6.3.1.1$^{1,4}$.0$^{5,12}$]tridec-7-yl)-2-(trifluoromethyl)benzonitrile (107)

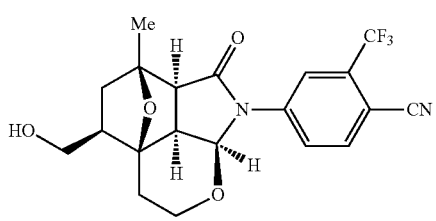

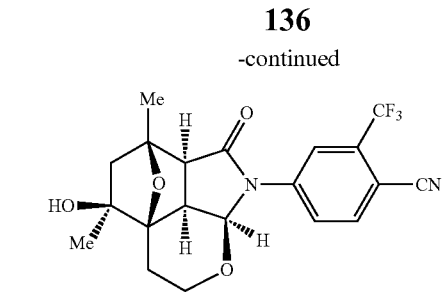

Examples 106 and 107 were prepared from Example 89 by the general method described for Preparations 1D and 1E in a ratio of 20:1 by mass.

Example 106

HPLC: 2.307 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=409 $[M+H]^+$.

Example 107

HPLC: 2.113 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=409 $[M+H]^+$.

Examples 108 and 109

1-(4-(8-(2-Chlorophenoxy)[1,2,4]-triazolo[4,3-b]pyridazin-3-yl)phenyl)-3-(2-(trifluoromethyl)phenyl)urea (109)

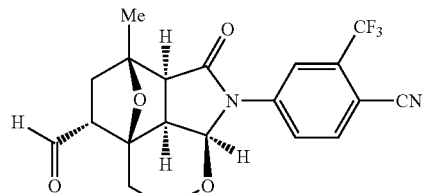

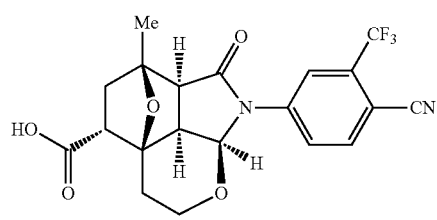

To a solution of Example 106 (361 mg, 0.885 mmol) in $CH_2Cl_2$ (10 mL) was added Dess-Martin periodinane (750 mg, 1.77 mmol). The reaction mixture was stirred at room temperature for 2.5 h and then concentrated in vacuo. The resulting residue was purified by ISCO column (12 g column, EtOAc/hexane=0-40%, 30 mL/min) to give Example 108 (113 mg, 31%) as yellow semi-solid. The column was flushed with 10% MeOH/$CH_2Cl_2$, the desired fractions were combined, concentrated to afford Example 109 (105 mg, 28%) as a yellow solid.

Example 108

HPLC: 2.472 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=439 [M+H+MeOH]$^+$.

Example 109

HPLC: 2.680 min (RT) (Chromolith SpeedROD column 4.6×50 mm, 10-90% aqueous MeOH over 4 minutes containing 0.2% phosphoric acid, 4 mL/min, monitoring at 220 nM). MS (ES): m/z=423 [M+H]$^+$.

Examples 110 to 126

(1S,3R,4S,5S,8S,12R)-7-(4-chloro-3-(trifluoromethyl)phenyl)-3-hydroxy-4-methyl-9,13-dioxa-7-azatetracyclo[6.3.1.1$^{1,4}$.0$^{5,12}$]tridecan-6-one (110)

(1R,2S,4R,5S,8S,12R)-7-(4-bromo-3-(trifluoromethyl)phenyl)-2-hydroxy-4-methyl-9,13-dioxa-7-azatetracyclo[6.3.1.1$^{1,4}$.0$^{5,12}$]tridecan-6-one (111)

(1R,2S,4R,5S,8S,12R)-7-(4-chloro-2-methyl-3-(trifluoromethyl)phenyl)-2-hydroxy-4-methyl-9,13-dioxa-7-azatetracyclo[6.3.1.1$^{1,4}$.0$^{5,12}$]tridecan-6-one (112)

(1R,2S,4R,5S,8S,12R)-7-(3,4-dichlorophenyl)-2-hydroxy-4-methyl-9,13-dioxa-7-azatetracyclo[6.3.1.1$^{1,4}$.0$^{5,12}$]tridecan-6-one (113)

(1R,2S,4R,5S,8S,12R)-7-(3-bromo-4-chlorophenyl)-2-hydroxy-4-methyl-9,13-dioxa-7-azatetracyclo[6.3.1.1$^{1,4}$.0$^{5,12}$]tridecan-6-one (114)

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-3-methyl-2-(trifluoromethyl)benzonitrile (115)

2-Chloro-3-fluoro-4-4(1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (116)

(1R,2S,4R,5S,8S,12R)-7-(3,5-dichlorophenyl)-2-hydroxy-4-methyl-9,13-dioxa-7-azatetracyclo[6.3.1.1$^{1,4}$.0$^{5,12}$]tridecan-6-one (117)

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-iodobenzonitrile (118)

2-Chloro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (119)

2-Chloro-5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (120)

2-Fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-3-methylbenzonitrile (121)

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-methylbenzonitrile (122)

4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-methoxybenzonitrile (123); and 4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2,6-dimethylbenzonitrile (124)

Examples 110 to 126 listed in Table 1 below were prepared according to the general procedure described in Example 15.

TABLE 1

| # | $R^x$ | $R^y$ | $R^z$ | $R^m$ | HPLC Ret. time (min) | Molecular mass [M + H]$^+$ |
|---|---|---|---|---|---|---|
| 110[d,i] | H | CF$_3$ | Cl | H | 2.503[a] | 404 |
| 111[d] | H | CF$_3$ | Br | H | 3.04[b] | 506.1[c] |
| 112[e] | Me | CF$_3$ | Cl | H | 2.988[b] | 418.1 |
| 113[d] | H | Cl | Cl | H | 2.820[b] | 370.1 |
| 114[f,j] | H | Br | Cl | H | 2.378[a] | 414 |
| 115[e] | Me | CF$_3$ | CN | H | 2.007[a] | 409 |
| 116[d] | F | Cl | CN | H | 2.195[b] | 379.1 |
| 117[d] | H | Cl | H | Cl | 2.881[b] | 429.2[c] |
| 118[g] | H | I | CN | H | 1.818[a] | 453 |
| 119[d] | H | Cl | CN | H | 2.228[b] | 361.3 |
| 120[d] | H | CN | Cl | H | 2.301[b] | 361.1 |
| 121[d] | Me | F | CN | H | 2.488[b] | 359.2 |
| 122[d] | H | Me | CN | H | 2.337[b] | 341.2 |
| 123[h] | H | OMe | CN | H | 2.208[b] | 357.2 |
| 124[d] | H | Me | CN | Me | 2.63[b] | 355.2 |
| 125 | H | CF$_3$ | NO$_2$ | H | 3.125[b] | 415.2 |
| 126 | H | H | H | H | 1.668[b] | 302.2 |

[a]Chromolith column 4.6 × 50 mm eluting with 10-90% aqueous MeOH over 4 minutes containing 0.1% TFA, 4 mL/min, monitoring at 220 nm.
[b]YMC Combiscreen ODS-A S5 column (4.6 × 50 mm). 10-90% aq. MeOH over 4 min with 0.2% phosphoric acid, 4 mL/min, monitoring @ 220 nm
[c][M + OAc]$^-$
[d]aniline required for synthesis via procedure described in Example 15 was commercially available
[e]Aniline prepared by the methods described in: Salvati, Mark E et al. Preparation of fused succinimides as modulators of nuclear hormone receptor function. PCT Int. Appl. (2003), 763 pp. WO 2003062241 A1 20030731
[f]Aniline prepared by the methods described in: Novak, Michael; Rovin, Lise H.; Pelecanou, Maria; Mulero, Julio J.; Lagerman, Robert K. Journal of Organic Chemistry (1987), 52(10), 2002-10.
[g]Aniline prepared by the methods described in: Van Dort, Marcian E.; Robins, Diane M.; Wayburn, Bess. Journal of Medicinal Chemistry (2000), 43(17), 3344-3347.
[h]Aniline prepared by the methods described in: Mackman, Richard L.; Katz, Bradley A.; Breitenbucher, J. Guy; Hui, Hon C.; Verner, Erik; Luong, Christine; Liu, Liang; Sprengeler, Paul A. Journal of Medicinal Chemistry (2001), 44(23), 3856-3871.
[i][α]$_D$ = −10.20 deg in MeOH at 25° C. (10.0 mg/mL). X-ray crystallography confirms absolute stereochemistry.
[j][α]$_D$ = −6.58 deg in MeOH at 25° C. (10.35 mg/mL). X-ray crystallography and VCD analysis confirms absolute stereochemistry.

Examples 127 to 135

2-Bromo-4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (127)

(1R,2R,4R,5S,8S,12R)-7-(4-chloro-2-methyl-3-(trifluoromethyl)phenyl)-2-hydroxy-4-methyl-9,13-dioxa-7-azatetracyclo[6.3.1.1$^{1,4}$.0$^{5,12}$]tridecan-6-one (128)

2-Fluoro-4-(1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (129)

2-Chloro-6-fluoro-4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (130)

3-Fluoro-4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (131)

2-Chloro-4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (132)

(1R,2R,4R,5S,8S,12R)-7-(3-Bromo-4-chlorophenyl)-2-hydroxy-4-methyl-9,13-dioxa-7-azatetracyclo[6.3.1.1$^{1,4}$.0$^{5,12}$]tridecan-6-one (133)

2-Chloro-4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (134); and 4-((1R,2R,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethoxy)benzonitrile (135)

Examples 127 to 135 listed in Table 2 below were prepared according to the general procedures described in Examples 5 and 6.

TABLE 2

| # | $R^x$ | $R^y$ | $R^z$ | $R^m$ | HPLC Ret. time (min) | Molecular mass [M + H]$^+$ |
|---|---|---|---|---|---|---|
| 127 | H | Br | CN | H | 2.671$^b$ | 464.1$^c$ |
| 128 | Me | CF$_3$ | Cl | H | 3.201$^b$ | 418.2$^c$ |
| 129 | H | CF$_3$ | CN | F | 2.665$^a$ | 413.0 |
| 130 | H | Cl | CN | F | 3.346$^b$ | 379.1 |
| 131 | F | CF$_3$ | CN | H | 2.36$^a$ | 413 |
| 132 | H | Cl | CN | H | 2.53$^b$ | 359.2$^c$ |
| 133 | H | Br | Cl | H | 3.425$^b$ | 416.3 |

TABLE 2-continued

| # | $R^x$ | $R^y$ | $R^z$ | $R^m$ | HPLC Ret. time (min) | Molecular mass [M + H]$^+$ |
|---|---|---|---|---|---|---|
| 134 | H | CF$_3$ | CN | Cl | 3.80$^a$ | 429 |
| 135 | H | OCF$_3$ | CN | H | 2.88$^b$ | 411.0 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$

Examples 136 to 155

(1S,3R,4S,5S,8S,12R)-7-(4-chloro-3-(trifluoromethyl)phenyl)-3-hydroxy-4-methyl-9,13-dioxa-7-azatetracyclo[6.3.1.1$^{1,4}$.0$^{5,12}$]tridecan-6-one (136)

2-Fluoro-4-((1S,3R,4S,5S,8S,12R)-3-hydroxy-4-methyl-6-oxo-9,13-dioxa-7-azatetracyclo[6.3.1.1$^{1,4}$.0$^{5,12}$]tridec-7-yl)benzonitrile (137)

(1S,3R,4S,5S,8S,12R)-7-(4-chloro-3-fluorophenyl)-3-hydroxy-4-methyl-9,13-dioxa-7-azatetracyclo[6.3.1.1$^{1,4}$.0$^{5,12}$]tridecan-6-one (138)

2-Fluoro-4-((1S,3R,4S,5S,8S,12R)-3-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (139)

(1S,3R,4S,5S,8S,12R)-7-(4-chloro-2-methyl-3-(trifluoromethyl)phenyl)-3-hydroxy-4-methyl-9,13-dioxa-7-azatetracyclo[6.3.1.1$^{1,4}$.0$^{5,12}$]tridecan-6-one (140)

(1S,3R,4S,5S,8S,12R)-7-(3-bromo-4-chlorophenyl)-3-hydroxy-4-methyl-9,13-dioxa-7-azatetracyclo[6.3.1.1$^{1,4}$.0$^{5,12}$]tridecan-6-one (141)

4-((1S,3R,4S,5S,8S,12R)-3-hydroxy-4-methyl-6-oxo-9,13-dioxa-7-azatetracyclo[6.3.1.1$^{1,4}$.0$^{5,12}$]tridec-7-yl)-3-methyl-2-(trifluoromethyl)benzonitrile (142)

(1S,3R,4S,5S,8S,12R)-7-(3,4-dichlorophenyl)-3-hydroxy-4-methyl-9,13-dioxa-7-azatetracyclo[6.3.1.1$^{1,4}$.0$^{5,12}$]tridecan-6-one (143)

2-Chloro-3-fluoro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)benzonitrile (144)

(1S,3R,4S,5S,8S,12R)-7-(4-chloro-3-ethynylphenyl)-3-hydroxy-4-methyl-9,13-dioxa-7-azatetracyclo[6.3.1.1^{1,4}.0^{5,12}]tridecan-6-one (145)

2-Bromo-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)benzonitrile (146)

3-Fluoro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)-2-(trifluoromethyl)benzonitrile (147)

2,6-Dichloro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)benzonitrile (148)

(1S,3R,4S,5S,8S,12R)-7-(3,5-dichlorophenyl)-3-hydroxy-4-methyl-9,13-dioxa-7-azatetracyclo[6.3.1.1^{1,4}.0^{5,12}]tridecan-6-one (149)

2-Chloro-6-fluoro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)benzonitrile (150)

4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)-2-methoxybenzonitrile (151)

2-Chloro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)-3-methylbenzonitrile (152)

2-Chloro-4-((1S,3R,4S,5S,8S,12R)-3-hydroxy-4-methyl-6-oxo-9,13-dioxa-7-azatetracyclo[6.3.1.1^{1,4}.0^{5,12}]tridec-7-yl)-6-(trifluoromethyl)benzonitrile (153); and Rac-4-((1R,3S,4R,5R,8R,12S)-3-hydroxy-4-methyl-6-oxo-9,13-dioxa-7-azatetracyclo[6.3.1.1^{1,4}.0^{5,12}]tridec-7-yl)-2-methylbenzonitrile (154)

Examples 136 to 155 listed in Table 3 below were prepared according to the general procedure described in Example 16.

TABLE 3

| # | $R^x$ | $R^y$ | $R^z$ | $R^m$ | HPLC Ret. time (min) | Molecular mass $[M + H]^+$ |
|---|---|---|---|---|---|---|
| 136 | H | $CF_3$ | Cl | H | 2.641[a] | 404 |
| 137 | H | F | CN | H | 1.638[a] | 345 |
| 138 | H | F | Cl | H | 2.13[a] | 354 |
| 139 | H | $CF_3$ | CN | F | 2.437[a] | 413 |
| 140 | Me | $CF_3$ | Cl | H | 2.685[a] | 418 |
| 141 | H | Br | Cl | H | 2.470[a] | 414 |
| 142 | Me | $CF_3$ | CN | H | 2.193[a] | 409 |
| 143 | H | Cl | Cl | H | 2.405[a] | 370 |
| 144 | F | Cl | CN | H | 1.818[a] | 379 |
| 145 | H | —CCH | Cl | H | 2.117[a] | 360 |
| 146 | H | Br | CN | H | 1.920[a] | 405 |
| 147 | F | $CF_3$ | CN | H | 2.15[a] | 413 |
| 148 | H | Cl | CN | Cl | 2.373[a] | 395 |
| 149 | H | Cl | H | Cl | 2.542[a] | 370 |
| 150 | H | Cl | CN | F | 3.091[b] | 379.1 |
| 151 | H | $OCH_3$ | CN | H | 2.353[b] | 357.2 |
| 152 | Me | Cl | CN | H | 2.845[b] | 375.2 |
| 153 | H | $CF_3$ | CN | Cl | 2.58[a] | 429 |
| 154 | H | $CH_3$ | CN | H | 2.493[b] | 341.2 |
| 155 | H | cyclopropyl | CN | H | 2.04[a] | 367 |

[a] Chromolith column 4.6 × 50 mm eluting with 10-90% aqueous MeOH over 4 minutes containing 0.1% TFA, 4 mL/min, monitoring at 220 nm.
[b] YMC Combiscreen ODS-A S5 column (4.6 × 50 mm). 10-90% aq. MeOH over 4 min with 0.2% phosphoric acid, 4 mL/min, monitoring @ 220 nm
[c] [M + OAc]−

Examples 156 to 159

4-((1S,3S,4S,5S,8S,12R)-3-hydroxy-4-methyl-6-oxo-9,13-dioxa-7-azatetracyclo[6.3.1.1^{1,4}.0^{5,12}]tridec-7-yl)-2-(trifluoromethyl)benzonitrile (156)

3-Fluoro-4-((1S,3S,4S,5S,8S,12R)-3-hydroxy-4-methyl-6-oxo-9,13-dioxa-7-azatetracyclo[6.3.1.1^{1,4}.0^{5,12}]tridec-7-yl)-2-(trifluoromethyl)benzonitrile (157); and 2,6-Dichloro-4-((1S,3S,4S,5S,8S,12R)-3-hydroxy-4-methyl-6-oxo-9,13-dioxa-7-azatetracyclo[6.3.1.1^{1,4}.0^{5,12}]tridec-7-yl)benzonitrile (158)

Examples 156 to 159 listed in Table 4 below were prepared according to the general procedures described in Examples 5 and 6.

TABLE 4

| # | $R^x$ | $R^y$ | $R^z$ | $R^m$ | HPLC Ret. time (min) | Molecular mass $[M + H]^+$ |
|---|---|---|---|---|---|---|

TABLE 4-continued

| | | | | | | |
|---|---|---|---|---|---|---|
| 156 | H | CF$_3$ | CN | H | 2.453[a] | 395 |
| 157 | F | CF$_3$ | CN | H | 2.42[a] | 413 |
| 158 | H | Cl | CN | Cl | 2.673[a] | 395 |
| 159 | H | Cl | CN | H | 2.203[a] | 361 |

[a]Chromolith column 4.6 × 50 mm eluting with 10-90% aqueous MeOH over 4 minutes containing 0.1% TFA, 4 mL/min, monitoring at 220 nm.

Examples 160 to 173

Ethyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (160)

Isopropyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (161)

2-Hydroxyethyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (162)

2-Methoxyethyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (163)

2-(4-Morpholinyl)ethyl ((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (164)

Methyl ((1R,2S,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (165)

Methyl ((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)carbamate (166)

Isopropyl ((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)carbamate (167)

Isopropyl ((1R,2S,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (168)

Methyl ((1R,2S,4R,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-2-yl)carbamate (169)

Methyl ((1R,2S,4R,5S,8S,12R)-7-(3-bromo-4-cyanophenyl)-4-methyl-6-oxo-9,13-dioxa-7-azatetracyclo[6.3.1.1$^{1,4}$.0$^{5,12}$]tridec-2-yl)carbamate (170); and Methyl ((1R,2S,4R,5S,8S,12R)-7-(3-bromo-4-chlorophenyl)-4-methyl-6-oxo-9,13-dioxa-7-azatetracyclo[6.3.1.1$^{1,4}$.0$^{5,12}$]tridec-2-yl)carbamate (171)

Examples 160 to 173 listed in Table 5 below were prepared from the corresponding exo amine according to the general procedure described in Example 8.

TABLE 5

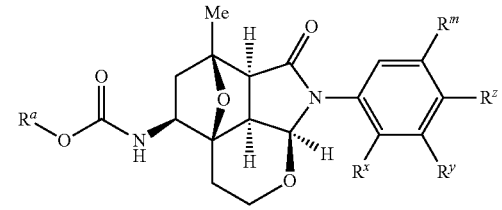

| # | R$^a$ | R$^x$ | R$^y$ | R$^z$ | R$^m$ | HPLC Ret. time (min) | Molecular mass [M + H]$^+$ |
|---|---|---|---|---|---|---|---|
| 160 | Et | H | CF$_3$ | CN | H | 2.660[a] | 466 |
| 161 | i-Pr | H | CF$_3$ | CN | H | 2.868[a] | 480 |
| 162 | —CH$_2$CH$_2$OH | H | CF$_3$ | CN | H | 2.193[a] | 482 |
| 163 | —CH$_2$CH$_2$OMe | H | CF$_3$ | CN | H | 2.483[a] | 496 |
| 164 | morpholinoethyl | H | CF$_3$ | CN | H | 1.930[a] | 551 |
| 165 | Me | H | CF$_3$ | Cl | H | 2.858[a] | 461 |

TABLE 5-continued

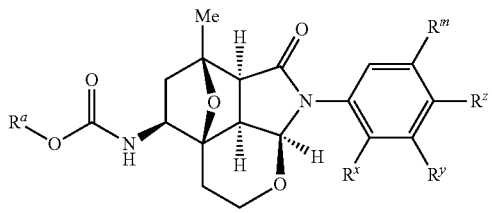

| # | $R^a$ | $R^x$ | $R^y$ | $R^z$ | $R^m$ | HPLC Ret. time (min) | Molecular mass $[M + H]^+$ |
|---|---|---|---|---|---|---|---|
| 166 | Me | H | Cl | CN | H | $2.480^b$ | $450.2^c$ |
| 167 | i-Pr | H | Cl | CN | H | $3.071^b$ | $505.2^c$ |
| 168 | i-Pr | H | $CF_3$ | Cl | H | $3.34^b$ | 489.4 |
| 169 | Me | H | Cl | CN | Cl | $3.431^b$ | 452.3 |
| 170 | Me | H | Br | CN | H | $3.06^b$ | 462.3 |
| 171 | Me | H | Br | Cl | H | $3.48^b$ | 473.3 |
| 172 | Me | H | $CF_3$ | CN | Cl | $2.82^a$ | 486 |
| 173 | Me | F | $CF_3$ | CN | H | $2.43^a$ | 470 |

[a]Chromolith column 4.6 × 50 mm eluting with 10-90% aqueous MeOH over 4 minutes containing 0.1% TFA, 4 mL/min, monitoring at 220 nm.
[b]YMC Combiscreen ODS-A S5 column (4.6 × 50 mm). 10-90% aq. MeOH over 4 min with 0.2% phosphoric acid, 4 mL/min, monitoring @ 220 nm Examples 174 to 191

N-((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)ethanesulfonamide (174)

N-((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)benzenesulfonamide (175)

N-((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)methanesulfonamide (176)

N-((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)methanesulfonamide (177)

N-((1R,2S,4R,5S,8S,12R)-7-(3-Bromo-4-chlorophenyl)-4-methyl-6-oxo-9,13-dioxa-7-azatetracyclo[6.3.1.1$^{1,4}$.0$^{5,12}$]tridec-2-yl)ethanesulfonamide (178)

N-((1R,2S,4R,5S,8S,12R)-7-(3-Bromo-4-cyanophenyl)-4-methyl-6-oxo-9,13-dioxa-7-azatetracyclo[6.3.1.1$^{1,4}$.0$^{5,12}$]tridec-2-yl)ethanesulfonamide (179)

N-((1R,2S,4R,5S,8S,12R)-7-(4-Chloro-3-(trifluoromethyl)phenyl)-4-methyl-6-oxo-9,13-dioxa-7-azatetracyclo[6.3.1.1$^{1,4}$.0$^{5,12}$]tridec-2-yl)methanesulfonamide (180)

N-((1R,2S,4R,5S,8S,12R)-7-(4-Cyano-3-(trifluoromethoxy)phenyl)-4-methyl-6-oxo-9,13-dioxa-7-azatetracyclo[6.3.1.1$^{1,4}$.0$^{5,12}$]tridec-2-yl)benzenesulfonamide (181)

N-((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)cyclopropanesulfonamide (182)

N-((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)-2-pyridinesulfonamide (183)

N-((1R,2S,4R,5S,8S,12R)-7-(4-Chloro-3-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (184)

N-((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)-2,2,2-trifluoroethanesulfonamide (185)

N-((1R,2S,4R,5S,8S,12R)-7-(3,5-Dichloro-4-cyanophenyl)-4-methyl-6-oxo-9,13-dioxa-7-azatetracyclo[6.3.1.1$^{1,4}$.0$^{5,12}$]tridec-2-yl)ethanesulfonamide (186)

N-((1R,2S,4R,5S,8S,12R)-7-(3-Chloro-4-cyano-5-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (187)

N-((1R,2S,4R,5S,8S,12R)-7-(4-Cyano-3-(trifluoromethoxy)phenyl)-4-methyl-6-oxo-9,13-dioxa-7-azatetracyclo[6.3.1.1$^{1,4}$.0$^{5,12}$]tridec-2-yl)ethanesulfonamide (188)

N-(4-(((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)sulfamoyl)phenyl)acetamide (189); and N-((1R,2S,4R,5S,8S,12R)-7-(4-Cyano-2-fluoro-3-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (190)

Examples 174 to 191 listed in Table 6 below were prepared from the corresponding exo amine according to the general procedure described in Example 9.

TABLE 6

| # | $R^a$ | $R^x$ | $R^y$ | $R^z$ | $R^m$ | HPLC Ret. time (min) | Molecular mass $[M + H]^+$ |
|---|---|---|---|---|---|---|---|
| 174 | Et | H | $CF_3$ | CN | H | $2.480^b$ | 450.2 |
| 175 | Ph | H | Cl | CN | H | $2.815^b$ | 411.1 |
| 176 | Me | H | Cl | CN | H | $2.32^b$ | 438.0 |
| 177 | Me | H | $CF_3$ | CN | H | $2.097^b$ | 472 |
| 178 | Et | H | Br | Cl | H | $3.34^b$ | 507.3 |
| 179 | Et | H | Br | CN | H | $2.88^b$ | 498.3 |
| 180 | Me | H | $CF_3$ | Cl | H | $3.39^b$ | 481.3 |
| 181 | Ph | H | $OCF_3$ | CN | H | $3.08^b$ | $548.0^c$ |
| 182 | cyclopropyl | H | Cl | CN | H | $2.50^b$ | $462.0^c$ |
| 183 | pyridin-3-yl | H | Cl | CN | H | $2.58^b$ | $500.9^c$ |
| 184 | Et | H | $CF_3$ | Cl | H | $3.47^b$ | 495.3 |
| 185 | $CH_2CF_3$ | H | Cl | CN | H | $2.71^b$ | $504.1^c$ |
| 186 | Et | H | Cl | CN | Cl | $3.28^b$ | 486.3 |
| 187 | Et | H | $CF_3$ | CN | Cl | $2.65^b$ | 520 |
| 188 | Et | H | $OCF_3$ | CN | H | $2.70^b$ | $500.0^c$ |
| 189 | 4-(acetamido)phenyl | H | Cl | CN | H | $2.68^b$ | $550.0^c$ |
| 190 | Et | F | $CF_3$ | CN | H | $2.28^a$ | 504 |
| 191 | Me | H | Br | Cl | H | 2.52 | 493.2 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$ Examples 192 to 200

N-((1R,2R,4R,5S,8S,12R)-7-(3-bromo-4-cyanophenyl)-4-methyl-6-oxo-9,13-dioxa-7-azatetracyclo[6.3.1.1$^{1,4}$.0$^{5,12}$]tridec-2-yl)ethanesulfonamide (192)

N-((1R,2R,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)ethanesulfonamide (193)

N-((1R,2R,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)benzenesulfonamide (194)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (195)

N-((1R,2R,4R,5S,8S,12R)-7-(4-Cyano-3-(trifluoromethyl)phenyl)-4-methyl-6-oxo-9,13-dioxa-7-azatetracyclo[6.3.1.1$^{1,4}$.0$^{5,12}$]tridec-2-yl)cyclopropanesulfonamide (196)

N-((1R,2R,4R,5S,8S,12R)-7-(4-cyano-3-fluoro-5-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (197)

N-41R,2R,4R,5S,8S,12R)-7-(3-amino-4-cyano-5-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (198)

N-((1R,2R,4R,5S,8S,12R)-7-(3-chloro-4-cyano-5-fluorophenyl)-4-methyl-6-oxo-9,13-dioxa-7-azatetracyclo[6.3.1.1$^{1,4}$.0$^{5,12}$]tridec-2-yl)ethanesulfonamide (199); and N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)methanesulfonamide (200)

Examples 192 to 200 listed in Table 7 below were prepared from the corresponding endo amine according to the general procedure described in Example 9.

TABLE 7

| # | R$^a$ | R$^y$ | R$^z$ | R$^m$ | HPLC Ret. time (min) | Molecular mass [M + H]$^+$ |
|---|---|---|---|---|---|---|
| 192 | Et | Br | CN | H | 2.890$^b$ | 496.1 |
| 193 | Et | Cl | CN | H | 2.895$^b$ | 450.1 |
| 194 | Ph | Cl | CN | H | 3.353$^b$ | 498.1 |
| 195 | Et | CF$_3$ | CN | H | 2.570$^a$ | 486 |
| 196 | cyclopropyl | CF$_3$ | CN | H | 2.69$^a$ | 498 |
| 197 | Et | CF$_3$ | CN | F | 3.286$^b$ | 504 |
| 198 | Et | CF$_3$ | CN | NH$_2$ | 2.86$^b$ | 501.1 |
| 199 | Et | Cl | CN | F | 3.553$^b$ | 470.1 |
| 200 | Me | CF$_3$ | CN | H | 2.455$^b$ | 472 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$ Examples 201 to 206

Methyl ((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (201)

Methyl ((1R,2R,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (202)

Methyl ((1R,2R,4R,5S,8S,12R)-7-(3-bromo-4-cyanophenyl)-4-methyl-6-oxo-9,13-dioxa-7-azatetracyclo[6.3.1.1$^{1,4}$.0$^{5,12}$]tridec-2-yl)carbamate (203)

Methyl ((1R,2R,4R,5S,8S,12R)-7-(4-chloro-2-methyl-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (204)

Methyl ((41R,2R,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)carbamate (205); and Methyl ((1R,2R,4R,5S,8S,12R)-7-(4-cyano-3-fluoro-5-(trifluoromethyl)phenyl)-4-methyl-6-oxo-9,13-dioxa-7-azatetracyclo[6.3.1.1$^{1,4}$.0$^{5,12}$]tridec-2-yl)carbamate (206)

Examples 201 to 206 listed in Table 8 below were prepared from the corresponding endo amine according to the general procedure described in Example 8.

TABLE 8

| # | R$^x$ | R$^y$ | R$^z$ | R$^m$ | HPLC Ret. time (min) | Molecular mass [M + H]$^+$ |
|---|---|---|---|---|---|---|
| 201 | H | CF$_3$ | CN | H | 2.676$^a$ | 452 |
| 202 | H | CF$_3$ | Cl | H | 2.908$^a$ | 461 |
| 203 | H | Br | CN | H | 2.901$^b$ | 460.1$^c$ |
| 204 | Me | CF$_3$ | CN | H | 3.428$^b$ | 475.1 |
| 205 | H | Cl | CN | H | 2.885$^b$ | 418.1 |
| 206 | H | CF$_3$ | CN | F | 3.30$^b$ | 470 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$ Examples 207 to 212

Methyl ((1R,3R,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (207)

Methyl ((1R,3R,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)carbamate (208)

Isopropyl ((1R,3R,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)carbamate (209)

Methyl ((1R,3R,4S,5S,8S,12R)-7-(4-cyano-2-fluoro-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (210); and Methyl ((1R,3R,4S,5S,8S,12R)-7-(3-bromo-4-chlorophenyl)-4-methyl-6-oxo-9,13-dioxa-7-azatetracyclo[6.3.1.1$^{1,4}$.0$^{5,12}$]tridec-3-yl)carbamate (211)

Examples 207 to 212 listed in Table 9 below were prepared from the corresponding exo amine according to the general procedure described in Example 8.

TABLE 9

| # | R$^a$ | R$^x$ | R$^y$ | R$^z$ | R$^m$ | HPLC Ret. time (min) | Molecular mass [M + H]$^+$ |
|---|---|---|---|---|---|---|---|
| 207 | Me | H | CF$_3$ | CN | H | 2.405$^a$ | 452 |
| 208 | Me | H | Cl | CN | Cl | 2.602$^a$ | 452 |
| 209 | i-Pr | H | Cl | CN | Cl | 2.908$^a$ | 452 |
| 210 | Me | F | CF$_3$ | CN | H | 2.38$^a$ | 470 |
| 211 | Me | H | Br | Cl | H | 3.44$^b$ | 473.3 |
| 212 | Me | H | Cl | CN | H | 2.913$^a$ | 418 |

$^a$Chromolith column 4.6 × 50 mm eluting with 10-90% aqueous MeOH over 4 minutes containing 0.1% TFA, 4 mL/min, monitoring at 220 nm.

Examples 213 to 214

N-((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)propanamide (213); and N-((1R,2S,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)propanamide (214)

Examples 213 to 214 listed in Table 10 below were prepared from the corresponding exo amine according to the general procedure described in Example 11.

TABLE 10

| # | R$^a$ | R$^y$ | HPLC Ret. time (min) | Molecular mass [M + H]$^+$ |
|---|---|---|---|---|
| 213 | Et | CF$_3$ | 2.427$^a$ | 450 |
| 214 | Et | Cl | 2.646$^b$ | 474.1$^c$ |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$ Examples 215 to 221

N-((1R,2R,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)propanamide (215)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)acetamide (216)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)-2-methylpropanamide (217)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)-2-methoxyacetamide (218)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)-N$^2$,N$^2$-dimethylglycinamide (219)

N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)-3-(4-morpholinyl)propanamide (220); and N-((1R,2R,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)propanamide (221)

Examples 215 to 221 listed in Table 11 below were prepared from the corresponding endo amine according to the general procedure described in Example 11.

TABLE 11

[Structure with $R^a$, $R^y$, $R^z$ substituents on methyl-oxo-dioxa-azatetracyclo scaffold with phenyl group]

| # | $R^a$ | $R^y$ | $R^z$ | HPLC Ret. time (min) | Molecular mass $[M + H]^+$ |
|---|---|---|---|---|---|
| 215 | Et | $CF_3$ | Cl | $2.860^a$ | 459 |
| 216 | Me | $CF_3$ | CN | $2.370^a$ | 436 |
| 217 | i-Pr | $CF_3$ | CN | $2.590^a$ | 464 |
| 218 | —$CH_2OCH_3$ | $CF_3$ | CN | $2.403^a$ | 466 |
| 219 | [CH₂CH₂N(Me)₂ group] | $CF_3$ | CN | $2.095^a$ | 479 |
| 220 | [propyl-morpholine group] | $CF_3$ | CN | $2.157^a$ | 535 |
| 221 | Et | Cl | CN | $2.756^b$ | $474.1^c$ |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$

Examples 222 to 223

N-((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)ethanesulfonamide (222); and N-((1R,3S,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)ethanesulfonamide (223)

Examples 222 to 223 listed in Table 12 below were prepared from the corresponding endo amine according to the general procedure described in Example 9.

TABLE 12

[Structure with sulfonamide $R^a$, $R^y$, $R^m$ substituents]

| # | $R^a$ | $R^y$ | $R^m$ | HPLC Ret. time (min) | Molecular mass $[M + H]^+$ |
|---|---|---|---|---|---|
| 222 | Et | $CF_3$ | H | $2.615^a$ | 486 |
| 223 | Et | Cl | Cl | $2.793^a$ | 486 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$

Examples 224 to 226

N-((1R,3R,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)ethanesulfonamide (224); and N-((1R,3R,4S,5S,8S,12R)-7-(3-Bromo-4-chlorophenyl)-4-methyl-6-oxo-9,13-dioxa-7-azatetracyclo[6.3.1.1$^{1,4}$.0$^{5,12}$]tridec-3-yl)ethanesulfonamide (225)

Examples 224 to 226 listed in Table 13 below were prepared from the corresponding exo amine according to the general procedure described in Example 9.

TABLE 13

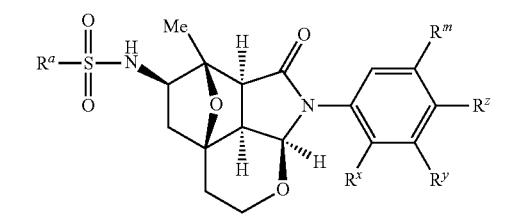

| # | $R^a$ | $R^x$ | $R^y$ | $R^z$ | $R^m$ | HPLC Ret. time (min) | Molecular mass $[M + H]^+$ |
|---|---|---|---|---|---|---|---|
| 224 | Et | H | Cl | CN | Cl | $2.408^a$ | 484 |
| 225 | Et | H | Br | Cl | H | $3.33^b$ | 507.3 |
| 226 | Et | H | Br | CN | H | $2.861^b$ | 498.2 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$

Examples 227 to 234

Ethyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (227)

Isopropyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (228)

2-Hydroxyethyl ((1S,3R,4R,5R,8R,12S)-7-(4-cyano-3-trifluoromethyl)phenyl)-4-methyl-6-oxo-9,13-dioxa-7-azatetracyclo[6.3.1.1$^{1,4}$.0$^{5,12}$]tridec-3-yl) carbamate (229)

2-Methoxyethyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl) carbamate (230)

2-(4-Morpholinyl)ethyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (231)

Methyl ((1S,3R,4R,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (232)

Methyl ((1S,3R,4R,5R,8R,12S)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)carbamate (233); and Methyl ((1S,3R,4R,5R,8R,12S)-7-(3-chloro-4-cyanophenyl)-4-methyl-6-oxo-9,13-dioxa-7-azatetracyclo[6.3.1.1$^{1,4}$.0$^{5,12}$]tridec-3-yl)carbamate (234)

Examples 227 to 234 listed in Table 14 below were prepared from the corresponding endo amine according to the general procedure described in Example 8.

TABLE 14

| # | R$^a$ | R$^y$ | R$^z$ | R$^m$ | HPLC Ret. time (min) | Molecular mass [M + H]$^+$ |
|---|---|---|---|---|---|---|
| 227 | Et | CF$_3$ | CN | H | 2.825$^a$ | 466 |
| 228 | i-Pr | CF$_3$ | CN | H | 2.996$^a$ | 480 |
| 229 | —CH$_2$CH$_2$OH | CF$_3$ | CN | H | 2.532$^a$ | 482 |
| 230 | —CH$_2$CH$_2$OCH$_3$ | CF$_3$ | CN | H | 2.530$^a$ | 496 |
| 231 | (morpholinylethyl) | CF$_3$ | CN | H | 2.375$^a$ | 551 |
| 232 | CH$_3$ | CF$_3$ | Cl | H | 2.975$^a$ | 461 |
| 233 | CH$_3$ | Cl | CN | Cl | 2.841$^a$ | 452 |
| 234 | CH$_3$ | Cl | CN | H | 2.447$^a$ | 418 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$ Example 235

Methyl ((1S,3S,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (235)

Example 235 listed in Table 15 below was prepared from the corresponding exo amine according to the general procedure described in Example 8.

TABLE 15

| # | R$^a$ | R$^x$ | R$^y$ | R$^z$ | HPLC Ret. time (min) | Molecular mass [M + H]$^+$ |
|---|---|---|---|---|---|---|
| 235 | CH$_3$ | H | CF$_3$ | CN | 2.402$^a$ | 452 |

$^a$Chromolith column 4.6 × 50 mm eluting with 10-90% aqueous MeOH over 4 minutes containing 0.1% TFA, 4 mL/min, monitoring at 220 nm.

Examples 236 to 237

N-((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)propanamide (236); and N-((1R,3S,4S,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-3-yl)propanamide (237)

Examples 236 to 237 listed in Table 16 below were prepared from the corresponding endo amine according to the general procedure described in Example 11.

TABLE 16

| # | R$^a$ | R$^z$ | HPLC Ret. time (min) | Molecular mass [M + H]$^+$ |
|---|---|---|---|---|
| 236 | Et | CN | 2.545$^a$ | 450 |
| 237 | Et | Cl | 2.898$^a$ | 459 |

$^a$Chromolith column 4.6 × 50 mm eluting with 10-90% aqueous MeOH over 4 minutes containing 0.1% TFA, 4 mL/min, monitoring at 220 nm.

Examples 238 to 239

Methyl ((1S,2S,4S,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (238); and Methyl ((1S,2S,4S,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (239)

Examples 238 to 239 listed in Table 17 below were prepared from the corresponding endo amine according to the general procedure described in Example 8.

TABLE 17

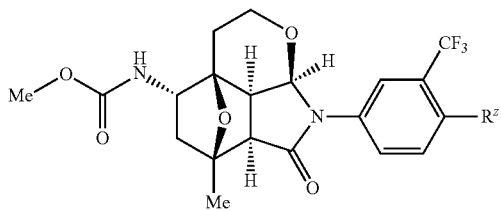

| # | R$^z$ | HPLC Ret. time (min) | Molecular mass [M + H]$^+$ |
|---|---|---|---|
| 238 | CN | 2.630$^a$ | 452 |
| 239 | Cl | 2.973$^a$ | 461 |

$^a$Chromolith column 4.6 × 50 mm eluting with 10-90% aqueous MeOH over 4 minutes containing 0.1% TFA, 4 mL/min, monitoring at 220 nm.

Examples 240 to 241

2-Bromo-4-((1S,2R,4S,5R,8R,12S)-2-hydroxy-4-methyl-6-oxo-9,13-dioxa-7-azatetracyclo[6.3.1.1$^{1,4}$.0$^{5,12}$]tridec-7-yl)benzonitrile (240); and 2-Fluoro-4-((1S,2R,4S,5R,8R,12S)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (241)

Examples 240 to 241 listed in Table 18 below were prepared according to the general procedure described in Example 15.

TABLE 18

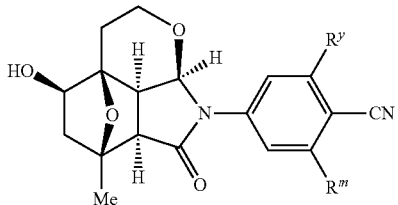

| # | R$^y$ | R$^m$ | HPLC Ret. time (min) | Molecular mass [M + H]$^+$ |
|---|---|---|---|---|
| 240 | Br | H | 2.285$^b$ | 464.2$^c$ |
| 241 | CF$_3$ | F | 2.75$^b$ | 413.2 |

$^a$Chromolithcolumn 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm
$^c$[M + OAc]$^-$

Examples 242 to 243

Methyl ((1S,2R,4S,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (242); and Methyl ((1S,2R,4S,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (243)

Examples 242 to 243 listed in Table 19 below were prepared from the corresponding exo amine according to the general procedure described in Example 8.

TABLE 19

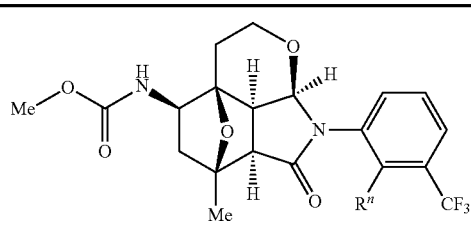

| # | R$^n$ | HPLC Ret. time (min) | Molecular mass [M + H]$^+$ |
|---|---|---|---|
| 242 | Cl | 2.886$^a$ | 461 |
| 243 | CN | 2.47$^a$ | 452 |

$^a$Chromolith column 4.6 × 50 mm eluting with 10-90% aqueous MeOH over 4 minutes containing 0.1% TFA, 4 mL/min, monitoring at 220 nm.

Examples 244 to 250

Methyl ((1R,2R,3R,4S,5S,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)carbamate (244)

N-((1R,2R,3R,4S,5S,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl) acetamide (245)

N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl) methanesulfonamide (246)

N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-2,2,2-trifluoroethanesulfonamide (247)

N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-4-fluorobenzenesulfonamide (248)

N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl) ethanesulfonamide (249); and N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl) cyclopropanesulfonamide (250)

Examples 244 to 250 listed in Table 20 below were prepared according to the general procedure described in Examples 30 and 32.

TABLE 20

| # | $R^a$ | HPLC Ret. time (min) | Molecular mass $[M + H]^+$ |
|---|---|---|---|
| 244 | —CO₂Me | 2.68[b] | 468.1 |
| 245 | —COMe | 2.50[b] | 450.1[c] |
| 246 | —SO₂CH₃ | 2.66[b] | 488.0 |
| 247 | —SO₂CH₂CF₃ | 3.00[b] | 554.0 |
| 248 | 4-fluorophenylsulfonyl | 3.11[b] | 566.0 |
| 249 | —SO₂CH₂CH₃ | 2.70[b] | 502.0 |
| 250 | cyclopropylsulfonyl | 3.80[b] | 514.0 |

[a]Chromolith column 4.6 × 50 mm eluting with 10-90% aqueous MeOH over 4 minutes containing 0.1% TFA, 4 mL/min, monitoring at 220 nm.
[b]YMC Combiscreen ODS-A S5 column (4.6 × 50 mm). 10-90% aq. MeOH over 4 min with 0.2% phosphoric acid, 4 mL/min, monitoring @ 220 nm.
[c][M + OAc]⁻

Examples 251 to 256

Methyl ((1S,2R,3R,4R,5R,8R,12S)-7-(4-cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)carbamate (251)

N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)methanesulfonamide (252)

N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)-2,2,2-trifluoroethanesulfonamide (253)

N-((1S,2R,3R,4R,5R,8R,12S)-7-(4-cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)acetamide (254)

N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)ethanesulfonamide (255); and N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1¹,⁴.0⁵,¹²]tridec-3-yl)-4-fluorobenzenesulfonamide (256)

Examples 251 to 256 listed in Table 21 below were prepared according to the general procedure described in Examples 31 and 32.

TABLE 21

| # | $R^a$ | HPLC Ret. time (min) | Molecular mass $[M + H]^+$ |
|---|---|---|---|
| 251 | —CO₂Me | 2.58[b] | 468.1 |
| 252 | —SO₂CH₃ | 2.50[b] | 488.0 |
| 253 | —SO₂CH₂CF₃ | 2.80[b] | 554.0 |
| 254 | —COMe | 2.40[b] | 452.1 |
| 255 | —SO₂CH₂CH₃ | 2.60[b] | 502.0 |
| 256 | 4-fluorophenylsulfonyl | 2.95[b] | 566.0 |

[a]Chromolith column 4.6 × 50 mm eluting with 10-90% aqueous MeOH over 4 minutes containing 0.1% TFA, 4 mL/min, monitoring at 220 nm.
[b]YMC Combiscreen ODS-A S5 column (4.6 × 50 mm). 10-90% aq. MeOH over 4 min with 0.2% phosphoric acid, 4 mL/min, monitoring @ 220 nm.
[c][M + OAc]⁻

Examples 257 to 263

2-Bromo-4-((1R,4R,5S,8S,12R)-4-methyl-2,6-dioxo-9,13-dioxa-7-azatetracyclo[6.3.1.1¹,⁴.0⁵,¹²]tridec-7-yl)benzonitrile (257)

(1R,4R,5S,8S,12R)-7-(4-chloro-2-methyl-3-(trifluoromethyl)phenyl)-4-methyl-9,13-dioxa-7-azatetracyclo[6.3.1.1¹,⁴.0⁵,¹²]tridecane-2,6-dione (258)

3-Fluoro-4-((1R,4R,5S,8S,12R)-4-methyl-2,6-dioxo-9,13-dioxa-7-azatetracyclo[6.3.1.1¹,⁴.0⁵,¹²]tridec-7-yl)-2-(trifluoromethyl)benzonitrile (259)

4-((1R,4R,5S,8S,12R)-4-Methyl-2,6-dioxo-9,13-dioxa-7-azatetracyclo[6.3.1.1¹,⁴.0⁵,¹²]tridec-7-yl)-2-(trifluoromethoxy)benzonitrile (260)

2-Chloro-4-((1R,4R,5S,8S,12R)-4-methyl-2,6-dioxo-9,13-dioxa-7-azatetracyclo[6.3.1.1¹,⁴.0⁵,¹²]tridec-7-yl)benzonitrile (261)

2-Chloro-4-((1R,4R,5S,8S,12R)-4-methyl-2,6-dioxo-9,13-dioxa-7-azatetracyclo[6.3.1.1¹,⁴.0⁵,¹²]tridec-7-yl)-6-(trifluoromethyl)benzonitrile (262); and 4-((1R,4R,5S,8S,12R)-4-Methyl-2,6-dioxo-9,13-dioxa-7-azatetracyclo[6.3.1.1¹,⁴.0⁵,¹²]tridec-7-yl)-2-(trifluoromethoxy)benzonitrile (263)

Examples 257 to 263 listed in Table 22 below were prepared according to the general procedure described in Example 5.

TABLE 22

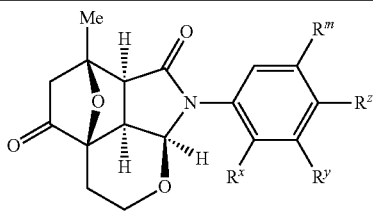

| # | $R^x$ | $R^y$ | $R^z$ | $R^m$ | HPLC Ret. time (min) | Molecular mass $[M + H]^+$ |
|---|---|---|---|---|---|---|
| 257 | H | Br | CN | H | 2.846[b] | 461.0[c] |
| 258 | Me | CF$_3$ | Cl | H | 3.405[b] | 416.1[c] |
| 259 | H | CF$_3$ | CN | F | 2.665[a] | 413.0 |
| 260 | H | OCF$_3$ | CN | H | 3.07[b] | 408.1 |
| 261 | H | Cl | CN | H | 2.80[b] | 417.0[c] |
| 262 | H | CF$_3$ | CN | Cl | 2.98[a] | 425[c] |
| 263 | H | OCF$_3$ | CN | H | 3.07[b] | 408 |

[a] Chromolith column 4.6 × 50 mm eluting with 10-90% aqueous MeOH over 4 minutes containing 0.1% TFA, 4 mL/min, monitoring at 220 nm.
[b] YMC Combiscreen ODS-A S5 column (4.6 × 50 mm). 10-90% aq. MeOH over 4 min with 0.2% phosphoric acid, 4 mL/min, monitoring @ 220 nm.
[c] [M + OAc]$^-$

Examples 264 to 268

3-chloro-5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-pyridinecarbonitrile (264)

5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-3-methyl-2-pyridinecarbonitrile (265)

5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-3-methoxy-2-pyridinecarbonitrile (266)

5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-3-(trifluoromethyl)-2-pyridinecarbonitrile (267); and 3-bromo-5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-pyridinecarbonitrile (268)

Examples 264 to 268 listed in Table 23 below were prepared according to the general procedure described in Example 15.

TABLE 23

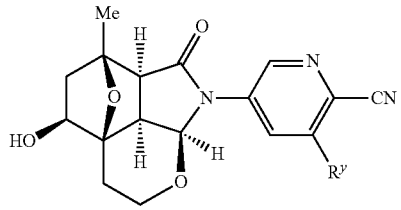

| # | $R^y$ | HPLC Ret. time (min) | Molecular mass $[M + H]^+$ |
|---|---|---|---|
| 264[d] | Cl | 2.15[b] | 420.1[c] |
| 265[d] | CH$_3$ | 1.75[b] | 342.2 |

TABLE 23-continued

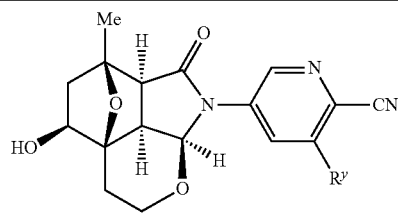

| # | $R^y$ | HPLC Ret. time (min) | Molecular mass $[M + H]^+$ |
|---|---|---|---|
| 266[d] | OCH$_3$ | 1.34[a] | 358 |
| 267[d] | CF$_3$ | 2.44[b] | 454.1[c] |
| 268[d] | Br | 2.20[b] | 464.0[c] |

[a] Chromolith column 4.6 × 50 mm eluting with 10-90% aqueous MeOH over 4 minutes containing 0.1% TFA, 4 mL/min, monitoring at 220 nm.
[b] YMC Combiscreen ODS-A S5 column (4.6 × 50 mm). 10-90% aq. MeOH over 4 min with 0.2% phosphoric acid, 4 mL/min, monitoring @ 220 nm.
[c] [M + OAc]$^-$
[d] For preparation of pyridyl amine starting materials see Salvati, Mark E et al. Preparation of fused succinimides as modulators of nuclear hormone receptor function. PCT Int. Appl. (2003), 763 pp. WO 2003062241 A1 20030731.

Examples 269 to 272

3-Fluoro-4-((1S,4S,5S,8S,12R)-4-methyl-3,6-dioxo-9,13-dioxa-7-azatetracyclo[6.3.1.1$^{1,4}$.0$^{5,12}$]tridec-7-yl)-2-(trifluoromethyl)benzonitrile (269)

(1S,4S,5S,8S,12R)-7-(3-Bromo-4-chlorophenyl)-4-methyl-9,13-dioxa-7-azatetracyclo[6.3.1.1$^{1,4}$.0$^{5,12}$]tridecane-3,6-dione (270)

4-((1S,4S,5S,8S,12R)-4-methyl-3,6-dioxo-9,13-dioxa-7-azatetracyclo[6.3.1.1$^{1,4}$.0$^{5,12}$]tridec-7-yl)-2-(trifluoromethyl)benzonitrile (271); and 2-Chloro-4-((1S,4S,5S,8S,12R)-4-methyl-3,6-dioxo-9,13-dioxa-7-azatetracyclo[6.3.1.1$^{1,4}$.0$^{5,12}$]tridec-7-yl)benzonitrile (272)

Examples 269 to 272 listed in Table 24 below were prepared according to the general procedure described in Example 5.

TABLE 24

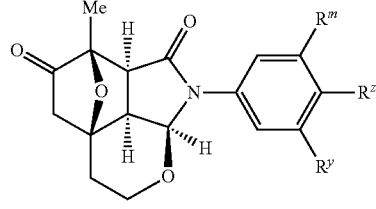

| # | $R^y$ | $R^z$ | $R^m$ | HPLC Ret. time (min) | Molecular mass $[M + H]^+$ |
|---|---|---|---|---|---|
| 269 | CF$_3$ | CN | F | 2.56[a] | 411 |
| 270 | Br | Cl | H | 3.65[b] | 414 |
| 271 | CF$_3$ | CN | H | 2.63[a] | 393 |
| 272 | Cl | CN | H | 2.407[a] | 359 |

[a] Chromolith column 4.6 × 50 mm eluting with 10-90% aqueous MeOH over 4 minutes containing 0.1% TFA, 4 mL/min, monitoring at 220 nm.
[b] YMC Combiscreen ODS-A S5 column (4.6 × 50 mm). 10-90% aq. MeOH over 4 min with 0.2% phosphoric acid, 4 mL/min, monitoring @ 220 nm.
[c] [M + OAc]$^-$

Examples 273 to 278

4-((1R,2E,4R,5S,8S,12R)-2-(Ethoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (273)

4-((1R,2E,4R,5S,8S,12R)-2-((Benzyloxy)imino)-4-methyl-6-oxo-9,13-dioxa-7-azatetracyclo[6.3.1.1$^{1,4}$.0$^{5,12}$]tridec-7-yl)-2-(trifluoromethyl)benzonitrile (274)

4-((1R,4R,5S,8S,12R)-2-(tert-Butoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (275)

4-((1R,4R,5S,8S,12R)-2-(Isopropoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (276)

4-((1R,2E,4R,5S,8S,12R)-4-Methyl-6-oxo-2-(phenoxyimino)-9,13-dioxa-7-azatetracyclo[6.3.1.1$^{1,4}$.0$^{5,12}$]tridec-7-yl)-2-(trifluoromethyl)benzonitrile (277); and 4-(1R,4R,5S,8S,12R)-4-Methyl-6-oxo-2-((tetrahydro-2H-pyran-2-yloxy)imino)-9,13-dioxa-7-azatetracyclo[6.3.1.1$^{1,4}$.0$^{5,12}$]tridec-7-yl)-2-(trifluoromethyl)benzonitrile (278)

Examples 273 to 278 listed in Table 25 below were prepared according to the general procedure described in Example 30.

TABLE 25

| # | R$^a$ | HPLC Ret. time (min) | Molecular mass [M + H]$^+$ |
|---|---|---|---|
| 273 | Et | 3.87$^b$ | 436.5 |
| 274 | PhCH$_2$- | 3.49$^b$ | 498.4 |
| 275 | t-Bu | 4.15$^b$ | 464.5 |
| 276 | i-Pr | 4.055$^b$ | 450.3 |
| 277 | Ph | 4.263$^b$ | 484.3 |
| 278 | tetrahydropyran-2-yl | 3.838$^b$ | 492.4 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$

Examples 279 to 284

4-((1R,3E,4S,5S,8S,12R)-3-(Methoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (279)

4-((1R,3E,4S,5S,8S,12R)-3-(Ethoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (280)

4-(1R,4S,5S,8S,12R)-3-((Benzyloxy)imino)-4-methyl-6-oxo-9,13-dioxa-7-azatetracyclo[6.3.1.1$^{1,4}$.0$^{5,12}$]tridec-7-yl)-2-(trifluoromethyl)benzonitrile (281)

4-((1R,3E,4S,5S,8S,12R)-3-(tert-Butoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (282)

4-((1R,4S,5S,8S,12R)-3-(Isopropoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (283); and 4-((1R,4S,5S,8S,12R)-4-Methyl-6-oxo-3-(phenoxyimino)-9,13-dioxa-7-azatetracyclo[6.3.1.1$^{1,4}$.0$^{5,12}$]tridec-7-yl)-2-(trifluoromethyl)benzonitrile (284)

Examples 279 to 284 listed in Table 26 below were prepared according to the general procedure described in Example 30.

TABLE 26

| # | R$^a$ | HPLC Ret. time (min) | Molecular mass [M + H]$^+$ |
|---|---|---|---|
| 279 | Me | 3.64$^b$ | 422.5 |
| 280 | Et | 3.83$^b$ | 436.5 |
| 281 | PhCH$_2$- | 4.13$^b$ | 498.4 |
| 282 | t-Bu | 3.39$^b$ | 464.5 |
| 283 | i-Pr | 4.006$^b$ | 450.3 |
| 284 | Ph | 4.230$^b$ | 484.3 |

$^a$Chromolith column 4.6 × 50 mm eluting with 10-90% aqueous MeOH over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$

Examples 285 to 291

Methyl ((1R,3S,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)carbamate (285)

Methyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (286)

Ethyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (287)

Isopropyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (288)

2-Hydroxyethyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (289)

2-Methoxyethyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (290); and Methyl ((1R,3S,4S,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (291)

Examples 285 to 291 listed in Table 27 below were prepared from the corresponding endo amine according to the general procedure described in Example 8.

TABLE 27

| # | $R^a$ | $R^y$ | $R^z$ | $R^m$ | HPLC Ret. time (min) | Molecular mass [M + H]$^+$ |
|---|---|---|---|---|---|---|
| 285 | Me | Cl | CN | Cl | 2.805$^a$ | 452 |
| 286 | Me | CF$_3$ | CN | H | 2.656$^a$ | 452 |
| 287 | Et | CF$_3$ | CN | H | 2.841$^a$ | 466 |
| 288 | i-Pr | CF$_3$ | CN | H | 3.010$^a$ | 480 |
| 289 | —CH$_2$CH$_2$OH | CF$_3$ | CN | H | 2.535$^a$ | 482 |
| 290 | —CH$_2$CH$_2$OCH$_3$ | CF$_3$ | CN | H | 2.711$^a$ | 496 |
| 291 | Me | CF$_3$ | Cl | H | 2.975$^a$ | 461 |

$^a$Chromolith column 4.6 × 50 mm eluting with 10-90% aqueous methanol over 4 minutes containing 0.1% TFA, 4 mL/min, monitoring at 220 nm.
$^b$YMC Combiscreen ODS-A S5 column (4.6 × 50 mm). 10-90% aq. MeOH over 4 min with 0.2% phosphoric acid, 4 mL/min, monitoring @ 220 nm.
$^c$[M + OAc]$^-$

Example 292

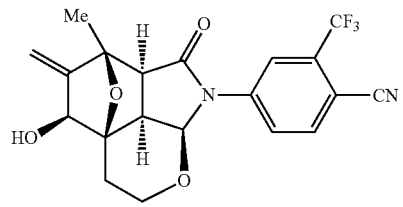

A mixture of Example 49 (30 mg, 0.077 mmol), SeO$_2$ (15 mg, 0.14 mmol) in 95% EtOH (1.3 ml) was heated at 150° C. under microwave for 5 h. The mixture was cooled to RT, concentrated and purified by ISCO silica gel column (4 g column, 15 mL/min, EtOAc/Hexane 0-90%) to give Example 292 (25.0 mg, 80%) as a white solid.

HPLC: 2.47 min (RT) (Chromolith column 4.6×50 mm eluting with 10-90% aqueous MeOH over 4 minutes containing 0.1% TFA, 4 mL/min, monitoring at 220 nm). MS (ES): m/z=407 [M+H]$^+$.

Examples 293 and 294

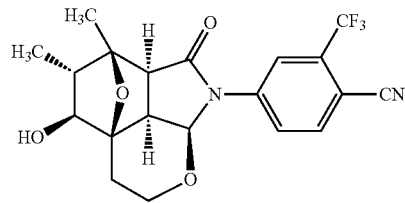

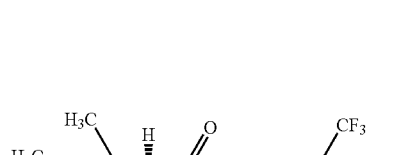

A mixture of Example 292 (20 mg, 0.049 mmol) and 10% Pd/C (9.8 mmol) in MeOH (5 mL) was stirred under hydrogen balloon for 2 h. The catalyst was filtered off through celite. The filtrate was concentrated, and purified by Chiralpak AD prep HPLC column. (100 mL/min, MeOH/EtOH/Heptane=15/15/70) to give Examples 293 (3.9 mg, 19%) and 294 (12.8 mg, 64%) both as white solids.

Example 293

HPLC: 2.15 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]+.

Example 294

HPLC: 2.15 min (RT) (Chromolith column 4.6×50 mm eluting with 10-90% aqueous MeOH over 4 minutes containing 0.1% TFA, 4 mL/min, monitoring at 220 nm). MS (ES): m/z=409 [M+H]+.

Example 295

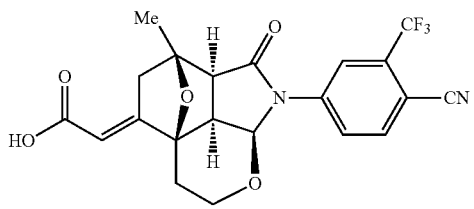

To a solution of Example 103 (89 mg, 0.199 mmol) in THF/MeOH/H₂O (2 mL/2 mL/1 mL) was added LiOH monohydrate (52.4 mg, 1.2 mmol). The reaction mixture was stirred at RT overnight. Next, the reaction mixture was acidified with 1N HCl (2 mL), concentrated and extracted thrice with EtOAc. The extracts were washed with brine, dried over Na₂SO₄, concentrated to give Example 295 (93 mg, 100%) as white solid.

HPLC: 2.691 min (RT) (Chromolith column 4.6×50 mm eluting with 10-90% aqueous MeOH over 4 minutes containing 0.1% TFA, 4 mL/min, monitoring at 220 nm). MS (ES): m/z=433 [M−H]⁻.

Example 296

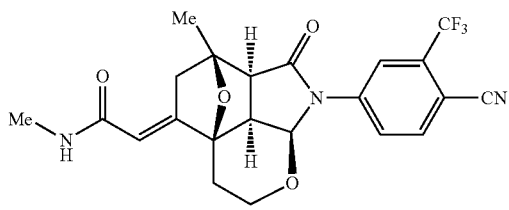

To a solution of Example 295 (19.7 mg, 0.047 mmol) in THF (1 mL) was added a 2 M solution of CH₃NH₂ in THF (0.24 mL, 0.48 mmol), followed by HATU (27 mg, 0.070 mmol) and TEA (25 µL, 0.18 mmol). The reaction mixture was stirred for 1 h, concentrated and purified by reverse-phase preparative HPLC to give Example 296 (17.3 mg, 85%) as a white solid.

HPLC: 2.532 min (RT) (Chromolith column 4.6×50 mm eluting with 10-90% aqueous MeOH over 4 minutes containing 0.1% TFA, 4 mL/min, monitoring at 220 nm). MS (ES): m/z=448 [M+H]+.

Examples 297 and 298

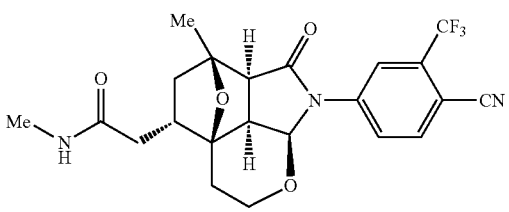

297

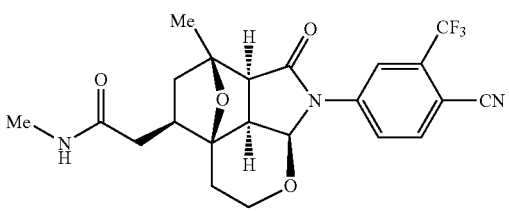

298

A mixture of Example 296 (27 mg, 0.06 mmol) and 10% Pd/C (12 mg) in MeOH/EtOAc (5 mL/3 mL) was stirred under hydrogen balloon at RT for 5 h. The catalyst was filtered off, and the filtrate was concentrated and purified by prep HPLC to give Examples 297 (6.0 mg, 22%) and 298 (13.2 mg, 49%) both as white solids.

Example 297

HPLC: 2.218 min (RT) (Chromolith column 4.6×50 mm eluting with 10-90% aqueous MeOH over 4 minutes containing 0.1% TFA, 4 mL/min, monitoring at 220 nm). MS (ES): m/z=450 [M+H]+.

Example 298

HPLC: 2.325 min (RT) (Chromolith column 4.6×50 mm eluting with 10-90% aqueous MeOH over 4 minutes containing 0.1% TFA, 4 mL/min, monitoring at 220 nm). MS (ES): m/z=450 [M+H]+.

Example 299

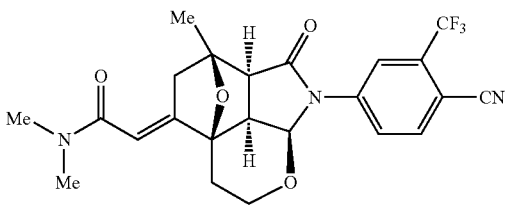

Example 299 was prepared from Example 295 by the general procedure described in Example 296.

HPLC: 2.618 min (RT) (Chromolith column 4.6×50 mm eluting with 10-90% aqueous MeOH over 4 minutes containing 0.1% TFA, 4 mL/min, monitoring at 220 nm). MS (ES): m/z=462 [M+H]+.

Examples 300 and 301

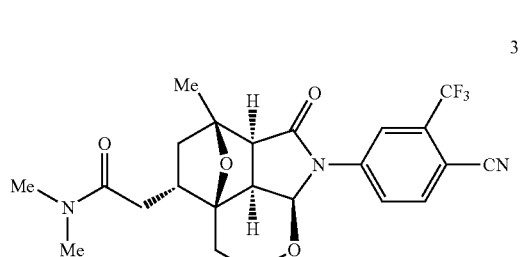

300

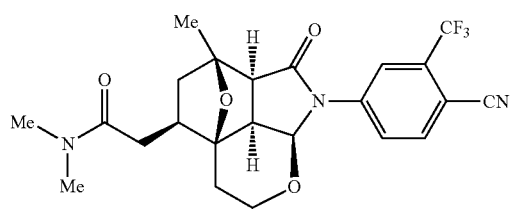

301

Examples 300 and 301 were prepared from Example 299 by the general procedure described in Example 297.

Example 300

HPLC: 2.533 min (RT) (Chromolith column 4.6×50 mm eluting with 10-90% aqueous MeOH over 4 minutes containing 0.1% TFA, 4 mL/min, monitoring at 220 nm). MS (ES): m/z=464 [M+H]+.

Example 301

HPLC: 2.493 min (RT) (Chromolith column 4.6×50 mm eluting with 10-90% aqueous MeOH over 4 minutes containing 0.1% TFA, 4 mL/min, monitoring at 220 nm). MS (ES): m/z=464 [M+H]+.

Example 302

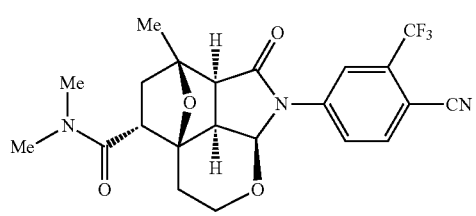

Example 302 was prepared from Example 109 by the general procedure described in Example 296.

HPLC: 2.597 min (RT) (Chromolith column 4.6×50 mm eluting with 10-90% aqueous MeOH over 4 minutes containing 0.1% TFA, 4 mL/min, monitoring at 220 nm). MS (ES): m/z=450 [M+H]+.

Example 303

To a solution of Example 108 (100 mg, 0.246 mmol) in MeOH (2 mL) was added K₂CO₃ (51 mg, 0.369 mmol). The reaction mixture was stirred at RT for 2 h. The solution was concentrated, water was added and mixture was extracted thrice. The combined extracts were washed with brine, dried over MgSO₄, filtered and concentrated. The residue was purified by ISCO silica gel column (4 g column, 15 mL/min, EtOAc/Hexane=1/1) to give Example 303 (33 mg, 33%) and recovered Example 108 (15 mg).

HPLC: 2.418 min (RT) (Chromolith column 4.6×50 mm eluting with 10-90% aqueous MeOH over 4 minutes containing 0.1% TFA, 4 mL/min, monitoring at 220 nm). MS (ES): m/z=407 [M+H]+.

Example 304

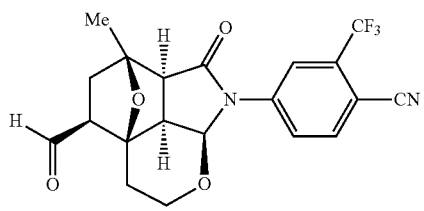

To a solution of Example 303 (28 mg, 0.069 mmol) in 1,4-dioxane (1 mL) was added a solution of NaH₂PO₄ (36 mg, 0.3 mmol) in H₂O (0.25 mL), followed by sulfamic acid (11.6 mg, 0.12 mmol). The reaction mixture was then cooled to 0° C. and a solution of 80% sodium chlorite (11.3 mg, 0.1 mmol) in H₂O (0.2 mL), was added by pipette. After 10 min, sodium sulfite (14 mg, 0.11 mmol) was added, and stirred for 20 min. The reaction mixture was purified by reverse-phase preparative HPLC to give acid Example 304 (19.5 mg, 66%) as white solid.

HPLC: 2.155 min (RT) (Chromolith column 4.6×50 mm eluting with 10-90% aqueous MeOH over 4 minutes containing 0.1% TFA, 4 mL/min, monitoring at 220 nm). MS (ES): m/z=421 [M+H]⁺.

Example 305

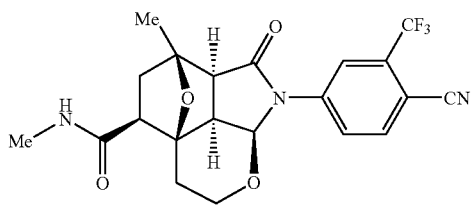

Example 305 was prepared from Example 304 by the general procedure described in Example 296.

HPLC: 2.115 min (RT) (Chromolith column 4.6×50 mm eluting with 10-90% aqueous MeOH over 4 minutes containing 0.1% TFA, 4 mL/min, monitoring at 220 nm). MS (ES): m/z=436 [M+H]⁺.

Example 306

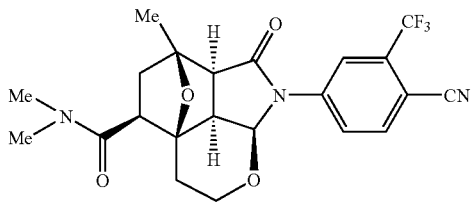

Example 306 was prepared from Example 304 by the general procedure described in Example 296.

HPLC: 2.217 min (RT) (Chromolith column 4.6×50 mm eluting with 10-90% aqueous MeOH over 4 minutes containing 0.1% TFA, 4 mL/min, monitoring at 220 nm). MS (ES): m/z=450 [M+H]⁺.

Example 307

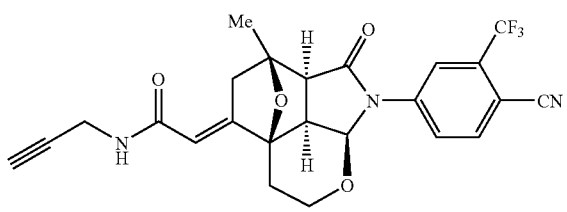

Example 307 was prepared from Example 295 by the general procedure described in Example 296.

HPLC: 2.597 min (RT) (Chromolith column 4.6×50 mm eluting with 10-90% aqueous MeOH over 4 minutes containing 0.1% TFA, 4 mL/min, monitoring at 220 nm). MS (ES): m/z=472 [M+H]⁺.

Examples 308 and 309

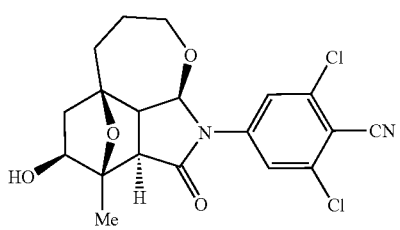

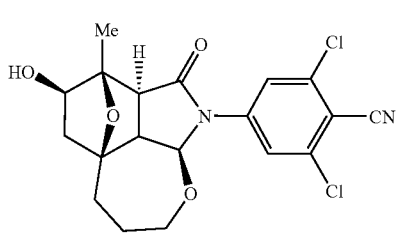

Examples 308 and 309 were prepared by the general procedures shown for Examples 41 and 42.

Example 308

MS (ES): m/z=410 [M+H]⁺; HPLC: 2.28 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 7.52 min (Chiralpak OJ 250×4.6 mm, 10 micro column, 30% isocratic elution, heptane/(EtOH:MeOH 1:1), 1 mL/min, monitoring at 254 nm). The absolute stereochemistry of Example 308 has not been established. Although the compound represents a single antipode, the nomenclature and structure shown does not reflect the absolute stereochemistry of the compound.

Example 309

MS (ES): m/z=410 [M+H]⁺; HPLC: 2.28 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 12.47 min (Chiralpak OJ 250×4.6 mm, 10 micron, 30% isocratic elution, heptane/(EtOH:MeOH 1:1), 1 mL/min, monitoring at 254 nm). The absolute stereochemistry of Example 309 has not been established. Although the compound represents a single antipode, the nomenclature and structure shown does not reflect the absolute stereochemistry of the compound.

Examples 310 and 311

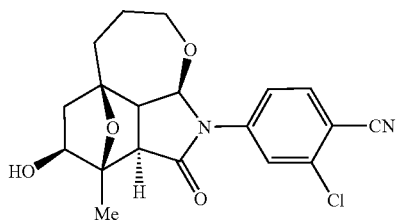

310

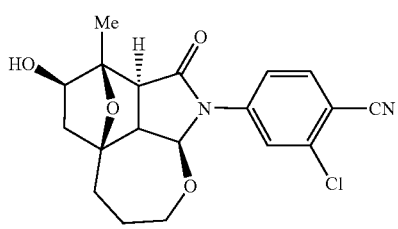

311

Examples 310 and 311 were prepared by the general procedures shown for Examples 41 and 42.

Example 310

MS (ES): m/z=375 [M+H]$^+$; HPLC: 1.83 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 7.54 min (Chiralpak OJ 250×4.6 mm, 10 micro column, 30% isocratic elution, heptane/(EtOH:MeOH 1:1), 1 mL/min, monitoring at 254 nm). The absolute stereochemistry of Example 310 has not been established. Although the compound represents a single antipode, the nomenclature and structure shown does not reflect the absolute stereochemistry of the compound.

Example 311

MS (ES): m/z=375 [M+H]$^+$; HPLC: 1.83 min (RT) (Chromolith SpeedROD column 4.6×50 mm, 10-90% aqueous methanol over 4 minutes containing 0.2% phosphoric acid, 4 mL/min, monitoring at 220 nm); Chiral HPLC: 98% ee, at 14.69 min (Chiralpak OJ 250×4.6 mm, 10 micron, 30% isocratic elution, heptane/(EtOH:MeOH 1:1), 1 mL/min, monitoring at 254 nm). The absolute stereochemistry of Example 311 has not been established. Although the compound represents a single antipode, the nomenclature and structure shown does not reflect the absolute stereochemistry of the compound.

Examples 312 and 313

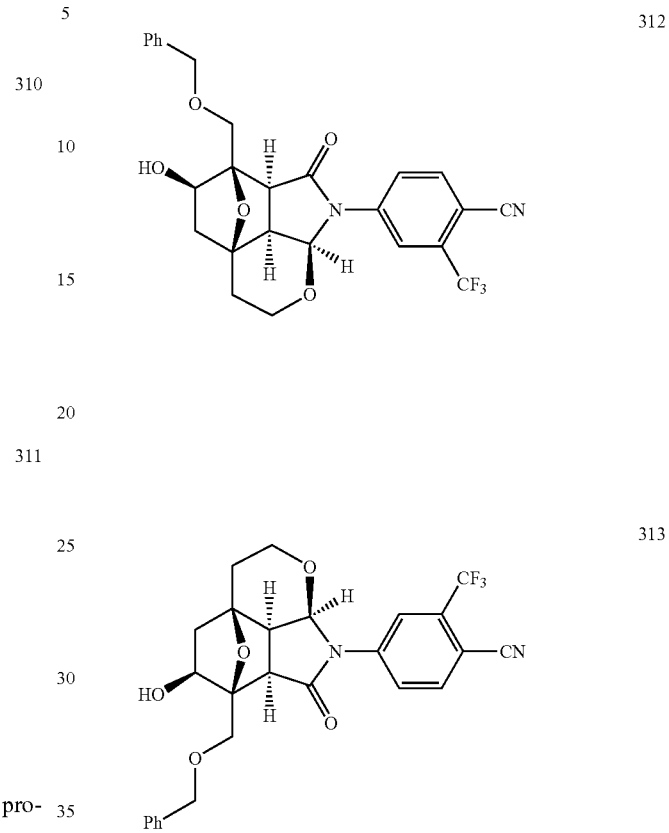

312

313

Preparation 312A

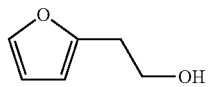

To a solution of furan (100.0 g, 1.469 mol) in THF (700 mL) cooled to −80° C. was added n-Butyl lithium (571.2 mL, 2.7 M, 1.544 mol). The reaction mixture was slowly warmed to r.t. and stirred overnight. The reaction mixture was again cooled to −80° C. and a cooled THF (100 mL) solution of ethylene oxide (180 mL, 2.936 mol) was added slowly. The reaction mixture was allowed to reach r.t. and stirred 14 h. Reaction progress was monitored by GC analysis. The reaction mixture was cooled to 0° C. and saturated ammonium chloride (200 mL) was added slowly. The product was extracted with ethyl acetate (2×500 mL) and the organic layer was washed with water, brine solution, dried over sodium sulfate and concentrated under reduced pressure to give product. The material was purified by vacuum distillation. Yield: 95 g (58%) of Preparation 312A as a colorless liquid.

$^1$H NMR (400 MHz, CDCl$_3$) δ 7.35 (m, 1H), 6.32 (m, 1H), 6.11 (m, 1H), 3.89 (m, 2H), 2.90 (m, 2H), 1.90 (s, 1H).

Preparation 312B

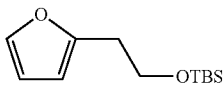

To solution of Preparation 312A (100.0 g, 0.892 mol) in dry CH$_2$Cl$_2$ (500 mL) was added imidazole (78.66 g, 1.155 mol) followed by cooling to 0° C. TBDMSCl (148.0 g, 0.982 mol) in CH$_2$Cl$_2$ (300 ml) was added drop-wise. After addition, reaction mixture was stirred at r.t. for 4 h. After completion of the reaction, water was added and stirred for 5 min and the organic layer was separated. The organic layer was washed with water and brine solution. The organic layer was dried over Na$_2$SO$_4$ and concentrated under reduced pressure. The material was purified by flash chromatography using hexane as eluent to give Preparation 312B as a colorless liquid 180 g (92%).

$^1$H NMR (400 MHz, CDCl$_3$) δ 7.31 (t, 1H, $^3J_{HH}$=1.2), 6.28 (m, 1H), 6.06 (m, 1H), 3.86 (t, 2H, $^3J_{HH}$=7.2), 2.86 (t, 2H, $^3J_{HH}$=7.2), 0.89 (s, 9H), 0.02 (s, 6H).

Preparation 312C

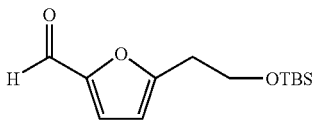

To a solution of Preparation 312B (60.0 g, 0.265 mol) in THF (600 mL) cooled to −78° C. was added n-butyl lithium (104.3 mL, 2.8 M, 0.292 mol) followed by warming to r.t. and stirring for 4 h. The reaction mixture was again cooled to −78° C. and dry DMF (41.0 mL, 0.53 mol) was added drop-wise. The reaction mixture was stirred at −78° C. for 45 min and at r.t. for 1 h. The reaction mixture was quenched with saturated ammonium chloride (200 mL) and the product was extracted in ethyl acetate. The organic layer was washed with water and brine solution, dried over sodium sulfate and concentrated under reduced pressure. The product was purified by flash chromatography using 20% ethyl acetate in hexane to give 40 g of Preparation 312C as a brown liquid (60%).

$^1$H NMR (400 MHz, CDCl$_3$) δ 9.53 (s, 1H), 7.18 (d, 1H, $^3J_{HH}$=3.6), 6.33 (d, 1H, $^3J_{HH}$=3.6), 3.92 (t, 2H, $^3J_{HH}$=6.4), 2.96 (t, 2H, $^3J_{HH}$=6.4), 0.88 (s, 9H), 0.005 (s, 6H).

Preparation 312D

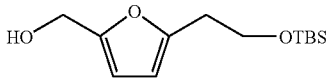

To a solution of Preparation 312C (64.9 g, 0.255 mol) in dry THF (400 mL) was added NaBH$_4$ (14.47 g, 0.383 mol) as portions at 0° C. under N$_2$ and stirred at r.t. for 3 h. The reaction was monitored by TLC. The reaction mixture was quenched by adding saturated Na$_2$HCO$_3$ solution drop-wise over 1 h. The aqueous layer was extracted thrice with ethyl acetate, dried over sodium sulfate, and concentrated under reduced pressure. Preparation 312D was isolated as a yellow liquid (50 g, 77%) and was taken to the next step without further purification.

$^1$H NMR (400 MHz, CDCl$_3$) δ 6.20 (d, 1H, $^3J_{HH}$=4), 6.02 (d, 1H, $^3J_{HH}$=4), 4.56 (s, 1H), 3.86 (t, 2H, $^3J_{HH}$=8), 2.85 (t, 2H, $^3J_{HH}$=8), 0.88 (s, 9H), 0.02 (s, 6H). MS: m/z=255 (M−1).

Preparation 312E

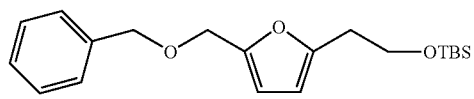

Preparation 312D (26 g, 0.102 mol) in THF (100 mL) was added drop-wise to a suspension of NaH (60% 10.13 g, 0.2535 mol) in THF (200 mL) at 0° C. The reaction mixture was stirred at the same temperature for 1 h. Benzyl bromide (12.7 mL, 0.1064 mol) was added drop-wise while maintaining the reaction temperature at 0° C. The reaction mixture was warmed to r.t. and stirred overnight. After completion of the reaction as measured by TLC, ice cold water was added slowly and the mixture extracted thrice with ethyl acetate. The combined organic layer was washed twice with water, brine dried over sodium sulfate, and concentrated. The product was purified by column chromatography using 5% ethyl acetate in petroleum ether as eluent, to yield 28 g (80%) of Preparation 312E as a yellow liquid.

$^1$H NMR (400 MHz, CDCl$_3$) δ 7.37 (m, 5H), 6.23 (dd, 1H), 6.04 (dd, 1H), 4.56 (s, 1H), 4.45 (s, 1H), 3.88 (t, 2H, $^3J_{HH}$=4), 2.87 (t, 2H, $^3J_{HH}$=4), 0.89 (s, 9H), 0.04 (s, 6H), MS: m/z=347 (M+1).

Preparation 312F

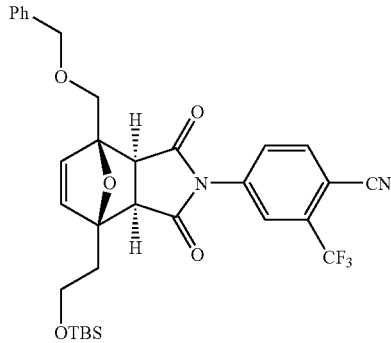

To a solution of Preparation 312E (5.0 g, 0.0144 mol) in a mixture of IPA and THF (15:1) (12.5 mL) was added 4-(2,5-dioxo-2,5-dihydro-1H-pyrrol-1-yl)-2-(trifluoromethyl)benzonitrile (3.0 g, 0.0112 mol). The reaction mixture was stirred at 80° C. for 1.5 h to give a clear solution and stirred further at 55° C. for 48 h. The reaction progress was monitored by TLC until ~70% conversion. The reaction mixture was concentrated under reduced pressure and dried under high vacuum to yield 6.5 g of Preparation 312F.

MS: m/z=613 (M+1).

Preparation 312G and 312H

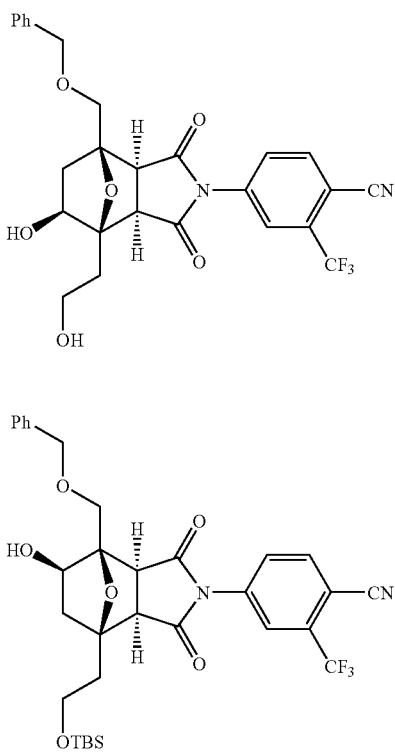

To a solution of Preparation 312F (6.5 g) in THF (70 mL) cooled to 0° C. was added borane dimethyl sulfide complex (3.5 mL, 36.9 mmol). After the addition was complete, the temperature was raised to r.t. and stirred for 30 min. The reaction mixture was cooled to −10° C. and phosphate buffer (pH=7.2) solution (90 mL) was added drop-wise while maintaining inner temperature below 20° C. $H_2O_2$ (30%, 40 mL) was added drop-wise while maintaining inner temperature below 20° C. The reaction mixture was warmed to r.t., ethyl acetate was added and the organic layer was separated. The aqueous layer was extracted twice with ethyl acetate. The combined organic layer was concentrated to minimize the volume of ethyl acetate. The organic layer was cooled to 0° C. and 10% sodium sulfite solution was added. The organic layer was washed with water, brine and concentrated. The product was purified by gradient chromatography on neutral alumina using pet-ether/ethyl acetate mixture. Preparation 312H (1.3 g) was isolated as a white foamy solid eluting with 30% ethyl acetate in pet-ether as eluent. Preparation 312G (0.80 g) was isolated as a white solid eluting with 70% ethyl acetate in pet-ether.

Preparation 312G: $^1$H NMR (400 MHz, CDCl$_3$) δ 7.89 (d, 1H, $^3J_{HH}$=8), 7.83 (s, 1H), 7.64 (dd, 1H), 7.34 (m, 5H), 4.69 (d, 2H, $^2J_{HH}$=12), 4.20-4.12 (m, 3H), 4.05 (d, 1H, $^2J_{HH}$=10.7), 3.92 (d, 1H, $^2J_{HH}$=10.7), 3.24 (d, 1H, $^3J_{HH}$=7.24), 3.19 (d, 1H, $^3J_{HH}$=7.24), 2.5-2.00 (m, 4H), 0.95 (s, 9H), 0.05 (s, 6H). MS: m/z=517 (M+1).

Preparation 312H: $^1$H NMR (400 MHz, CDCl$_3$) δ 7.88 (d, 1H, $^3J_{HH}$=8.4), 7.83 (s, 1H), 7.66 (dd, 1H), 7.34 (m, 5H), 4.69 (d, 1H, $^2J_{HH}$=12), 4.53 (d, 1H, $^2J_{HH}$=12), 4.14 (m, 2H), 4.06 (s, 1H), 3.96 (m, 2H), 3.16 (d, 1H, $^3J_{HH}$=8), 3.10 (d, 1H, $^3J_{HH}$=8), 2.36-2.31 (m, 4H), 0.95 (s, 9H), 0.05 (s, 6H). MS: m/z=631 [M+H]$^+$.

Preparation 312I

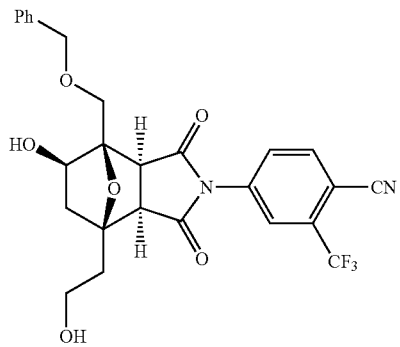

To a solution of Preparation 312H (2.0 g, 0.0031 mol) in ethyl acetate was added 2M HCl (40 mL) and stirred at r.t for 2 h. After the consumption of the starting material, the reaction mixture was twice extracted with ethyl acetate and the combined organic layer was washed with water, dried over sodium sulfate, and concentrated to give Preparation 312I as a white solid (1.2 g, 75%). $^1$H NMR (400 MHz, CDCl$_3$) δ 7.92 (d, 1H, $^3J_{HH}$=8.32), 7.84 (s, 1H), 7.66 (dd, 1H), 7.34 (m, 5H), 4.74 (d, 1H, $^2J_{HH}$=11.4), 4.58 (d, 1H, $^2J_{HH}$=11.4), 4.26-4.04 (m, 4H), 3.78 (m, 2H), 3.40 (d, 1H, $^3J_{HH}$=7.3), 3.17 (d, 1H, $^3J_{HH}$=7.3), 2.41 (m, 2H), 2.17 (m, 2H). MS: m/z=517 [M+H]$^+$.

Examples 312 and 313

Preparation 312I (2.2 g, 0.0043 mol) in THF (22 mL) and MeOH (2.2 mL) was cooled to −5° C. and NaBH$_4$ (0.21 g, 0.00554 mol) was added in portions over 15 min. The reaction mixture was monitored by TLC. After the disappearance of the starting material, the reaction mixture was slowly quenched with 2 M aq. HCl (20 mL). The reaction mixture was concentrated under vacuum to remove some THF. Oil started to come out of solution and was re-dissolved by addition of a minimum amount of THF (2 mL). To the mixture was added more 2M aq. HCl (20 mL) and stirred at r.t. for 48 h. The oily reaction mass was extracted thrice with ethyl acetate. The combined organic layer was washed with water, dried over sodium sulfate and concentrated. The racemic mixture was purified by flash chromatography using 30% ethyl acetate in petroleum ether to give 1.3 g as a white solid. The mixture of enantiomers was separated by chiral preparative HPLC using OD-H SC/191 column (250 mm×20 mm, 5μ, detection wave length: 210 nm).

Example 312

Chiral HPLC: 27.4 minutes (RT) (OD-H SC/601 (250 mm×4.6 mm, 5μ, detection wave length: 210 nm. Mobile Phase: Hexane/IPA (80:20). Flow rate: 1.0 ml/min) $^1$H NMR (400 MHz, CD$_3$OD) δ 8.10 (s, 1H), 7.95 (d, 1H, $^3J_{HH}$=8.56), 7.85 (d, 1H, $^3J_{HH}$=8.56), 7.39 (m, 5H), 5.86 (d, 1H, $^3J_{HH}$=7.6), 4.80 (d, 1H, $^2J_{HH}$=11.56), 4.66 (d, 1H, $^2J_{HH}$=11.6), 4.39 (d, 1H, $^2J_{HH}$=9.56), 4.26 (m, 1H), 4.15 (d, 1H, $^2J_{HH}$=9.56), 3.62 (m, 2H), 3.01 (d, 1H, $^3J_{HH}$=7.88), 2.91 (s, 1H), 2.48 (t, 1H, $^3J_{HH}$=7.68), 2.13 (m, 1H), 2.06 (m, 2H)

1.59 (m, 1H). LC-MS: 2.35 minutes (RT) (Column: ATLANTIS dC18 75×4.6 mm 5μ, mobile phase: 0.1% HCOOH/CH$_3$CN; Flow: 0.8 ml/min.), m/z=500 [M+H]$^+$. The absolute stereochemistry of Example 312 has not been established. Although the compound represents a single antipode, the nomenclature and structure shown does not reflect the absolute stereochemistry of the compound.

Example 313

Chiral HPLC: 38.65 minutes (RT) (OD-H SC/601 (250 mm×4.6 mm, 5μ, detection wave length: 210 nm. Mobile Phase: Hexane/IPA (80:20). Flow rate: 1.0 ml/min) $^1$H NMR (400 MHz, CD$_3$OD) δ 8.10 (s, 1H), 7.95 (d, 1H, $^3$J$_{HH}$=8.56), 7.85 (d, 1H, $^3$J$_{HH}$=8.56), 7.39 (m, 5H), 5.86 (d, 1H, $^3$J$_{HH}$=7.6), 4.80 (d, 1H, $^2$J$_{HH}$=11.56), 4.66 (d, 1H, $^2$J$_{HH}$=11.6), 4.39 (d, 1H, $^2$J$_{HH}$=9.56), 4.26 (m, 1H), 4.15 (d, 1H, $^2$J$_{HH}$=9.56), 3.62 (m, 2H), 3.01 (d, 1H, $^3$J$_{HH}$=7.88), 2.91 (s, 1H), 2.48 (t, 1H, $^3$J$_{HH}$=7.68), 2.13 (m, 1H), 2.06 (m, 2H) 1.59 (m, 1H). LC-MS: 2.35 minutes (RT) (Column: ATLANTIS dC18 75×4.6 mm 5μ, mobile phase: 0.1% HCOOH/CH$_3$CN; Flow: 0.8 ml/min.), m/z=500 [M+H]$^+$. The absolute stereochemistry of Example 313 has not been established. Although the compound represents a single antipode, the nomenclature and structure shown does not reflect the absolute stereochemistry of the compound.

Examples 314 and 315

Example 314

Chiral HPLC: 16.0 minutes (RT) (Column: AD-H SC/600 (250 mm×4.6 mm, 5μ, detection wave length: 210 nm). Mobile Phase: Hexane/IPA (80:20). Flow rate: 1.0 ml/min); $^1$H NMR (400 MHz, CD$_3$OD) δ 8.19 (s, 1H), 8.00 (dd, 2H), 6.02 (d, 1H, $^3$J$_{HH}$=7.24), 4.25-4.14 (m, 3H), 3.63-3.56 (m, 2H), 3.14 (d, 1H, $^3$J$_{HH}$=8), 2.63 (t, 1H, $^3$J$_{HH}$=8), 2.29 (m, 1H), 2.22-1.93 (m, 2H), 1.49 (dd, 1H). LC-MS: 1.3 minutes (RT) (Column: ATLANTIS dC18 75×4.6 mm 5μ, mobile phase: 0.1% HCOOH/CH$_3$CN Flow: 0.8 ml/min), m/z=411 (M+1). The absolute stereochemistry of Example 314 has not been established. Although the compound represents a single antipode, the nomenclature and structure shown does not reflect the absolute stereochemistry of the compound.

Example 315

Chiral HPLC: 42.8 minutes (RT) (Column: AD-H SC/600 (250 mm×4.6 mm, 5μ, detection wave length: 210 nm). Mobile Phase: Hexane/IPA (80:20). Flow rate: 1.0 ml/min); $^1$H NMR (400 MHz, CD$_3$OD) δ 8.19 (s, 1H), 8.00 (dd, 2H), 6.02 (d, 1H, $^3$J$_{HH}$=7.24), 4.25-4.14 (m, 3H), 3.63-3.56 (m, 2H), 3.14 (d, 1H, $^3$J$_{HH}$=8), 2.63 (t, 1H, $^3$J$_{HH}$=8), 2.29 (m, 1H), 2.22-1.93 (m, 2H), 1.49 (dd, 1H). LC-MS: 1.3 minutes (RT) (Column: ATLANTIS dC18 75×4.6 mm 5μ, mobile phase: 0.1% HCOOH/CH$_3$CN Flow: 0.8 ml/min), m/z=411 (M+1). The absolute stereochemistry of Example 315 has not been established. Although the compound represents a single antipode, the nomenclature and structure shown does not reflect the absolute stereochemistry of the compound.

Example 316

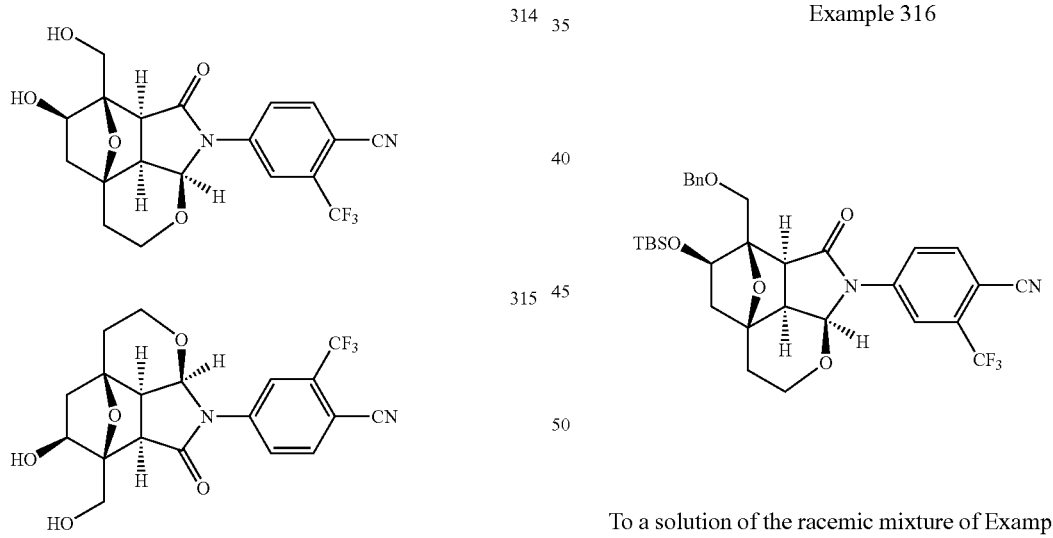

To a solution of the racemic mixture of Examples 312 and 313 (2.3 g, 0.0046 mol) in dry CH$_2$Cl$_2$ (25 mL) at −78° C. was added boron trichloride (15 mL, 1M solution in DCM) dropwise and stirred for 1 h. The reaction mixture was slowly quenched with MeOH (20 mL) followed by the addition of sat. NaHCO$_3$ solution and extracted with CH$_2$Cl$_2$. The organic layer was dried over sodium sulfate and concentrated to give 1.5 g of the mixture of Examples 314 and 315 as a white solid. The two enantiomers were separated by chiral preparative HPLC using chiral AD-H SC/531 (250 mm×20 mm, 5μ, detection wave length: 210 nm).

To a solution of the racemic mixture of Examples 312 and 313 (2.0 g, 0.004 mol) in dry DMF (50 mL) was added imidazole (0.544 g, 0.008 mol) and the solution was cooled to 0° C. TBDMSCl (0.75 g, 0.005 mol) was added to the reaction mixture followed by a catalytic amount of DMAP. The reaction mixture was stirred at r.t. for 2 h. After the completion of the reaction as measured by TLC, water was added slowly and the resulting mixture was extracted with ethyl acetate (3×30 mL). The combined organic layer was washed with water, brine, dried over sodium sulfate, and concentrated. The material was purified by column chromatography using 20% ethyl acetate in pet-ether as eluent to give 2.3 g of racemic Example 316 as a foamy solid.

MS: m/z=615 [M+H]$^+$.

Example 317

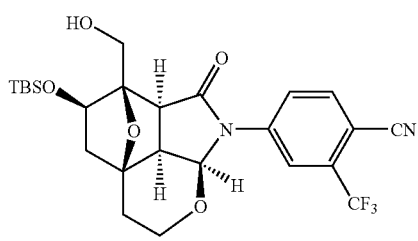

Example 316 (0.3 g, 0.0037 mol, 1 eq) in dry CH$_2$Cl$_2$ (25.0 mL) was cooled to −100° C. and boron trichloride in CH$_2$Cl$_2$ (20 mL, 1M in CH$_2$Cl$_2$) was added drop-wise. The reaction mixture was stirred at the same temperature for 1 h and slowly quenched with MeOH (20 mL) followed by the addition of sat. NaHCO$_3$ solution. The product was extracted with CH$_2$Cl$_2$ (2×50 mL), dried over sodium sulfate and concentrated to give Example 317 (1.6 g, 84%) as a white solid.

LC-MS: 4.177 minutes (RT) (Column: ATLANTIS dC18 75×4.6 mm, 5μ, mobile phase: 0.1% HCOOH/CH$_3$CN; Flow: 0.8 ml/min.), m/z=523 [M+H]$^+$.

Example 318

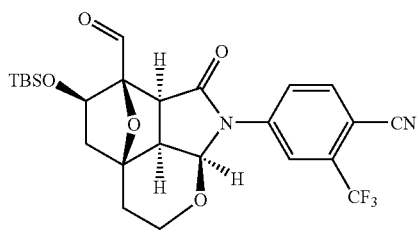

To a solution of Example 317 (1.8 g, 0.0034 mol) in dry DCM (20 mL) was added 2,2,6,6-tetramethylpiperidine-1-oxyl (TEMPO) (53 mg, 0.00034 mol), KBr (25 mg, 0.00034 mol) followed by water (1.8 mL). The reaction mixture was cooled to 0° C., followed by the drop-wise addition of sodium hypochlorite (while adjusting pH to approximately 9.5 using 5% NaHCO$_3$, 25 mL). The reaction mixture was stirred at r.t. for 2 h. The aqueous layer was extracted with ethyl acetate (3×25 mL). The combined organic layers were washed with water, brine dried over sodium sulfate and concentrated. Yield: 1.2 g, (66%) as a yellow liquid.

MS: m/z=521 [M+H]$^+$.

Example 319

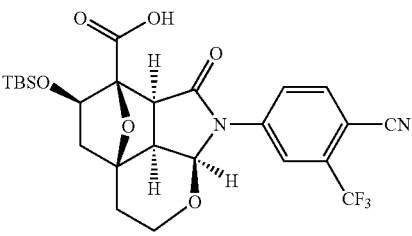

To a solution of Example 318 (1.2 g, 0.0023 mol) in tert-butanol (25 mL) and water (10 mL) cooled to 0° C., was added sodium chlorite (0.645 g, 0.009 mol), sodium dihydrogen phosphate (0.925 g, 0.009 mol) followed by the slow addition of 2-methyl-2-butene (1.5 mL, 0.0138 mol). The mixture was stirred at r.t. for 4 h. The reaction progress was monitored by TLC. Over the course of the reaction, a white solid precipitated out and this was filtered and dried under vacuum to give 0.80 g of Example 319 as a white solid.

LC-MS: 2.94 minutes (RT) (Column: ATLANTIS dC18 75×4.6 mm 5μ, mobile phase: 0.1% HCOOH/CH$_3$CN; Flow: 0.8 ml/min), m/z=539 [M+H]$^+$.

Example 320

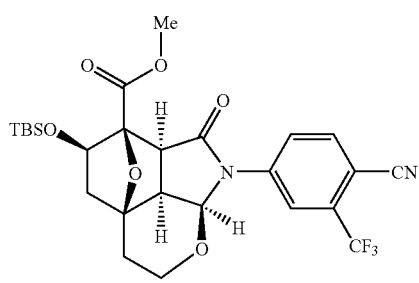

Example 319 (0.6 g, 0.0011 mol) was dissolved in dry CH$_2$Cl$_2$ (10 mL), cooled to 0° C., and trimethylsilyl diazomethane (10 mL, 3 M solution in diethyl ether) was added drop-wise. The reaction mixture was stirred at 0° C. for 1 h. After the disappearance of the starting material as measured by TLC, the reaction mixture was directly concentrated under reduce pressure. The product was purified by flash column chromatography using 10% ethyl acetate in pet-ether as eluent to give 0.42 g of Example 320 as a white solid.

LC-MS: 3.922 minutes (RT) (Column: ATLANTIS dC18 75×4.6 mm 5μ, mobile phase: 0.1% HCOOH/CH₃CN; Flow: 0.8 ml/min), m/z=552 [M+H]⁺.

Examples 321 and 322

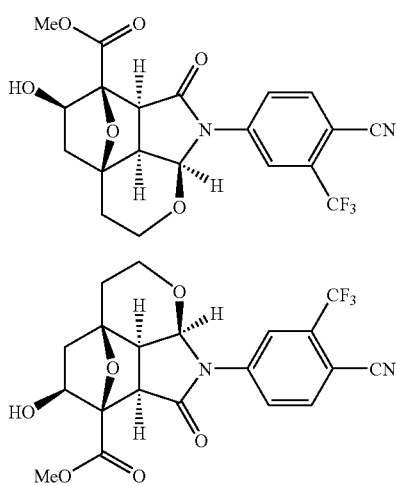

Example 320 (0.4 g, 0.0007 mol) was dissolved in dry DMF (7.0 mL) under N₂ and cesium fluoride (0.32 g, 0.0021 mol) was added. The reaction mixture was heated to 70° C. for 1 h. The reaction mixture was quenched with water and extracted with ethyl acetate (3×20 mL). The combined organic layer was washed thrice with water, dried over Na₂SO₄, and concentrated. The product was purified by flash column chromatography using 3% MeOH in CHCl₃ as eluent to give 0.021 g (68%) of the racemic mixture of Examples 321 and 322 as a white solid. The enantiomers were separated by chiral preparative HPLC (Agillent 1200 series) using AD-H SC/531 column (250 mm×20 mm, 5μ, detection wave length: 210 nm).

Example 321

Chiral HPLC: 16.53 minutes (RT) (Column: AD-H SC/600 (250 mm×4.6 mm, 5μ, detection wave length: 210 nm). Mobile Phase: Hexane/IPA (80:20). Flow rate: 1.0 ml/min); ¹H NMR (400 MHz, CD₃OD): δ 8.21 (s, 1H), 8.02-7.95 (dd, 2H), 6.05 (d, 1H, ³J$_{HH}$=7.2), 4.42 (m, 1H), 3.88 (s, 3H), 3.63-3.33 (m, 3H), 2.65 (t, 1H, ³J$_{HH}$=8), 2.27 (m, 1H), 2.09 (m, 2H), 1.58 (dd, 1H). LC-MS: 1.35 minutes (RT) (Column: ATLANTIS dC18 75×4.6 mm 5μ, mobile phase: 0.1% HCOOH/CH₃CN; Flow: 0.8 ml/min), m/z=438 [M+H]⁺. The absolute stereochemistry of Example 321 has not been established. Although the compound represents a single antipode, the nomenclature and structure shown does not reflect the absolute stereochemistry of the compound.

Example 322

Chiral HPLC: 29.07 minutes (RT) (Column: AD-H SC/600 (250 mm×4.6 mm, 5μ, detection wave length: 210 nm). Mobile Phase: Hexane/IPA (80:20). Flow rate: 1.0 ml/min); ¹H NMR (400 MHz, CD₃OD): δ 8.21 (s, 1H), 8.02-7.95 (dd, 2H), 6.05 (d, 1H, ³J$_{HH}$=7.2), 4.42 (m, 1H), 3.88 (s, 3H), 3.63-3.33 (m, 3H), 2.65 (t, 1H, ³J$_{HH}$=8), 2.27 (m, 1H), 2.09 (m, 2H), 1.58 (dd, 1H). LC-MS: 1.35 minutes (RT) (Column: ATLANTIS dC18 75×4.6 mm 5μ, mobile phase: 0.1% HCOOH/CH₃CN; Flow: 0.8 ml/min), m/z=438 [M+H]⁺. The absolute stereochemistry of Example 322 has not been established. Although the compound represents a single antipode, the nomenclature and structure shown does not reflect the absolute stereochemistry of the compound.

Example 323

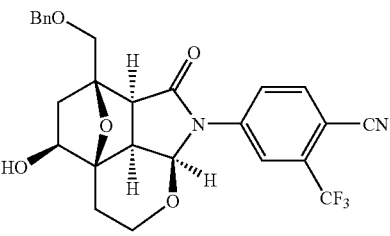

To a solution of racemic Preparation 312G (2.2 g, 0.0043 mol) in THF (22 mL) and MeOH (2.2 mL) cooled in an ice/salt bath was added in portions NaBH₄ (0.21 g, 0.00554 mol) over 15 min. The reaction mixture was monitored by TLC. After the disappearance of the starting material, the reaction mixture was slowly quenched with 2M aq. HCl (20 mL). The reaction mixture was concentrated under vacuum to remove some THF. Oil started to come out of solution and was re-dissolved by addition of minimum amount of THF (2 mL). To the mixture was added more 2M aq. HCl (20 mL) and stirred at r.t. for 48 h. The oily reaction mass was extracted thrice with ethyl acetate. The combine organic layer was washed with water, dried over sodium sulfate and concentrated. The product was purified by flash chromatography using 60% ethyl acetate with petroleum ether to give 1.2 g of Example 323 as a white solid.

¹H NMR (400 MHz, CD₃OD) δ 8.10 (s, 1H), 7.91 (d, 1H, ³J$_{HH}$=8.48), 7.83 (d, 1H, ³J$_{HH}$=8.48), 7.35 (m, 5H), 5.93 (d, 1H, ³J$_{HH}$=7.20), 4.75 (d, 1H, ²J$_{HH}$=12), 4.63 (d, 1H, ²J$_{HH}$=12), 4.19 (d, 1H, ²J$_{HH}$=10.8), 4.08 (d, 1H, ²J$_{HH}$=10.8), 3.79 (m, 1H), 3.66-3.55 (m, 2H), 2.91 (d, 1H, ³J$_{HH}$=7.72), 2.39 (t, 1H, ³J$_{HH}$=7.6), 2.18-1.97 (m, 6H). LC-MS: 2.02 minutes (RT) (Column: ATLANTIS dC18 75×4.6 mm 5μ, mobile phase: 0.1% HCOOH/CH₃CN; Flow: 0.8 ml/min), m/z=500 [M+H]⁺.

Examples 324 and 325

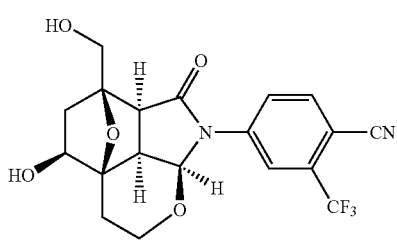

325

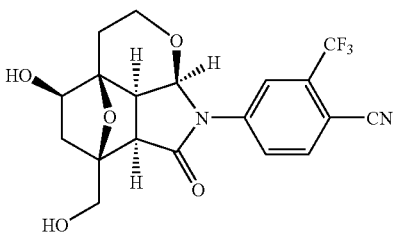

To a solution of Example 323 (2.3 g, 0.0046 mol) in dry CH$_2$Cl$_2$ (25 mL) at −78° C. was added boron trichloride (18 mL, 1M solution in DCM) and the mixture was stirred for 1 h. The reaction mixture was then slowly quenched with MeOH (20 mL) followed by sat. NaHCO$_3$ solution and extracted with CH$_2$Cl$_2$. The organic layer was dried over sodium sulfate and concentrated to give 1.5 g of the racemic mixture of Examples 324 and 325 as a white solid. The two enantiomers were separated by chiral preparative HPLC using OD-H SC/191 (250 mm×20 mm, 5μ, detection wave length: 210 nm).

Example 324

Chiral HPLC: 13.0 minutes (RT) (Column: AD-H SC/600 (250 mm×4.6 mm, 5μ, detection wave length: 210 nm). Mobile Phase: 0.1% TFA in Hexane/IPA (80:20). Flow rate: 1.0 ml/min); $^1$H NMR (400 MHz, CD$_3$OD) δ 8.19 (s, 1H), 7.99 (dd, 2H), 6.06 (d, 1H, $^3J_{HH}$=8), 4.15 (d, 2H, $^3J_{HH}$=4), 3.84 (d, 1H, $^3J_{HH}$=8), 3.60-3.55 (m, 2H), 3.05 (d, 1H, $^3J_{HH}$=4), 2.55 (t, 1H, $^3J_{HH}$=8), 2.20 (m, 1H), 2.07-1.92 (m, 3H). LC-MS: 1.20 minutes (RT) (Column: ATLANTIS dC18 75×4.6 mm 5μ, mobile phase: 0.1% HCOOH/CH$_3$CN Flow: 0.8 ml/min), m/z=411 [M+H]$^+$. The absolute stereochemistry of Example 324 has not been established. Although the compound represents a single antipode, the nomenclature and structure shown does not reflect the absolute stereochemistry of the compound.

Example 325

Chiral HPLC: 14.6 minutes (RT) (Column: AD-H SC/600 (250 mm×4.6 mm, 5μ, detection wave length: 210 nm). Mobile Phase: 0.1% TFA in Hexane/IPA (80:20). Flow rate: 1.0 ml/min); $^1$H NMR (400 MHz, CD$_3$OD) δ 8.19 (s, 1H), 7.99 (dd, 2H), 6.06 (d, 1H, $^3J_{HH}$=8), 4.15 (d, 2H, $^3J_{HH}$=4), 3.84 (d, 1H, $^3J_{HH}$=8), 3.60-3.55 (m, 2H), 3.05 (d, 1H, $^3J_{HH}$=4), 2.55 (t, 1H, $^3J_{HH}$=8), 2.20 (m, 1H), 2.07-1.92 (m, 3H). LC-MS: 1.20 minutes (RT) (Column: ATLANTIS dC18 75×4.6 mm 5μ, mobile phase: 0.1% HCOOH/CH$_3$CN Flow: 0.8 ml/min), m/z=411 [M+H]$^+$. The absolute stereochemistry of Example 325 has not been established. Although the compound represents a single antipode, the nomenclature and structure shown does not reflect the absolute stereochemistry of the compound.

Examples 326 and 327

326

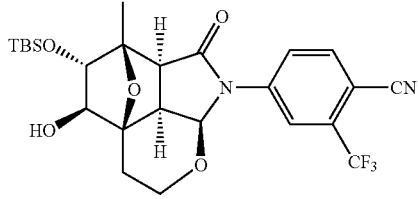

327

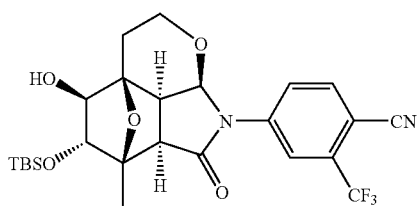

Preparation 326A

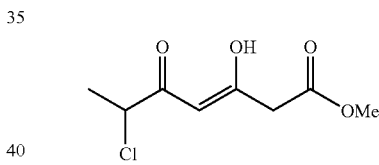

A solution of methyl 3-oxobutanoate (10.0 g, 86 mmol) in THF (60 mL) was added via additional funnel to a suspension of sodium hydride (3.44 mL, 103 mmol) in THF (500 mL) in a 3-neck 2 L round bottom flask at 0° C. under nitrogen. The speed of addition was controlled so that the internal temperature did not reach above 3° C. After the addition was complete, the color of solution changed to grey. The reaction mixture was stirred at 0° C. for 20 min. Then butyllithium (53.8 mL, 86 mmol) was added slowly so that the internal temperature was maintained below 3° C. The mixture was stirred at 0° C. for 20 min. The color of the solution changed to a yellow tint. The reaction was then cooled to −78° C. and methyl 2-chloropropanoate (11.78 mL, 103 mmol) was added via additional funnel followed by boron trifluoride ethyl ether complex (12.71 mL, 103 mmol). The reaction mixture was slowly warmed to 0° C. for 3 h. Next, saturated NH$_4$Cl and EtOAc were added to quench the reaction. The organic layer was separated and washed with brine and dried over MgSO$_4$. The resulting product was filtered to remove the solvent and the residue was dissolved in CH$_2$Cl$_2$ and purified with flash chromatography in ISCO using 330 column, Flow rate: 100 mL/min, solvent A: CH$_2$Cl$_2$, solvent B: EtOAc. Gradient: 0% B to 70% B in 25 minutes. Preparation 326A was eluted with about 40% B to give 7.8 g of yellow oil.

HPLC (RT): 2.063 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=205.2 [M−H]⁻.

Preparation 326B

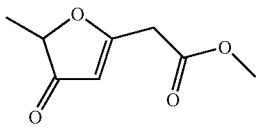

To a solution of Preparation 326A ((Z)-methyl 6-chloro-3-hydroxy-5-oxohept-3-enoate) (6.7 g, 32.4 mmol) in THF (100 mL) at 22° C. was added 1,8-Diazabicyclo[5.4.0]undec-7-ene (9.70 ml, 64.9 mmol). The reaction mixture was stirred at 22° C. for 16 h, and the diluted with EtOAc and 1N HCl. The organic phase was separated and washed with brine, dried over $MgSO_4$, concentrated and purified with flash chromatography in ISCO using 120 g column, Flow rate: 85 mL/min, solvent A: Hexane, solvent B: EtOAc. Gradient: 0% B to 100% B in 25 minutes. Preparation 326B eluted with 50% B to give 3.2 g of light yellow oil.

HPLC (RT): 1.2 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=171.06 [M+H]⁺.

Preparation 326C

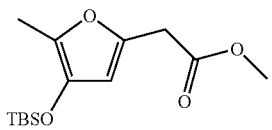

To a solution of Preparation 326B (methyl 2-(5-methyl-4-oxo-4,5-dihydrofuran-2-yl)acetate) (3.2 g, 18.81 mmol) in $CH_2Cl_2$ (50 mL) at 0° C. was added TEA (2.87 mL, 20.69 mmol) followed by t-butyldimethylsilyl triflate (4.54 mL, 19.75 mmol). The reaction was stirred at 0° C. for 2 h. The material was purified with flash chromatography in ISCO using 120 g column, Flow rate: 30 mL/min, solvent A: Hexane, solvent B: EtOAc. Gradient: 0% B to 50% B in 25 minutes. Preparation 326C was eluted with 15% B to give 3.6 g of a yellow liquid.

HPLC (RT): 3.97 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=285.21 [M+H]⁺.

Preparation 326D

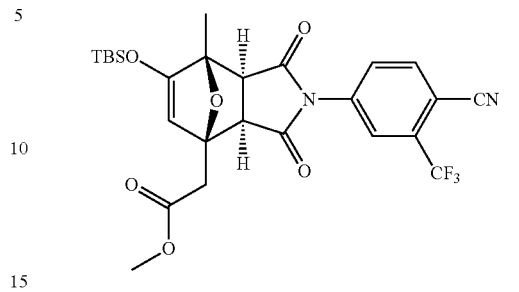

Preparation 326C (Ethyl 2-(4-(tert-butyldimethylsilyloxy)-5-methylfuran-2-yl)acetate) (3.6 g, 12.66 mmol) and 4-(2,5-dioxo-2,5-dihydro-1H-pyrrol-1-yl)-2-(trifluoromethyl)benzonitrile (3.37 g, 12.66 mmol) were mixed in a 50 mL flask. THF (10 mL) was added so that it formed an homogeneous solution. The reaction mixture was stirred at r.t. under $N_2$ for 16 h (reaction was complete within 30 min.). Solvent was removed by reduced pressure and the residue was dissolved in $CH_2Cl_2$ and purified with flash chromatography in ISCO using 330 g column, Flow rate: 100 mL/min, solvent A: Hexane, solvent B: EtOAc. Gradient: 0% B to 100% B in 25 minutes to give 2.60 g of Preparation 326D as a white solid.

HPLC (RT): 4.11 min (YMC ODS-A column 4.6×50 mm eluting with 10-90% aqueous MeOH over 4 minutes containing 0.1% $H_3PO_4$, 4 mL/min, monitoring at 220 nm).

Preparation 326E

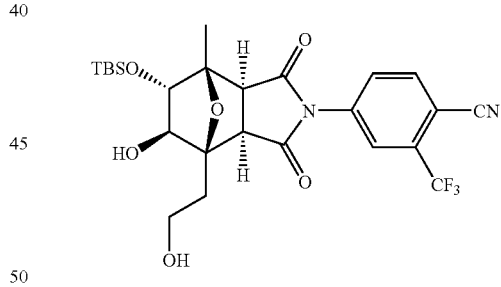

To a solution of Preparation 326D (2.6 g, 4.72 mmol) in THF at 0° C. was added $BH_3$.THF complex (1.0 M in THF, 5.0 mL, 5.0 mmol) slowly. The reaction was stirred at 0° C. for 15 min followed by the two separate addition of 5 mL of $BH_3$.THF complex The reaction mixture was stirred at 0° C. for 3 h and then it was warmed up to room temperature for 30 min. The reaction mixture was then cooled to 0° C. and pH 7 phosphate buffer (15 mL) was added followed by 30% $H_2O_2$ in water (10 mL). The reaction mixture was stirred at 0° C. and warmed up to r.t. and stirred at r.t. for 16 h. EtOAc was added. Organic was separated and washed with brine, dried over $MgSO_4$, concentrated and the material was purified with flash chromatography in ISCO using 120 g column, (Flow rate: 85 mL/min, solvent A: Hexane, solvent B: EtOAc. Gradient: 0% B to 100% B in 25 minutes) to give 1.60 g of Preparation 326E as a white solid.

HPLC (RT): 3.83 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=541.1 $[M+H]^+$.

Examples 326 and 327

To a solution of Preparation 326E (1.1 g, 2.035 mmol) in THF/MeOH (20 mL) at 0° C. was added sodium borohydride (0.385 g, 10.17 mmol). The reaction was stirred at 0° C. for 1 h. Saturated $NH_4Cl$ and EtOAc were added. The organic layers were separated and washed with brine, dried with $MgSO_4$, and concentrated to give 1.1 g of the intermediate aminal as a white solid.

The above-prepared aminal was dissolved in $CH_2Cl_2$ (20 mL) at 0° C. and TFA (3 mL) was added drop-wise. The reaction was then stirred at room temperature for 2 h. Solvent was removed and the residue was purified with flash chromatography in ISCO using 80 g column (Flow rate: 50 mL/min, solvent A: Hexane, solvent B: EtOAc. Gradient: 0% B to 80% B in 25 minutes) to give 0.800 g of the racemic mixture of Examples 325 and 326 as a white solid.

HPLC (RT): 3.8 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=523.1 $[M-H]^-$.

The racemic mixture (660 mg) was separated by SFC chiral HPLC. A Chiracel OJ-H column (3 cm×25 cm) was used at 100 bar, eluting with 90/10 $CO_2$/MeOH at 130 mL/min (35° C.), monitoring at 270 nm.

Example 326

0.23 g obtained, (RT)=2.34 min. The absolute stereochemistry of Example 325 has not been established. Although the compound represents a single antipode, the nomenclature and structure shown does not reflect the absolute stereochemistry of the compound.

Example 327

0.23 g obtained, (RT)=6.69 min. The absolute stereochemistry of Example 326 has not been established. Although the compound represents a single antipode, the nomenclature and structure shown does not reflect the absolute stereochemistry of the compound.

Example 328

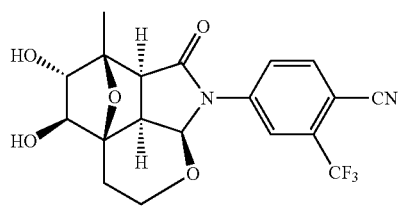

To the racemic mixture of Examples 326 and 327 (150 mg, 0.286 mmol) was added 10% HCl in THF (1 mL). The reaction was stirred under $N_2$ at 22° C. for 16 h. Solvent was removed and to the resulting residue was added $CH_2Cl_2$. The solid was collected by filtration to give 90 mg of racemic Example 328 as a white solid.

HPLC (RT): 2.4 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=411.0 $[M-H]^-$.

Examples 329 and 330

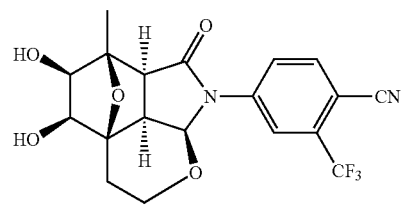

328

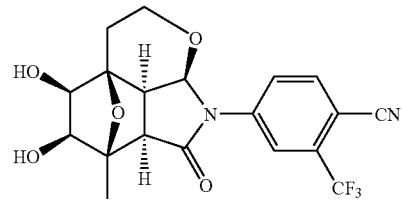

329

The racemic Example 31 (1.0 g) was separated by SFC chiral HPLC. A Chiracel OJ-H column (3 cm×25 cm) was used at 100 bar, eluting with 90/10 $CO_2$/MeOH at 150 mL/min (35° C.), monitoring at 270 nm.

Example 329

0.4 g obtained, (RT)=4.42 min. The absolute stereochemistry of Example 328 has not been established. Although the compound represents a single antipode, the nomenclature and structure shown does not reflect the absolute stereochemistry of the compound.

Example 330

0.4 g obtained, (RT)=6.27 min. The absolute stereochemistry of Example 329 has not been established. Although the compound represents a single antipode, the nomenclature and structure shown does not reflect the absolute stereochemistry of the compound.

Examples 331 and 332

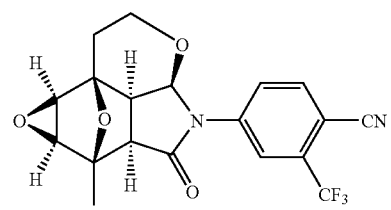

331

-continued

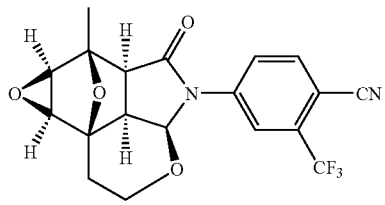
332

The racemic mixture Example 71 (460 mg) was separated by SFC chiral HPLC. A Chiracel AD-H column (0.46 cm×25 cm) was used at 100 bar, eluting with 80/20 $CO_2$/MeOH at 3 mL/min (35° C.), monitoring at 270 nm.

Example 331

0.23 g obtained, (RT)=2.7 min. The absolute stereochemistry of Example 330 has not been established. Although the compound represents a single antipode, the nomenclature and structure shown does not reflect the absolute stereochemistry of the compound.

Example 332

0.23 g obtained, (RT)=3.5 min. The absolute stereochemistry of Example 331 has not been established. Although the compound represents a single antipode, the nomenclature and structure shown does not reflect the absolute stereochemistry of the compound.

Example 333

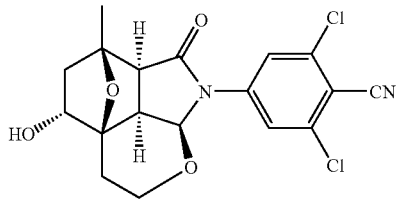

Example 333 was prepared from Example 70 by the general procedures shown in Examples 5 and 6.

HPLC (RT): 3.481 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=395.16 $[M+H]^+$.

Example 334

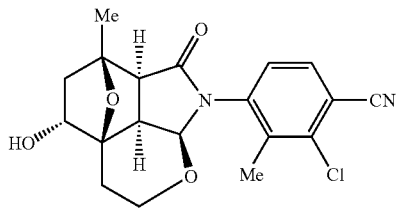

Example 334 was prepared by the general procedures shown in Examples 5 and 6.

HPLC (RT): 3.025 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=375.38 $[M+H]^+$.

Example 335

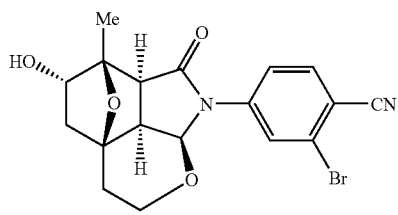

Example 335 was prepared from Example 146 by the general procedures shown in Examples 5 and 6.

HPLC (RT): 3.106 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=405.12 $[M+H]^+$.

Example 336

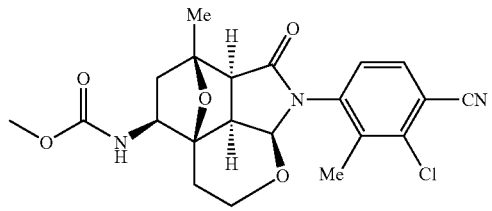

Example 336 was prepared from Example 334 by the general procedures shown in Examples 7 and 8.

HPLC (RT): 3.083 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=432.50 $[M+H]^+$.

Example 337

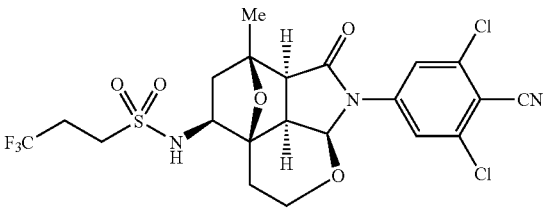

Example 337 was prepared from Example 333 by the general procedures shown in Examples 7 and 9.

HPLC (RT): 3.650 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=554.1 [M+H]$^+$.

Example 338

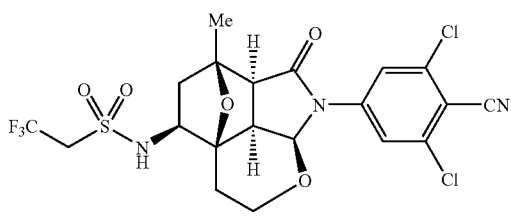

Example 338 was prepared from Example 333 by the general procedures shown in Examples 7 and 9.

HPLC (RT): 3.548 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=540.07 [M+H]$^+$.

Example 339

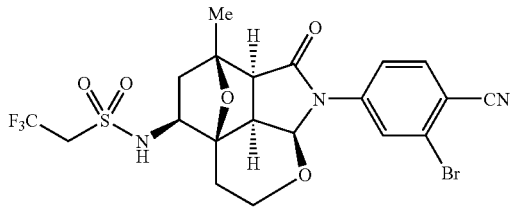

Example 339 was prepared from Example 127 by the general procedures shown in Examples 7 and 9.

HPLC (RT): 3.246 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=552.37 [M+H]$^+$.

Example 340

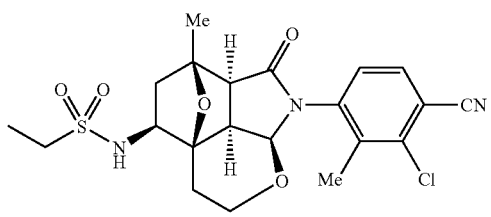

Example 340 was prepared from Example 334 by the general procedures shown in Examples 7 and 9.

HPLC (RT): 2.891 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=466.38 [M+H]$^+$.

Example 341

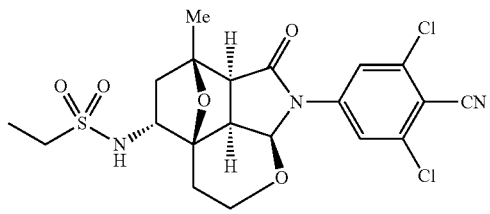

Example 341 was prepared from Example 70 by the general procedures shown in Examples 10 and 9.

HPLC (RT): 3.270 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=418.25 [M+H]$^+$.

Example 342

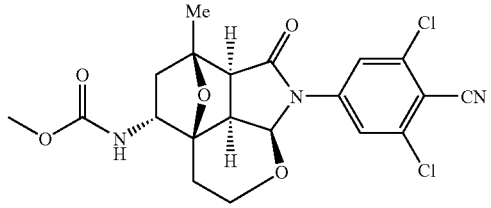

Example 342 was prepared from Example 70 by the general procedures shown in Examples 10 and 8.

HPLC (RT): 3.676 min (YMC ODS-A column 4.6×50 mm eluting with 10-90% aqueous MeOH over 4 minutes containing 0.1% $H_3PO_4$, 4 mL/min, monitoring at 220 nm). MS (ES): m/z=452.17 [M+H]$^+$.

Example 343

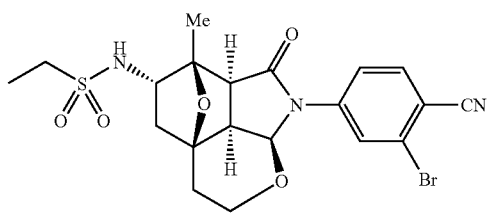

Example 343 was prepared from Example 146 by the general procedures shown in Examples 10 and 9.

HPLC (RT): 3.395 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=497.10 [M+H]$^+$.

Example 344

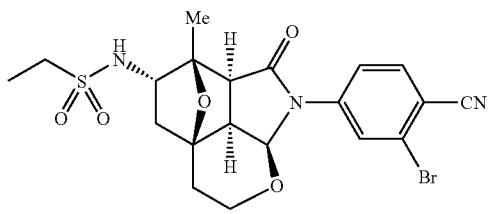

Example 344 was prepared from Example 16 by the general procedures shown in Examples 10 and 9.

HPLC (RT): 3.253 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=452.24 [M+H]$^+$.

Example 345

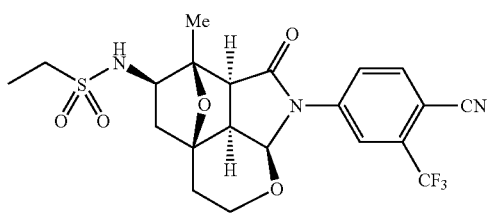

Example 345 was prepared from Example 156 by the general procedures shown in Examples 7 and 9.

HPLC (RT): 3.063 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=486.17 [M+H]$^+$.

Example 346

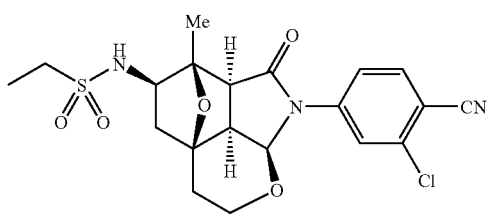

Example 346 was prepared from Example 159 by the general procedures shown in Examples 7 and 9.

HPLC (RT): 2.92 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=452.30 [M+H]$^+$.

Example 347

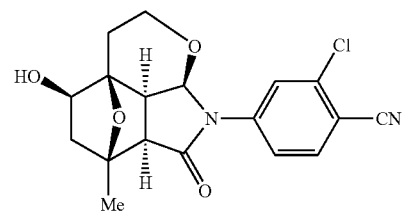

Example 347 was prepared from 2-chloro-4-(2,5-dioxo-2,5-dihydro-1H-pyrrol-1-yl)benzonitrile and Preparation 1B by the general procedures shown in Examples 1 and 3.

HPLC (RT): 2.23 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=361.3 [M+H]$^+$.

Example 348

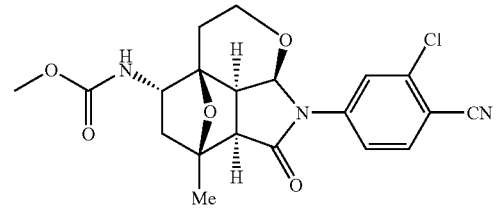

Example 347 was prepared from Example 348 by the general procedures shown in Examples 10 and 8.

HPLC (RT): 3.270 min (YMC ODS-A column 4.6×50 mm eluting with 10-90% aqueous MeOH over 4 minutes containing 0.1% H$_3$PO$_4$, 4 mL/min, monitoring at 220 nm). MS (ES): m/z=418.25 [M+H]$^+$.

Example 349

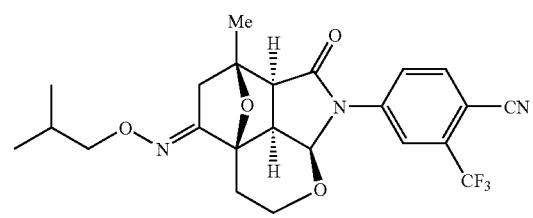

Example 349 was prepared from Example 29 by the general procedure shown in Example 30.

HPLC (RT): 4.218 min (YMC ODS-A column 4.6×50 mm eluting with 10-90% aqueous MeOH over 4 minutes containing 0.1% H₃PO₄, 4 mL/min, monitoring at 220 nm). MS (ES): m/z=464.31 [M+H]⁺.

Example 350

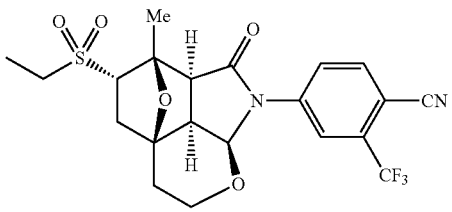

Example 350 was prepared from Example 1 by the general procedures shown in Examples 34A and 88.

HPLC (RT): 3.380 min (YMC ODS-A column 4.6×50 mm eluting with 10-90% aqueous MeOH over 4 minutes containing 0.1% H₃PO₄, 4 mL/min, monitoring at 220 nm). MS (ES): m/z=471.39 [M+H]⁺.

Example 351

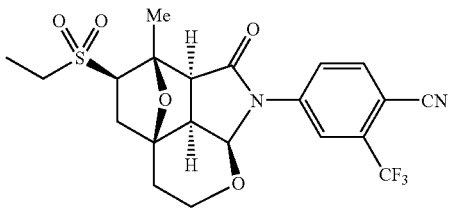

Example 351 was prepared from Example 156 by the general procedures shown in Examples 34A and 88.

HPLC (RT): 3.220 min (YMC ODS-A column 4.6×50 mm eluting with 10-90% aqueous MeOH over 4 minutes containing 0.1% H₃PO₄, 4 mL/min, monitoring at 220 nm). MS (ES): m/z=471.30 [M+H]⁺.

Example 352

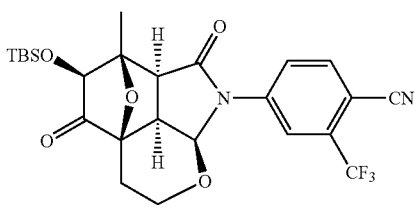

To a solution of racemic Example 32 (0.78 g, 1.487 mmol) in CH₂Cl₂ (50 mL) at 25° C. was added Dess-Martin periodinane (1.261 g, 2.97 mmol). The reaction was stirred at 25° C. for 48 h. Then 5% Na₂SO₃ in water (40 mL) was added. The reaction was stirred at 25° C. for 20 min. Organic phases was separated, washed with saturated NaHCO₃, brine and dried over anhydrous magnesium sulfate and filtered. The filtrate was concentrated in vacuo to give 0.78 g of Example 352 as a white solid.

HPLC (RT): 4.1 min (YMC ODS-A column 4.6×50 mm eluting with 10-90% aqueous MeOH over 4 minutes containing 0.1% H₃PO₄, 4 mL/min, monitoring at 220 nm). MS (ES): m/z=523.0 [M+H]⁺.

Example 353

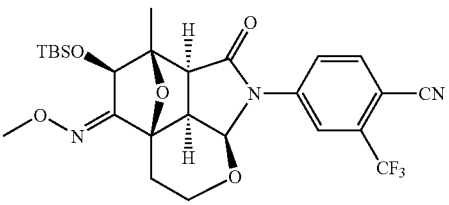

Racemic Example 353 was prepared from Example 352 by the general procedure shown for Example 30. MS (ES): m/z=552.3 [M+H]⁺.

Example 354

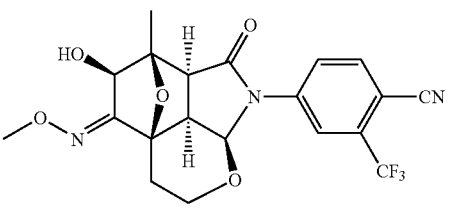

Racemic Example 354 was prepared from Example 353 by the general procedure shown in Preparation 15D.

HPLC (RT): 3.201 min (YMC ODS-A column 4.6×50 mm eluting with 10-90% aqueous MeOH over 4 minutes containing 0.1% H₃PO₄, 4 mL/min, monitoring at 220 nm). MS (ES): m/z=438.23 [M+H]⁺. ¹H NMR (500 MHz, d⁶-DMSO) δ ppm 1.49 (s, 3H) 1.82-1.91 (m, 1H) 2.04-2.22 (m, 1H) 2.58 (t, J=7.84 Hz, 1H) 3.07 (d, J=7.97 Hz, 1H) 3.44-3.69 (m, 2H) 3.79 (s, 3H) 4.37 (d, J=6.87 Hz, 1H) 5.64 (d, J=6.87 Hz, 1H) 6.04 (d, J=7.70 Hz, 1H) 7.93 (dd, J=8.52, 1.92 Hz, 1H) 8.12 (d, J=1.65 Hz, 1H) 8.20 (d, J=8.52 Hz, 1H).

Biological Testing of Compounds

AR Binding Assay

For the whole cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, are incubated at 37° C. to remove any endogenous ligand that might be complexed with the receptor in the cells. After 48 hours, either a saturation analysis to determine the $K_d$ for tritiated dihydrotestosterone, [³H]-DHT, or a competitive binding assay to evaluate the ability of test compounds to compete with [³H]-DHT is performed. For the saturation analysis, media (RPMI 1640 or DMEM-0.2% CA-FBS) containing [³H]-DHT (in concentrations ranging from 0.1 nM to 16 nM) in the absence (total binding) or presence (non-specific binding) of a 500-fold molar excess of unlabeled DHT are added to the cells. After 4 hours at 37° C., an aliquot of the total binding media at each concentration of [³H]-DHT is removed to estimate the amount of free [³H]-

DHT. The remaining media is removed, cells are washed three times with PBS and harvested onto UniFilter GF/B plates (Packard), Microscint (Packard) is added and plates counted in a Top-Counter (Packard) to evaluate the amount of bound [³H]-DHT.

For the saturation analysis, the difference between the total binding and the non-specific binding is defined as specific binding. The specific binding is evaluated by Scatchard analysis to determine the $K_d$ for [³H]-DHT. See e.g. D. Rodbard, *Mathematics and Statistics of Ligand Assays: An Illustrated Guide*: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 2 nM [³H]-DHT and compounds of the invention ("test compounds") in concentrations ranging from $10^{-10}$ to $10^{-5}$ M are added to the cells. Two replicates are used for each sample. After 90 min at 37° C., cells are washed, harvested, and counted as described above. The data is plotted as the amount of [³H]-DHT (% of control in the absence of test compound) remaining over the range of the dose response curve for a given compound. The concentration of test compound that inhibited 50% of the amount of [³H]-DHT bound in the absence of competing ligand is quantified ($IC_{50}$) after log-logit transformation. The $K_I$ values are determined by application of the Cheng-Prusoff equation to the $IC_{50}$ values, where:

$$K_I = \frac{IC_{50}}{(1 + [^3H\text{-}DHT]/K_d \text{ for } ^3H\text{-}DHT)}.$$

After correcting for non-specific binding, $IC_{50}$ values are determined The $IC_{50}$ is defined as the concentration of competing ligand needed to reduce specific binding by 50%. The $K_d$ values for [³H]-DHT for MDA 453 is 0.7 nM.

Compounds described herein, e.g., in the examples, were tested and found to show affinity to the androgen receptor.

AR Binding Assay

For the whole cell binding assay, human breast adenocarcinoma MDA-MB-453 cells (American Type Culture Collection, Rockville, Md., ATCC #: HTB-131), expressing a functional endogenous wild type AR, are grown to near confluency in T-225 tissue culture flasks containing Dulbecco's Modified Eagle Medium (DMEM) (Mediatech CAT #45000-668) supplemented with 10% fetal bovine serum (FBS) (Invitrogen/GIBCO Life Science). In order to remove any endogenous ligand that might be complexed with the receptor in the cells, the tissue culture media is removed and the cells are incubated overnight at 37° C. in serum-free DMEM. The next day, cells are rinsed with magnesium and calcium free Phosphate Buffered Saline (PBS) (Invitrogen/GIBCO Life Science), harvested using Cell Stripper Buffer (Mediatech) and re-suspended in serum-free DMEM to achieve a final assay concentration of $4 \times 10^5$ cells/well of a 96-well assay plate. Saturation analysis or competitive binding assays with tritiated dihydrotestosterone ([³H]-DHT) are used to evaluate $K_d$ and $K_i$ values of the test compounds, respectively. For the saturation analysis, media (DMEM—10% charcoal stripped CA-FBS, Hyclone) containing [³H]-DHT (in concentrations ranging from 0.1 nM to 16 nM) in the absence (total binding) or presence (non-specific binding) of a 500-fold molar excess of unlabeled DHT are added to the cells. After 90 minutes at room temperature, an aliquot of the total binding media at each concentration of [³H]-DHT is removed to estimate the amount of free [³H]-DHT. After the remaining media is removed, cells are washed three times with PBS and harvested onto UniFilter GF/B plates (PerkinElmer). Microscint 20 solution (PerkinElmer) is added and the plates are counted on a TopCount detector (Packard) to evaluate the amount of bound [³H]-DHT. The specific binding is evaluated by Scatchard analysis to determine the $K_d$ for [³H]-DHT.

For the competition studies, media containing 2 nM [³H]-DHT and test compounds in concentrations ranging from $10^{-10}$ to $10^{-5}$ M are added to the cells. Two replicates are used for each sample. After 90 minutes at room temperature, cells are harvested by filtering through a GF/B filter plate (PerkinElmer) followed by washing with ice-cold 1×PBS (without calcium and magnesium) to remove unbound label. The competition data of the test compounds over the range of concentrations is plotted as percentage inhibition of [³H]-DHT specific bound in the absence of test compounds (percent of total signal). After correcting for non-specific binding, $IC_{50}$ values are determined. The $IC_{50}$ value is defined as the concentration of competing ligand needed to reduce specific binding by 50%. The concentration of test compound that inhibited 50% of the amount of [³H]-DHT specific bound ($IC_{50}$) is quantified using the four parameter logistic equation to fit the data. The $K_i$ values are determined by application of the Cheng-Prusoff equation to the $IC_{50}$ values where:

$$K_I = \frac{IC_{50}}{(1 + [^3H\text{-}DHT]/K_d \text{ for } ^3H\text{-}DHT)}$$

The $K_d$ for [³H]-DHT for MDA-MB-453 was 0.4 nM.

The specific binding is evaluated by Scatchard analysis to determine the $K_d$ for [³H]-DHT. See e.g. D. Rodbard, *Mathematics and Statistics of Ligand Assays: An Illustrated Guide*: In: J. Langon and J. J. Clapp, eds., Ligand Assay, Masson Publishing U.S.A., Inc., New York, pp. 45-99, (1981).

Androgen Receptor Transactivation Assay Using MDA-MB-453 or 22 RV1 Cell Lines

Compounds can be tested in a cell based transactivation assay used to measure the antagonism of androgen receptor (AR) transcriptional activity. The transactivation assay provides a means of identifying antagonists that inhibit the effects of the native hormone dihydrotestosterone (DHT). The human breast adenocarcinoma MDA-MB-453 cell line (American Type Culture Collection, Rockville, Md., ATCC #: HTB-131), expressing a functional endogenous wild type AR, was transiently transfected with a reporter plasmid and tested for AR dependent transactivation activity in the absence or presence of test compounds. The pGL3 PSA-Luc reporter plasmid is comprised of the cDNA for the firefly luciferase gene and the upstream promoter sequences containing the androgen response elements (AREs) of the prostate specific antigen (PSA). This plasmid functions as a reporter for the transcription-modulating activity of the AR. In order to detect antagonists, the transactivation assay is conducted in the presence of constant concentration of the natural AR hormone (DHT) to induce a defined reporter signal. Addition of increasing concentrations of the suspected antagonist will decrease the reporter signal (luciferase activity).

MDA-MB-453 and 22 RV1 cells were maintained in DMEM (Cellgro, Cat. #10-014-CM) or RPMI 1640 (Gibco Cat. #11875-085) respectively and supplemented with 10% FBS (Invitrogen/GIBCO Life Science). Cells were bulk transfected in flasks with 1.3 ug/ml pGL3 PSA-Luc plasmid by using the Lipofectamine 2000 Reagent (Invitrogen, Cat.

11668-019) and serum-free Opti-MEM I media (Invitrogen, Cat #31985-070) according to the manufacturer's optimized conditions. Transfection was conducted at 37° C. with 5% $CO_2$ for 16-18 hours. Following transfection, cells were washed, treated with trypsin, counted, and seeded in a 96-well plate at 30,000 cells per well in DMEM containing 10% Charcoal/Dextran Treated Fetal Bovine Serum (Gibco Cat. #11054-020) for MDA-MB-453 cells or RPMI 1640 (Gibco Cat. #110835) containing 10% FBS (Invitrogen/GIBCO Life Science) for 22 RV1 cells.

Following transfection, cells were incubated in the absence (blank) or presence (control) of 3 nM DHT (Sigma, Cat. #A-8380) and in the presence or absence of the standard antiandrogen bicalutamide or test compounds ranging in concentrations from $10^{-10}$ to $10^{-5}$M. Duplicates were used for each sample. The compound dilutions were performed by the Tecan Genesis (Tecan, Triangle Park, N.C.). After a 48 hour incubation, luciferase activity was measured using the Steady-Glo Luciferase Assay System (Promega, Cat. #E2550) according to manufacturer's specifications and luminescence was measured on a Packard TopCount (PerkinElmer). For each luciferase sample reading, the percent control (in absence of compounds) was calculated as:

% Control=100×[average$_{sample}$−average$_{blank}$]/ [average$_{control}$−average$_{blank}$]

Data was plotted and the $IC_{50}$ value was defined as the concentration of compound that inhibited 50% of the luciferase activity for the controls.

Compounds described herein were tested in the AR transactivation assay described immediately above, using MDA-MB-453 cells. The following results were obtained.

TABLE 28

MDA-MB-453 Androgen Receptor Transactivation Assay

| Example | $IC_{50}$ (nM) |
|---|---|
| 1 | 177 |
| 2 | 11000 |
| 3 | 175 |
| 6 | 281 |
| 12 | >7500 |
| 13 | >7500 |
| 14 | 185 |
| 15 | 10450 |
| 19 | 5317 |
| 22 | >7500 |
| 23 | 1198 |
| 24 | 5453 |
| 25 | >7500 |
| 26 | >7500 |
| 30 | 31 |
| 37 | 1158 |
| 38 | 1086 |
| 39 | 719 |
| 45 | 12750 |
| 47 | 1605 |
| 50 | 42 |
| 51 | 1806 |
| 53 | 1203 |
| 55 | 10760 |
| 57 | 7500 |
| 59 | 7500 |
| 61 | 7500 |
| 62 | 1924 |
| 66 | 195 |
| 113 | 1343 |
| 117 | 2477 |
| 119 | 183 |
| 120 | 1652 |
| 122 | 1708 |
| 137 | 6241 |

TABLE 28-continued

MDA-MB-453 Androgen Receptor Transactivation Assay

| Example | $IC_{50}$ (nM) |
|---|---|
| 138 | 6053 |
| 139 | 60 |
| 142 | 950 |
| 145 | 1722 |
| 149 | 1095 |
| 156 | 304 |
| 162 | 1959 |
| 174 | 335 |
| 179 | 141 |
| 183 | 1056 |
| 185 | 147 |
| 186 | 220 |
| 188 | 383 |
| 190 | 2273 |
| 196 | 46 |
| 207 | 54 |
| 208 | 118 |
| 214 | 5652 |
| 222 | 58 |
| 236 | 104 |
| 240 | 6380 |
| 246 | 280 |
| 254 | 4946 |
| 267 | 427 |
| 291 | 45 |

Immature Rat Prostate Weight (IRPW) Assay

The activity of compounds of Formula (I) as AR antagonists can be investigated in an immature male rat model, as described in L. G. Hershberger et al., *Proc. Soc. Expt. Biol. Med.*, 83, 175 (1953); P. C. Walsh and R. F. Gittes, "Inhibition of extratesticular stimuli to prostate growth in the castrated rat by antiandrogens", *Endocrinology*, 86, 624 (1970); and B. J. Furr et al., "ICI 176,334: A novel non-steroid, peripherally selective antiandrogen", *J. Endocrinol.*, 113, R7-9 (1987), the disclosures of which are herein incorporated by reference.

Male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells in the testis under the control of the pituitary luteinizing hormone (LH) and follicle stimulating hormone (FSH). Testosterone is converted to the more active form, dihydrotestosterone, (DHT), within the prostate by 5α-reductase. Adrenal androgens also contribute about 20% of total DHT in the rat prostate, compared to 40% of that in 65-year-old men. F. Labrie et al. *Clin. Invest. Med.*, 16, 475-492 (1993). However, this is not a major pathway, since in both animals and humans, castration leads to almost complete involution of the prostate and seminal vesicles without concomitant adrenalectomy. Therefore, under normal conditions, the adrenals do not support significant growth of prostate tissues. M. C. Luke and D. S. Coffey, "*The Physiology of Reproduction*" ed. by E. Knobil and J. D. Neill, 1, 1435-1487 (1994). Since the male sex organs are the tissues most responsive to modulation of the androgen activity, this model is used to determine the androgen dependent growth of the sex accessory organs in immature castrated rats.

Male immature rats (19-20 days old Sprague-Dawley, Harlan Sprague-Dawley) are castrated under metofane anesthesia. Five days after surgery these castrated rats (60-70 g, 23-25 day-old) are dosed for 3 days. Animals are dosed subcutaneously (s.c.) 1 mg/kg with Testosterone Proprionate (TP) in arachis oil vehicle and anti-androgen test compounds (compounds of formula (I)) are dosed orally by gavage (p.o.)

in dissolved/suspensions of 80% PEG 400 and 20% Tween 80 surfactant (PEGTW). Animals are dosed (v/w) at 0.5 ml of vehicle/100 g body weight. Experimental groups are as follows:
 1. Control vehicle
 2. Testosterone Propionate (TP) (3 mg/rat/day, subcutaneous)
 3. TP plus bicalutamide (administered p.o. in PEGTW, QD), a recognized antiandrogen, as a reference compound.
 4. To demonstrate antagonist activity, a compound of formula (I) ("test compound") is administered (p.o. in PEGTW, QD) with TP (s.c. as administered in group 2) in a range of doses.
 5. To demonstrate agonist activity a compound of formula (I) ("test compound") is administered alone (p.o. in PEGTW, QD) in a range of doses.

At the end of the 3-day treatment, the animals are sacrificed, and the ventral prostate weighed. To compare data from different experiments, the sexual organs weights are first standardized as mg per 100 g of body weight, and the increase in organ weight induced by TP was considered as the maximum increase (100%). ANOVA followed by one-tailed Student or Fischer's exact test is used for statistical analysis.

The gain and loss of sexual organ weight reflect the changes of the cell number (DNA content) and cell mass (protein content), depending upon the serum androgen concentration. See Y. Okuda et al., *J. Urol.*, 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases seminal vesicles (SV) and the ventral prostate (VP) in a dose dependent manner.

The maximum increase in organ weight is 4 to 5-fold when dosing 3 mg/rat/day of testosterone (T) or 1 mg/rat/day of testosterone propionate (TP) for 3 days. The $EC_{50}$ of T and TP are about 1 mg and 0.03 mg, respectively. The increase in the weight of the VP and SV also correlates with the increase in the serum T and DHT concentration. Although administration of T shows 5-times higher serum concentrations of T and DHT at 2 hours after subcutaneous injection than that of TP, thereafter, these high levels decline very rapidly. In contrast, the serum concentrations of T and DHT in TP-treated animals are fairly consistent during the 24 hours, and therefore, TP showed about 10-30-fold higher potency than free T.

[$^3$H]-Thymidine Incorporation

Flag-AR-LNCaP cells are derived from prostate cancer LnCap cells with a wild-type AR fused with a Flag tag stable transfected into parental LnCap cells. These cells with increased AR level confer resistance to antiandrogens. Flag-AR-LnCap cells are maintained in RPMI medium with 10% serum and 800 ug/ml G418 for selection. In [$^3$H]-Thymidine Incorporation assays, LnCap or Flag-AR-LnCap cells are seeded at 6000 cells/well in 96 well plates and maintained in phenol red-free RPMI medium supplemented with 5% charcoal dextran-stripped serum. After 24 hours, compounds are added to the cells in the presence of final concentration of 0.5 nM DHT. Four days after the compound treatment, [$^3$H]-thymidine pulsing for 4 hours is followed by plate harvesting and counting using TOPCOUNT detector.

For each replicate, the % Inhibition (compared to controls in the absence of compounds) is calculated as:

% Inhibition=100×[1−[[average$_{sample}$−average$_{blank}$]/[average$_{control}$−average$_{blank}$]]]

Data is plotted and the $IC_{50}$ is defined as the concentration of compound that exhibited an inhibition of 50% of the [$^3$H]-thymidine incorporation observed in the controls in the absence of compounds.

Compounds described herein, e.g., in the examples, were tested in the immature rate prostate weight test described above. The following results were obtained.

TABLE 29

Immature Rat Prostate Weight (IRPW) Assay (3 mpk PO QD × 4 days)

| Example | IRPW SV/FB (% control) |
|---|---|
| 1 | 54[a] |
| 3 | 41 |
| 6 | 37 |
| 14 | 35 |
| 30 | 37 |
| 50 | 46 |
| 62 | 108 |
| 66 | 38 |
| 113 | 68 |
| 119 | 39 |
| 120 | 80 |
| 122 | 90 |
| 139 | 35 |
| 156 | 64 |
| 174 | 42 |
| 179 | 31 |
| 185 | 31 |
| 186 | 39 |
| 188 | 33 |
| 207 | 37 |
| 208 | 37 |
| 236 | 62 |
| 246 | 98 |
| 267 | 40 |
| 291 | 35 |
| — | — |

[a]Compound tested at 5 mpk, PO, QD × 4 days

Human Tumor Xenograft Assay

Three human tumor xenografts are utilized: CWR-22 (Wainstein et al., 1994), LuCap 23.1 (Ellis et al., 1996), and LuCap 35 (Linja et al., 2001). The CWR-22 line was obtained from Dr. T. Prestlow (Case Western Reserve), and the LuCap 23.1 and LuCap 35 lines were received from Dr. Robert Vesella (University of Washington, Seattle, Wash.).

The tumor lines are maintained in Balb/c athymic (nu/nu) mice. Tumors are propagated as subcutaneous transplants in adult male nude mice (4-6 weeks old) using tumor fragments obtained from donor mice. Tumor passage occurs every 5-6 weeks.

For antitumor efficacy trial, the required number of animals needed to detect a meaningful response are pooled at the start of the experiment and each is given a subcutaneous implant of a tumor fragment (~50 mg) with a 13-gauge trocar. Tumors are allowed to grow to approximately 100-200 mg (tumors outside the range were excluded) and animals are evenly distributed to various treatment and control groups. Treatment of each animal is based on individual body weight. Treated animals are checked daily for treatment related toxicity/mortality. Each group of animals is weighed before the initiation of treatment ($Wt_1$) and then again following the last treatment dose ($Wt_2$). The difference in body weight ($Wt_2-Wt_1$) provides a measure of treatment-related toxicity.

Tumors are measured weekly for the LuCap 23.1 and LuCap 35 studies, and twice weekly for the CWR-22 studies.

Tumor size (mm³) is calculated from the formula: Tumor weight=(length×width²)÷2. Body weights are obtained weekly.

Tumor response end-point is expressed in terms of tumor growth inhibition (% T/C), defined as the ratio of median tumor weights of the treated tumors (T) to that of the control group (C).

To estimate tumor cell kill, the tumor volume doubling time is first calculated with the formula:

$TVDT$=[(Median time (days) for control tumors to reach target size)−(Median time (days) for control tumors to reach half the target size)].

And, Log cell kill=(T−C)÷(3.32×TVDT)

Statistical evaluations of data are performed using Gehan's generalized Wilcoxon test.

What is claimed is:
1. A compound of Formula (I):

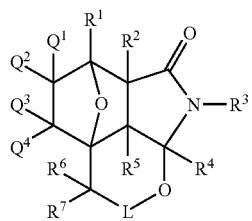

(I)

or a pharmaceutically-acceptable salt or stereoisomer thereof, wherein:

L is a bond, $CR^8R^9$, or $CR^8R^9CR^{10}R^{11}$;

$R^1$ is H, $C_{1-4}$alkyl optionally substituted with OH, —CH$_2$OCH$_2$(phenyl), —C(=O)OR$^a$ wherein R$^a$ is H or $C_{1-4}$alkyl, or —C(=O)NR$^b$R$^c$ wherein R$^b$ and R$^c$ are independently H and/or $C_{1-4}$alkyl;

$R^2$ is
  i) H,
  ii) $C_{1-4}$alkyl optionally substituted with OH,
  iii) -C(=O)OR$^a$ wherein R$^a$ is H or $C_{1-4}$alkyl optionally substituted with aryl, or
  iv) -C(=O)NHR$^c$ wherein R$^c$ is phenyl or $C_{1-2}$alkyl optionally substituted with aryl or —CF$_3$;

$R^3$ is 1- or 2-ring aryl or heteroaryl which is optionally substituted with 1-3 substituents independently selected from methyl, cyclopropyl, —CF$_3$, halogen, —C≡CH, —CN, —NH$_2$, —NO$_2$, and/or —OR$_a$ wherein each R$_a$ is independently $C_{1-3}$ alkyl optionally substituted with 1 or more halogens;

$R^4$, $R^5$, $R^6$, $R^7$, $R^8$, $R^9$, $R^{10}$, and $R^{11}$ are independently H and/or $C_{1-4}$alkyl; and $Q^1$, $Q^2$, $Q^3$, and $Q^4$ are each independently:
  i) H,
  ii) OH,
  iii) —N$_3$,
  iv) CN,
  v) $C_{1-4}$alkyl optionally substituted with OH, —C(=O)NHCH$_3$, or —C(=O)N(CH$_3$)$_2$
  vi) monocyclic heterocycle,
  vii) —NHOR$^a$ wherein R$^a$ is $C_{1-4}$alkyl,
  viii) —C(=O)R$^b$ wherein R$^b$ is H or $C_{1-4}$alkyl;
  ix) —C(=O)OR$^a$ wherein R$^a$ is H or $C_{1-4}$alkyl,
  x) —C(=O)NR$^b$R$^c$ wherein R$^b$ and R$^c$ are independently H or $C_{1-4}$alkyl,
  xi) —NHC(=O)OR$^a$ wherein R$^a$ is $C_{1-4}$alkyl optionally substituted with OH, OCH$_3$, or monocyclic heterocycle,
  xii) —NHC(=O)R$^a$ wherein R$^a$ is $C_{1-4}$alkyl optionally substituted with —OCH$_3$, —N(CH$_3$)$_2$, or monocyclic heterocycle,
  xiii) —NR$^b$R$^c$ wherein R$^b$ and R$^c$ are independently H or monocyclic heterocycle optionally substituted with halogen or —CF$_3$,
  xiv) —NHSO$_2$R$^a$ wherein R$^a$ is monocyclic heterocycle, $C_{1-4}$alkyl optionally substituted with —CF$_3$, $C_{3-6}$cycloalkyl, or phenyl, or phenyl optionally substituted with halogen or —NHC(=O)(C$_{1-4}$alkyl),
  xv) —NHSO$_2$NR$^b$R$^c$ wherein R$^b$ and R$^c$ are independently H and/or $C_{1-4}$alkyl, or
  xvi) —SO$_2$R$^a$ wherein R$^a$ is $C_{1-4}$alkyl or phenyl optionally substituted with halogen; or $Q^1$ and $Q^2$ together or $Q^3$ and $Q^4$ together are:
  i) =CHR$^d$ wherein R$^d$ is H, —C(=O)OR$^a$ or —C(=O)NR$^b$R$^c$ wherein R$^a$, R$^b$, and R$^c$ are independently H and/or $C_{1-4}$alkyl,
  ii) =O,
  iii) =NOR$^b$ wherein R$^b$ is H, phenyl, monocyclic heterocycle, or $C_{1-4}$alkyl optionally substituted with phenyl,
  iv) =NR$^d$ wherein R$^d$ is monocyclic heterocycle,
  v) =NNR$^c$R$^d$ wherein R$^c$ and R$^d$ are independently H or $C_{1-4}$alkyl; or $Q^1$ and $Q^3$ together are =O wherein $Q^2$ and $Q^4$ are each H.

2. The compound according to claim 1 or a pharmaceutically-acceptable salt or stereoisomer thereof, wherein:

$R^1$ is H, methyl, ethyl, —C(=O)NHCH$_3$, —C(=O)N(CH$_3$)$_2$, —CH$_2$OH, —C(=O)OH, or —C(=O)OCH$_3$;

$R^2$ is H, methyl, —CH$_2$OH, —C(=O)OCH$_2$-phenyl, —C(=O)NHCH$_2$-phenyl, —C(=O)NHCH$_2$CF$_3$, —C(=O)NHCH$_2$CH$_3$, or —C(=O)NH-phenyl;

$R^3$ is i) phenyl, or ii) phenyl, naphthyl, pyridyl, or quinolinyl substituted with 1-3 substituents independently selected from methyl, cyclopropyl, —CF$_3$, halogen, —C≡CH, —CN, —NH$_2$, —OCF$_3$, and —NO$_2$;

$R^4$ is H or methyl;

$R^5$, $R^6$, $R^7$, $R^{10}$, and $R^{11}$ are each H;

$R^8$ and $R^9$ are independently H and/or methyl; and $Q^1$, $Q^2$, $Q^3$, and $Q^4$ are each independently H, OH, —CH$_3$, —CH$_2$OH, —CN, —N$_3$, —NH$_2$, —NHOCH$_3$, —C(=O)H, —C(=O)OH, —C(=O)NHCH$_3$, —C(=O)N(CH$_3$)$_2$, —NHC(=O)OCH$_3$, —NHC(=O)OCH$_2$CH$_3$, —NHC(=O)OCH(CH$_3$)$_2$, —NHC(=O)OCH$_2$CH$_2$OH, —NHC(=O)OCH$_2$CH$_2$OCH$_3$, —NHC(=O)CH$_3$, —NHC(=O)CH$_2$CH$_3$, —CH$_2$C(=O)NHCH$_3$, —CH$_2$C(=O)N(CH$_3$)$_2$, —NHC(=O)CH(CH$_3$)$_2$, —NHC(=O)CH$_2$OCH$_3$, —NHC(=O)CH$_2$N(CH$_3$)$_2$,

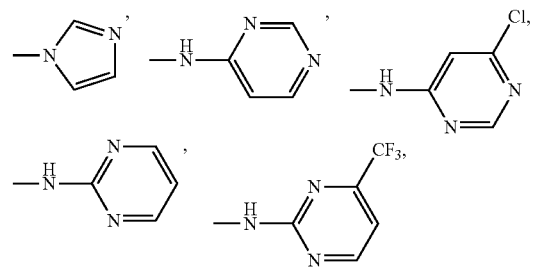

-continued

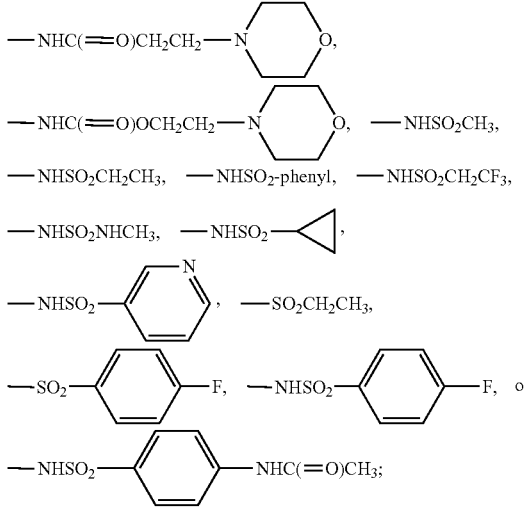

or Q¹ and Q² together or Q³ and Q⁴ together are =CH₂, =CHC(=O)OH, =CHC(=O)NHCH₃, =CHC(=O)OCH₃, =CHC(=O)N(CH₃)₂, =O, =NOH, =NOCH₃, =NOCH₂CH₃, =NOCH(CH₃)₂, =NOC(CH₃)₃, =N—O-phenyl, =N—NHCH₃,

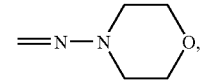

=N—OCH₂-phenyl, or

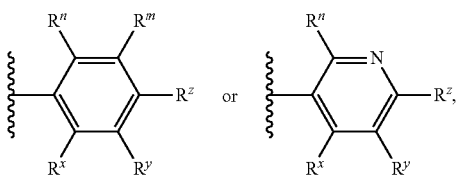

Q¹ and Q³ together are =O wherein Q² and Q⁴ are each H.

3. The compound according to claim 1 or a pharmaceutically-acceptable salt or stereoisomer thereof, wherein L is $CR^8R^9$.

4. The compound according to claim 3 or a pharmaceutically-acceptable salt or stereoisomer thereof, wherein at least two of Q¹, Q², Q³, and Q⁴ are H.

5. The compound according to claim 4 or a pharmaceutically-acceptable salt or stereoisomer thereof, wherein R³ is:

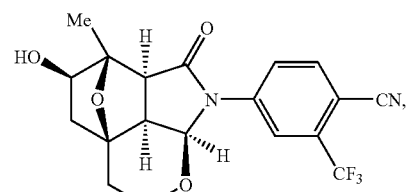

wherein:
$R^n$, $R^m$, $R^x$, $R^y$, and $R^z$ are each independently H, $C_{1-4}$alkyl, substituted $C_{1-4}$alkyl, cyclopropyl, substituted cyclopropyl, alkynyl, substituted alkynyl, $OR^e$, halo, and/or CN; and
$R^e$ is alkyl or substituted alkyl;
provided that at least one of $R^n$, $R^m$, $R^x$, $R^y$, and $R^z$ is not H.

6. The compound according to claim 1 or a pharmaceutically-acceptable salt or stereoisomer thereof, wherein:
L is —CH₂—;
R¹ is methyl;
R², R⁴, R⁵, R⁶, R⁷, R⁸ and R⁹ are H; and
R³ is substituted aryl or substituted heteroaryl.

7. The compound according to claim 1, wherein said compound is:

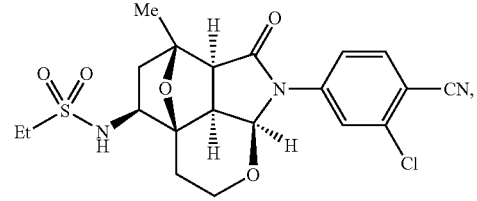

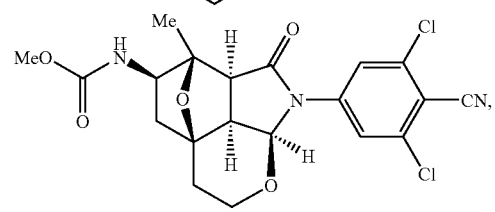

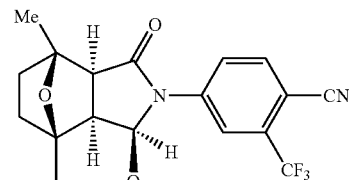

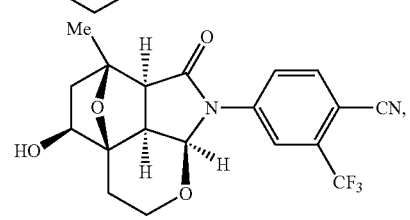

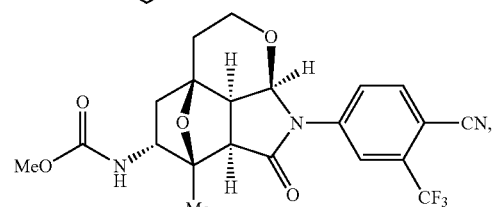

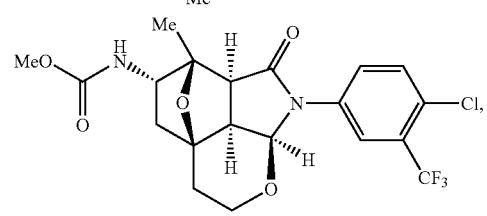

-continued

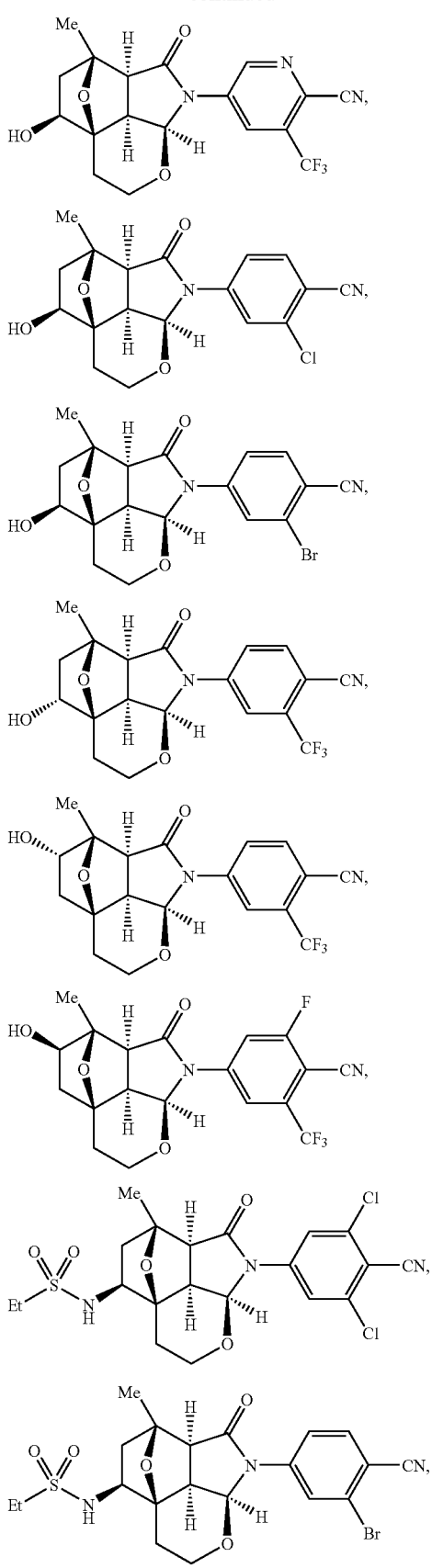

-continued

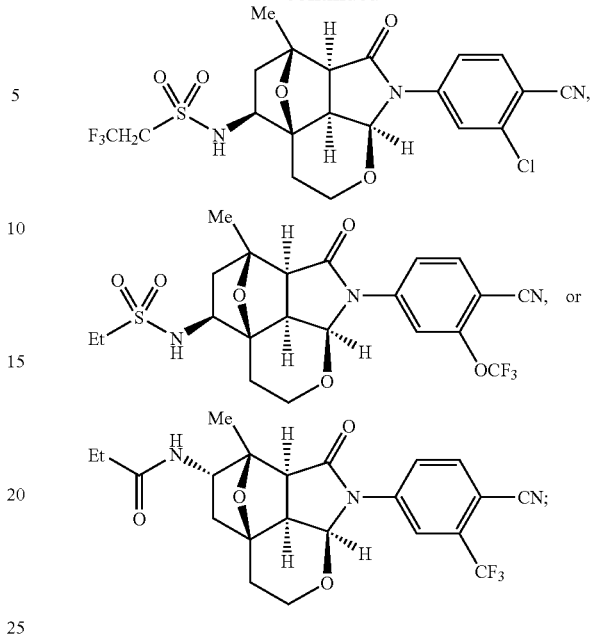

or a pharmaceutically-acceptable salt or stereoisomer thereof.

8. A pharmaceutical composition comprising at least one compound according to claim 1 or a pharmaceutically-acceptable salt or stereoisomer thereof; and a pharmaceutically-acceptable carrier or diluent.

9. The compound according to claim 1 or a pharmaceutically-acceptable salt or stereoisomer thereof, wherein said compound is selected from: 4-((1S,3R,4S,5S,8S,12R)-3-hydroxy-4-methyl-6-oxo-9,13-dioxa-7-azatetracyclo [6.3.1.1$^{1,4}$.0$^{5,12}$]tridec-7-yl)-2-(trifluoromethyl)benzonitrile (1); 4-((1R,3S,4R,5R,8R,12S)-3-hydroxy-4-methyl-6-oxo-9,13-dioxa-7-azatetracyclo [6.3.1.1$^{1,4}$.0$^{5,12}$] tridec-7-yl)-2-(trifluoromethyl)benzonitrile (2); 4-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-(trifluoromethyl)benzonitrile (3); 4-((1S,2R,4S,5R,8R,12S)-2-hydroxy-4-methyl-6-oxo-9,13-dioxa-7-azatetracyclo [6.3.1.1$^{1,4}$.0$^{5,12}$] tridec-7-yl)-2-(trifluoromethyl)benzonitrile (4); 4-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-(trifluoromethyl)benzonitrile (3); 4-((1R,4R,5S,8S,12R)-4-methyl-2,6-dioxo-9,13-dioxa-7-azatetracyclo [6.3.1.1$^{1,4}$.0$^{5,12}$]tridec-7-yl)-2-(trifluoromethyl)benzonitrile (5); 4-((1R,2R,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-(trifluoromethyl)benzonitrile (6); Methyl ((1R,2S,4R,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-2-yl)carbamate (8); N-((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$] tridec-2-yl)ethanesulfonamide (9); N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl) propanamide (11); 4-((1S,3R,4R,5R,8R,12S)-3-azido-4-methyl-6-oxo-9,13-dioxa-7-azatetracyclo [6.3.1.1$^{1,4}$.0$^{5,12}$] tridec-7-yl)-2-(trifluoromethyl)benzonitrile (12); 4-((1S,3R,4R,5R,8R,12S)-3-amino-4-methyl-6-oxo-9,13-dioxa-7-azatetracyclo [6.3.1.1$^{1,4}$.0$^{5,12}$]tridec-7-yl)-2-(trifluoromethyl)benzonitrile (13); Methyl ((1S,3R,4R,5R,8R,12S)-7-(4-cyano-3-(trifluoromethyl)phenyl)-4-methyl- 6-oxo-9,13-dioxa-7-azatetracyclo[6.3.1.1$^{1,4}$.0$^{5,12}$]tridec-3-yl)carbamate (14); 1R,2S,4R,5S,8S,12R)-7-(3-chloro-4-fluorophenyl)-2-hydroxy-4-methyl-9,13-dioxa-7-azatetracyclo[6.3.1.1$^{1,4}$.0$^{5,12}$]tridecan-6-one (15); 2-Chloro-4-[((1S,3R,4S,5S,8S,12R)-3-hydroxy-4-methyl-6-oxo-9,13-dioxa-7-azatetracyclo [6.3.1.1$^{1,4}$.0$^{5,12}$]tridec-7-yl) benzonitrile (16); (1R,2S,4R,5S,8S,12R)-7-(4-Cyano-3-(trifluoromethyl)phenyl)-N-ethyl-2-hydroxy-4-methyl-6-oxo-9,13-dioxa-7-azatetracyclo [6.3.1.1$^{1,4}$.0$^{5,12}$]tridecane-5-carboxamide (17); Benzyl (1S,3R,4S,5R,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$] tridecane-5-carboxylate (18); (1R,3S)—N-((1R,2S)-2-(((4S)-4-(4-Chlorophenyl)-4-hydroxy-3,3-dimethyl-1-piperidinyl) carbonyl)cyclohexyl)-3-hydroxycyclopentanecarboxamide (19); (1S,3R,4S,5S,8S,12R)-7-(4-Cyano-3-(trifluoromethyl) phenyl)-N-ethyl-3-hydroxy-4-methyl-6-oxo-9,13-dioxa-7-azatetracyclo[6.3.1.1$^{1,4}$.0$^{5,12}$]tridecane-5-carboxamide (21); (1R,3S,4R,5R,8R,12S)-7-(4-Cyano-3-(trifluoromethyl)phenyl)-N-ethyl-3-hydroxy-4-methyl-6-oxo-9,13-dioxa-7-azatetracyclo[6.3.1.1$^{1,4}$.0$^{5,12}$]tridecane-5-carboxamide (22); Benzyl (1R,2S,4R,5R,8S,12R)-7-(4-cyano-3-(trifluoromethyl)phenyl)-2-hydroxy-4-methyl-6-oxo-9,13-dioxa-7-azatetracyclo [6.3.1.1$^{1,4}$.0$^{5,12}$]tridecane-5-carboxylate (23); 4-((1R,2S,4R,5R,8S,12R)-2-hydroxy-5-(hydroxymethyl)-4-methyl-6-oxo-9,13-dioxa-7-azatetracyclo[6.3.1.1$^{1,4}$.0$^{5,12}$] tridec-7-yl)-2-(trifluoromethyl)benzonitrile (24); 4-((1S,3R,4S,5S,8S,12R)-3-hydroxy-4,8-dimethyl-6-oxo-9,13-dioxa-7-azatetracyclo [6.3.1.1$^{1,4}$.0$^{5,12}$]tridec-7-yl)-2-(trifluoromethyl)benzonitrile (25); 4-((1R,3S,4R,5R,8R,12S)-3-hydroxy-4,8-dimethyl-6-oxo-9,13-dioxa-7-azatetracyclo[6.3.1.1$^{1,4}$.0$^{5,12}$] tridec-7-yl)-2-(trifluoromethyl)benzonitrile (26); 4-((1R,2E,4R,5S,8S,12R)-2-(hydroxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (27); 4-((1R,2E,4R,5S,8S,12R)-2-(methoxyimino)-4-methyl-6-oxo-9,13-dioxa-7-azatetracyclo [6.3.1.1$^{1,4}$.0$^{5,12}$]tridec-7-yl)-2-(trifluoromethyl)benzonitrile (30); Rac-4-((1R,2S,3R,4S,5S,8S,12R)-2,3-dihydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (31); Rac-4-((1R,2S,3R,4S,5S,8S,12R)-3-((tert-butyl(dimethyl) silyl)oxy)-2-hydroxy-4-methyl-6-oxo-9,13-dioxa-7-azatetracyclo[6.3.1.1$^{1,4}$.0$^{5,12}$] tridec-7-yl)-2-(trifluoromethyl)benzonitrile (32); Rac-4-((1R,2S,3R,4S,5S,8S,12R)-2-((tert-butyl(dimethyl)silyl) oxy)-3-hydroxy-4-methyl-6-oxo-9,13-dioxa-7-azatetracyclo [6.3.1.1$^{1,4}$.0$^{5,12}$]tridec-7-yl)-2-(trifluoromethyl)benzonitrile (33); Rac-N-((1R,2R,3R,4S,5S,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-4-fluorobenzenesulfonamide (34); N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1$^{1,4}$.0$^{5,12}$] tridec-3-yl)-4-fluorobenzenesulfonamide (35); 4-((1R,2S,4R,5S,8S,10S,12R)-2-hydroxy-4,10-dimethyl-6-oxo-9,13-dioxa-7-azatetracyclo[6.3.1.1$^{1,4}$.0$^{5,12}$]tridec-7-yl)-2-(trifluoromethyl)benzonitrile (36); 4-((1R,2R,4R,5S,8S,12R)-2-hydroxy-2,4-dimethyl-6-oxo-9,13-dioxa-7-azatetracyclo[6.3.1.1$^{1,4}$.0$^{5,12}$] tridec-7-yl)-2-(trifluoromethyl)benzonitrile (37); 4-((1S,4S,7S,8R,10S,11R)-10-Hydroxy-8-methyl-6-oxo-3,12-dioxa-5-azatetracyclo [5.3.1.1$^{1,8}$.0$^{4,11}$]dodec-5-yl)-2-(trifluoromethyl)benzonitrile (38); 4-((1R, 4S,7S,8R,10S,11R)-10-Hydroxy-8-methyl-6-oxo-3,12-dioxa-5-azatetracyclo [5.3.1.1$^{1,8}$.0$^{4,11}$] dodec-5-yl)-2-(trifluoromethyl)benzonitrile (39); 2-Cyclopropyl-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (40); 4-((1R,2S,4R,5S,8S,13R)-2-Hydroxy-4-methyl-6-oxo-9,14-dioxa-7-azatetracyclo[6.4.1.1$^{1,4}$.0$^{5,13}$] tetradec-7-yl)-2-(trifluoromethyl)benzonitrile (42); 4-((1R,2S,4R,5S,12R)-2-amino-4-methyl-6-oxo-9,13-dioxa-7-azatetracyclo [6.3.1.1$^{1,4}$.0$^{5,12}$]tridec-7-yl)-2-chlorobenzonitrile (45); 2-Chloro-4-((1R,2S,4R,5S,8S,12R)-2-((6-chloro-4-pyrimidinyl)amino)-4-methyl-6-oxo-9,13-dioxa-7-azatetracyclo [6.3.1.1$^{1,4}$.0$^{5,12}$]tridec-7-yl)benzonitrile (46); N-((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)-N'-methylsulfamide (47); 4-((1S,3S,4S,5S,8S,12R)-3-hydroxy-3,4-dimethyl-6-oxo-9,13-dioxa-7-azatetracyclo [6.3.1.1$^{1,4}$.0$^{5,12}$]tridec-7-yl)-2-(trifluoromethyl)benzonitrile (48); 4-((1R,4S,5S,8S,12R)-4-methyl-3-methylene-6-oxo-9,13-dioxa-7-azatetracyclo [6.3.1.1$^{1,4}$.0$^{5,12}$]tridec-7-yl)-2-(trifluoromethyl)benzonitrile (49); 4-((1R,4R,5S,8S,12R)-4-methyl-6-oxo-9,13-dioxa-7-azatetracyclo[6.3.1.1$^{1,4}$.0$^{5,12}$] tridec-7-yl)-2-(trifluoromethyl)benzonitrile (50); 4-((1S,4S,5R,8R,12S)-4-methyl-6-oxo-9,13-dioxa-7-azatetracyclo [6.3.1.1$^{1,4}$.0$^{5,12}$]tridec-7-yl)-2-(trifluoromethyl)benzonitrile (51); 4-((1R,4R,5S,8S,12R)-6-oxo-9,13-dioxa-7-azatetracyclo [6.3.1.1$^{1,4}$.0$^{5,12}$]tridec-7-yl)-2-(trifluoromethyl)benzonitrile (52); 4-((1S,4S,5R,8R,12S)-6-oxo-9,13-dioxa-7-azatetracyclo[6.3.1.1$^{1,4}$.0$^{5,12}$]tridec-7-yl)-2-(trifluoromethyl) benzonitrile (53); 4-((1R,2S,4R,5S,8S,12R)-2-hydroxy-6-oxo-9,13-dioxa-7-azatetracyclo [6.3.1.1$^{1,4}$.0$^{5,12}$]tridec-7-yl)-2-(trifluoromethyl)benzonitrile (54); 4-((1S,2R,4S,5R,8R,12S)-2-hydroxy-6-oxo-9,13-dioxa-7-azatetracyclo [6.3.1.1$^{1,4}$.0$^{5,12}$]tridec-7-yl)-2-(trifluoromethyl)benzonitrile (55); 4-((1S,3R,4S,5S,8S,12R)-3-hydroxy-6-oxo-9,13-dioxa-7-azatetracyclo [6.3.1.1$^{1,4}$.0$^{5,12}$]tridec-7-yl)-2-(trifluoromethyl)benzonitrile (56); 4-((1R,3S,4R,5R,8R,12S)-3-hydroxy-6-oxo-9,13-dioxa-7-azatetracyclo[6.3.1.1$^{1,4}$.0$^{5,12}$] tridec-7-yl)-2-(trifluoromethyl)benzonitrile (57); 4-((1R,2S,4R,5S,8S,12R)-4-ethyl-2-hydroxy-6-oxo-9,13-dioxa-7-azatetracyclo [6.3.1.1$^{1,4}$.0$^{5,12}$]tridec-7-yl)-2-(trifluoromethyl)benzonitrile (58); 4-((1S,2R,4S,5R,8R,12S)-4-ethyl-2-hydroxy-6-oxo-9,13-dioxa-7-azatetracyclo [6.3.1.1$^{1,4}$.0$^{5,12}$]tridec-7-yl)-2-(trifluoromethyl)benzonitrile (59); 4-((1S,3R,4S,5S,8S,12R)-4-ethyl-3-hydroxy-6-oxo-9,13-dioxa-7-azatetracyclo [6.3.1.1$^{1,4}$.0$^{5,12}$]tridec-7-yl)-2-(trifluoromethyl)benzonitrile (60); 4-((1R,3S,4R,5R,8R,12S)-4-ethyl-3-hydroxy-6-oxo-9,13-dioxa-7-azatetracyclo [6.3.1.1$^{1,4}$.0$^{5,12}$]tridec-7-yl)-2-(trifluoromethyl)benzonitrile (61); 2-Ethynyl-4-((1R,2S,4R,5S,8S,12R)-2-hydroxy-4-methyl-6-oxo-9,13-dioxa-7-azatetracyclo[6.3.1.1$^{1,4}$.0$^{5,12}$] tridec-7-yl)benzonitrile (62); (1R,2S,4R,5S,8S,12R)-7-(4-chloro-3-ethynylphenyl)-2-hydroxy-4-methyl-9,13-dioxa-7-azatetracyclo[6.3.1.1$^{1,4}$.0$^{5,12}$]tridecan-6-one (63); 2-Fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (64); 2-Chloro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-6-(trifluoromethyl)benzonitrile (65); 2-Bromo-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)benzonitrile (66); 4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethoxy)benzonitrile (67); 3-Fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-(trifluoromethyl)benzonitrile (68); 2-Chloro-6-fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)

benzonitrile (69); 2,6-Dichloro-4-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)benzonitrile (70); Rac-4-((1R, 5S,8S,9S,10R,12S,13R)-9-methyl-7-oxo-4,11,14-trioxa-6-azapentacyclo [6.4.1.1$^{1,9}$.0$^{5,13}$.0$^{10,12}$]tetradec-6-yl)-2-(trifluoromethyl)benzonitrile (71); 4-((1S,3S,4S,5S,8S,12R)-3-hydroxy-3-(hydroxymethyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (72); 4-((1S,3R,4S,5S,8S,12R)-3-hydroxy-4,5-dimethyl-6-oxo-9,13-dioxa-7-azatetracyclo [6.3.1.1$^{1,4}$.0$^{5,12}$]tridec-7-yl)-2-(trifluoromethyl)benzonitrile (73); Methyl ((1R,3S,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$] tridec-3-yl)carbamate (74); 4-((1S,3S,4S,5S,8S,12R)-3-hydroxy-4,5-dimethyl-6-oxo-9,13-dioxa-7-azatetracyclo [6.3.1.1$^{1,4}$.0$^{5,12}$]tridec-7-yl)-2-(trifluoromethyl)benzonitrile (75); 4-((1R,3R,4S,5S,8S,12R)-3-azido-4,5-dimethyl-6-oxo-9,13-dioxa-7-azatetracyclo [6.3.1.1$^{1,4}$.0$^{5,12}$]tridec-7-yl)-2-(trifluoromethyl)benzonitrile (76); Methyl ((1R,3R,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$] tridec-3-yl)carbamate (77); Isopropyl ((1R,3R,4S,5S,8S,12R)-7-(4-cyano-3-(trifluoromethyl)phenyl)-4,5-dimethyl-6-oxo-9,13-dioxa-7-azatetracyclo[6.3.1.1$^{1,4}$.0$^{5,12}$]tridec-3-yl)carbamate (78); 4-((1R,2S,4R,5S,8S,12R)-2-hydroxy-4,5-dimethyl-6-oxo-9,13-dioxa-7-azatetracyclo[6.3.1.1$^{1,4}$. 0$^{5,12}$] tridec-7-yl)-2-(trifluoromethyl)benzonitrile (79); (1R, 3S,4S,5S,8S,12R)-3-azido-7-(4-chloro-3-(trifluoromethyl) phenyl)-4-methyl-9,13-dioxa-7-azatetracyclo[6.3.1.1$^{1,4}$. 0$^{5,12}$]tridecan-6-one (80); 4-((1R,3R,4S,5S,8S,12R)-3-azido-4-methyl-6-oxo-9,13-dioxa-7-azatetracyclo [6.3.1.1$^{1,4}$.0$^{5,12}$]tridec-7-yl)-2-(trifluoromethyl)benzonitrile (81); 4-((1R,3S,4S,5S,8S,12R)-3-azido-4-methyl-6-oxo-9, 13-dioxa-7-azatetracyclo [6.3.1.1$^{1,4}$.0$^{5,12}$]tridec-7-yl)-2-(trifluoromethyl)benzonitrile (82); 4-((1R,3R,4S,5S,8S,12R)-3-azido-4-methyl-6-oxo-9,13-dioxa-7-azatetracyclo [6.3.1.1$^{1,4}$. 0$^{5,12}$]tridec-7-yl)-2,6-dichlorobenzonitrile (83); (1R,2S,4R,5S,8S,12R)-2-azido-7-(4-chloro-3-(trifluoromethyl)phenyl)-4-methyl-9,13-dioxa-7-azatetracyclo [6.3.1.1$^{1,4}$.0$^{5,12}$]tridecan-6-one (84); 2-Chloro-4-((1R,2S,4R,5S,8S,12R)-4-methyl-6-oxo-2-((4-(trifluoromethyl)-2-pyrimidinyl)amino)-9,13-dioxa-7-azatetracyclo[6.3.1.1$^{1,4}$. 0$^{5,12}$]tridec-7-yl)benzonitrile (85); 2-Chloro-4-((1R,2S,4R, 5S,8S,12R)-4-methyl-6-oxo-2-(2-pyrimidinylamino)-9,13-dioxa-7-azatetracyclo[6.3.1.1$^{1,4}$.0$^{5,12}$]tridec-7-yl)benzonitrile (86); 2-Chloro-4-((1R,2S,4R,5S,8S,12R)-4-methyl-6-oxo-2-(4-pyrimidinylamino)-9,13-dioxa-7-azatetracyclo [6.3.1.1$^{1,4}$.0$^{5,12}$]tridec-7-yl)benzonitrile (87); 2-Chloro-4-((1R,2S,4R,5S,8S,12R)-2-((4-fluorophenyl)sulfonyl)-4-methyl-6-oxo-9,13-dioxa-7-azatetracyclo [6.3.1.1$^{1,4}$.0$^{5,12}$] tridec-7-yl)benzonitrile (88); N-(5-cyclopropyl-1H-pyrazol-3-yl)-2-(3-(3-pyridinyl)-1-pyrrolidinyl)pyrrolo[2,1-f][1,2,4] triazin-4-amine (89); 4-((1R,2S,4R,5S,8S,12R)-2-(Methoxyamino)-4-methyl-6-oxo-9,13-dioxa-7-azatetracyclo[6.3.1.1$^{1,4}$.0$^{5,12}$]tridec-7-yl)-2-(trifluoromethyl)benzonitrile (90); 4-((1R,2R,4R,5S,8S,12R)-2-(Methoxyamino)-4-methyl-6-oxo-9,13-dioxa-7-azatetracyclo[6.3.1.1$^{1,4}$.0$^{5,12}$]tridec-7-yl)-2-(trifluoromethyl)benzonitrile (91); 4-((1R,2E,4R,5S,8S,12R)-4-Methyl-2-(4-morpholinylimino)-6-oxo-9,13-dioxa-7-azatetracyclo [6.3.1.1$^{1,4}$.0$^{5,12}$]tridec-7-yl)-2-(trifluoromethyl)benzonitrile (92); 4-((1R,3E,4S,5S,8S,12R)-4-Methyl-3-(4-morpholinylimino)-6-oxo-9,13-dioxa-7-azatetracyclo[6.3.1.1$^{1,4}$.0$^{5,12}$]tridec-7-yl)-2-(trifluoromethyl)benzonitrile (93); 4-((1R,2E,4S,5S,8S,12R)-4-Methyl-2-(methylhydrazono)-6-oxo-9,13-dioxa-7-azatetracyclo[6.3.1.1$^{1,4}$.0$^{5,12}$]tridec-7-yl)-2-(trifluoromethyl)benzonitrile (94); 2-Chloro-4-((1R,4S,5S,8S,12R)-4-methyl-3-methylene-6-oxo-9,13-dioxa-7-azatetracyclo [6.3.1.1$^{1,4}$.0$^{5,12}$]tridec-7-yl)benzonitrile (95); 2-Chloro-4-((1R,2S,4R,5S,8S,12R)-2-(1H-imidazol-1-yl)-4-methyl-6-oxo-9,13-dioxa-7-azatetracyclo[6.3.1.1$^{1,4}$.0$^{5,12}$]tridec-7-yl) benzonitrile (96); 4-((1R,2R,4R,5S,8S,12R)-2-[((4-Fluorophenyl)sulfonyl)-4-methyl-6-oxo-9,13-dioxa-7-azatetracyclo [6.3.1.1$^{1,4}$.0$^{5,12}$]tridec-7-yl)-2-(trifluoromethyl)benzonitrile (97); 4-((1R,2R,4R,5S,8S,12R)-2-(Ethylsulfonyl)-4-methyl-6-oxo-9,13-dioxa-7-azatetracyclo[6.3.1.1$^{1,4}$.0$^{5,12}$]tridec-7-yl)-2-(trifluoromethyl)benzonitrile (98); (1S,3R,4S,5S,8S,12R)-7-(4-Cyano-3-(trifluoromethyl)phenyl)-3-hydroxy-4-methyl-6-oxo-N-(2,2,2-trifluoroethyl)-9,13-dioxa-7-azatetracyclo [6.3.1.1$^{1,4}$.0$^{5,12}$] tridecane-5-carboxamide (99); (1S,3R,4S, 5S,8S,12R)-7-(4-Cyano-3-(trifluoromethyl)phenyl)-3-hydroxy-4-methyl-6-oxo-N-(2,2,2-trifluoroethyl)-9,13-dioxa-7-azatetracyclo[6.3.1.1$^{1,4}$.0$^{5,12}$] tridecane-5-carboxamide (100); (1R,2S,4R,5S,8S,12R)—N-Benzyl-7-(4-cyano-3-(trifluoromethyl)phenyl)-2-hydroxy-4-methyl-6-oxo-9,13-dioxa-7-azatetracyclo[6.3.1.1$^{1,4}$.0$^{5,12}$]tridecane-5-carboxamide (101); Methyl (2E)-((1R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-ylidene) acetate (103); 4-((1R,2S,4R,5S,8S,12R)-2-Hydroxy-2,4-dimethyl-6-oxo-9,13-dioxa-7-azatetracyclo[6.3.1.1$^{1,4}$.0$^{5,12}$] tridec-7-yl)-2-(trifluoromethyl)benzonitrile (107); 1-(4-(8-(2-Chlorophenoxy)[1,2,4]triazolo[4,3-b]pyridazin-3-yl) phenyl)-3-(2-(trifluoromethyl)phenyl)urea (109); (1S,3R,4S, 5S,8S,12R)-7-(4-chloro-3-(trifluoromethyl)phenyl)-3-hydroxy-4-methyl-9,13-dioxa-7-azatetracyclo[6.3.1.1$^{1,4}$. 0$^{5,12}$] tridecan-6-one (110); (1R,2S,4R,5S,8S,12R)-7-(4-bromo-3-(trifluoromethyl)phenyl)-2-hydroxy-4-methyl-9, 13-dioxa-7-azatetracyclo[6.3.1.1$^{1,4}$.0$^{5,12}$]tridecan-6-one (111); (1R,2S,4R,5S,8S,12R)-7-(4-chloro-2-methyl-3-(trifluoromethyl)phenyl)-2-hydroxy-4-methyl-9,13-dioxa-7-azatetracyclo [6.3.1.1$^{1,4}$.0$^{5,12}$]tridecan-6-one (112); (1R,2S,4R,5S,8S,12R)-7-(3,4-dichlorophenyl)-2-hydroxy-4-methyl-9,13-dioxa-7-azatetracyclo[6.3.1.1$^{1,4}$.0$^{5,12}$]tridecan-6-one (113); (1R,2S,4R,5S,8S,12R)-7-(3-bromo-4-chlorophenyl)-2-hydroxy-4-methyl-9,13-dioxa-7-azatetracyclo[6.3.1.1$^{1,4}$.0$^{5,12}$] tridecan-6-one (114); 4-((1R, 2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-3-methyl-2-(trifluoromethyl)benzonitrile (115); 2-Chloro-3-fluoro-4-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl) benzonitrile (116); (1R,2S,4R,5S,8S,12R)-7-(3,5-dichlorophenyl)-2-hydroxy-4-methyl-9,13-dioxa-7-azatetracyclo[6.3.1.1$^{1,4}$.0$^{5,12}$]tridecan-6-one (117); 4-((1R, 2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-iodobenzonitrile (118); 2-Chloro-4-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)benzonitrile (119); 2-Chloro-5-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)benzonitrile (120); 2-Fluoro-4-((1R,2S,4R,5S,8S,12R)-2-hydroxy-4-methyl-6-oxo-9,13-dioxa-7-azatetracyclo [6.3.1.1$^{1,4}$.0$^{5,12}$] tridec-7-yl)-3-methylbenzonitrile (121); 4-((1R,2S,4R,5S, 8S,12R)-2-hydroxy-4-methyl-6-oxo-9,13-dioxa-7-azatetracyclo [6.3.1.1$^{1,4}$.0$^{5,12}$]tridec-7-yl)-2-methylbenzonitrile (122); 4-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-methoxybenzonitrile (123); 4-((1R,2S,4R,5S,8S,12R)-2-hydroxy-4-methyl-6-oxo-9,13-dioxa-7-azatetracyclo

[6.3.1.1¹,⁴.0⁵,¹²]tridec-7-yl)-2,6-dimethylbenzonitrile (124); 2-Bromo-4-((1R,2R,4R,5S,8S,12R)-2-hydroxy-4-methyl-6-oxo-9,13-dioxa-7-azatetracyclo [6.3.1.1¹,⁴.0⁵,¹²]tridec-7-yl) benzonitrile (127); (1R,2R,4R,5S,8S,12R)-7-(4-chloro-2-methyl-3-(trifluoromethyl)phenyl)-2-hydroxy-4-methyl-9,13-dioxa-7-azatetracyclo[6.3.1.1¹,⁴.0⁵,¹²]tridecan-6-one (128); 2-Fluoro-4-(1R,2R,4R,5S,8S,12R)-2-hydroxy-4-methyl-6-oxo-9,13-dioxa-7-azatetracyclo[6.3.1.1¹,⁴.0⁵,¹²]tridec-7-yl)-6-(trifluoromethyl)benzonitrile (129); 2-Chloro-6-fluoro-4-((1R,2R,4R,5S,8S,12R)-2-hydroxy-4-methyl-6-oxo-9,13-dioxa-7-azatetracyclo[6.3.1.1¹,⁴.0⁵,¹²]tridec-7-yl) benzonitrile (130); 3-Fluoro-4-((1R,2R,4R,5S,8S,12R)-2-hydroxy-4-methyl-6-oxo-9,13-dioxa-7-azatetracyclo [6.3.1.1¹,⁴.0⁵,¹²]tridec-7-yl)-2-(trifluoromethyl)benzonitrile (131); 2-Chloro-4-((1R,2R,4R,5S,8S,12R)-2-hydroxy-4-methyl-6-oxo-9,13-dioxa-7-azatetracyclo[6.3.1.1¹,⁴.0⁵,¹²] tridec-7-yl)benzonitrile (132); (1R,2R,4R,5S,8S,12R)-7-(3-Bromo-4-chlorophenyl)-2-hydroxy-4-methyl-9,13-dioxa-7-azatetracyclo [6.3.1.1¹,⁴.0⁵,¹²]tridecan-6-one (133); 2-Chloro-4-((1R,2R,4R,5S,8S,12R)-2-hydroxy-4-methyl-6-oxo-9,13-dioxa-7-azatetracyclo [6.3.1.1¹,⁴.0⁵,¹²]tridec-7-yl)-6-(trifluoromethyl)benzonitrile (134); 4-((1R,2R,4R,5S,8S,12R)-2-hydroxy-4-methyl-6-oxo-9,13-dioxa-7-azatetracyclo [6.3.1.1¹,⁴.0⁵,¹²]tridec-7-yl)-2-(trifluoromethoxy)benzonitrile (135); (1S,3R,4S,5S,8S,12R)-7-(4-chloro-3-(trifluoromethyl)phenyl)-3-hydroxy-4-methyl-9,13-dioxa-7-azatetracyclo[6.3.1.1¹,⁴.0⁵,¹²]tridecan-6-one (136); 2-Fluoro-4-((1S,3R,4S,5S,8S,12R)-3-hydroxy-4-methyl-6-oxo-9,13-dioxa-7-azatetracyclo [6.3.1.1¹,⁴.0⁵,¹²] tridec-7-yl)benzonitrile (137); (1S,3R,4S,5S,8S,12R)-7-(4-chloro-3-fluorophenyl)-3-hydroxy-4-methyl-9,13-dioxa-7-azatetracyclo [6.3.1.1¹,⁴.0⁵,¹²] tridecan-6-one (138); 2-Fluoro-4-((1S,3R,4S,5S,8S,12R)-3-hydroxy-4-methyl-6-oxo-9,13-dioxa-7-azatetracyclo [6.3.1.1¹,⁴.0⁵,¹²]tridec-7-yl)-6-(trifluoromethyl)benzonitrile (139); (1S,3R,4S,5S,8S,12R)-7-(4-chloro-2-methyl-3-(trifluoromethyl)phenyl)-3-hydroxy-4-methyl-9,13-dioxa-7-azatetracyclo[6.3.1.1¹,⁴.0⁵,¹²]tridecan-6-one (140); (1S,3R,4S,5S,8S,12R)-7-(3-bromo-4-chlorophenyl)-3-hydroxy-4-methyl-9,13-dioxa-7-azatetracyclo[6.3.1.1¹,⁴.0⁵,¹²]tridecan-6-one (141); 4-((1S,3R,4S,5S,8S,12R)-3-hydroxy-4-methyl-6-oxo-9,13-dioxa-7-azatetracyclo[6.3.1.1¹,⁴.0⁵,¹²] tridec-7-yl)-3-methyl-2-(trifluoromethyl)benzonitrile (142); (1S,3R,4S,5S,8S,12R)-7-(3,4-dichlorophenyl)-3-hydroxy-4-methyl-9,13-dioxa-7-azatetracyclo[6.3.1.1¹,⁴.0⁵,¹²] tridecan-6-one (143); 2-Chloro-3-fluoro-4-((1S,3R,4S,5S,8S,12R)-3-hydroxy-4-methyl-6-oxo-9,13-dioxa-7-azatetracyclo[6.3.1.1¹,⁴.0⁵,¹²] tridec-7-yl)benzonitrile (144); (1S,3R,4S,5S,8S,12R)-7-(4-chloro-3-ethynylphenyl)-3-hydroxy-4-methyl-9,13-dioxa-7-azatetracyclo[6.3.1.1¹,⁴.0⁵,¹²]tridecan-6-one (145); 2-Bromo-4-((1S,3R,4S,5S,8S,12R)-3-hydroxy-4-methyl-6-oxo-9,13-dioxa-7-azatetracyclo [6.3.1.1¹,⁴.0⁵,¹²]tridec-7-yl) benzonitrile (146); 3-Fluoro-4-((1S,3R,4S,5S,8S,12R)-3-hydroxy-4-methyl-6-oxo-9,13-dioxa-7-azatetracyclo [6.3.1.1¹,⁴.0⁵,¹²]tridec-7-yl)-2-(trifluoromethyl)benzonitrile (147); 2,6-Dichloro-4S, 3R,4S,5S,8S,12R)-3-hydroxy-4-methyl-6-oxo-9,13-dioxa-7-azatetracyclo [6.3.1.1¹,⁴.0⁵,¹²]tridec-7-yl)benzonitrile (148); (1S,3R,4S,5S,8S,12R)-7-(3,5-dichlorophenyl)-3-hydroxy-4-methyl-9,13-dioxa-7-azatetracyclo[6.3.1.1¹,⁴.0⁵,¹²]tridecan-6-one (149); 2-Chloro-6-fluoro-4-((1S,3R,4S,5S,8S,12R)-3-hydroxy-4-methyl-6-oxo-9,13-dioxa-7-azatetracyclo [6.3.1.1¹,⁴.0⁵,¹²] tridec-7-yl)benzonitrile (150); 4-((1S,3R,4S,5S,8S,12R)-3-hydroxy-4-methyl-6-oxo-9,13-dioxa-7-azatetracyclo [6.3.1.1¹,⁴.0⁵,¹²]tridec-7-yl)-2-methoxybenzonitrile (151); 2-Chloro-4-((1S,3R,4S,5S,8S,12R)-3-hydroxy-4-methyl-6-oxo-9,13-dioxa-7-azatetracyclo [6.3.1.1¹,⁴.0⁵,¹²] tridec-7-yl)-3-methylbenzonitrile (152); 2-Chloro-4-((1S,3R,4S,5S,8S,12R)-3-hydroxy-4-methyl-6-oxo-9,13-dioxa-7-azatetracyclo [6.3.1.1¹,⁴.0⁵,¹²]tridec-7-yl)-6-(trifluoromethyl)benzonitrile (153); Rac-4-((1R,3S,4R,5R,8R,12S)-3-hydroxy-4-methyl-6-oxo-9,13-dioxa-7-azatetracyclo [6.3.1.1¹,⁴.0⁵,¹²]tridec-7-yl)-2-methylbenzonitrile (154); 4-((1S,3S,4S,5S,8S,12R)-3-hydroxy-4-methyl-6-oxo-9,13-dioxa-7-azatetracyclo [6.3.1.1¹,⁴.0⁵,¹²]tridec-7-yl)-2-(trifluoromethyl)benzonitrile (156); 3-Fluoro-4-((1S,3S,4S,5S,8S,12R)-3-hydroxy-4-methyl-6-oxo-9,13-dioxa-7-azatetracyclo [6.3.1.1¹,⁴.0⁵,¹²] tridec-7-yl)-2-(trifluoromethyl)benzonitrile (157); 2,6-Dichloro-4-((1S,3S,4S,5S,8S,12R)-3-hydroxy-4-methyl-6-oxo-9,13-dioxa-7-azatetracyclo [6.3.1.1¹,⁴.0⁵,¹²]tridec-7-yl) benzonitrile (158); Ethyl ((1R,2S,4R,5S,8S,12R)-7-(4-cyano-3-(trifluoromethyl)phenyl)-4-methyl-6-oxo-9,13-dioxa-7-azatetracyclo[6.3.1.1¹,⁴.0⁵,¹²]tridec-2-yl)carbamate (160); Isopropyl ((1R,2S,4R,5S,8S,12R)-7-(4-cyano-3-(trifluoromethyl)phenyl)-4-methyl-6-oxo-9,13-dioxa-7-azatetracyclo[6.3.1.1¹,⁴.0⁵,¹²]tridec-2-yl)carbamate (161); 2-Hydroxyethyl ((1R,2S,4R,5S,8S,12R)-7-(4-cyano-3-(trifluoromethyl)phenyl)-4-methyl-6-oxo-9,13-dioxa-7-azatetracyclo[6.3.1.1¹,⁴.0⁵,¹²] tridec-2-yl)carbamate (162); 2-Methoxyethyl ((1R,2S,4R,5S,8S,12R)-7-(4-cyano-3-(trifluoromethyl)phenyl)-4-methyl-6-oxo-9,13-dioxa-7-azatetracyclo [6.3.1.1¹,⁴.0⁵,¹²]tridec-2-yl)carbamate (163); 2-(4-Morpholinyl)ethyl ((1R,2S,4R,5S,8S,12R)-7-(4-cyano-3-(trifluoromethyl)phenyl)-4-methyl-6-oxo-9,13-dioxa-7-azatetracyclo[6.3.1.1¹,⁴.0⁵,¹²] tridec-2-yl)carbamate (164); Methyl ((1R,2S,4R,5S,8S,12R)-7-(4-chloro-3-(trifluoromethyl)phenyl)-4-methyl-6-oxo-9,13-dioxa-7-azatetracyclo [6.3.1.1¹,⁴.0⁵,¹²]tridec-2-yl)carbamate (165); Methyl ((1R,2S,4R,5S,8S,12R)-7-(3-chloro-4-cyanophenyl)-4-methyl-6-oxo-9,13-dioxa-7-azatetracyclo[6.3.1.1¹,⁴.0⁵,¹²]tridec-2-yl) carbamate (166); Isopropyl ((1R,2S,4R,5S,8S,12R)-7-(3-chloro-4-cyanophenyl)-4-methyl-6-oxo-9,13-dioxa-7-azatetracyclo[6.3.1.1¹,⁴.0⁵,¹²]tridec-2-yl)carbamate (167); Isopropyl ((1R,2S,4R,5S,8S,12R)-7-(4-chloro-3-(trifluoromethyl)phenyl)-4-methyl-6-oxo-9,13-dioxa-7-azatetracyclo[6.3.1.1¹,⁴.0⁵,¹²]tridec-2-yl)carbamate (168); Methyl ((1R,2S,4R,5S,8S,12R)-7-(3,5-dichloro-4-cyanophenyl)-4-methyl-6-oxo-9,13-dioxa-7-azatetracyclo[6.3.1.1¹,⁴.0⁵,¹²]tridec-2-yl)carbamate (169); Methyl ((1R,2S,4R,5S,8S,12R)-7-(3-bromo-4-cyanophenyl)-4-methyl-6-oxo-9,13-dioxa-7-azatetracyclo[6.3.1.1¹,⁴.0⁵,¹²]tridec-2-yl)carbamate (170); Methyl ((1R,2S,4R,5S,8S,12R)-7-(3-bromo-4-chlorophenyl)-4-methyl-6-oxo-9,13-dioxa-7-azatetracyclo [6.3.1.1¹,⁴.0⁵,¹²]tridec-2-yl)carbamate (171); N-((1R,2S,4R,5S,8S,12R)-7-(3-chloro-4-cyanophenyl)-4-methyl-6-oxo-9,13-dioxa-7-azatetracyclo[6.3.1.1¹,⁴.0⁵,¹²]tridec-2-yl) ethanesulfonamide (174); N-((1R,2S,4R,5S,8S,12R)-7-(3-chloro-4-cyanophenyl)-4-methyl-6-oxo-9,13-dioxa-7-azatetracyclo[6.3.1.1¹,⁴.0⁵,¹²]tridec-2-yl) benzenesulfonamide (175); N-((1R,2S,4R,5S,8S,12R)-7-(3-chloro-4-cyanophenyl)-4-methyl-6-oxo-9,13-dioxa-7-azatetracyclo [6.3.1.1¹,⁴.0⁵,¹²]tridec-2-yl) methanesulfonamide (176); N-((1R,2S,4R,5S,8S,12R)-7-(4-cyano-3-(trifluoromethyl)phenyl)-4-methyl-6-oxo-9,13-dioxa-7-azatetracyclo[6.3.1.1¹,⁴.0⁵,¹²] tridec-2-yl) methanesulfonamide (177); N-((1R,2S,4R,5S,8S,12R)-7-(3-Bromo-4-chlorophenyl)-4-methyl-6-oxo-9,13-dioxa-7-azatetracyclo[6.3.1.1¹,⁴.0⁵,¹²] tridec-2-yl) ethanesulfonamide (178); N-((1R,2S,4R,5S,8S,12R)-7-(3-Bromo-4-cyanophenyl)-4-methyl-6-oxo-9,13-dioxa-7-azatetracyclo [6.3.1.1¹,⁴.0⁵,¹²] tridec-2-yl) ethanesulfonamide (179); N-((1R,2S,4R,5S,8S,12R)-7-(4-Chloro-3-(trifluoromethyl)phenyl)-4-methyl-6-oxo-9,13- dioxa-7-azatetracyclo [6.3.1.1$^{1,4}$.0$^{5,12}$]tridec-2-yl) methanesulfonamide (180); N-((1R,2S,4R,5S,8S,12R)-7-(4-Cyano-3-(trifluoromethoxy)phenyl)-4-methyl-6-oxo-9,13-dioxa-7-azatetracyclo[6.3.1.1$^{1,4}$.0$^{5,12}$]tridec-2-yl) benzenesulfonamide (181); N-((1R,2S,4R,5S,8S,12R)-7-(3-Chloro-4-cyanophenyl)-4-methyl-6-oxo-9,13-dioxa-7-azatetracyclo [6.3.1.1$^{1,4}$.0$^{5,12}$]tridec-2-yl) cyclopropanesulfonamide (182); N-((1R,2S,4R,5S,8S,12R)-7-(3-Chloro-4-cyanophenyl)-4-methyl-6-oxo-9,13-dioxa-7-azatetracyclo[6.3.1.1$^{1,4}$.0$^{5,12}$]tridec-2-yl)-2-pyridinesulfonamide (183); N-((1R,2S,4R,5S,8S,12R)-7-(4-Chloro-3-(trifluoromethyl)phenyl)-4-methyl-6-oxo-9,13-dioxa-7-azatetracyclo[6.3.1.1$^{1,4}$.0$^{5,12}$] tridec-2-yl) ethanesulfonamide (184); N-((1R,2S,4R,5S,8S,12R)-7-(3-Chloro-4-cyanophenyl)-4-methyl-6-oxo-9,13-dioxa-7-azatetracyclo [6.3.1.1$^{1,4}$.0$^{5,12}$] tridec-2-yl)-2,2,2-trifluoroethanesulfonamide (185); N-((1R,2S,4R,5S,8S,12R)-7-(3,5-Dichloro-4-cyanophenyl)-4-methyl-6-oxo-9,13-dioxa-7-azatetracyclo[6.3.1.1$^{1,4}$.0$^{5,12}$]tridec-2-yl) ethanesulfonamide (186); N-((1R,2S,4R,5S,8S,12R)-7-(3-Chloro-4-cyano-5-(trifluoromethyl)phenyl)-4-methyl-6-oxo-9,13-dioxa-7-azatetracyclo[6.3.1.1$^{1,4}$.0$^{5,12}$]tridec-2-yl) ethanesulfonamide (187); N-((1R,2S,4R,5S,8S,12R)-7-(4-Cyano-3-(trifluoromethoxy)phenyl)-4-methyl-6-oxo-9,13-dioxa-7-azatetracyclo[6.3.1.1$^{1,4}$.0$^{5,12}$] tridec-2-yl) ethanesulfonamide (188); N-(4-(((1R,2S,4R,5S,8S,12R)-7-(3-Chloro-4-cyanophenyl)-4-methyl-6-oxo-9,13-dioxa-7-azatetracyclo [6.3.1.1$^{1,4}$.0$^{5,12}$] tridec-2-yl)sulfamoyl)phenyl) acetamide (189); N-((1R,2S,4R,5S,8S,12R)-7-(4-Cyano-2-fluoro-3-(trifluoromethyl)phenyl)-4-methyl-6-oxo-9,13-dioxa-7-azatetracyclo [6.3.1.1$^{1,4}$.0$^{5,12}$]tridec-2-yl) ethanesulfonamide (190); N-((1R,2R,4R,5S,8S,12R)-7-(3-bromo-4-cyanophenyl)-4-methyl-6-oxo-9,13-dioxa-7-azatetracyclo[6.3.1.1$^{1,4}$.0$^{5,12}$]tridec-2-yl)ethanesulfonamide (192); N-((1R,2R,4R,5S,8S,12R)-7-(3-chloro-4-cyanophenyl)-4-methyl-6-oxo-9,13-dioxa-7-azatetracyclo[6.3.1.1$^{1,4}$.0$^{5,12}$]tridec-2-yl)ethanesulfonamide (193); N-((1R,2R,4R,5S,8S,12R)-7-(3-chloro-4-cyanophenyl)-4-methyl-6-oxo-9,13-dioxa-7-azatetracyclo [6.3.1.1$^{1,4}$.0$^{5,12}$]tridec-2-yl)benzenesulfonamide (194); N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl) ethanesulfonamide (195); N-((1R,2R,4R,5S,8S,12R)-7-(4-Cyano-3-(trifluoromethyl)phenyl)-4-methyl-6-oxo-9,13-dioxa-7-azatetracyclo[6.3.1.1$^{1,4}$.0$^{5,12}$]tridec-2-yl) cyclopropanesulfonamide (196); N-((1R,2R,4R,5S,8S,12R)-7-(4-cyano-3-fluoro-5-(trifluoromethyl)phenyl)-4-methyl-6-oxo-9,13-dioxa-7-azatetracyclo[6.3.1.1$^{1,4}$.0$^{5,12}$]tridec-2-yl)ethanesulfonamide (197); N-((1R,2R,4R,5S,8S,12R)-7-(3-amino-4-cyano-5-(trifluoromethyl)phenyl)-4-methyl-6-oxo-9,13-dioxa-7-azatetracyclo[6.3.1.1$^{1,4}$.0$^{5,12}$]tridec-2-yl) ethanesulfonamide (198); N-((1R,2R,4R,5S,8S,12R)-7-(3-chloro-4-cyano-5-fluorophenyl)-4-methyl-6-oxo-9,13-dioxa-7-azatetracyclo[6.3.1.1$^{1,4}$.0$^{5,12}$]tridec-2-yl) ethanesulfonamide (199); N-((1R,2R,4R,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-2-yl) methanesulfonamide (200); Methyl ((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl) carbamate (201); Methyl ((1R,2R,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (202); Methyl ((1R,2R,4R,5S,8S,12R)-7-(3-bromo-4-cyanophenyl)-4-methyl-6-oxo-9,13-dioxa-7-azatetracyclo [6.3.1.1$^{1,4}$.0$^{5,12}$]tridec-2-yl)carbamate (203); Methyl ((1R,2R,4R,5S,8S,12R)-7-(4-chloro-2-methyl-3-(trifluoromethyl)phenyl)-4-methyl-6-oxo-9,13-dioxa-7-azatetracyclo[6.3.1.1$^{1,4}$.0$^{5,12}$] tridec-2-yl)carbamate (204); Methyl ((1R,2R,4R,5S,8S,12R)-7-(3-chloro-4-cyanophenyl)-4-methyl-6-oxo-9,13-dioxa-7-azatetracyclo[6.3.1.1$^{1,4}$. 0$^{5,12}$] tridec-2-yl) carbamate (205); Methyl ((1R,2R,4R,5S,8S,12R)-7-(4-cyano-3-fluoro-5-(trifluoromethyl)phenyl)-4-methyl-6-oxo-9,13-dioxa-7-azatetracyclo[6.3.1.1$^{1,4}$.0$^{5,12}$] tridec-2-yl)carbamate (206); Methyl ((1R,3R,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl) carbamate (207); Methyl ((1R,3R,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl) carbamate (208); Isopropyl ((1R,3R,4S,5S,8S,12R)-7-(3,5-dichloro-4-cyanophenyl)-4-methyl-6-oxo-9,13-dioxa-7-azatetracyclo [6.3.1.1$^{1,4}$.0$^{5,12}$]tridec-3-yl)carbamate (209); Methyl ((1R,3R,4S,5S,8S,12R)-7-(4-cyano-2-fluoro-3-(trifluoromethyl) phenyl)-4-methyl-6-oxo-9,13-dioxa-7-azatetracyclo [6.3.1.1$^{1,4}$.0$^{5,12}$]tridec-3-yl)carbamate (210); Methyl ((1R,3R,4S,5S,8S,12R)-7-(3-bromo-4-chlorophenyl)-4-methyl-6-oxo-9,13-dioxa-7-azatetracyclo[6.3.1.1$^{1,4}$.0$^{5,12}$]tridec-3-yl) carbamate (211); N-((1R,2S,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)propanamide (213); N-((1R,2S,4R,5S,8S,12R)-7-(3-chloro-4-cyanophenyl)-4-methyl-6-oxo-9,13-dioxa-7-azatetracyclo[6.3.1.1$^{1,4}$. 0$^{5,12}$]tridec-2-yl) propanamide (214); N-((1R,2R,4R,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl) propanamide (215); N-((1R,2R,4R,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)acetamide (216); N-((1R,2R,4R,5S,8S,12R)-7-(4-cyano-3-(trifluoromethyl) phenyl)-4-methyl-6-oxo-9,13-dioxa-7-azatetracyclo [6.3.1.1$^{1,4}$.0$^{5,12}$]tridec-2-yl)-2-methylpropanamide (217); N-((1R,2R,4R,5S,8S,12R)-7-(4-cyano-3-(trifluoromethyl) phenyl)-4-methyl-6-oxo-9,13-dioxa-7-azatetracyclo [6.3.1.1$^{1,4}$.0$^{5,12}$]tridec-2-yl)-2-methoxyacetamide (218); N-((1R,2R,4R,5S,8S,12R)-7-(4-cyano-3-(trifluoromethyl) phenyl)-4-methyl-6-oxo-9,13-dioxa-7-azatetracyclo [6.3.1.1$^{1,4}$.0$^{5,12}$] tridec-2-yl)-N$^2$,N$^2$-dimethylglycinamide (219); N-((1R,2R,4R,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-2-yl)-3-(4-morpholinyl)propanamide (220); N-((1R,2R,4R,5S,8S,12R)-7-(3-chloro-4-cyanophenyl)-4-methyl-6-oxo-9,13-dioxa-7-azatetracyclo[6.3.1.1$^{1,4}$. 0$^{5,12}$]tridec-2-yl)propanamide (221); N-((1R,3S,4S,5S,8S,12R)-7-(4-cyano-3-(trifluoromethyl)phenyl)-4-methyl-6-oxo-9,13-dioxa-7-azatetracyclo[6.3.1.11,4.05,12]tridec-3-yl)ethanesulfonamide (222); N-((1R,3S,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl) ethanesulfonamide (223); N-((1R,3R,4S,5S,8S,12R)-7-(3,5-dichloro-4-cyanophenyl)-4-methyl-6-oxo-9,13-dioxa-7-azatetracyclo[6.3.1.1$^{1,4}$.0$^{5,12}$]tridec-3-yl)ethanesulfonamide (224); N-((1R,3R,4S,5S,8S,12R)-7-(3-Bromo-4-chlorophenyl)-4-methyl-6-oxo-9,13-dioxa-7-azatetracyclo[6.3.1.1$^{1,44}$. 0$^{5,12}$]tridec-3-yl)ethanesulfonamide (225); Ethyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$] tridec-3-yl)carbamate (227); Isopropyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl) carbamate (228); 2-Hydroxyethyl ((1S,3R,4R,5R,8R,12S)-7-(4-cyano-3-trifluoromethyl)phenyl)-4-methyl-6-oxo-9,13-dioxa-7-azatetracyclo[6.3.1.1$^{1,4}$.0$^{5,12}$] tridec-3-yl) carbamate (229); 2-Methoxyethyl ((1S,3R,4R,5R,8R,12S)-

7-(4-cyano-3-(trifluoromethyl)phenyl)-4-methyl-6-oxo-9,13-dioxa-7-azatetracyclo[6.3.1.1$^{1,4}$.0$^{5,12}$] tridec-3-yl) carbamate (230); 2-(4-Morpholinyl)ethyl ((1S,3R,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$] tridec-3-yl)carbamate (231); Methyl ((1S,3R,4R,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (232); Methyl ((1S,3R,4R,5R,8R,12S)-7-(3,5-dichloro-4-cyanophenyl)-4-methyl-6-oxo-9,13-dioxa-7-azatetracyclo [6.3.1.1$^{1,4}$.0$^{5,12}$]tridec-3-yl)carbamate (233); Methyl ((1S,3R,4R,5R,8R,12S)-7-(3-chloro-4-cyanophenyl)-4-methyl-6-oxo-9,13-dioxa-7-azatetracyclo[6.3.1.1$^{1,4}$.0$^{5,12}$]tridec-3-yl)carbamate (234); Methyl ((1S,3S,4R,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (235); N-((1R,3S,4S,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-3-yl)propanamide (236); N-((1R,3S,4S,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$] tridec-3-yl)propanamide (237); Methyl ((1S,2S,4S,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl) carbamate (238); Methyl ((1S,2S,4S,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (239); 2-Bromo-4-((1S,2R,4S,5R,8R,12S)-2-hydroxy-4-methyl-6-oxo-9,13-dioxa-7-azatetracyclo[6.3.1.1$^{1,4}$.0$^{5,12}$] tridec-7-yl)benzonitrile (240); 2-Fluoro-4-((1S,2R,4S,5R,8R,12S)-2-hydroxy-4-methyl-6-oxo-9,13-dioxa-7-azatetracyclo [6.3.1.1$^{1,4}$.0$^{5,12}$]tridec-7-yl)-6-(trifluoromethyl)benzonitrile (241); Methyl ((1S,2R,4S,5R,8R,12S)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (242); Methyl ((1S,2R,4S,5R,8R,12S)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-2-yl)carbamate (243); Methyl ((1R,2R,3R,4S,5S,8S,12R)-7-(4-cyano-3-(trifluoromethyl)phenyl)-3-hydroxy-4-methyl-6-oxo-9,13-dioxa-7-azatetracyclo [6.3.1.1$^{1,4}$.0$^{5,12}$]tridec-2-yl)carbamate (244); N-((1R,2R,3R,4S,5S,8S,12R)-7-(4-cyano-3-(trifluoromethyl)phenyl)-3-hydroxy-4-methyl-6-oxo-9,13-dioxa-7-azatetracyclo[6.3.1.1$^{1,4}$.0$^{5,12}$] tridec-2-yl)acetamide (245); N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo [6.3.1.1$^{1,4}$.0$^{5,12}$]tridec-2-yl)methanesulfonamide (246); N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-2,2,2-trifluoroethanesulfonamide (247); N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)-4-fluorobenzenesulfonamide (248); N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo [6.3.1.1$^{1,4}$.0$^{5,12}$]tridec-2-yl)ethanesulfonamide (249); N-((1R,2R,3R,4S,5S,8S,12R)-7-(4-Cyano-3-(trifluoromethyl)phenyl)-3-hydroxy-4-methyl-6-oxo-9,13-dioxa-7-azatetracyclo[6.3.1.1$^{1,4}$.0$^{5,12}$]tridec-2-yl)cyclopropanesulfonamide (250); Methyl ((1S,2R,3R,4R,5R,8R,12S)-7-(4-cyano-3-(trifluoromethyl)phenyl)-2-hydroxy-4-methyl-6-oxo-9,13-dioxa-7-azatetracyclo[6.3.1.1$^{1,4}$.0$^{5,12}$]tridec-3-yl) carbamate (251); N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo [6.3.1.1$^{1,4}$.0$^{5,12}$]tridec-3-yl) methanesulfonamide (252); N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo[6.3.1.1$^{1,4}$.0$^{5,12}$] tridec-3-yl)-2,2,2-trifluoroethanesulfonamide (253); N-((1S,2R,3R,4R,5R,8R,12S)-7-(4-cyano-3-(trifluoromethyl)phenyl)-2-hydroxy-4-methyl-6-oxo-9,13-dioxa-7-azatetracyclo [6.3.1.1$^{1,4}$.0$^{5,12}$] tridec-3-yl)acetamide (254); N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo [6.3.1.1$^{1,4}$.0$^{5,12}$]tridec-3-yl)ethanesulfonamide (255); N-((1R,2S,3S,4S,5S,8S,12R)-7-(4-Cyano-3-(trifluoromethyl)phenyl)-2-hydroxy-4-methyl-6-oxo-9,13-dioxa-7-azatetracyclo [6.3.1.1$^{1,4}$.0$^{5,12}$]tridec-3-yl)-4-fluorobenzenesulfonamide (256); 2-Bromo-4-((1R,4R,5S,8S,12R)-4-methyl-2,6-dioxo-9,13-dioxa-7-azatetracyclo [6.3.1.1$^{1,4}$.0$^{5,12}$]tridec-7-yl)benzonitrile (257); (1R,4R,5S,8S,12R)-7-(4-chloro-2-methyl-3-(trifluoromethyl)phenyl)-4-methyl-9,13-dioxa-7-azatetracyclo [6.3.1.1$^{1,4}$.0$^{5,12}$]tridecane-2,6-dione (258); 3-Fluoro-4-((1R,4R,5S,8S,12R)-4-methyl-2,6-dioxo-9,13-dioxa-7-azatetracyclo [6.3.1.1$^{1,4}$.0$^{5,12}$] tridec-7-yl)-2-(trifluoromethyl)benzonitrile (259); 4-((1R,4R,5S,8S,12R)-4-Methyl-2,6-dioxo-9,13-dioxa-7-azatetracyclo [6.3.1.1$^{1,4}$.0$^{5,12}$]tridec-7-yl)-2-(trifluoromethoxy) benzonitrile (260); 2-Chloro-4-((1R,4R,5S,8S,12R)-4-methyl-2,6-dioxo-9,13-dioxa-7-azatetracyclo [6.3.1.1$^{1,4}$.0$^{5,12}$]tridec-7-yl)benzonitrile (261); 2-Chloro-4-((1R,4R,5S,8S,12R)-4-methyl-2,6-dioxo-9,13-dioxa-7-azatetracyclo [6.3.1.1$^{1,4}$.0$^{5,12}$] tridec-7-yl)-6-(trifluoromethyl)benzonitrile (262); 4-((1R,4R,5S,8S,12R)-4-Methyl-2,6-dioxo-9,13-dioxa-7-azatetracyclo [6.3.1.1$^{1,4}$.0$^{5,12}$]tridec-7-yl)-2-(trifluoromethoxy)benzonitrile (263); 3-chloro-5-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-2-pyridinecarbonitrile (264); 5-((1R,2S,4R,5S,8S,12R)-2-hydroxy-4-methyl-6-oxo-9,13-dioxa-7-azatetracyclo [6.3.1.1$^{1,4}$.0$^{5,12}$] tridec-7-yl)-3-methyl-2-pyridinecarbonitrile (265); 5-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-3-methoxy-2-pyridinecarbonitrile (266); 5-((1R,2S,4R,5S,8S,12R)-2-hydroxy-4-methyl-6-oxo-9,13-dioxa-7-azatetracyclo [6.3.1.1$^{1,4}$.0$^{5,12}$]tridec-7-yl)-3-(trifluoromethyl)-2-pyridinecarbonitrile (267); 3-bromo-5-((1R,2S,4R,5S,8S,12R)-2-hydroxy-4-methyl-6-oxo-9,13-dioxa-7-azatetracyclo[6.3.1.1$^{1,4}$.0$^{5,12}$]tridec-7-yl)-2-pyridinecarbonitrile (268); 3-Fluoro-4-((1S,4S,5S,8S,12R)-4-methyl-3,6-dioxo-9,13-dioxa-7-azatetracyclo [6.3.1.1$^{1,4}$.0$^{5,12}$]tridec-7-yl)-2-(trifluoromethyl)benzonitrile (269); (1S,4S,5S,8S,12R)-7-(3-Bromo-4-chlorophenyl)-4-methyl-9,13-dioxa-7-azatetracyclo[6.3.1.1$^{1,4}$.0$^{5,12}$]tridecane-3,6-dione (270); 4-((1S,4S,5S,8S,12R)-4-methyl-3,6-dioxo-9,13-dioxa-7-azatetracyclo[6.3.1.1$^{1,4}$.0$^{5,12}$] tridec-7-yl)-2-(trifluoromethyl)benzonitrile (271); 2-Chloro-4-((1S,4S,5S,8S,12R)-4-methyl-3,6-dioxo-9,13-dioxa-7-azatetracyclo[6.3.1.1$^{1,4}$.0$^{5,12}$] tridec-7-yl)benzonitrile (272); 4-((1R,2E,4R,5S,8S,12R)-2-(Ethoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (273); 4-((1R,2E,4R,5S,8S,12R)-2-((Benzyloxy)imino)-4-methyl-6-oxo-9,13-dioxa-7-azatetracyclo[6.3.1.1$^{1,4}$.0$^{5,12}$]tridec-7-yl)-2-(trifluoromethyl)benzonitrile (274); 4-((1R,4R,5S,8S,12R)-2-(tert-Butoxyimino)-4-methyl-6-oxo-9,13-dioxa-7-azatetracyclo [6.3.1.1$^{1,4}$.0$^{5,12}$]tridec-7-yl)-2-(trifluoromethyl)benzonitrile (275); 4-((1R,4R,5S,8S,12R)-2-(Isopropoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (276); 4-((1R,2E,4R,5S,8S,12R)-4-Methyl-6-oxo-2-(phenoxyimino)-9,13-dioxa-7-azatetracyclo[6.3.1.1$^{1,4}$.0$^{5,12}$]tridec-7-yl)-2-(trifluoromethyl)benzonitrile (277); 4-((1R,4R,5S,8S,12R)-

4-Methyl-6-oxo-2-((tetrahydro-2H-pyran-2-yloxy)imino)-9,13-dioxa-7-azatetracyclo[6.3.1.1$^{1,4}$.0$^{5,12}$]tridec-7-yl)-2-(trifluoromethyl)benzonitrile (278); 4-((1R,3E,4S,5S,8S,12R)-3-(Methoxyimino)-4-methyl-6-oxo-9,13-dioxa-7-azatetracyclo [6.3.1.1$^{1,4}$.0$^{5,12}$]tridec-7-yl)-2-(trifluoromethyl)benzonitrile (279); 4-((1R,3E,4S,5S,8S,12R)-3-(Ethoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (280); 4-((1R,4S,5S,8S,12R)-3-((Benzyloxy)imino)-4-methyl-6-oxo-9,13-dioxa-7-azatetracyclo[6.3.1.1$^{1,4}$.0$^{5,12}$]tridec-7-yl)-2-(trifluoromethyl)benzonitrile (281); 4-((1R,3E,4S,5S,8S,12R)-3-(tert-Butoxyimino)-4-methyl-6-oxo-9,13-dioxa-7-azatetracyclo [6.3.1.1$^{1,4}$.0$^{5,12}$]tridec-7-yl)-2-(trifluoromethyl)benzonitrile (282); 4-((1R,4S,5S,8S,12R)-3-(Isopropoxyimino)-4-methyl-6-oxo-9,13-dioxa-7-azatetracyclo[6.3.1.1$^{1,4}$.0$^{5,12}$]tridec-7-yl)-2-(trifluoromethyl)benzonitrile (283); 4-((1R,4S,5S,8S,12R)-4-Methyl-6-oxo-3-(phenoxyimino)-9,13-dioxa-7-azatetracyclo[6.3.1.1$^{1,4}$.0$^{5,12}$]tridec-7-yl)-2-(trifluoromethyl)benzonitrile (284); Methyl ((1R,3S,4S,5S,8S,12R)-7-(3,5-dichloro-4-cyanophenyl)-4-methyl-6-oxo-9,13-dioxa-7-azatetracyclo [6.3.1.1$^{1,4}$.0$^{5,12}$]tridec-3-yl) carbamate (285); Methyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (286); Ethyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (287); Isopropyl ((1R,3S,4S,5S,8S,12R)-7-(4-cyano-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (288); 2-Hydroxyethyl ((1R,3S,4S,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-3-yl)carbamate (289); 2-Methoxyethyl ((1R,3S,4S,5S,8S,12R)-7-(4-cyano-3-(trifluoromethyl)phenyl)-4-methyl-6-oxo-9,13-dioxa-7-azatetracyclo [6.3.1.1$^{1,4}$.0$^{5,12}$]tridec-3-yl)carbamate (290); and Methyl ((1R,3S,4S,5S,8S,12R)-7-(4-chloro-3-(trifluoromethyl)phenyl)-4-methyl-6-oxo-9,13-dioxa-7-azatetracyclo[6.3.1.1$^{1,4}$.0$^{5,12}$]tridec-3-yl)carbamate (291).

\* \* \* \* \*

UNITED STATES PATENT AND TRADEMARK OFFICE
CERTIFICATE OF CORRECTION

PATENT NO. : 8,067,582 B2  
APPLICATION NO. : 12/666423  
DATED : November 29, 2011  
INVENTOR(S) : Derek Norris et al.

Page 1 of 1

It is certified that error appears in the above-identified patent and that said Letters Patent is hereby corrected as shown below:

In the Claims:

Col. 205, claim 1, line 61, delete "$(CH_3)_2$" and insert -- $(CH_3)_2$, --, therefor;

Col. 210, claim 9, lines 51-52, delete "$[6.3.1.1^{1,}{}_{4}.0^{5,12}]$" and insert -- $[6.3.1.1^{1,4}.0^{5,12}]$ --, therefor;

Col. 215, claim 9, line 56, delete "2,6-Dichloro-4S, 3R," and insert -- 2,6-Dichloro-4-((1S,3R, --, therefor; and Col. 218, claim 9, lines 57-58, delete "$[6.3.1.1^{1,44}.0^{5,12}]$" and insert -- $[6.3.1.1^{1,4}.0^{5,12}]$ --, therefor.

Signed and Sealed this  
Twenty-second Day of May, 2012

David J. Kappos  
*Director of the United States Patent and Trademark Office*